US012637450B2

(12) United States Patent
Stocking et al.

(10) Patent No.: US 12,637,450 B2
(45) **Date of Patent: *May 26, 2026**

(54) TRI-SUBSTITUTED ARYL AND HETEROARYL DERIVATIVES AS MODULATORS OF PI3-KINASE AND AUTOPHAGY PATHWAYS

(71) Applicant: Global Cancer Technology Inc., San Diego, CA (US)

(72) Inventors: Emily M. Stocking, Encinitas, CA (US); Wolfgang J. Wrasidlo, La Jolla, CA (US)

(73) Assignee: Global Cancer Technology Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/741,572

(22) Filed: Jun. 12, 2024

(65) Prior Publication Data

US 2024/0327396 A1 Oct. 3, 2024

Related U.S. Application Data

(63) Continuation of application No. 17/982,425, filed on Nov. 7, 2022, now Pat. No. 12,049,462, which is a continuation of application No. 17/046,746, filed as application No. PCT/US2019/026634 on Apr. 9, 2019, now Pat. No. 11,492,348.

(60) Provisional application No. 62/655,741, filed on Apr. 10, 2018.

(51) Int. Cl.

| | |
|---|---|
| *C07D 413/14* | (2006.01) |
| *C07D 413/10* | (2006.01) |
| *C07D 413/12* | (2006.01) |

(52) U.S. Cl.

CPC ......... *C07D 413/14* (2013.01); *C07D 413/10* (2013.01); *C07D 413/12* (2013.01)

(58) Field of Classification Search

CPC ................ C07D 413/14; C07D 413/12; C07D 413/10

USPC ..................................................... 514/210.21

See application file for complete search history.

(56) References Cited

U.S. PATENT DOCUMENTS

| | | | | |
|---|---|---|---|---|
| 8,921,361 | B2 | 12/2014 | Cmiljanovic | |
| 11,236,079 | B2 | 2/2022 | Stocking | |
| 11,492,348 | B2 * | 11/2022 | Stocking | A61P 25/00 |
| 12,049,462 | B2 * | 7/2024 | Stocking | C07D 413/14 |
| 2009/0163545 | A1 | 6/2009 | Goldfarb | |
| 2010/0249126 | A1 | 9/2010 | Burger | |
| 2011/0230476 | A1 | 9/2011 | Niu | |
| 2012/0252802 | A1 | 10/2012 | Brown | |

FOREIGN PATENT DOCUMENTS

| | | | |
|---|---|---|---|
| CN | 101389622 | A | 3/2009 |
| CN | 102625708 | A | 8/2012 |
| CN | 103582636 | A | 2/2014 |
| EP | 3235816 | A1 | 10/2017 |
| JP | 2009527464 | A | 7/2009 |
| JP | 2010512338 | A | 4/2010 |
| JP | 2011507910 | A | 3/2011 |
| JP | 2011522865 | A | 8/2011 |
| JP | 2012508223 | A | 4/2012 |
| JP | 2013504325 | A | 2/2013 |
| JP | 2014509647 | A | 4/2014 |
| JP | 2014511395 | A | 5/2014 |
| JP | 2017513888 | A | 6/2017 |
| JP | 2017538730 | A | 12/2017 |
| WO | 2007084786 | A1 | 7/2007 |
| WO | 2008070740 | A1 | 6/2008 |
| WO | 2008098058 | A1 | 8/2008 |
| WO | 2009066084 | A1 | 5/2009 |
| WO | 2009150230 | A1 | 12/2009 |
| WO | 2010052569 | A2 | 5/2010 |
| WO | 2011031896 | A2 | 3/2011 |
| WO | 2012122383 | A2 | 9/2012 |
| WO | 2012135160 | A1 | 10/2012 |
| WO | 2015162084 | A1 | 10/2015 |
| WO | 2017140843 | A1 | 8/2017 |
| WO | 2017210545 | A1 | 12/2017 |
| WO | 2019199864 | A1 | 10/2019 |
| WO | 2019199874 | A1 | 10/2019 |

OTHER PUBLICATIONS

Bagshawe, K.D. (1995). "Antibody-Directed Enzyme Prodrug Therapy: A Review," Drug Dev. Res. 34:220-230.

Beaulieu, C. et al. (2004). "A Mild and Efficient New Synthesis of Aryl Sulfones From Boronic Acids and Sulfinic Acid Salts," Tetrahedron Letters 45(16):3233-3236.

Berge, S.M. et al. (Jan. 1977). "Pharmaceuticals Salts," J. Pharmaceutical Sciences 66(1):1-19.

Bertolini, G. et al. (1997). "A New Rational Hypothesis For The Pharmacophore Of The Active Metabolite Of Leflunomide, A Potent Immunosuppressive Drug," J. Med. Chem. 40(13):2011-2016.

Bhaskar, K. (Mar. 16, 2009). "The PI3K-Akt-mTOR Pathway Regulates Abeta Oligomer Induced Neuronal Cell Cycle Events," Molecular Neurodegeneration 4(14):18 pages.

Bodor, N. (1984). "Novel Approaches to the Design of Safer Drugs: Soft Drugs and Site-Specific Chemical Delivery Systems," Adv. Drug Res. 13:255-331.

Brooks, D.J. (Apr. 2005). "Positron Emission Tomography and Single-Photon Emission Computed Tomography in Central Nervous System Drug Development," NeuroRx 2(2):226-236.

Bruno, N.C. et al. (2013). "Design and Preparation of New Palladium Precatalysts for C—C and C—N Cross-coupling Reactions," Chem. Sci. 4:916-920.

(Continued)

*Primary Examiner* — Kahsay Habte

(74) *Attorney, Agent, or Firm* — MORRISON & FOERSTER LLP

(57) ABSTRACT

The present disclosure relates to tri-substituted aryl and heteroaryl derivatives, pharmaceutical compositions containing them, and methods of using them, including methods for modulating autophagy or preventing, reversing, slowing or inhibiting the PI3K-AKT-MTOR pathway, and methods of treating diseases that are associated with autophagy or the PI3K-AKT-MTOR pathway.

20 Claims, No Drawings

(56) References Cited

OTHER PUBLICATIONS

CAS Registry No. 300706-72-3, STN Entry Date: Nov. 1, 2000; 4-(4,4"-diethoxy[1,1':3',1"-terphenyl]-5'-yl)-morpholine.
CAS Registry No. 301171-51-7, STN entry date: Nov. 3, 2000; 4-[4,6-bis(4-methoxyphenyl)-2-pyridinyl]-morpholine.
CAS Registry No. 848987-07-5, STN entry date: Apr. 22, 2005; 4-(3,3",4,4"-tetramethoxy[1,1':3',1"-terphenyl]-5'-yl)-morpholine.
CAS Registry No. 858850-19-8; STN Entry Date: Aug. 8, 2005; 1-(3,5-di-p-tolylphenyl)-piperidine.
Cherra, S. J. et al. (May 2008). "Autophagy in Neuroprotection and Neurodegeneration: A Question Of Balance," Future Neurol. 3(3):309-323.
Codogno, P. et al. (2005). "Autophagy and Signaling: Their Role In Cell Survival And Cell Death," Cell Death and Differ. 12(S2):1509-1518.
International Preliminary Report on Patentability issued Oct. 13, 2020 for Patent Application No. PCT/US2019/026634, filed Apr. 9, 2019, 6 pages.
International Search Report and Written Opinion of the International Searching Authority mailed Jun. 5, 2019, for International Patent Application No. PCT/US2019/026634, filed Apr. 9, 2019, 11 pages.
Katritzky, A.R et al. (1997). "Benzotriazole-Assisted Preparations Of 2-(Substituted Amino) Pyridines and Pyrid-2-ones," J Organic Chemistry 62(18):6210-6214.
Katritzky, A.R. et al. (2000). "Syntheses of 2-Alkylamino- and 2-Dialkylamino-4,6-diarylpyridines and 2,4,6-Trisubstituted Pyrimidines Using Solid-Phase-Bound Chalcones," J Combinatorial Chemistry 2(2):182-185.
Martinez-Vicente, M. et al. (May 2010). "Cargo Recognition Failure Is Responsible For Inefficient Autophagy In Huntington's Disease," Nat. Neurosci. 13(5):567-576.
Meredith, E.L. et al. (2010, e-pub. Jul. 14, 2010). "Identification of Potent and Selective Amidobipyridyl Inhibitors of Protein Kinase D," Journal of Medicinal Chemistry, 53(15):5422-5438.
Nalini et al. (2018, e-pub. Oct. 23, 2017). "Computational Design of New Protein Kinase D 1 (PKD1) Inhibitors: Homology-Based Active Site Prediction, Energy-Optimized Pharmacophore, Docking and Database Screening," Molecular Diversity 22(1):47-56 and Supplemental Information, 25 pages.
Reddy, K.R. et al., (Aug. 1995). "Cycloaromatization Of Methyl (E)-4-lithio-3-(1-pyrrolidinyl)-2-butenoate With α-oxoketene N,S-Acetals: Direct Synthesis of 3,5-Vis(cycloalkylamino)biphenyls," Synthesis 8:929-930.
Ronan, B. et al. (Dec. 2014, e-pub. Oct. 19, 2014). "A Highly Potent and Selective Vps34 Inhibitor Alters Vesicle Trafficking and Autophagy," 10(21):1013-1019.
Shan, D. et al. (Jul. 1997). "Prodrug Strategies Based On Intramolecular Cyclization Reactions," J. Pharm. Sci. 86 (7):765-767.

* cited by examiner

TRI-SUBSTITUTED ARYL AND HETEROARYL DERIVATIVES AS MODULATORS OF PI3-KINASE AND AUTOPHAGY PATHWAYS

CROSS-REFERENCE TO RELATED APPLICATIONS

This application is a continuation of U.S. patent application Ser. No. 17/982,425, filed Nov. 7, 2022, now issued as U.S. Pat. No. 12,049,462, which is a continuation of U.S. patent application Ser. No. 17/046,746, filed Oct. 9, 2020, now issued as U.S. Pat. No. 11,492,348, which is a national stage application under 35 U.S.C. § 371 of International Application No. PCT/US2019/026634, filed internationally on Apr. 9, 2019, which claims priority to U.S. Provisional Application No. 62/655,741, filed Apr. 10, 2018, entitled "TRI-SUBSTITUTED ARYL AND HETEROARYL DERIVATIVES AS MODULATORS OF PI3-KINASE AND AUTOPHAGY PATHWAYS," the content of which is hereby incorporated by reference in its entirety for all purposes.

TECHNICAL FIELD

The present disclosure relates to tri-substituted aryl and heteroaryl compounds, pharmaceutical compositions containing them, and methods of using them, including methods for modulating the PI3K-AKT-MTOR pathway, methods for activating, increasing or stimulating autophagy by preventing, reversing, slowing, or inhibiting the PI3K-AKT-MTOR pathway, and methods for treating diseases that are associated with mis-regulation of the PI3K-AKT-MTOR pathway.

BACKGROUND

Autophagy, a principal mechanism for the clearance of cellular constituents, plays an important role in development, cellular differentiation, homeostasis, and cell survival. Mis-regulation of autophagy has been linked to a number of different neurodegenerative disorders including amyotrophic lateral sclerosis, Alzheimer's disease (AD), Parkinson's disease (PD), and Huntington's disease (HD). Therapeutic agents that activate autophagy may be beneficial in the treatment of these neurodegenerative disorders (Martinez-Vicente et al. *Nat. Neurosci.* 2010, 13(5), 567-576).

The PI3K-AKT-mTOR (PI3 kinase/Akt/mammalian target of rapamycin) pathway regulates the expression of cell survival genes and cell energetics. This pathway is also a key negative regulator of autophagy (Codogno and Meijer, *Cell Death Differ.* 2005, 12(S2), 1509-1518, Bhaskar, et al. *Molecular Neurodegeneration* 2009, 4, 14; Cherra and Chu, Future Neurol. 2008, 3(3), 309-323). Thus, inhibition of the PI3K-AKT-mTOR pathway may be an ideal way to up regulate autophagy, promote cell survival, and treat peripheral degenerative disorders and neurodegenerative disorders.

Intracellular systems, which regulate reactive oxygen and reactive nitrogen species (ROS/RNA) formation as well as ROS/RNS transformation, are central to maintaining cellular oxidation-reduction homeostasis. Aberrant, unregulated ROS/RNS formation results in enzyme dysfunction, increased protein misfolding and activation of pathogenic cellular processes, which underlie multiple neurodegenerative disorders. PI3K plays a central role in the regulation of ROS/RNS formation through modulation of nitrogen oxide synthase (NOS) and nicotinamide adenine dinucleotide phosphate (NADPH) oxidase (NOX) signaling pathways. Indeed, PI3K inhibition reduces ROS and oxidative stress signaling. Therapeutic agents that inhibit PI3K would likely be beneficial in the treatment of neurodegenerative diseases which exhibit pathogenic, oxidative stress mechanisms, including hypoxia-ischemia, traumatic brain injury, synucleinopathies, AD, HD, spinal cord injury and seizure.

Additionally, the PI3K/AKT pathway has recently emerged as a clinically relevant target for inflammatory diseases, including dermatological disorders. Modulators of the PI3K/AKT pathway may have utility in the treatment of dermatological disorders such as atopic dermatitis, rosacea, acne, and psoriasis.

There remains a need for compounds that affect autophagy with desirable pharmaceutical properties. The present disclosure provides certain tri-substituted aryl and heteroaryl compounds have been found to inhibit the PI3K-AKT-MTOR pathway. These compounds inhibit phosphorylation of AKT and mTOR. Consequently, these compounds also increase markers of autophagy and increase cellular clearance of toxic protein aggregates. These compounds may thus have utility in the treatment of neurodegenerative disorders and other disorders associated with the PI3K-AKT-mTOR signaling pathway, such as Alzheimer's Disease, Parkinson's Disease, fronto-temporal dementia, dementia with Lewy Bodies, PD dementia, multiple system atrophy, Huntington's disease, Amyotrophic lateral sclerosis, cancer, infection, dermatological disorders, Crohn's disease, heart disease, Paget's disease, Charcot-Marie-Tooth Disease, macular degeneration, cardiomyopathy, and aging.

SUMMARY

In one aspect, the present disclosure provides a compound of Formula (I):

(I)

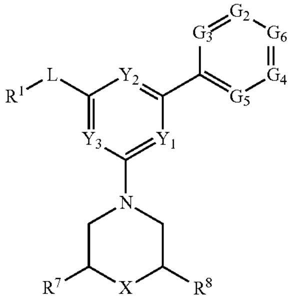

wherein $R^1$ is $-(CR^aR^b)_m$-aryl, $-CH{=}CH$-aryl, $-(CR^cR^d)_n$-heteroaryl, $-(CR^eR^f)_o$-heterocycloalkyl, or $-(CR^gR^h)_p$-cycloalkyl; wherein m, n, o, and p are each independently 0, 1, or 2;

$R^a$, $R^b$, $R^c$, $R^d$, $R^e$, $R^f$, $R^g$, and $R^h$ are each independently H, halo, or $C_{1-4}$alkyl, or $R^a$ and $R^b$ are taken together with the carbon to which they are attached to form a cycloalkyl ring, or $R^a$ and $R^b$ are taken together to form $=CH_2$ or $=O$;

each aryl, heteroaryl, heterocycloalkyl, or cycloalkyl present in $R^1$ is unsubstituted or substituted with one or two $R^x$ substituents;

wherein each $R^x$ substituent is independently halo, $C_{1-4}$alkyl, cycloalkyl, $-C_{1-2}$-haloalkyl, $-OH$, $-OC_{1-4}$alkyl, $-O-C_{1-2}$-haloalkyl, cyano, —$C(O)C_{1-4}$alkyl, —$C(O)NR^iR^j$, —$SO_2C_{1-4}$alkyl, —$SO_2NR^kR^l$, —$NR^qR^r$, —C(O)-cycloalkyl, —C(O)-aryl (optionally substituted with methyl or halo), —$CO_2C_{1-4}$alkyl, —$CO_2$aryl, —C(O)$CH_2$-aryl (optionally substituted with methyl or halo), —$CH_2$-aryl (optionally substituted with methyl or halo), or monocyclic heterocycloalkyl (optionally substituted with methyl, —$C(O)C_{1-4}$ alkyl, or —$CO_2C_{1-4}$alkyl);

wherein $R^1$, $R^j$, $R^k$, and $R^l$ are each independently H, $C_{1-4}$alkyl, —$C_{1-4}$alkyl-OH, or —$C_{1-4}$alkyl-O—$C_{1-4}$alkyl, wherein $R^q$ and $R^r$ are each independently H, $C_{1-4}$alkyl, —$C_{1-4}$alkyl-OH, —$C_{1-4}$alkyl-O—$C_{1-4}$alkyl, —$C(O)C_{1-4}$alkyl, —$CO_2C_{1-4}$alkyl, or —$SO_2C_{1-4}$alkyl;

L is absent, —$S(O)_2$—, —C(O)—, —O—, —$CH_2$—, —$CF_2$—, $C(CH_3)_2$, —C(=$CH_2$)—, or —$CR^sR^t$—;

wherein $R^s$ and $R^t$ are independently H or alkyl, or $R^s$ and $R^t$ are taken together with the carbon atom to which they are attached to form a cycloalkyl ring;

X is O, S, NH, N($CO_2C_{1-4}$alkyl), N($SO_2C_{1-4}$alkyl), N($SO_2$cycloalkyl), or $CH_2$;

$Y_1$, $Y_2$, and $Y_3$ are each independently CH or N; wherein when L is other than —$S(O)_2$—, $Y_2$ and $Y_3$ are each CH;

$G_2$ is N or $CR^2$;

$G_3$ is N or $CR^3$;

$G_4$ is N, $NR^{4b}$, or $CR^{4a}$;

$G_5$ is N or $CR^5$; and $G_6$ is N or $CR^6$;

wherein $R^2$, $R^3$, $R^{4a}$, $R^5$, and $R^6$ are each independently hydrogen, halogen, —OH, -alkyl, —Oalkyl, -haloalkyl, —O-haloalkyl, or —$NR^uR^v$;

or $R^{4b}$ is taken together with $R^6$ and the atoms to which they are attached to form a heteroaryl or heterocyclic ring; wherein the heteroaryl ring comprising $R^{4b}$ and $R^6$ comprises no more than one N and is optionally substituted with alkyl, and the heterocyclic ring comprising $R^{4b}$ and $R^6$ is optionally substituted with oxo, $R^u$ is H or $C_{1-4}$alkyl;

$R^v$ is H, $C_{1-4}$alkyl, monocyclic cycloalkyl, —$C(O)C_{1-4}$ alkyl, or —$C(O)NR^wR^y$;

wherein each alkyl present in $R^v$ is unsubstituted or substituted with —OH, —$NH_2$, —NH($C_{1-4}$alkyl), or —N($C_{1-4}$alkyl)$_2$, $R^w$ and $R^v$ are each independently H or $C_{1-4}$alkyl; wherein

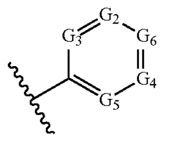

is not unsubstituted phenyl; and $R^7$ and $R^8$ are each independently hydrogen or $C_{1-4}$alkyl, or $R^7$ and $R^8$ are taken together to form —$CH_2CH_2$—;

or a pharmaceutically acceptable salt thereof.

In certain embodiments, the compound of Formula (I) is a compound selected from those species described or exemplified in the detailed description herein.

In some embodiments of Formula (I) or any variation thereof, $R^1$ is —$(CR^aR^b)_m$-aryl. In some embodiments, $R^1$ is $(CR^cR^d)_n$-heteroaryl. In some embodiments, $R^1$ is $(CR^eR^f)_o$-heterocycloalkyl or $(CR^gR^h)_p$-cycloalkyl.

In some embodiments of Formula (I) or any variation thereof, L is —$S(O)_2$—. In some embodiments, L is —C(O)—, —$CH_2$—, —$CF_2$—, $C(CH_3)_2$, —C(=$CH_2$)—, or —$CR^sR^t$—. In other embodiments, L is —C(O)—, —O—, —$CH_2$—, —$CF_2$—, $C(CH_3)_2$, —C(=$CH_2$)—, or —$CR^sR^t$—. In some embodiments, L is absent.

Provided in other aspects are compounds of Formula (II):

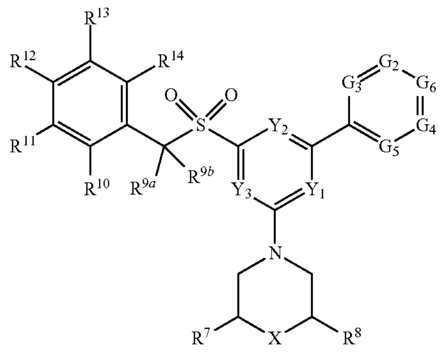

(II)

wherein

X is O, S, NH, N($CO_2C_{1-4}$alkyl), N($SO_2C_{1-4}$alkyl), N($SO_2$cycloalkyl), or $CH_2$;

$Y_1$, $Y_2$, and $Y_3$ are each independently CH or N;

$G_2$ is N or $CR^2$;

$G_3$ is N or $CR^3$;

$G_4$ is N, $NR^{4b}$, or $CR^{4a}$;

$G_5$ is N or $CR^5$; and $G_6$ is N or $CR^6$;

wherein $R^2$, $R^3$, $R^{4a}$, $R^5$, and $R^6$ are each independently hydrogen, halogen, —OH, -alkyl, —Oalkyl, -haloalkyl, —O-haloalkyl, or —$NR^uR^v$;

or $R^{4b}$ is taken together with $R^6$ and the atoms to which they are attached to form a heteroaryl or heterocyclic ring; wherein the heteroaryl ring comprising $R^{4b}$ and $R^6$ comprises no more than one N and is optionally substituted with alkyl, and the heterocyclic ring comprising $R^{4b}$ and $R^6$ is optionally substituted with oxo, $R^u$ is H or $C_{1-4}$alkyl;

$R^v$ is H, $C_{1-4}$alkyl, monocyclic cycloalkyl, —$C(O)C_{1-4}$ alkyl, or —$C(O)NR^wR^y$;

wherein each alkyl present in $R^v$ is unsubstituted or substituted with —OH, —$NH_2$, —NH($C_{1-4}$alkyl), or —N($C_{1-4}$alkyl)$_2$, and $R^w$ and $R^v$ are each independently H or $C_{1-4}$alkyl; wherein

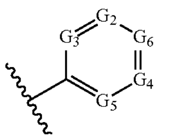

is not unsubstituted phenyl;

$R^7$ and $R^8$ are each independently hydrogen or $C_{1-4}$alkyl, or $R^7$ and $R^8$ are taken together to form —$CH_2CH_2$—;

$R^{9a}$ and $R^{9b}$ are each independently hydrogen or halogen;

$R^{10}$, $R^{11}$, $R^{12}$, $R^{13}$, and $R^{14}$ are each independently hydrogen, halogen, —OH, —CN, -alkyl, —Oalkyl, -haloalkyl, heterocycloalkyl, —O-haloalkyl, —$SO_2C_{1-4}$alkyl, or —$NR^{aa}R^{bb}$;

$R^{aa}$ is hydrogen, $C_{1-4}$alkyl, or —$C_{1-4}$alkyl-OH;

$R^{bb}$ is hydrogen or $C_{1-4}$alkyl;

or $R^{9a}$ is taken together with $R^{10}$ and the interposed atoms to form a heteroaryl or heterocyclic ring;

or $R^{11}$ is taken together with $R^{12}$ and the atoms to which they are attached to form a heteroaryl or heterocyclic ring;

or a pharmaceutically acceptable salt thereof.

Provided in other aspects are compounds of Formula (III):

(III)

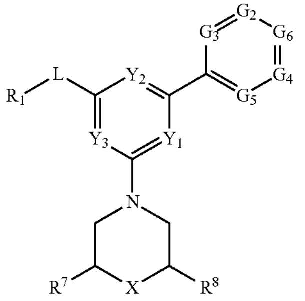

wherein $R^1$ is —$(CR^aR^b)_m$-aryl, —CH═CH-aryl, $(CR^cR^d)_n$-heteroaryl, $(CR^eR^f)_o$— heterocycloalkyl, or $(CR^gR^h)_p$-cycloalkyl, wherein when L is $SO_2$, the heteroaryl and the heterocycloalkyl present in $R^1$ are each monocyclic;

m is 0 or 2;

n, o, and p are each independently 0, 1, or 2;

$R^a$, $R^b$, $R^c$, $R^d$, $R^e$, $R^f$, $R^g$, and $R^h$ are each independently H, halo, or $C_{1-4}$alkyl, or $R^a$ and $R^b$ are taken together with the carbon to which they are attached to form a cycloalkyl ring, or $R^a$ and $R^b$ are taken together to form ═$CH_2$ or ═O;

each aryl, heteroaryl, heterocycloalkyl, or cycloalkyl present in $R^1$ is unsubstituted or substituted with one or two $R^x$ substituents;

wherein each $R^x$ substituent is independently halo, $C_{1-4}$alkyl, cycloalkyl, —$C_{1-2}$-haloalkyl, —OH, —$OC_{1-4}$alkyl, —O—$C_{1-2}$-haloalkyl, cyano, —C(O)$C_{1-4}$alkyl, —C(O)$NR^iR^j$, —$SO_2C_{1-4}$alkyl, —$SO_2NR^kR^l$, —$NR^qR^r$, —C(O)-cycloalkyl, —C(O)-aryl (optionally substituted with methyl or halo), —$CO_2C_{1-4}$alkyl, —$CO_2$aryl, —C(O)$CH_2$-aryl (optionally substituted with methyl or halo), —$CH_2$-aryl (optionally substituted with methyl or halo), or monocyclic heterocycloalkyl (optionally substituted with methyl, —C(O)$C_{1-4}$alkyl, or —$CO_2C_{1-4}$alkyl);

wherein $R^i$, $R^j$, $R^k$, and $R^l$ are each independently H, $C_{1-4}$alkyl, —$C_{1-4}$alkyl-OH, or —$C_{1-4}$alkyl-O—$C_{1-4}$ alkyl, wherein $R^q$ and $R^r$ are each independently H, $C_{1-4}$alkyl, —$C_{1-4}$alkyl-OH, —$C_{1-4}$alkyl-O—$C_{1-4}$alkyl, —C(O)$C_{1-4}$alkyl, —$CO_2C_{1-4}$alkyl, or —$SO_2C_{1-4}$alkyl;

or $R^1$ is

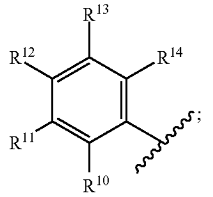

wherein $R^{10}$, $R^{11}$, $R^{12}$, $R^{13}$, and $R^{14}$ are each independently hydrogen, halogen, —OH, —CN, -alkyl, —Oalkyl, -haloalkyl, heterocycloalkyl, —O-haloalkyl, —$SO_2C_{1-4}$alkyl, or —$NR^{aa}R^{bb}$;

$R^{aa}$ is hydrogen, $C_{1-4}$alkyl, or —$C_{1-4}$alkyl-OH;

$R^{bb}$ is hydrogen or $C_{1-4}$alkyl;

or $R^{10}$ is taken together with $R^{11}$ and the atoms to which they are attached to form a heteroaryl or heterocyclic ring;

or $R^{11}$ is taken together with $R^{12}$ and the atoms to which they are attached to form a heteroaryl or heterocyclic ring;

L is absent, —$S(O)_2$—, —C(O)—, —O—, —$CH_2$—, —$CF_2$—, $C(CH_3)_2$, —C(═$CH_2$)—, or —$CR^sR^t$—; where $R^s$ and $R^t$ are independently H or alkyl, or $R^s$ and $R^t$ are taken together with the carbon atom to which they are attached to form a cycloalkyl ring;

X is O, S, NH, N($CO_2C_{1-4}$alkyl), N($SO_2C_{1-4}$alkyl), N($SO_2$cyclo-alkyl), or $CH_2$;

$Y_1$, $Y_2$, and $Y_3$ are each independently CH or N; wherein when L is other than —$S(O)_2$—, $Y_2$ and $Y_3$ are each CH;

$G_2$ is N or $CR^2$;

$G_3$ is N or $CR^3$;

$G_4$ is N, $NR^{4b}$, or $CR^{4a}$;

$G_5$ is N or $CR^5$; and $G_6$ is N or $CR^6$;

wherein $R^2$, $R^3$, $R^{4a}$, $R^5$, and $R^6$ are each independently hydrogen, halogen, —OH, -alkyl, —Oalkyl, -haloalkyl, —O-haloalkyl, or —$NR^uR^v$;

or $R^{4b}$ is taken together with $R^6$ and the atoms to which they are attached to form a heteroaryl or heterocyclic ring; wherein the heteroaryl ring comprising $R^{4b}$ and $R^6$ comprises no more than one N and is optionally substituted with alkyl, and the heterocylic ring comprising $R^{4b}$ and $R^6$ is optionally substituted with oxo, $R^u$ is H or $C_{1-4}$alkyl;

$R^v$ is H, $C_{1-4}$alkyl, monocyclic cycloalkyl, —C(O)$C_{1-4}$alkyl, or —C(O)$NR^wR^y$;

wherein each alkyl present in $R^v$ is unsubstituted or substituted with —OH, —$NH_2$, —NH($C_{1-4}$alkyl), or —N($C_{1-4}$alkyl$)_2$, $R^w$ and $R^y$ are independently H or $C_{1-4}$alkyl;

wherein

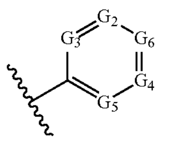

is not unsubstituted phenyl; and $R^7$ and $R^8$ are each independently hydrogen or $C_{1-4}$alkyl, or $R^7$ and $R^8$ are taken together to form —$CH_2CH_2$—; or a pharmaceutically acceptable salt thereof.

In some embodiments of any of the compounds of Formula (I), (II), or (III), $Y_1$, $Y_2$, and $Y_3$ are each CH. In some embodiments, $Y_1$ is N and $Y_2$ and $Y_3$ are each CH. In some embodiments, $Y_2$ is N and $Y_1$ and $Y_3$ are each CH. In some embodiments, $Y_3$ is N and $Y_1$ and $Y_2$ are each CH.

In some embodiments of any of the compounds of Formula (I), (II), or (III), X is O. In some embodiments, X is NH, $N(CO_2C_{1-4}alkyl)$, $N(SO_2C_{1-4}alkyl)$, or $N(SO_2cycloalkyl)$.

In some embodiments of any of the compounds of Formula (I), (II), or (III), $G_2$ and $G_4$ are each N, and $G_6$ is $CR^6$. In some embodiments of any of the compounds of Formula (I), (II), or (III), $G_3$ is $CR^3$ and $G_5$ is $CR^5$. In some embodiments of any of the compounds of Formula (I), (II), or (III), one of $G_2$ and $G_4$ is N.

In some embodiments of any of the compounds of Formula (I), (II), or (III), $R^6$ is $—NR^uR^v$. In some embodiments of any of the compounds of Formula (I), (II), or (III), $R^{4b}$ is taken together with $R^6$ and the atoms to which they are attached to form a heteroaryl or heterocyclic ring.

In a further aspect, the present disclosure provides a pharmaceutical composition comprising at least one compound of Formula (I), (II), or (III) or a pharmaceutically acceptable salt thereof. Pharmaceutical compositions according to the embodiments may further comprise a pharmaceutically acceptable excipient. Provided in some embodiments is a pharmaceutical composition that contains (a) at least one compound of Formula (I), (II) or (III), or a pharmaceutically acceptable salt thereof, and (b) a pharmaceutically acceptable excipient.

The present disclosure also provides a compound of Formula (I), (II), or (III) or a pharmaceutically acceptable salt thereof for use as a medicament. In some aspects, the compound of Formula (I), (II) or (III), or a pharmaceutically acceptable salt thereof, or a pharmaceutical composition containing a compound of Formula (I), (II) or (III), is used in the treatment of a disease or medical condition associated with autophagy or the PI3K-AKT-MTOR pathway. In some embodiments, the disease or medical condition is a neurodegenerative disorder. In other embodiments, the disease or medical condition is a peripheral degenerative disorder. In some embodiments, the disease or medical condition is Alzheimer's Disease, Parkinson's Disease, fronto-temporal dementia, dementia with Lewy Bodies, PD dementia, multiple system atrophy, Huntington's disease, Amyotrophic lateral sclerosis, cancer, infection, Crohn's disease, heart disease, Paget's disease, Charcot-Marie-Tooth Disease, macular degeneration, cardiomyopathy, and aging. In some embodiments, the disease or medical condition is a dermatological disorder. In some embodiments, the dermatological disorder is selected from rosacea, acne, psoriasis, and atopic dermatitis.

In another aspect, the present disclosure provides a method of treating a disease or medical condition associated with autophagy or the PI3K-AKT-mTOR pathway, comprising administering to a subject in need of such treatment an effective amount of at least one compound of Formula (I), (II), or (III) or a pharmaceutically acceptable salt thereof. In some embodiments, the disease or medical condition is a neurodegenerative disease or condition. In other embodiments, the disease or medical condition is a peripheral degenerative disorder. In some embodiments, the disease or medical condition is Alzheimer's Disease, Parkinson's Disease, fronto-temporal dementia, dementia with Lewy Bodies, PD dementia, multiple system atrophy, Huntington's disease, Amyotrophic lateral sclerosis, cancer, infection, Crohn's disease, heart disease, Paget's disease, Charcot-Marie-Tooth Disease, macular degeneration, cardiomyopathy, and aging. In some embodiments, the disease or medical condition is a dermatological disorder. In some embodiments, the dermatological disorder is selected from rosacea, acne, psoriasis, and atopic dermatitis.

The present disclosure provides use of a compound of Formula (I), (II), or (III) in the preparation of a medicament for the treatment of such diseases and medical conditions, and the use of such compounds and salts for treatment of such diseases and medical conditions. In some embodiments, provided is the use of at least one compound of Formula (I), (II) or (III), or a pharmaceutically acceptable salt thereof, or a pharmaceutical composition a compound of Formula (I), (II) or (III), in the manufacture of a medicament for the treatment of a disease or medical condition associated with autophagy or the PI3K-AKT-MTOR pathway. In some embodiments, the disease or medical condition is a neurodegenerative disorder. In other embodiments, the disease or medical condition is a peripheral degenerative disorder. In some embodiments, the disease or medical condition is Alzheimer's Disease, Parkinson's Disease, frontotemporal dementia, dementia with Lewy Bodies, PD dementia, multiple system atrophy, Huntington's disease, Amyotrophic lateral sclerosis, cancer, infection, Crohn's disease, heart disease, Paget's disease, Charcot-Marie-Tooth Disease, macular degeneration, cardiomyopathy, or aging. In some embodiments, the disease or medical condition is a dermatological disorder. In some embodiments, the dermatological disorder is selected from rosacea, acne, psoriasis, and atopic dermatitis.

In yet another aspect, the present disclosure provides a method of interfering with the process of autophagy in a cell modulating, activating, increasing or stimulating autophagy in a cell or preventing, reversing, slowing or inhibiting the PI3K-AKT-mTOR pathway, comprising contacting the cell with an effective amount of at least one compound of Formula (I), (II), or (III) or a salt thereof, and/or with at least one pharmaceutical composition of the embodiments, wherein the contacting is in vitro, ex vivo, or in vivo.

Additional embodiments, features, and advantages of the present disclosure will be apparent from the following detailed description and through practice of the present disclosure.

DETAILED DESCRIPTION

The present disclosure relates to aryl and heteroaryl compounds, pharmaceutical compositions containing them, and methods of using them, including methods for modulating, activating, increasing or stimulating autophagy by preventing, reversing, slowing or inhibiting the PI3K-AKT-MTOR pathway, and methods of treating diseases that are associated with regulating autophagy.

It is to be understood that this disclosure is not limited to particular embodiments described, as such may, of course, vary. It is also to be understood that the terminology used herein is for the purpose of describing particular embodiments only, and is not intended to be limiting.

As used herein and in the appended claims, the singular forms "a," "an," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As used herein, the terms “including,” “containing,” and “comprising” are used in their open, non-limiting sense.

To provide a more concise description, some of the quantitative expressions given herein are not qualified with the term “about.” It is understood that, whether the term “about” is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value. Whenever a yield is given as a percentage, such yield refers to a mass of the entity for which the yield is given with respect to the maximum amount of the same entity that could be obtained under the particular stoichiometric conditions. Concentrations that are given as percentages refer to mass ratios, unless indicated differently.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure. All publications mentioned herein are incorporated herein by reference to disclose and describe the methods and/or materials in connection with which the publications are cited.

Except as otherwise noted, the methods and techniques of the present embodiments are generally performed according to conventional methods well known in the art and as described in various general and more specific references that are cited and discussed throughout the present specification. See, e.g., Loudon, Organic Chemistry, $4^{th}$ edition, New York: Oxford University Press, 2002, pp. 360-361, 1084-1085; Smith and March, March’s Advanced Organic Chemistry: Reactions, Mechanisms, and Structure, $5^{th}$ edition, Wiley-Interscience, 2001.

The nomenclature used herein to name the subject compounds is illustrated in the Examples herein. This nomenclature has generally been derived using the commercially-available ChemBioDraw Ultra software, Version 13.0.2.3021.

It is appreciated that certain features of the disclosure, which are, for clarity, described in the context of separate embodiments, may also be provided in combination in a single embodiment. Conversely, various features of the disclosure, which are, for brevity, described in the context of a single embodiment, may also be provided separately or in any suitable subcombination. All combinations of the embodiments pertaining to the chemical groups represented by the variables are specifically embraced by the present disclosure and are disclosed herein just as if each and every combination was individually and explicitly disclosed, to the extent that such combinations embrace compounds that are stable compounds (i.e., compounds that can be isolated, characterized, and tested for biological activity). In addition, all subcombinations of the chemical groups listed in the embodiments describing such variables are also specifically embraced by the present disclosure and are disclosed herein just as if each and every such sub-combination of chemical groups was individually and explicitly disclosed herein.

Terms

The following terms have the following meanings unless otherwise indicated. Any undefined terms have their art recognized meanings.

The term “alkyl” refers to a saturated straight- or branched-chain hydrocarbon group having from 1 to 12 carbon atoms in the chain. Examples of alkyl groups include methyl (Me), ethyl (Et), n-propyl, isopropyl, butyl, isobutyl, sec-butyl, tert-butyl (tBu), pentyl, isopentyl, tert-pentyl, hexyl, isohexyl, and groups that in light of the ordinary skill in the art and the teachings provided herein would be considered equivalent to any one of the foregoing examples. In some instances, alkyl groups are $C_{1-4}$alkyl.

“Haloalkyl” refers to an alkyl group as described above, wherein one or more hydrogen atoms on the alkyl group have been substituted with a halo group. Examples of such groups include, without limitation, fluoroalkyl groups, such as fluoroethyl, trifluoromethyl, difluoromethyl, trifluoroethyl, and the like.

The term “oxo” represents a carbonyl oxygen. For example, a cyclopentyl substituted with oxo is cyclopentanone.

“Aryl” or “Ar” refers to a monovalent aromatic carbocyclic group of from 6 to 18 annular carbon atoms having a single ring (such as is present in a phenyl group) or a ring system having multiple condensed rings (examples of such aromatic ring systems include naphthyl, anthryl and indanyl) which condensed rings may or may not be aromatic, provided that the point of attachment is through an atom of an aromatic ring. This term includes, by way of example, phenyl and naphthyl.

“Cycloalkyl” refers to cyclic hydrocarbon groups of from 3 to 10 carbon atoms having single or multiple cyclic rings including fused, bridged, and spiro ring systems. Examples of suitable cycloalkyl groups include, for instance, adamantyl, cyclopropyl, cyclobutyl, cyclopentyl, cyclooctyl and the like. Such cycloalkyl groups include, by way of example, single ring structures such as cyclopropyl, cyclobutyl, cyclopentyl, cyclooctyl, and the like, or multiple ring structures such as adamantanyl, and the like. In some instances, the cycloalkyl is a monocyclic ring. In some instances, cycloalkyl is a 3- to 6-membered ring.

The term “heteroaryl” refers to a monocyclic, fused bicyclic, or fused polycyclic aromatic heterocycle (ring structure having ring atoms selected from carbon atoms and up to four heteroatoms selected from nitrogen, oxygen, and sulfur) having from 5 to 12 ring atoms per heterocycle. Such heteroaryl groups comprise at least one ring within the ring system that is aromatic, provided that the point of attachment is through an atom of an aromatic ring. In certain embodiments, the nitrogen and/or sulfur ring atom(s) of the heteroaryl group are optionally oxidized to provide for the N-oxide ($N \rightarrow O$), sulfinyl, or sulfonyl moieties. In some instances, heteroaryl groups are 5-, 6-, 8-, 9-, or 10-membered ring systems.

Examples of heteroaryls include, but are not limited to, pyrrole, furan, thiophenyl, imidazole, pyrazole, thiazole, oxazole, isoxazole, isothiazole, triazole, oxadiazole, thiadiazole, tetrazole, pyridine, pyrazine, pyrimidine, pyridazine, indole, benzofuran, benzothiophene, indazole, benzimidazole, benzothiazole, benzoxazole, indolizine, isoindole, purine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, phenoxazine, phenothiazine, phthalimide, and the like.

“Heterocycloalkyl” refers to a saturated or partially unsaturated group having a single ring or multiple condensed rings, including fused, bridged, or spiro ring systems, and having from 3 to 20 ring atoms, including 1 to 10 hetero atoms. These ring atoms are selected from the group consisting of carbon, nitrogen, sulfur, or oxygen, wherein, in fused ring systems, one or more of the rings can be cycloalkyl, aryl, or heteroaryl, provided that the point of attachment is through the non-aromatic ring. In certain embodiments, the nitrogen and/or sulfur atom(s) of the heterocyclic group are optionally oxidized to provide for N-oxide, —S(O)—, or —$SO_2$— moieties. Examples of heterocycloalkyls include, but are not limited to, azetidine, oxetane, tetrahydrofuran, pyrrolidine, piperazine, piperidine, morpholine, thiomorpholine, 1,1-dioxothiomorpholinyl, dihydroindole, indazole, quinolizine, imidazolidine, imidazoline, indoline, 1,2,3,4-tetrahydroisoquinoline, thiazolidine, and the like. In some instances, heterocycloalkyl groups are 4-, 5-, or 6-membered rings. In some instances, the heterocycloalkyl comprises a fused phenyl ring.

"Cyano" refers to the group —CN.

"Halo" or "halogen" refers to fluoro, chloro, bromo, and iodo.

"Hydroxy" or "hydroxyl" refers to the group —OH.

In addition to the disclosure herein, the term "substituted," when used to modify a specified group or radical, can also mean that one or more hydrogen atoms of the specified group or radical are each, independently of one another, replaced with the same or different substituent groups as defined below. Substituent groups include, but are not limited to, alkoxy, acyl, acyloxy, carbonylalkoxy, acylamino, amino, aminoacyl, aminocarbonylamino, aminocarbonyloxy, cycloalkyl, cycloalkenyl, aryl, heteroaryl, aryloxy, cyano, azido, halo, hydroxyl, nitro, carboxyl, thiol, thioalkyl, cycloalkyl, cycloalkenyl, alkyl, alkenyl, alkynyl, heterocyclyl, aralkyl, aminosulfonyl, sulfonylamino, sulfonyl, oxo, carbonylalkylenealkoxy and the like. The term "unsubstituted" means that the specified group bears no substituents. The term "optionally substituted" means that the specified group is unsubstituted or substituted by one or more substituents. Where the term "substituted" is used to describe a structural system, the substitution is meant to occur at any valency-allowed position on the system. When a group or moiety bears more than one substituent, it is understood that the substituents may be the same or different from one another. In some embodiments, a substituted group or moiety bears from one to five substituents. In some embodiments, a substituted group or moiety bears one substituent. In some embodiments, a substituted group or moiety bears two substituents. In some embodiments, a substituted group or moiety bears three substituents. In some embodiments, a substituted group or moiety bears four substituents. In some embodiments, a substituted group or moiety bears five substituents.

Any formula depicted herein is intended to represent a compound of that structural formula as well as certain variations or forms. For example, a formula given herein is intended to include a racemic form, or one or more enantiomeric, diastereomeric, or geometric isomers, or a mixture thereof. Additionally, any formula given herein is intended to refer also to a hydrate, solvate, or polymorph of such a compound, or a mixture thereof.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the present disclosure include isotopes of hydrogen, carbon, nitrogen, oxygen, phosphorous, fluorine, chlorine, and iodine, such as $^{2}H$, $^{3}H$, $^{11}C$, $^{13}C$, $^{14}C$, $^{15}N$, $^{18}O$, $^{17}O$, $^{31}P$, $^{32}P$, $^{35}S$, $^{18}F$, $^{36}Cl$, and $^{125}I$, respectively. Such isotopically labeled compounds are useful in metabolic studies (preferably with $^{14}C$), reaction kinetic studies (with, for example $^{2}H$ or $^{3}H$), detection or imaging techniques [such as positron emission tomography (PET) or single-photon emission computed tomography (SPECT)] including drug or substrate tissue distribution assays, or in radioactive treatment of patients. In particular, an $^{18}F$ or $^{11}C$ labeled compound may be particularly preferred for PET or SPECT studies. PET and SPECT studies may be performed as described, for example, by Brooks, D. J., "Positron Emission Tomography and Single-Photon Emission Computed Tomography in Central Nervous System Drug Development," *NeuroRx* 2005, 2(2), 226-236, and references cited therein. Further, substitution with heavier isotopes such as deuterium (i.e., $^{2}H$) may afford certain therapeutic advantages resulting from greater metabolic stability, for example increased in vivo half-life or reduced dosage requirements. Isotopically labeled compounds of the present disclosure and prodrugs thereof can generally be prepared by carrying out the procedures disclosed in the schemes or in the examples and preparations described below by substituting a readily available isotopically labeled reagent for a non-isotopically labeled reagent.

The nomenclature "$C_{i-j}$" with j>i, when applied herein to a class of substituents, is meant to refer to embodiments of the present disclosure for which each and every one of the number of carbon members, from i to j including i and j, is independently realized. By way of example, the term $C_{1-3}$ refers independently to embodiments that have one carbon member ($C_1$), embodiments that have two carbon members ($C_2$), and embodiments that have three carbon members ($C_3$).

Any disubstituent referred to herein is meant to encompass the various attachment possibilities when more than one of such possibilities are allowed. For example, reference to disubstituent -A-B—, where A≠B, refers herein to such disubstituent with A attached to a first substituted member and B attached to a second substituted member, and it also refers to such disubstituent with A attached to the second substituted member and B attached to the first substituted member.

As to any of the groups disclosed herein which contain one or more substituents, it is understood, of course, that such groups do not contain any substitution or substitution patterns which are sterically impractical and/or synthetically non-feasible. In addition, the subject compounds include all stereochemical isomers arising from the substitution of these compounds.

The present disclosure also includes pharmaceutically acceptable salts of the compounds represented by Formula (I), preferably of those described above and of the specific compounds exemplified herein, and pharmaceutical compositions comprising such salts, and methods of using such salts.

A "pharmaceutically acceptable salt" is intended to mean a salt of a free acid or base of a compound represented herein that is non-toxic, biologically tolerable, or otherwise biologically suitable for administration to the subject. See, generally, S. M. Berge, et al., "Pharmaceutical Salts," J. Pharm. Sci., 1977, 66, 1-19. Preferred pharmaceutically acceptable salts are those that are pharmacologically effective and suitable for contact with the tissues of subjects without undue toxicity, irritation, or allergic response. A compound described herein may possess a sufficiently acidic group, a sufficiently basic group, both types of functional groups, or more than one of each type, and accordingly react with a number of inorganic or organic bases, and inorganic and organic acids, to form a pharmaceutically acceptable salt.

Examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, methylsulfonates, propylsulfonates, besylates, tosylates, xylenesulfonates, naphthalene-1-sulfonates, naphthalene-2-sulfonates, edisylates, phenylacetates, phenylpropionates, phenylbutyrates, citrates, lactates, 7-hydroxybutyrates, glycolates, tartrates, and mandelates. Lists of other suitable pharmaceutically acceptable salts are found in Remington's Pharmaceutical Sciences, 17th Edition, Mack Publishing Company, Easton, Pa., 1985.

For a compound of Formula (I) that contains a basic nitrogen, a pharmaceutically acceptable salt may be prepared by any suitable method available in the art, for example, treatment of the free base with an inorganic acid, such as hydrochloric acid, hydrobromic acid, sulfuric acid, sulfamic acid, nitric acid, boric acid, phosphoric acid, and the like, or with an organic acid, such as acetic acid, phenylacetic acid, propionic acid, stearic acid, lactic acid, ascorbic acid, maleic acid, hydroxymaleic acid, isethionic acid, succinic acid, valeric acid, fumaric acid, malonic acid, pyruvic acid, oxalic acid, glycolic acid, salicylic acid, oleic acid, palmitic acid, lauric acid, a pyranosidyl acid, such as glucuronic acid or galacturonic acid, an alpha-hydroxy acid, such as mandelic acid, citric acid, or tartaric acid, an amino acid, such as aspartic acid or glutamic acid, an aromatic acid, such as benzoic acid, 2-acetoxybenzoic acid, naphthoic acid, or cinnamic acid, a sulfonic acid, such as laurylsulfonic acid, p-toluenesulfonic acid, methanesulfonic acid, ethanesulfonic acid, ethanedisulfonic acid or any compatible mixture of acids such as those given as examples herein, and any other acid and mixture thereof that are regarded as equivalents or acceptable substitutes in light of the ordinary level of skill in this technology.

"Solvate" refers to a complex formed by combination of solvent molecules with molecules or ions of the solute. The solvent can be an organic compound, an inorganic compound, or a mixture of both. Some examples of solvents include, but are not limited to, methanol, N,N-dimethylformamide, tetrahydrofuran, dimethylsulfoxide, and water. When the solvent is water, the solvate formed is a hydrate.

"Stereoisomer" and "stereoisomers" refer to compounds that have same atomic connectivity but different atomic arrangement in space. Stereoisomers include cis-trans isomers, E and Z isomers, enantiomers, and diastereomers.

"Tautomer" refers to alternate forms of a molecule that differ only in electronic bonding of atoms and/or in the position of a proton, such as enol-keto and imine-enamine tautomers, or the tautomeric forms of heteroaryl groups containing a —N═C(H)—NH— ring atom arrangement, such as pyrazoles, imidazoles, benzimidazoles, triazoles, and tetrazoles. A person of ordinary skill in the art would recognize that other tautomeric ring atom arrangements are possible.

It will be appreciated that the term "or a salt or solvate or stereoisomer thereof" is intended to include all permutations of salts, solvates and stereoisomers, such as a solvate of a pharmaceutically acceptable salt of a stereoisomer of subject compound.

Compounds

Compounds and salts thereof (such as pharmaceutically acceptable salts) are detailed herein, including in the Summary and in the appended claims. Also provided are the use of all of the compounds described herein, including salts and solvates of the compounds described herein, as well as methods of making such compounds. Any compound described herein may also be referred to as a drug.

In one aspect, provided are compounds of Formula (I):

(I)

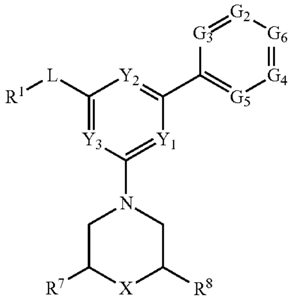

wherein $R^1$ is —$(CR^aR^b)_m$-aryl, —CH═CH-aryl, —$(CR^cR^d)_n$-heteroaryl, —$(CR^eR^f)_o$-heterocycloalkyl, or —$(CR^gR^h)_p$-cycloalkyl; wherein m, n, o, and p are each independently 0, 1, or 2;

$R^a$, $R^b$, $R^c$, $R^d$, $R^e$, $R^f$, $R^g$, and $R^h$ are each independently H, halo, or $C_{1-4}$alkyl, or $R^a$ and $R^b$ are taken together with the carbon to which they are attached to form a cycloalkyl ring, or $R^a$ and $R^b$ are taken together to form ═$CH_2$ or ═O;

each aryl, heteroaryl, heterocycloalkyl, or cycloalkyl present in $R^1$ is unsubstituted or substituted with one or two $R^x$ substituents;

wherein each $R^x$ substituent is independently halo, $C_{1-4}$alkyl, cycloalkyl, —$C_{1-2}$-haloalkyl, —OH, —$OC_{1-4}$alkyl, —O—$C_{1-2}$-haloalkyl, cyano, —$C(O)C_{1-4}$alkyl, —$C(O)NR^iR^j$, —$SO_2C_{1-4}$alkyl, —$SO_2NR^kR^l$, —$NR^qR^r$, —C(O)-cycloalkyl, —C(O)-aryl (optionally substituted with methyl or halo), —$CO_2C_{1-4}$alkyl, —$CO_2$aryl, —C(O)$CH_2$-aryl (optionally substituted with methyl or halo), —$CH_2$-aryl (optionally substituted with methyl or halo), or monocyclic heterocycloalkyl (optionally substituted with methyl, —$C(O)C_{1-4}$ alkyl, or —$CO_2C_{1-4}$alkyl);

wherein $R^i$, $R^j$, $R^k$, and $R^l$ are each independently H, $C_{1-4}$alkyl, —$C_{1-4}$alkyl-OH, or —$C_{1-4}$alkyl-O—$C_{1-4}$alkyl, wherein $R^q$ and $R^r$ are each independently H, $C_{1-4}$alkyl, —$C_{1-4}$alkyl-OH, —$C_{1-4}$alkyl-O—$C_{1-4}$alkyl, —$C(O)C_{1-4}$alkyl, —$CO_2C_{1-4}$alkyl, or —$SO_2C_{1-4}$alkyl;

L is absent, —$S(O)_2$—, —C(O)—, —O—, —$CH_2$—, —$CF_2$—, $C(CH_3)_2$, —C(═$CH_2$)—, or —$CR^sR^t$—; wherein $R^s$ and $R^t$ are independently H or alkyl, or $R^s$ and $R^t$ are taken together with the carbon atom to which they are attached to form a cycloalkyl ring;

X is O, S, NH, N($CO_2C_{1-4}$alkyl), N($SO_2C_{1-4}$alkyl), N($SO_2$cycloalkyl), or $CH_2$;

$Y_1$, $Y_2$, and $Y_3$ are each independently CH or N; wherein when L is other than —$S(O)_2$—, $Y_2$ and $Y_3$ are each CH;

$G_2$ is N or $CR^2$;

$G_3$ is N or $CR^3$;

$G_4$ is N, $NR^{4b}$, or $CR^{4a}$;

$G_5$ is N or $CR^5$; and $G_6$ is N or $CR^6$;

wherein $R^2$, $R^3$, $R^{4a}$, $R^5$, and $R^6$ are each independently hydrogen, halogen, —OH, -alkyl, —Oalkyl, -haloalkyl, —O-haloalkyl, or —$NR^uR^v$;

or $R^{4b}$ is taken together with $R^6$ and the atoms to which they are attached to form a heteroaryl or heterocyclic ring; wherein the heteroaryl ring comprising $R^{4b}$ and $R^6$ comprises no more than one N and is optionally substituted with alkyl, and the heterocyclic ring comprising $R^{4b}$ and $R^6$ is optionally substituted with oxo, $R^u$ is H or $C_{1-4}$alkyl;

$R^v$ is H, $C_{1-4}$alkyl, monocyclic cycloalkyl, —C(O)$C_{1-4}$ alkyl, or —C(O)$NR^wR^y$;

wherein each alkyl present in $R^v$ is unsubstituted or substituted with —OH, —$NH_2$, —NH($C_{1-4}$alkyl), or —N($C_{1-4}$alkyl)$_2$, $R^w$ and $R^y$ are each independently H or $C_{1-4}$alkyl; wherein

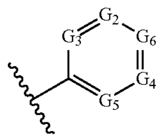

is not unsubstituted phenyl; and $R^7$ and $R^8$ are each independently hydrogen or $C_{1-4}$alkyl, or $R^7$ and $R^8$ are taken together to form —$CH_2CH_2$—;

or a pharmaceutically acceptable salt thereof.

In some embodiments of Formula (I), $R^1$ is —$(CR^aR^b)_m$-aryl, —CH═CH-aryl, or —$(CR^cR^d)_n$-heteroaryl, each unsubstituted or substituted with one or two $R^x$ substituents. In some embodiments, $R^1$ is —$(CR^eR^f)_o$-heterocycloalkyl or —$(CR^gR^h)_p$-cycloalkyl, each unsubstituted or substituted with one or two $R^x$ substituents. In some embodiments, $R^1$ is —$(CR^aR^b)_m$-aryl, wherein $R^a$ and $R^b$ are each independently H, halo, or $C_{1-4}$alkyl, and m is 0, 1, or 2, and wherein the aryl present in $R^1$ is unsubstituted or substituted with one or two $R^x$ substituents. In some embodiments, $R^1$ is —$(CR^aR^b)_m$-aryl, wherein $R^a$ and $R^b$ are taken together with the carbon to which they are attached to form a cycloalkyl, or $R^a$ and $R^b$ are taken together to form ═$CH_2$ or ═O, and the aryl present in $R^1$ is unsubstituted or substituted with one or two $R^x$ substituents. In some embodiments, $R^1$ is aryl, unsubstituted or substituted with one or two $R^x$ substituents. In some embodiments, $R^1$ is —$CH_2$-aryl, unsubstituted or substituted with one or two $R^x$ substituents. In some embodiments, $R^1$ is —$CH_2CH_2$-aryl, unsubstituted or substituted with one or two $R^x$ substituents. In some embodiments, $R^1$ is —$(CR^aR^b)_m$-aryl, wherein the aryl is phenyl or naphthyl, each unsubstituted or substituted with one or two $R^x$ substituents. In some embodiments, $R^1$ is phenyl. In other embodiments, $R^1$ is napthyl. In some embodiments, $R^1$ is aryl, —$CH_2$-aryl, —$CH_2CH_2$-aryl, —CH═CH-aryl, each unsubstituted or substituted with one or two $R^x$ substituents independently selected from the group consisting of halo, $C_{1-4}$alkyl, —$C_{1-2}$-haloalkyl, —OH, —O$C_{1-4}$alkyl, —O—$C_{1-2}$-haloalkyl, cyano, —$NR^qR^r$, and monocyclic heterocycloalkyl (optionally substituted with methyl, —C(O)$C_{1-4}$alkyl, or —$CO_2C_{1-4}$alkyl), wherein $R^q$ and $R^r$ are each independently H, $C_{1-4}$alkyl, —$C_{1-4}$alkyl-OH, —$C_{1-4}$ alkyl-O—$C_{1-4}$alkyl, —C(O)$C_{1-4}$alkyl, —$CO_2C_{1-4}$alkyl, or —$SO_2C_{1-4}$alkyl. In some embodiments, $R^1$ is phenyl, —$CH_2$-phenyl, —$CH_2CH_2$-phenyl, —CH═CH-phenyl, napthyl, —$CH_2$-napthyl, —$CH_2CH_2$-napthyl, or —CH═CH— napthyl. In some embodiments, $R^1$ is phenyl, —$CH_2$-phenyl, —$CH_2CH_2$-phenyl, —CH═CH-phenyl, napthyl, —$CH_2$-napthyl, —$CH_2CH_2$-napthyl, or —CH═CH— napthyl, each substituted with one or two $R^x$ substituents independently selected from the group consisting of F, Cl, —$CF_3$, —$OCF_3$, cyano, —$CH_3$, —$OCH_3$, —NHC(O)$CH_3$, —$NHCH_2C(CH_3)_2OH$, morpholinyl, tetrahydrofuranyl, tetrahydropyranyl, pyrindinyl, and —NHS(O)$_2CH_3$.

In some embodiments, $R^1$ is —$(CR^cR^d)_n$-heteroaryl, wherein $R^c$ and $R^d$ are each independently H, halo, or $C_{1-4}$alkyl, and n is 0, 1, or 2, wherein the heteroaryl present in $R^1$ is unsubstituted or substituted with one or two $R^x$ substituents. In some embodiments, $R^1$ is heteroaryl, unsubstituted or substituted with one or two $R^x$ substituents. In some embodiments, $R^1$ is —$CH_2$-heteroaryl, unsubstituted or substituted with one or two $R^x$ substituents. In some embodiments, $R^1$ is —$CH_2CH_2$-heteroaryl, unsubstituted or substituted with one or two $R^x$ substituents. In some embodiments, $R^1$ is —$(CR^cR^d)_n$-heteroaryl, wherein the heteroaryl is a monocyclic heteroaryl. In some embodiments, $R^1$ is —$(CR^cR^d)_n$-heteroaryl, wherein the heteroaryl is a bicyclic heteroaryl. In any of these embodiments, the heteroaryl includes one or two nitrogen ring members. In some embodiments, $R^1$ is —$(CR^cR^d)_n$-heteroaryl, wherein the heteroaryl is pyrrole, furan, thiophenyl, imidazole, pyrazole, thiazole, oxazole, isoxazole, isothiazole, triazole, oxadiazole, thiadiazole, tetrazole, pyridine, pyrazine, pyrimidine, pyridazine, indole, isoindole, benzofuran, benzothiophene, benzimidazole, benzothiazole, or benzoxazole, each unsubstituted or substituted with one or two $R^x$ substituents. In some embodiments, $R^1$ is —$CH_2$-heteroaryl. or —$CH_2CH_2$-heteroaryl, each unsubstituted or substituted with one or two $R^x$ substituents independently selected from the group consisting of halo, $C_{1-4}$alkyl, —$C_{1-2}$-haloalkyl, —OH, —O$C_{1-4}$ alkyl, —O—$C_{1-2}$-haloalkyl, cyano, —$NR^qR^r$, and monocyclic heterocycloalkyl (optionally substituted with methyl, —C(O)$C_{1-4}$alkyl, or —$CO_2C_{1-4}$alkyl), wherein $R^q$ and $R^r$ are each independently H, $C_{1-4}$alkyl, —$C_{1-4}$alkyl-OH, —$C_{1-4}$alkyl-O—$C_{1-4}$alkyl, —C(O)$C_{1-4}$alkyl, —$CO_2C_{1-4}$alkyl, or —$SO_2C_{1-4}$alkyl. In some embodiments, $R^1$ is pyrrole, furan, thiophenyl, imidazole, pyrazole, thiazole, oxazole, isoxazole, isothiazole, triazole, oxadiazole, thiadiazole, tetrazole, pyridine, pyrazine, pyrimidine, pyridazine, indole, isoindole, benzofuran, benzothiophene, benzimidazole, benzothiazole, or benzoxazole. In some embodiments, $R^1$ is pyrrole, furan, thiophenyl, imidazole, pyrazole, thiazole, oxazole, isoxazole, isothiazole, triazole, oxadiazole, thiadiazole, tetrazole, pyridine, pyrazine, pyrimidine, pyridazine, indole, isoindole, benzofuran, benzothiophene, benzimidazole, benzothiazole, or benzoxazole, each substituted with one or two $R^x$ substituents independently selected from the group consisting of F, Cl, —$CF_3$, —$OCF_3$, cyano, —$CH_3$, —$OCH_3$, —NHC(O)$CH_3$, —$NHCH_2C(CH_3)_2OH$, morpholinyl, tetrahydrofuranyl, tetrahydropyranyl, pyrindinyl, and —NHS(O)$_2CH_3$.

In some embodiments, $R^1$ is —$(CR^eR^f)_o$-heterocycloalkyl, wherein $R^e$ and $R^f$ are each independently H, halo, or $C_{1-4}$alkyl, o is 0, 1, or 2, wherein the heterocycloalkyl present in $R^1$ is unsubstituted or substituted with one or two $R^x$ substituents. In some embodiments, $R^1$ is heterocycloalkyl, unsubstituted or substituted with one or two $R^x$ substituents. In some embodiments, $R^1$ is —$CH_2$-heterocycloalkyl, unsubstituted or substituted with one or two $R^x$ substituents. In some embodiments, $R^1$ is —$CH_2CH_2$-heterocycloalkyl, unsubstituted or substituted with one or two $R^x$ substituents. In some embodiments, $R^1$ is —$(CR^eR^f)_o$-heterocycloalkyl, wherein the heterocycloalkyl is monocyclic, and in some embodiments, the heterocycloalkyl is a 4- to 6-membered ring. In some embodiments, $R^1$ is —$(CR^eR^f)_o$-heterocycloalkyl, wherein the heterocycloalkyl is azetidine, tetrahydrofuran, pyrrolidine, tetrahydropyran, piperidine, piperazine, morpholine, thiomorpholine, 1,1-dioxothiomorpholine, azepine, or diazepine. In some embodiments, the heterocycloalkyl is attached to the remainder of the structure through a carbon atom (a C-linked heterocycloalkyl). In some embodiments, $R^1$ is —$CH_2$-heterocycloalkyl. or —$CH_2CH_2$-heterocycloalkyl, each unsubstituted or substituted with one or two $R^x$ substituents independently selected from the group consisting of halo, $C_{1-4}$alkyl, —$C_{1-2}$-haloalkyl, —OH, —$OC_{1-4}$alkyl, —O—$C_{1-2}$-haloalkyl, cyano, —$NR^qR^r$, and monocyclic heterocycloalkyl (optionally substituted with methyl, —$C(O)C_{1-4}$alkyl, or —$CO_2C_{1-4}$alkyl), wherein $R^q$ and $R^r$ are each independently H, $C_{1-4}$alkyl, —$C_{1-4}$alkyl-OH, —$C_{1-4}$alkyl-O—$C_{1-4}$alkyl, —$C(O)C_{1-4}$alkyl, —$CO_2C_{1-4}$alkyl, or —$SO_2C_{1-4}$alkyl. In some embodiments, $R^1$ is azetidine, tetrahydrofuran, pyrrolidine, tetrahydropyran, piperidine, piperazine, morpholine, thiomorpholine, 1,1-dioxothiomorpholine, azepine, or diazepine. In some embodiments, $R^1$ is azetidine, tetrahydrofuran, pyrrolidine, tetrahydropyran, piperidine, piperazine, morpholine, thiomorpholine, 1,1-dioxothiomorpholine, azepine, or diazepine, each substituted with one or two $R^x$ substituents independently selected from the group consisting of F, Cl, —$CF_3$, —$OCF_3$, cyano, —$CH_3$, —$OCH_3$, —$NHC(O)CH_3$, —$NHCH_2C(CH_3)_2OH$, morpholinyl, tetrahydrofuranyl, tetrahydropyranyl, pyrindinyl, and —$NHS(O)_2CH_3$.

In some embodiments, $R^1$ is —$(CR^gR^h)_p$-cycloalkyl, wherein $R^g$ and $R^h$ are each independently H, halo, or $C_{1-4}$alkyl, and p is 0, 1, or 2, and wherein the cycloalkyl present in $R^1$ is unsubstituted or substituted with one or two $R^x$ substituents. In some embodiments, $R^1$ is cycloalkyl, unsubstituted or substituted with one or two $R^x$ substituents. In some embodiments, $R^1$ is —$CH_2$-cycloalkyl, unsubstituted or substituted with one or two $R^x$ substituents. In some embodiments, $R^1$ is —$CH_2CH_2$-cycloalkyl, unsubstituted or substituted with one or two $R^x$ substituents. In some embodiments, $R^1$ is —$(CR^gR^h)_p$-cycloalkyl, wherein the cycloalkyl is cyclopropyl, cyclobutyl, cyclopentyl, or cyclohexyl. In some embodiments, $R^1$ is cycloalkyl, —$CH_2$-cycloalkyl. or —$CH_2CH_2$-cycloalkyl, each unsubstituted or substituted with one or two $R^x$ substituents independently selected from the group consisting of halo, $C_{1-4}$alkyl, —$C_{1-2}$-haloalkyl, —OH, —$OC_{1-4}$alkyl, —O—$C_{1-2}$-haloalkyl, cyano, —$NR^qR^r$, and monocyclic heterocycloalkyl (optionally substituted with methyl, —$C(O)C_{1-4}$ alkyl, or —$CO_2C_{1-4}$alkyl), wherein $R^q$ and $R^r$ are each independently H, $C_{1-4}$alkyl, —$C_{1-4}$alkyl-OH, —$C_{1-4}$alkyl-O—$C_{1-4}$alkyl, —$C(O)C_{1-4}$alkyl, —$CO_2C_{1-4}$alkyl, or —$SO_2C_{1-4}$alkyl. In some embodiments, $R^1$ is cyclopropyl, cyclobutyl, cyclopentyl, or cyclohexyl. In some embodiments, $R^1$ is cyclopropyl, cyclobutyl, cyclopentyl, or cyclohexyl, each substituted with one or two $R^x$ substituents independently selected from the group consisting of F, Cl, —$CF_3$, —$OCF_3$, cyano, —$CH_3$, —$OCH_3$, —$NHC(O)CH_3$, —$NHCH_2C(CH_3)_2OH$, morpholinyl, tetrahydrofuranyl, tetrahydropyranyl, pyrindinyl, and —$NHS(O)_2CH_3$.

In some embodiments, $R^1$ is phenyl, naphthyl, dihydrobenzofuran, benzofuran, benzyl, indolylmethyl, phenethyl, 1,1-difluoro(phenyl)methyl, imidazolylmethyl, benzimdazolylmethyl, pyridinylmethyl, cyclohexyl, cyclohexylmethyl, azetidine, tetrahydrofuran, tetrahydrofuranylmethyl, pyrrolidine, tetrahydropyran, tetrahydropyranylmethyl, or piperidine, each unsubstituted or substituted with one or two $R^x$ substituents.

In each instance, $R^1$ is unsubstituted or substituted with one or two $R^x$ substituents. In some embodiments, there is one $R^x$ substituent, and in others there are two $R^x$ substituents.

In some embodiments, each $R^x$ is independently halo, $C_{1-4}$alkyl, cycloalkyl, —$C_{1-2}$-haloalkyl, —OH, —$OC_{1-4}$alkyl, —O—$C_{1-2}$-haloalkyl, cyano, —$C(O)C_{1-4}$alkyl, —$C(O)NR^iR^j$, —$SO_2C_{1-4}$alkyl, —$SO_2NR^kR^l$, —$NR^qR^r$, —C(O)-cycloalkyl, —C(O)-aryl (optionally substituted with methyl or halo), —$CO_2C_{1-4}$alkyl, —$C(O)CH_2$-aryl (optionally substituted with methyl or halo), —$CH_2$-aryl (optionally substituted with methyl or halo), or monocyclic heterocycloalkyl (optionally substituted with methyl, —$C(O)C_{1-4}$alkyl, or —$CO_2C_{1-4}$alkyl). In some embodiments, each $R^x$ is independently halo, $C_{1-4}$alkyl, cycloalkyl, —$C_{1-2}$-haloalkyl, —OH, —$OC_{1-4}$alkyl, —O—$C_{1-2}$-haloalkyl, cyano, —$C(O)C_{1-4}$alkyl, —$C(O)NR^iR^j$, —$SO_2C_{1-4}$alkyl, —$SO_2NR^kR^l$, —$NR^qR^r$, —C(O)-cycloalkyl, —C(O)-aryl (optionally substituted with methyl or halo), —$CO_2C_{1-4}$alkyl, —$CO_2$aryl, —$C(O)CH_2$-aryl (optionally substituted with methyl or halo), —$CH_2$-aryl (optionally substituted with methyl or halo), or monocyclic heterocycloalkyl (optionally substituted with methyl, —$C(O)C_{1-4}$alkyl, or —$CO_2C_{1-4}$alkyl). In some embodiments, each $R^x$ is independently halo (such as fluoro, chloro, bromo), methyl, ethyl, propyl, isopropyl, —$C(O)NH_2$, —$C(O)NHC_{1-4}$alkyl, —$C(O)NMe_2$, acetyl, —C(O)ethyl, —C(O)-isopropyl, —C(O)-tert-butyl, —C(O)-cyclopropyl, —$CO_2$-tert-butyl, —$C(O)CH_2$-phenyl, —C(O)phenyl, —$C(O)NHC_{1-2}$alkyl-$OCH_3$, boc-piperidinyl, isopropyl, tetrahydropyranyl, cyano, morpholinyl, fluoro, chloro, —$CF_3$, methoxy, —$NHSO_2CH_3$, 2-hydroxy-2-methyl-1-aminopropyl, —NH-acetyl, or —$OCF_3$. In some embodiments, each $R^x$ is independently tetrahydrofuranyl, tetrahydropyranyl, or pyrindinyl, each optionally substituted. In each instance the aryl and heterocycloalkyl groups are optionally substituted as described above.

In some embodiments, $R^i$ and $R^j$ are each independently H, $C_{1-4}$alkyl, —$C_{1-4}$alkyl-OH, or —$C_{1-4}$alkyl-O—$C_{1-4}$alkyl. In some embodiments, $R^i$ and $R^j$ are each independently H, methyl, ethyl, propyl, isopropyl, butyl, isobutyl, sec-butyl, tert-butyl, hydroxymethyl, hydroxyethyl, 2-hydroxy-2-methylpropyl, methoxymethyl, or methoxyethyl.

In some embodiments, $R^k$ and $R^l$ are each independently H, $C_{1-4}$alkyl, —$C_{1-4}$alkyl-OH, —$C_{1-4}$alkyl-O—$C_{1-4}$alkyl, —$C(O)C_{1-4}$alkyl, —$CO_2C_{1-4}$alkyl, or —$SO_2C_{1-4}$alkyl. In some embodiments, $R^k$ and $R^l$ are each independently H, methyl, ethyl, propyl, isopropyl, —$C_{1-4}$alkyl-OH, acetyl, or —$CO_2$-tert-butyl.

In some embodiments of Formula (I), X is O. In some embodiments, X is S. In some embodiments, X is NH, $N(CO_2C_{1-4}alkyl)$, $N(SO_2C_{1-4}alkyl)$, or $N(SO_2cyclo\text{-}alkyl)$. In some embodiments, X is $CH_2$.

In some embodiments of Formula (I), $Y_1$, $Y_2$, and $Y_3$ are each CH. In some embodiments, $Y_1$, $Y_2$, and $Y_3$ are each N. In some embodiments, $Y_1$ is N, and $Y_2$ and $Y_3$ are each CH. In some embodiments, $Y_2$ is N, and $Y_1$ and $Y_3$ are each CH.

In some embodiments, $Y_3$ is N, and $Y_1$ and $Y_2$ are each CH. In some embodiments, $Y_1$ and $Y_2$ are each N, and $Y_3$ is CH. In some embodiments, $Y_1$ and $Y_3$ are each N, and $Y_2$ is CH. In some embodiments, $Y_2$ and $Y_3$ are each N, and $Y_1$ is CH.

In some embodiments of Formula (I) or any variation thereof, L is absent, —$S(O)_2$—, —C(O)—, —$CH_2$—, —$CF_2$—, $C(CH_3)_2$, —C(=$CH_2$)—, or —$CR^sR^t$—; wherein $R^s$ and $R^t$ are independently H or alkyl, or $R^s$ and $R^t$ are taken together with the carbon atom to which they are attached to form a cycloalkyl ring; and $R^1$, $R^2$, $R^3$, $R^{4a}$, $R^{4b}$, $R^5$, $R^6$, $R^7$, $R^1$, X, $Y_1$, $Y_2$, $Y_3$, $G_2$, $G_3$, $G_4$, $G_5$, $G_6$, $R^a$, $R^b$, $R^c$, $R^d$, $R^e$, $R^f$, $R^g$, $R^h$, $R^i$, $R^j$, $R^k$, $R^l$, $R^q$, $R^r$, $R^u$, $R^v$, $R^w$, $R^x$, $R^y$, m, n, o, and p are as defined for Formula (I) or any variation or embodiment thereof.

In some embodiments of Formula (I), L is —$S(O)_2$—. In some embodiments, L is absent. In some embodiments, L is —C(O)—, —O—, —$CH_2$—, —$CF_2$—, $C(CH_3)_2$, —C(=$CH_2$)—, or —$CR^sR^t$—. In some embodiments, L is —C(O)—, —$CH_2$—, —$CF_2$—, $C(CH_3)_2$, —C(=$CH_2$)—, or —$CR^sR^t$—. In some embodiments, L is absent, —C(O)—, —$CH_2$—, —$CF_2$—, $C(CH_3)_2$, —C(=$CH_2$)—, or —$CR^sR^t$—; and $Y_2$ and $Y_3$ are each CH.

In some embodiments of Formula (I), $G_2$ is $CR^2$, $G_3$ is $CR^3$, $G_4$ is $CR^{4a}$, $G_5$ is $CR^5$, and $G_6$ is $CR^6$. In some embodiments, one of $G_2$, $G_3$, $G_4$, $G_5$, and $G_6$ is N. In some embodiments, more than one of $G_2$, $G_3$, $G_4$, $G_5$, and $G_6$ are N. In some embodiments, two of $G_2$, $G_3$, $G_4$, $G_5$, and $G_6$ are N. In some embodiments, $G_2$ is N, $G_3$ is $CR^3$, $G_4$ is $CR^{4a}$, $G_5$ is $CR^5$, and $G_6$ is $CR^6$. In some embodiments, $G_2$ is $CR^2$, $G_3$ is $CR^3$, $G_4$ is $CR^{4a}$, $G_5$ is N, and $G_6$ is $CR^6$. In some embodiments, $G_2$ and $G_4$ are each N, $G_3$ is $CR^3$, $G_5$ is $CR^5$, and $G_6$ is $CR^6$. In some embodiments, $G_4$ and $G_5$ are each N, $G_2$ is $CR^2$, $G_3$ is $CR^3$, and $G_6$ is $CR^6$.

In some embodiments wherein none of $G_2$, $G_3$, $G_4$, $G_5$, and $G_6$ are N, $G_4$ is not N or $NR^{4b}$, and at least one of $R^2$, $R^3$, $R^{4a}$, $R^5$, and $R^6$ is not hydrogen. In some embodiments, $G_4$ is $NR^{41}$. In some embodiments, $R^{4b}$ is taken together with $R^6$ and the atoms to which they are attached to form a heteroaryl or heterocyclic ring. In some embodiments, the heteroaryl ring comprising $R^{4b}$ and $R^6$ comprises no more than one N. In some embodiments, the heteroaryl ring comprising $R^{4b}$ and $R^6$ is optionally substituted with alkyl, and the heterocylic ring is optionally substituted with oxo. In some embodiments, none of $G_2$, $G_3$, $G_4$, $G_5$, and $G_6$ are N, $G_4$ is not N or $NR^{4b}$, and at least one of $R^2$, $R^3$, $R^{4a}$, $R^5$, and $R^6$ is halogen, —OH, -alkyl, —Oalkyl, -haloalkyl, —O-haloalkyl, or —$NR^uR^v$.

In some embodiments of Formula (I), $R^7$ and $R^8$ are each hydrogen. In some embodiments, one of $R^7$ and $R^8$ is hydrogen and the other is $C_{1-4}$alkyl. In some embodiments, both of $R^7$ and $R^8$ is $C_{1-4}$alkyl. In some embodiments, $R^7$ and $R^8$ are taken together to form —$CH_2CH_2$—.

In some embodiments of Formula (I), L is —$S(O)_2$— and $R^1$ is —$(CR^aR^b)_m$-aryl, wherein $R^a$ and $R^b$ are each independently H, halo, or $C_{1-4}$alkyl, and m is 0, 1, or 2, and wherein the aryl is unsubstituted or substituted with one or two $R^x$ substituents. In some embodiments, L is —$S(O)_2$— and $R^1$ is —$(CR^cR^d)_n$-heteroaryl, wherein $R^c$ and $R^d$ are each independently H, halo, or $C_{1-4}$alkyl, and n is 0, 1, or 2, and wherein the heteroaryl is unsubstituted or substituted with one or two $R^x$ substituents. In some embodiments, L is —$S(O)_2$— and $R^1$ is —$(CR^eR^f)_o$-heterocycloalkyl, wherein $R^e$ and $R^f$ are each independently H, halo, or $C_{1-4}$alkyl, and o is 0, 1, or 2, and wherein the heterocycloalkyl is unsubstituted or substituted with one or two $R^x$ substituents. In other embodiments, L is —$S(O)_2$— and $R^1$ is —$(CR^gR^h)_p$-cycloalkyl; wherein $R^g$ and $R^h$ are each independently H, halo, or $C_{1-4}$alkyl, and p is 0, 1, or 2, and wherein the cycloalkyl is unsubstituted or substituted with one or two $R^x$ substituents. In yet other embodiments, L is —$S(O)_2$— and $R^1$ is —CH=CH-aryl.

In some embodiments, L is —$S(O)_2$—, $R^1$ is —$(CR^aR^b)_m$-aryl or —CH=CH-aryl, and X is O. In some embodiments, L is —$S(O)_2$—, $R^1$ is —$(CR^cR^d)_n$-heteroaryl, and X is O. In some embodiments, L is —$S(O)_2$—, $R^1$ is —$(CR^eR^f)_o$-heterocycloalkyl, and X is O. In other embodiments, L is —$S(O)_2$—, $R^1$ is —$(CR^gR^h)_p$-cycloalkyl, and X is O.

In some embodiments, L is —$S(O)_2$—, $R^1$ is —$(CR^aR^b)_m$-aryl or —CH=CH-aryl, X is O, and none of $G_2$, $G_3$, $G_4$, $G_5$, and $G_6$ are N. In some embodiments, L is —$S(O)_2$—, $R^1$ is —$(CR^aR^b)_m$-aryl or —CH=CH-aryl, X is O, and one of $G_2$, $G_3$, $G_4$, $G_5$, and $G_6$ is N. In some embodiments, L is —$S(O)_2$—, $R^1$ is —$(CR^aR^b)_m$-aryl or —CH=CH-aryl, X is O, and two of $G_2$, $G_3$, $G_4$, $G_5$, and $G_6$ are N. In some embodiments, L is —$S(O)_2$—, $R^1$ is —$(CR^aR^b)_m$-aryl or —CH=CH-aryl, X is O, $G_2$ and $G_4$ are each N, $G_3$ is $CR^3$, $G_5$ is $CR^5$, and $G_6$ is $CR^6$.

In some embodiments, L is —$S(O)_2$—, $R^1$ is —$(CR^cR^d)_n$-heteroaryl, X is O, and none of $G_2$, $G_3$, $G_4$, $G_5$, and $G_6$ are N. In some embodiments, L is —$S(O)_2$—, $R^1$ is —$(CR^cR^d)_n$-heteroaryl, X is O, and one of $G_2$, $G_3$, $G_4$, $G_5$, and $G_6$ is N. In some embodiments, L is —$S(O)_2$—, $R^1$ is —$(CR^cR^d)_n$-heteroaryl, X is O, and two of $G_2$, $G_3$, $G_4$, $G_5$, and $G_6$ are N. In some embodiments, L is —$S(O)_2$—, $R^1$ is —$(CR^cR^d)_n$-heteroaryl, X is O, $G_2$ and $G_4$ are each N, $G_3$ is $CR^3$, $G_5$ is $CR^5$, and $G_6$ is $CR^6$. In some embodiments, L is —$S(O)_2$—, $R^1$ is —$(CR^eR^f)_o$-heterocycloalkyl, X is O, and none of $G_2$, $G_3$, $G_4$, $G_5$, and $G_6$ are N. In some embodiments, L is —$S(O)_2$—, $R^1$ is —$(CR^eR^f)_o$-heterocycloalkyl, X is O, and one of $G_2$, $G_3$, $G_4$, $G_5$, and $G_6$ is N. In some embodiments, L is —$S(O)_2$—, $R^1$ is —$(CR^eR^f)_o$-heterocycloalkyl, X is O, and two of $G_2$, $G_3$, $G_4$, $G_5$, and $G_6$ are N. In some embodiments, L is —$S(O)_2$—, $R^1$ is —$(CR^eR^f)_o$-heterocycloalkyl, X is O, $G_2$ and $G_4$ are each N, $G_3$ is $CR^3$, $G_5$ is $CR^5$, and $G_6$ is $CR^6$.

In some embodiments of Formula (I), L is —C(O)— and $R^1$ is —$(CR^aR^b)_m$-aryl, wherein $R^a$ and $R^b$ are each independently H, halo, or $C_{1-4}$alkyl, and m is 0, 1, or 2, and wherein the aryl is unsubstituted or substituted with one or two $R^x$ substituents. In some embodiments, L is —C(O)— and $R^1$ is —$(CR^cR^d)_n$-heteroaryl, wherein $R^c$ and $R^d$ are each independently H, halo, or $C_{1-4}$alkyl, and n is 0, 1, or 2, and wherein the heteroaryl is unsubstituted or substituted with one or two $R^x$ substituents. In some embodiments, L is —C(O)— and $R^1$ is —$(CR^eR^f)_o$-heterocycloalkyl, wherein $R^e$ and $R^f$ are each independently H, halo, or $C_{1-4}$alkyl, and o is 0, 1, or 2, and wherein the heterocycloalkyl is unsubstituted or substituted with one or two $R^x$ substituents. In other embodiments, L is —C(O)— and $R^1$ is —$(CR^gR^h)_p$-cycloalkyl; wherein $R^g$ and $R^h$ are each independently H, halo, or $C_{1-4}$alkyl, and p is 0, 1, or 2, and wherein the cycloalkyl is unsubstituted or substituted with one or two $R^x$ substituents. In yet other embodiments, L is —C(O)— and $R^1$ is —CH=CH-aryl.

In some embodiments, L is —C(O)—, $R^1$ is —$(CR^aR^b)_m$-aryl or —CH=CH-aryl, and X is O. In some embodiments, L is —C(O)—, $R^1$ is —$(CR^cR^d)_n$-heteroaryl, and X is O. In some embodiments, L is —C(O)—, $R^1$ is —$(CR^eR^f)_o$-heterocycloalkyl, and X is O. In other embodiments, L is —C(O)—, $R^1$ is —$(CR^gR^h)_p$-cycloalkyl, and X is O.

In some embodiments, L is —C(O)—, $R^1$ is —$(CR^aR^b)_m$-aryl or —CH=CH-aryl, X is O, and none of $G_2$, $G_3$, $G_4$, $G_5$, and $G_6$ are N. In some embodiments, L is —C(O)—, $R^1$ is —$(CR^aR^b)_m$-aryl or —CH=CH-aryl, X is O, and one of $G_2$, $G_3$, $G_4$, $G_5$, and $G_6$ is N. In some embodiments, L is —C(O)—, $R^1$ is —$(CR^aR^b)_m$-aryl or —CH═CH-aryl, X is O, and two of $G_2$, $G_3$, $G_4$, $G_5$, and $G_6$ are N. In some embodiments, L is —C(O)—, $R^1$ is —$(CR^aR^b)_m$-aryl or —CH═CH-aryl, X is O, $G_2$ and $G_4$ are each N, $G_3$ is $CR^3$, $G_5$ is $CR^5$, and $G_6$ is $CR^6$.

In some embodiments, L is —C(O)—, $R^1$ is —$(CR^cR^d)_n$-heteroaryl, X is O, and none of $G_2$, $G_3$, $G_4$, $G_5$, and $G_6$ are N. In some embodiments, L is —C(O)—, $R^1$ is —$(CR^cR^d)_n$-heteroaryl, X is O, and one of $G_2$, $G_3$, $G_4$, $G_5$, and $G_6$ is N. In some embodiments, L is —C(O)—, $R^1$ is —$(CR^cR^d)_n$-heteroaryl, X is O, and two of $G_2$, $G_3$, $G_4$, $G_5$, and $G_6$ are N. In some embodiments, L is —C(O)—, $R^1$ is —$(CR^cR^d)_n$-heteroaryl, X is O, $G_2$ and $G_4$ are each N, $G_3$ is $CR^3$, $G_5$ is $CR^5$, and $G_6$ is $CR^6$. In some embodiments, L is —C(O)—, $R^1$ is —$(CR^eR^f)_o$-heterocycloalkyl, X is O, and none of $G_2$, $G_3$, $G_4$, $G_5$, and $G_6$ are N. In some embodiments, L is —C(O)—, $R^1$ is —$(CR^eR^f)_o$-heterocycloalkyl, X is O, and one of $G_2$, $G_3$, $G_4$, $G_5$, and $G_6$ is N. In some embodiments, L is —C(O)—, $R^1$ is —$(CR^eR^f)_o$-heterocycloalkyl, X is O, and two of $G_2$, $G_3$, $G_4$, $G_5$, and $G_6$ are N. In some embodiments, L is —C(O)—, $R^1$ is —$(CR^eR^f)_o$-heterocycloalkyl, X is O, $G_2$ and $G_4$ are each N, $G_3$ is $CR^3$, $G_5$ is $CR^5$, and $G_6$ is $CR^6$.

In some embodiments of Formula (I), L is —O—. In some embodiments, L is —O—, and $R^1$ is —$(CR^cR^d)_n$-heteroaryl, wherein $R^c$ and $R^d$ are each independently H, halo, or $C_{1-4}$alkyl, and n is 0, 1, or 2, and wherein the heteroaryl is unsubstituted or substituted with one or two $R^x$ substituents. In some embodiments, L is —O—, and $R^1$ is —$(CR^eR^f)_o$-heterocycloalkyl, wherein $R^e$ and $R^f$ are each independently H, halo, or $C_{1-4}$alkyl, and o is 0, 1, or 2, and wherein the heterocycloalkyl is unsubstituted or substituted with one or two $R^x$ substituents. In other embodiments, L is —O—, and $R^1$ is —$(CR^gR^h)_p$-cycloalkyl; wherein $R^g$ and $R^h$ are each independently H, halo, or $C_{1-4}$alkyl, and p is 0, 1, or 2, and wherein the cycloalkyl is unsubstituted or substituted with one or two $R^x$ substituents. In yet other embodiments, L is —O—, and $R^1$ is —CH═CH-aryl.

In some embodiments, L is —O—, $R^1$ is —$(CR^aR^b)_m$-aryl or —CH═CH-aryl, and X is O. In some embodiments, L is —O—, $R^1$ is —$(CR^cR^d)_n$-heteroaryl, and X is O. In some embodiments, L is —O—, $R^1$ is —$(CR^eR^f)_o$-heterocycloalkyl, and X is O. In other embodiments, L is —O—, $R^1$ is —$(CR^gR^h)_p$-cycloalkyl, and X is O.

In some embodiments, L is —O—, $R^1$ is —$(CR^aR^b)_m$-aryl or —CH═CH-aryl, X is O, and none of $G_2$, $G_3$, $G_4$, $G_5$, and $G_6$ are N. In some embodiments, L is —O—, $R^1$ is —$(CR^aR^b)_m$-aryl or —CH═CH-aryl, X is O, and one of $G_2$, $G_3$, $G_4$, $G_5$, and $G_6$ is N. In some embodiments, L is —O—, $R^1$ is —$(CR^aR^b)_m$-aryl or —CH═CH-aryl, X is O, and two of $G_2$, $G_3$, $G_4$, $G_5$, and $G_6$ are N. In some embodiments, L is —O—, $R^1$ is —$(CR^aR^b)_m$-aryl or —CH═CH-aryl, X is O, $G_2$ and $G_4$ are each N, $G_3$ is $CR^3$, $G_5$ is $CR^5$, and $G_6$ is $CR^6$.

In some embodiments, L is —O—, $R^1$ is —$(CR^cR^d)_n$-heteroaryl, X is O, and none of $G_2$, $G_3$, $G_4$, $G_5$, and $G_6$ are N. In some embodiments, L is —O—, $R^1$ is —$(CR^cR^d)_n$-heteroaryl, X is O, and one of $G_2$, $G_3$, $G_4$, $G_5$, and $G_6$ is N. In some embodiments, L is —O—, $R^1$ is —$(CR^cR^d)_n$-heteroaryl, X is O, and two of $G_2$, $G_3$, $G_4$, $G_5$, and $G_6$ are N. In some embodiments, L is —O—, $R^1$ is —$(CR^cR^d)_n$-heteroaryl, X is O, $G_2$ and $G_4$ are each N, $G_3$ is $CR^3$, $G_5$ is $CR^5$, and $G_6$ is $CR^6$. In some embodiments, L is —O—, $R^1$ is —$(CR^eR^f)_o$-heterocycloalkyl, X is O, and none of $G_2$, $G_3$, $G_4$, $G_5$, and $G_6$ are N. In some embodiments, L is —O—, $R^1$ is —$(CR^eR^f)_o$-heterocycloalkyl, X is O, and one of $G_2$, $G_3$, $G_4$, $G_5$, and $G_6$ is N. In some embodiments, L is —O—, $R^1$ is —$(CR^eR^f)_o$-heterocycloalkyl, X is O, and two of $G_2$, $G_3$, $G_4$, $G_5$, and $G_6$ are N. In some embodiments, L is —O—, $R^1$ is —$(CR^eR^f)_o$-heterocycloalkyl, X is O, $G_2$ and $G_4$ are each N, $G_3$ is $CR^3$, $G_5$ is $CR^5$, and $G_6$ is $CR^6$.

In some embodiments of Formula (I), L is —$CH_2$—, —$CF_2$—, $C(CH_3)_2$, —C(═$CH_2$)—, or —$CR^sR^t$—, and $R^1$ is —$(CR^aR^b)_m$-aryl, wherein $R^a$ and $R^b$ are each independently H, halo, or $C_{1-4}$alkyl, and m is 0, 1, or 2, and wherein the aryl is unsubstituted or substituted with one or two $R^x$ substituents. In some embodiments, L is —$CH_2$—, —$CF_2$—, $C(CH_3)_2$, —C(═$CH_2$)—, or —$CR^sR^t$—, and $R^1$ is —$(CR^cR^d)_n$-heteroaryl, wherein $R^c$ and $R^d$ are each independently H, halo, or $C_{1-4}$alkyl, and n is 0, 1, or 2, and wherein the heteroaryl is unsubstituted or substituted with one or two $R^x$ substituents. In some embodiments, L is —$CH_2$—, —$CF_2$—, $C(CH_3)_2$, —C(═$CH_2$)—, or —$CR^sR^t$—, and $R^1$ is —$(CR^eR^f)_o$-heterocycloalkyl, wherein $R^e$ and $R^f$ are each independently H, halo, or $C_{1-4}$alkyl, and o is 0, 1, or 2, and wherein the heterocycloalkyl is unsubstituted or substituted with one or two $R^x$ substituents. In other embodiments, L is —$CH_2$—, —$CF_2$—, $C(CH_3)_2$, —C(═$CH_2$)—, or —$CR^sR^t$—, and $R^1$ is —$(CR^gR^h)_p$-cycloalkyl; wherein $R^g$ and $R^h$ are each independently H, halo, or $C_{1-4}$alkyl, and p is 0, 1, or 2, and wherein the cycloalkyl is unsubstituted or substituted with one or two $R^x$ substituents. In yet other embodiments, L is —$CH_2$—, —$CF_2$—, $C(CH_3)_2$, —C(═$CH_2$)—, or —$CR^sR^t$—, and $R^1$ is —CH═CH-aryl.

In some embodiments, L is —$CH_2$—, —$CF_2$—, —$C(CH_3)_2$—, —C(═$CH_2$)—, or —$CR^sR^t$—, $R^1$ is —$(CR^aR^b)_m$-aryl or —CH═CH-aryl, and X is O. In some embodiments, L is —$CH_2$—, —$CF_2$—, $C(CH_3)_2$, —C(═$CH_2$)—, or —$CR^sR^t$—, $R^1$ is —$(CR^cR^d)_n$-heteroaryl, and X is O. In some embodiments, L is —$CH_2$—, —$CF_2$—, $C(CH_3)_2$, —C(═$CH_2$)—, or —$CR^sR^t$—, $R^1$ is —$(CR^eR^f)_o$-heterocycloalkyl, and X is O. In other embodiments, L is —$CH_2$—, —$CF_2$—, $C(CH_3)_2$, —C(═$CH_2$)—, or —$CR^sR^t$—, $R^1$ is —$(CR^gR^h)_p$-cycloalkyl, and X is O.

In some embodiments, L is —$CH_2$—, —$CF_2$—, $C(CH_3)_2$, —C(═$CH_2$)—, or —$CR^sR^t$—, $R^1$ is —$(CR^aR^b)_m$-aryl or —CH═CH-aryl, X is O, and none of $G_2$, $G_3$, $G_4$, $G_5$, and $G_6$ are N. In some embodiments, L is —$CH_2$—, —$CF_2$—, —$C(CH_3)_2$—, —C(═$CH_2$)—, or —$CR^sR^t$—, $R^1$ is —$(CR^aR^b)_m$ aryl or —CH═CH-aryl, X is O, and one of $G_2$, $G_3$, $G_4$, $G_5$, and $G_6$ is N. In some embodiments, L is —$CH_2$—, —$CF_2$—, $C(CH_3)_2$, —C(═$CH_2$)—, or —$CR^sR^t$—, $R^1$ is —$(CR^aR^b)_m$-aryl or —CH═CH-aryl, X is O, and two of $G_2$, $G_3$, $G_4$, $G_5$, and $G_6$ are N. In some embodiments, L is —$CH_2$—, —$CF_2$—, $C(CH_3)_2$, —C(═$CH_2$)—, or —$CR^sR^t$—, $R^1$ is —$(CR^aR^b)_m$-aryl or —CH═CH-aryl, X is O, $G_2$ and $G_4$ are each N, $G_3$ is $CR^3$, $G_5$ is $CR^5$, and $G_6$ is $CR^6$.

In some embodiments, L is —$CH_2$—, —$CF_2$—, —$C(CH_3)_2$—, —C(═$CH_2$)—, or —$CR^sR^t$—, $R^1$ is —$(CR^cR^d)_n$-heteroaryl, X is O, and none of $G_2$, $G_3$, $G_4$, $G_5$, and $G_6$ are N. In some embodiments, L is —$CH_2$—, —$CF_2$—, —$C(CH_3)_2$—, —C(═$CH_2$)—, or —$CR^sR^t$—, $R^1$ is —$(CR^cR^d)_n$-heteroaryl, X is O, and one of $G_2$, $G_3$, $G_4$, $G_5$, and $G_6$ is N. In some embodiments, L is —$CH_2$—, —$CF_2$—, $C(CH_3)_2$, —C(═$CH_2$)—, or —$CR^sR^t$—, $R^1$ is —$(CR^cR^d)_n$-heteroaryl, X is O, and two of $G_2$, $G_3$, $G_4$, $G_5$, and $G_6$ are N. In some embodiments, L is —$CH_2$—, —$CF_2$—, $C(CH_3)_2$, —C(═$CH_2$)—, or —$CR^sR^t$—, $R^1$ is —$(CR^cR^d)_n$-heteroaryl, X is O, $G_2$ and $G_4$ are each N, $G_3$ is $CR^3$, $G_5$ is $CR^5$, and $G_6$ is $CR^6$. In some embodiments, L is —$CH_2$—, —$CF_2$—, —$C(CH_3)_2$—, —C(═$CH_2$)—, or —$CR^sR^t$—, $R^1$ is $—(CR^eR^f)_o$-heterocycloalkyl, X is O, and none of $G_2$, $G_3$, $G_4$, $G_5$, and $G_6$ are N. In some embodiments, L is $—CH_2—$, $—CF_2—$, $—C(CH_3)_2—$, $—C(═CH_2)—$, or $—CR^sR^t—$, $R^1$ is $—(CR^eR^f)_o$-heterocycloalkyl, X is O, and one of $G_2$, $G_3$, $G_4$, $G_5$, and $G_6$ is N. In some embodiments, L is $—CH_2—$, $—CF_2—$, $C(CH_3)_2$, $—C(═CH_2)—$, or $—CR^sR^t—$, $R^1$ is $—(CR^eR^f)_o$-heterocycloalkyl, X is O, and two of $G_2$, $G_3$, $G_4$, $G_5$, and $G_6$ are N. In some embodiments, L is $—CH_2—$, $—CF_2—$, $C(CH_3)_2$, $—C(═CH_2)—$, or $—CR^sR^t—$, $R^1$ is $—(CR^eR^f)_o$-heterocycloalkyl, X is O, $G_2$ and $G_4$ are each N, $G_3$ is $CR^3$, $G_5$ is $CR^5$, and $G_6$ is $CR^6$.

In some embodiments of Formula (I), L is absent and $R^1$ is $—(CR^aR^b)_m$-aryl, wherein $R^a$ and $R^b$ are each independently H, halo, or $C_{1-4}$alkyl, and m is 0, 1, or 2, and wherein the aryl is unsubstituted or substituted with one or two $R^x$ substituents. In some embodiments, L is absent and $R^1$ is $—(CR^cR^d)_n$-heteroaryl, wherein $R^c$ and $R^d$ are each independently H, halo, or $C_{1-4}$alkyl, and n is 0, 1, or 2, and wherein the heteroaryl is unsubstituted or substituted with one or two $R^x$ substituents. In some embodiments, L is absent and $R^1$ is $—(CR^eR^f)_o$-heterocycloalkyl, wherein $R^e$ and $R^f$ are each independently H, halo, or $C_{1-4}$alkyl, and o is 0, 1, or 2, and wherein the heterocycloalkyl is unsubstituted or substituted with one or two $R^x$ substituents. In other embodiments, L is absent and $R^1$ is $—(CR^gR^h)_p$-cycloalkyl; wherein $R^g$ and $R^h$ are each independently H, halo, or $C_{1-4}$alkyl, and p is 0, 1, or 2, and wherein the cycloalkyl is unsubstituted or substituted with one or two $R^x$ substituents. In yet other embodiments, L is absent and $R^1$ is —CH═CH-aryl.

In some embodiments, L is absent, $R^1$ is $—(CR^aR^b)_m$-aryl or —CH═CH-aryl, and X is O. In some embodiments, L is absent, $R^1$ is $—(CR^cR^d)_n$-heteroaryl, and X is O. In some embodiments, L is absent, $R^1$ is $—(CR^eR^f)_o$-heterocycloalkyl, and X is O. In other embodiments, L is absent, $R^1$ is $—(CR^gR^h)_p$-cycloalkyl, and X is O.

In some embodiments, L is absent, $R^1$ is $—(CR^aR^b)_m$-aryl or —CH═CH-aryl, X is O, and none of $G_2$, $G_3$, $G_4$, $G_5$, and $G_6$ are N. In some embodiments, L is absent, $R^1$ is $—(CR^aR^b)_m$-aryl or —CH═CH-aryl, X is O, and one of $G_2$, $G_3$, $G_4$, $G_5$, and $G_6$ is N. In some embodiments, L is absent, $R^1$ is $—(CR^aR^b)_m$-aryl or —CH═CH-aryl, X is O, and two of $G_2$, $G_3$, $G_4$, $G_5$, and $G_6$ are N. In some embodiments, L is absent, $R^1$ is $—(CR^aR^b)_m$-aryl or —CH═CH-aryl, X is O, $G_2$ and $G_4$ are each N, $G_3$ is $CR^3$, $G_5$ is $CR^5$, and $G_6$ is $CR^6$.

In some embodiments, L is absent, $R^1$ is $—(CR^cR^d)_n$-heteroaryl, X is O, and none of $G_2$, $G_3$, $G_4$, $G_5$, and $G_6$ are N. In some embodiments, L is absent, $R^1$ is $—(CR^cR^d)_n$-heteroaryl, X is O, and one of $G_2$, $G_3$, $G_4$, $G_5$, and $G_6$ is N. In some embodiments, L is absent, $R^1$ is $—(CR^cR^d)_n$-heteroaryl, X is O, and two of $G_2$, $G_3$, $G_4$, $G_5$, and $G_6$ are N. In some embodiments, L is absent, $R^1$ is $—(CR^cR^d)_n$-heteroaryl, X is O, $G_2$ and $G_4$ are each N, $G_3$ is $CR^3$, $G_5$ is $CR^5$, and $G_6$ is $CR^6$. In some embodiments, L is absent, $R^1$ is $—(CR^eR^f)_o$-heterocycloalkyl, X is O, and none of $G_2$, $G_3$, $G_4$, $G_5$, and $G_6$ are N. In some embodiments, L is absent, $R^1$ is $—(CR^eR^f)_o$-heterocycloalkyl, X is O, and one of $G_2$, $G_3$, $G_4$, $G_5$, and $G_6$ is N. In some embodiments, L is absent, $R^1$ is $—(CR^eR^f)_o$-heterocycloalkyl, X is O, and two of $G_2$, $G_3$, $G_4$, $G_5$, and $G_6$ are N. In some embodiments, L is absent, $R^1$ is $—(CR^eR^f)_o$-heterocycloalkyl, X is O, $G_2$ and $G_4$ are each N, $G_3$ is $CR^3$, $G_5$ is $CR^5$, and $G_6$ is $CR^6$.

In another aspect, provided are compounds of Formula (II):

(II)

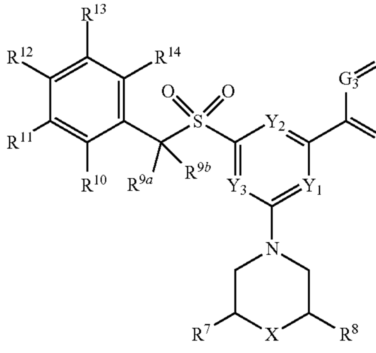

wherein

X is O, S, NH, $N(CO_2C_{1-4}alkyl)$, $N(SO_2C_{1-4}alkyl)$, $N(SO_2cycloalkyl)$, or $CH_2$;

$Y_1$, $Y_2$, and $Y_3$ are each independently CH or N;

$G_2$ is N or $CR^2$;

$G_3$ is N or $CR^3$;

$G_4$ is N, $NR^{4b}$, or $CR^{4a}$;

$G_5$ is N or $CR^5$; and $G_6$ is N or $CR^6$;

wherein $R^2$, $R^3$, $R^{4a}$, $R^5$, and $R^6$ are each independently hydrogen, halogen, —OH, -alkyl, —Oalkyl, -haloalkyl, —O-haloalkyl, or $—NR^uR^v$;

or $R^{4b}$ is taken together with $R^6$ and the atoms to which they are attached to form a heteroaryl or heterocyclic ring; wherein the heteroaryl ring comprising $R^{4b}$ and $R^6$ comprises no more than one N and is optionally substituted with alkyl, and the heterocyclic ring comprising $R^{4b}$ and $R^6$ is optionally substituted with oxo, $R^u$ is H or $C_{1-4}$alkyl;

$R^v$ is H, $C_{1-4}$alkyl, monocyclic cycloalkyl, $—C(O)C_{1-4}$ alkyl, or $—C(O)NR^wR^y$;

wherein each alkyl present in $R^v$ is unsubstituted or substituted with —OH, $—NH_2$, $—NH(C_{1-4}alkyl)$, or $—N(C_{1-4}alkyl)_2$, and $R^w$ and $R^y$ are each independently H or $C_{1-4}$alkyl;

wherein

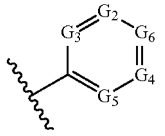

is not unsubstituted phenyl;

$R^7$ and $R^8$ are each independently hydrogen or $C_{1-4}$alkyl, or $R^7$ and $R^8$ are taken together to form $—CH_2CH_2—$;

$R^{9a}$ and $R^{9b}$ are each independently hydrogen or halogen;

$R^{10}$, $R^{11}$, $R^{12}$, $R^{13}$, and $R^{14}$ are each independently hydrogen, halogen, —OH, —CN, -alkyl, —Oalkyl, -haloalkyl, heterocycloalkyl, —O-haloalkyl, $—SO_2C_{1-4}alkyl$, or $—NR^{aa}R^{bb}$;

$R^{aa}$ is hydrogen, $C_{1-4}$alkyl, or $—C_{1-4}alkyl$-OH;

$R^{bb}$ is hydrogen or $C_{1-4}$alkyl;

or $R^{9a}$ is taken together with $R^{10}$ and the interposed atoms to form a heteroaryl or heterocyclic ring;

or $R^{11}$ is taken together with $R^{12}$ and the atoms to which they are attached to form a heteroaryl or heterocyclic ring;

or a pharmaceutically acceptable salt thereof.

In some embodiments of Formula (II), $Y_1$, $Y_2$, and $Y_3$ are each CH. In some embodiments, $Y_1$, $Y_2$, and $Y_3$ are each N. In some embodiments, $Y_1$ is N, and $Y_2$ and $Y_3$ are each CH. In some embodiments, $Y_2$ is N, and $Y_1$ and $Y_3$ are each CH. In some embodiments, $Y_3$ is N, and $Y_1$ and $Y_2$ are each CH. In some embodiments, $Y_1$ and $Y_2$ are each N, and $Y_3$ is CH. In some embodiments, $Y_1$ and $Y_3$ are each N, and $Y_2$ is CH. In some embodiments, $Y_2$ and $Y_3$ are each N, and $Y_1$ is CH.

In some embodiments of Formula (II), X is O. In some embodiments, X is S. In some embodiments, X is NH, $N(CO_2C_{1-4}alkyl)$, $N(SO_2C_{1-4}alkyl)$, or $N(SO_2cyclo\text{-}alkyl)$. In some embodiments, X is $CH_2$.

In some embodiments of Formula (II), $G_2$ is $CR^2$, $G_3$ is $CR^3$, $G_4$ is $CR^{4a}$, $G_5$ is $CR^5$, and $G_6$ is $CR^6$. In some embodiments, one of $G_2$, $G_3$, $G_4$, $G_5$, and $G_6$ is N. In some embodiments, more than one of $G_2$, $G_3$, $G_4$, $G_5$, and $G_6$ are N. In some embodiments, two of $G_2$, $G_3$, $G_4$, $G_5$, and $G_6$ are N. In some embodiments, $G_2$ is N, $G_3$ is $CR^3$, $G_4$ is $CR^{4a}$, $G_5$ is $CR^5$, and $G_6$ is $CR^6$. In some embodiments, $G_2$ is $CR^2$, $G_3$ is $CR^3$, $G_4$ is $CR^{4a}$, $G_5$ is N, and $G_6$ is $CR^6$. In some embodiments, $G_2$ and $G_4$ are each N, $G_3$ is $CR^3$, $G_5$ is $CR^5$, and $G_6$ is $CR^6$. In some embodiments, $G_4$ and $G_5$ are each N, $G_2$ is $CR^2$, $G_3$ is $CR^3$, and $G_6$ is $CR^6$.

In some embodiments wherein none of $G_2$, $G_3$, $G_4$, $G_5$, and $G_6$ are N, $G_4$ is not N or $NR^{4b}$, at least one of $R^2$, $R^3$, $R^{4a}$, $R^5$, and $R^6$ is not hydrogen. In some embodiments, $G_4$ is $NR^{4b}$. In some embodiments, $R^{4b}$ is taken together with $R^6$ and the atoms to which they are attached to form a heteroaryl or heterocyclic ring. In some embodiments, the heteroaryl ring comprising $R^{4b}$ and $R^6$ comprises no more than one N. In some embodiments, the heteroaryl ring comprising $R^{4b}$ and $R^6$ is optionally substituted with alkyl, and the heterocylic ring is optionally substituted with oxo.

In some embodiments of Formula (II), $R^{10}$, $R^{11}$, $R^{12}$, $R^{13}$, and $R^{14}$ are each hydrogen. In some embodiments, at least one of $R^{10}$, $R^{11}$, $R^{12}$, $R^{13}$, and $R^{14}$ is not hydrogen. In some embodiments, at least one of $R^{10}$, $R^{11}$, $R^{12}$, $R^{13}$, and $R^{14}$ is selected from the group consisting of halogen, —OH, —CN, -alkyl, —Oalkyl, -haloalkyl, heterocycloalkyl, —O-haloalkyl, —$SO_2C_{1-4}$alkyl, or —$NR^{aa}R^{bb}$. In some embodiments, $R^{10}$ is selected from the group consisting of halogen, —OH, —CN, -alkyl, —Oalkyl, -haloalkyl, heterocycloalkyl, —O— haloalkyl, —$SO_2C_{1-4}$alkyl, or —$NR^{aa}R^{bb}$. In some embodiments, $R^{12}$ is halo, and $R^{10}$, $R^{11}$, $R^{13}$, and $R^{14}$ are each hydrogen. In some embodiments, at least one of $R^{10}$, $R^{11}$, $R^{12}$, $R^{13}$, and $R^{14}$ is heterocycloalkyl. In some embodiments, at least one of $R^{10}$, $R^{11}$, $R^{12}$, $R^{13}$, and $R^{14}$ is a heterocycloalkyl selected from the group consisting of aziridinyl, pyrrolidinyl, pyrrolidino, piperidinyl, piperidino, piperazinyl, piperazino, morpholinyl, morpholino, thiomorpholinyl, thiomorpholino, tetrahydrofuranyl, tetrahydrothiofuranyl, tetrahydropyranyl, and pyranyl, each optionally substituted. In some embodiments, at least one of $R^{10}$, $R^{11}$, $R^{12}$, $R^{13}$, and $R^{14}$ is a heterocycloalkyl selected from the group consisting of morpholinyl, tetrahydrofuranyl, tetrahydropyranyl, and pyrindinyl, each optionally substituted.

In some embodiments of Formula (II), $R^{9a}$ is taken together with $R^{10}$ and the interposed atoms to form a heteroaryl or heterocyclic ring. In some embodiments, $R^{11}$ is taken together with $R^{12}$ and the atoms to which they are attached to form a heteroaryl or heterocyclic ring.

In some embodiments of Formula (II), $R^7$ and $R^8$ are each hydrogen. In some embodiments, one of $R^7$ and $R^8$ is hydrogen and the other is $C_{1-4}$alkyl. In some embodiments, both of $R^7$ and $R^8$ is $C_{1-4}$alkyl. In some embodiments, $R^7$ and $R^8$ are taken together to form —$CH_2CH_2$—.

In some embodiments of Formula (II), $Y_1$, $Y_2$, and $Y_3$ are each CH, $R^{9a}$ and $R^{9b}$ are each hydrogen, X is O, and none of $G_2$, $G_3$, $G_4$, $G_5$, and $G_6$ is N. In some embodiments, $Y_1$, $Y_2$, and $Y_3$ are each CH, $R^{9a}$ and $R^{9b}$ are each hydrogen, X is O, and one of $G_2$, $G_3$, $G_4$, $G_5$, and $G_6$ is N. In some embodiments, $Y_1$, $Y_2$, and $Y_3$ are each CH, $R^{9a}$ and $R^{9b}$ are each hydrogen, X is O, and two of $G_2$, $G_3$, $G_4$, $G_5$, and $G_6$ are N. In some embodiments, $Y_1$, $Y_2$, and $Y_3$ are each CH, $R^{9a}$ and $R^{9b}$ are both hydrogen, X is O, and $R^{4b}$ is taken together with $R^6$ and the atoms to which they are attached to form a heteroaryl or heterocyclic ring.

In another aspect, provided are compounds of Formula (III):

(III)

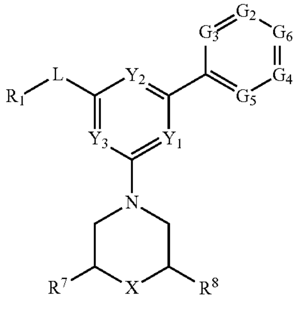

wherein $R^1$ is —$(CR^aR^b)_m$-aryl, —CH═CH-aryl, $(CR^cR^d)_n$-heteroaryl, $(CR^eR^f)_o$— heterocycloalkyl, or $(CR^gR^h)_p$-cycloalkyl, wherein when L is $SO_2$, the heteroaryl and the heterocycloalkyl present in $R^1$ are each monocyclic;

m is 0 or 2;

n, o, and p are each independently 0, 1, or 2;

$R^a$, $R^b$, $R^c$, $R^d$, $R^e$, $R^f$, $R^g$, and $R^h$ are each independently H, halo, or $C_{1-4}$alkyl, or $R^a$ and $R^b$ are taken together with the carbon to which they are attached to form a cycloalkyl ring, or $R^a$ and $R^b$ are taken together to form ═$CH_2$ or ═O;

each aryl, heteroaryl, heterocycloalkyl, or cycloalkyl present in $R^1$ is unsubstituted or substituted with one or two $R^x$ substituents;

wherein each $R^x$ substituent is independently halo, $C_{1-4}$alkyl, cycloalkyl, —$C_{1-2}$-haloalkyl, —OH, —$OC_{1-4}$alkyl, —O—$C_{1-2}$-haloalkyl, cyano, —C(O)$C_{1-4}$alkyl, —C(O)$NR^iR^j$, —$SO_2C_{1-4}$alkyl, —$SO_2NR^kR^l$, —$NR^qR^r$, —C(O)-cycloalkyl, —C(O)-aryl (optionally substituted with methyl or halo), —$CO_2C_{1-4}$alkyl, —$CO_2$aryl, —C(O)$CH_2$-aryl (optionally substituted with methyl or halo), —$CH_2$-aryl (optionally substituted with methyl or halo), or monocyclic heterocycloalkyl (optionally substituted with methyl, —C(O)$C_{1-4}$alkyl, or —$CO_2C_{1-4}$alkyl);

wherein $R^i$, $R^j$, $R^k$, and $R^l$ are each independently H, $C_{1-4}$alkyl, —$C_{1-4}$alkyl-OH, or —$C_{1-4}$alkyl-O—$C_{1-4}$alkyl, wherein $R^q$ and $R^r$ are each independently H, $C_{1-4}$alkyl, —$C_{1-4}$alkyl-OH, —$C_{1-4}$alkyl-O—$C_{1-4}$alkyl, —C(O)$C_{1-4}$alkyl, —$CO_2C_{1-4}$alkyl, or —$SO_2C_{1-4}$alkyl;

or $R^1$ is

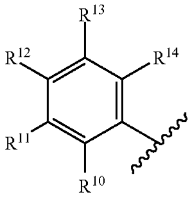

;

wherein $R^{10}$, $R^{11}$, $R^{12}$, $R^{13}$, and $R^{14}$ are each independently hydrogen, halogen, —OH, —CN, -alkyl, —Oalkyl, -haloalkyl, heterocycloalkyl, —O-haloalkyl, —$SO_2C_{1-4}$alkyl, or —$NR^{aa}R^{bb}$;

$R^{aa}$ is hydrogen, $C_{1-4}$alkyl, or —$C_{1-4}$alkyl-OH;

$R^{bb}$ is hydrogen or $C_{1-4}$alkyl;

or $R^{10}$ is taken together with $R^{11}$ and the atoms to which they are attached to form a heteroaryl or heterocyclic ring;

or $R^{11}$ is taken together with $R^{12}$ and the atoms to which they are attached to form a heteroaryl or heterocyclic ring;

L is absent, —$S(O)_2$—, —C(O)—, —O—, —$CH_2$—, —$CF_2$—, $C(CH_3)_2$, —C(=$CH_2$)—, or —$CR^sR^t$—; where $R^s$ and $R^t$ are independently H or alkyl, or $R^s$ and $R^t$ are taken together with the carbon atom to which they are attached to form a cycloalkyl ring;

X is O, S, NH, N($CO_2C_{1-4}$alkyl), N($SO_2C_{1-4}$alkyl), N($SO_2$cyclo-alkyl), or $CH_2$;

$Y_1$, $Y_2$, and $Y_3$ are each independently CH or N; wherein when L is other than —$S(O)_2$—, $Y_2$ and $Y_3$ are each CH;

$G_2$ is N or $CR^2$;

$G_3$ is N or $CR^3$;

$G_4$ is N, $NR^{4b}$, or $CR^{4a}$;

$G_5$ is N or $CR^5$; and $G_6$ is N or $CR^6$;

wherein $R^2$, $R^3$, $R^{4a}$, $R^5$, and $R^6$ are each independently hydrogen, halogen, —OH, -alkyl, —Oalkyl, -haloalkyl, —O-haloalkyl, or —$NR^uR^v$;

or $R^{4b}$ is taken together with $R^6$ and the atoms to which they are attached to form a heteroaryl or heterocyclic ring; wherein the heteroaryl ring comprising $R^{4b}$ and $R^6$ comprises no more than one N and is optionally substituted with alkyl, and the heterocyclic ring comprising $R^{4b}$ and $R^6$ is optionally substituted with oxo, $R^u$ is H or $C_{1-4}$alkyl;

$R^v$ is H, $C_{1-4}$alkyl, monocyclic cycloalkyl, —$C(O)C_{1-4}$ alkyl, or —$C(O)NR^wR^y$; wherein each alkyl present in $R^v$ is unsubstituted or substituted with —OH, —$NH_2$, —NH($C_{1-4}$alkyl), or —N($C_{1-4}$alkyl)$_2$, $R^w$ and $R^v$ are independently H or $C_{1-4}$alkyl;

wherein

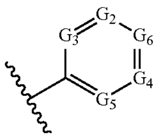

is not unsubstituted phenyl; and $R^7$ and $R^8$ are each independently hydrogen or $C_{1-4}$alkyl, or $R^7$ and $R^8$ are taken together to form —$CH_2CH_2$—;

or a pharmaceutically acceptable salt thereof.

In some embodiments of Formula (I), $R^1$ is —$(CR^aR^b)_m$-aryl, —CH=CH-aryl, or —$(CR^cR^d)_n$-heteroaryl, each unsubstituted or substituted with one or two $R^x$ substituents. In some embodiments, $R^1$ is —$(CR^eR^f)_o$-heterocycloalkyl or —$(CR^gR^h)_p$-cycloalkyl, each unsubstituted or substituted with one or two $R^x$ substituents. In some embodiments, $R^1$ is —$(CR^aR^b)_m$-aryl, wherein $R^a$ and $R^b$ are each independently H, halo, or $C_{1-4}$alkyl, and m is 0 or 2, wherein the aryl is unsubstituted or substituted with one or two $R^x$ substituents. In some embodiments, $R^1$ is —$(CR^aR^b)_2$-aryl, wherein $R^a$ and $R^b$ are taken together with the carbon to which they are attached to form a cycloalkyl, or $R^a$ and $R^b$ are taken together to form =$CH_2$ or =O, and the aryl present in $R^1$ is unsubstituted or substituted with one or two $R^x$ substituents. In some embodiments, $R^1$ is aryl, unsubstituted or substituted with one or two $R^x$ substituents. In some embodiments, $R^1$ is —$CH_2CH_2$-aryl, unsubstituted or substituted with one or two $R^x$ substituents. In some embodiments, $R^1$ is phenyl, naphthyl, —$(CR^aR^b)_2$-phenyl or —$(CR^aR^b)_2$-naphtyl, each unsubstituted or substituted with one or two $R^x$ substituents. In some embodiments, $R^1$ is phenyl. In other embodiments, $R^1$ is napthyl. In some embodiments, $R^1$ is aryl, —$CH_2CH_2$-aryl, or —CH=CH-aryl, each unsubstituted or substituted with one or two $R^x$ substituents independently selected from the group consisting of halo, $C_{1-4}$alkyl, —$C_{1-2}$-haloalkyl, —OH, —$OC_{1-4}$alkyl, —O—$C_{1-2}$-haloalkyl, cyano, —$NR^qR^r$, and monocyclic heterocycloalkyl (optionally substituted with methyl, —$C(O)C_{1-4}$alkyl, or —$CO_2C_{1-4}$alkyl), wherein $R^q$ and $R^r$ are each independently H, $C_{1-4}$alkyl, —$C_{1-4}$alkyl-OH, —$C_{1-4}$alkyl-O—$C_{1-4}$alkyl, —$C(O)C_{1-4}$alkyl, —$CO_2C_{1-4}$alkyl, or —$SO_2C_{1-4}$alkyl. In some embodiments, $R^1$ is phenyl, —$CH_2CH_2$-phenyl, —CH=CH-phenyl, napthyl, —$CH_2CH_2$-napthyl, or —CH=CH— napthyl. In some embodiments, $R^1$ is phenyl, —$CH_2CH_2$-phenyl, —CH=CH-phenyl, napthyl, —$CH_2CH_2$-napthyl, or —CH=CH— napthyl, each substituted with one or two $R^x$ substituents independently selected from the group consisting of F, Cl, —$CF_3$, —$OCF_3$, cyano, —$CH_3$, —$OCH_3$, —$NHC(O)CH_3$, —$NHCH_2C(CH_3)_2OH$, morpholinyl, tetrahydrofuranyl, tetrahydropyranyl, pyrindinyl, and —NHS$(O)_2CH_3$.

In some embodiments, $R^1$ is —$(CR^cR^d)_n$-heteroaryl, wherein $R^c$ and $R^d$ are each independently H, halo, or $C_{1-4}$alkyl, and n is 0, 1, or 2, wherein the heteroaryl is unsubstituted or substituted with one or two $R^x$ substituents. In some embodiments, $R^1$ is heteroaryl, unsubstituted or substituted with one or two $R^x$ substituents. In some embodiments, $R^1$ is —$CH_2$-heteroaryl, unsubstituted or substituted with one or two $R^x$ substituents. In some embodiments, $R^1$ is —$CH_2CH_2$-heteroaryl, unsubstituted or substituted with one or two $R^x$ substituents. In some embodiments, $R^1$ is —$(CR^cR^d)_n$-heteroaryl, wherein the heteroaryl is a monocyclic heteroaryl. In some embodiments, $R^1$ is —$(CR^cR^d)_n$-heteroaryl, wherein the heteroaryl is a bicyclic heteroaryl. In any of these embodiments, the heteroaryl includes one or two nitrogen ring members. In some embodiments, $R^1$ is —$(CR^cR^d)_n$-heteroaryl, wherein the heteroaryl is pyrrole, furan, thiophenyl, imidazole, pyrazole, thiazole, oxazole, isoxazole, isothiazole, triazole, oxadiazole, thiadiazole, tetrazole, pyridine, pyrazine, pyrimidine, pyridazine, indole, isoindole, benzofuran, benzothiophene, benzimidazole, benzothiazole, or benzoxazole, each unsubstituted or substituted with one or two $R^x$ substituents. In some embodiments, $R^1$ is —$CH_2$-heteroaryl. or —$CH_2CH_2$-heteroaryl, each unsubstituted or substituted with one or two $R^x$ substituents independently selected from the group consisting of halo, $C_{1-4}$alkyl, —$C_{1-2}$-haloalkyl, —OH, —$OC_{1-4}$alkyl, —O—$C_{1-2}$-haloalkyl, cyano, —$NR^qR^r$, and monocyclic heterocycloalkyl (optionally substituted with methyl, —C(O)$C_{1-4}$alkyl, or —$CO_2C_{1-4}$alkyl), wherein $R^q$ and $R^r$ are each independently H, $C_{1-4}$alkyl, —$C_{1-4}$alkyl-OH, —$C_{1-4}$alkyl-O—$C_{1-4}$alkyl, —C(O)$C_{1-4}$alkyl, —$CO_2C_{1-4}$alkyl, or —$SO_2C_{1-4}$alkyl. In some embodiments, $R^1$ is pyrrole, furan, thiophenyl, imidazole, pyrazole, thiazole, oxazole, isoxazole, isothiazole, triazole, oxadiazole, thiadiazole, tetrazole, pyridine, pyrazine, pyrimidine, pyridazine, indole, isoindole, benzofuran, benzothiophene, benzimidazole, benzothiazole, or benzoxazole. In some embodiments, $R^1$ is pyrrole, furan, thiophenyl, imidazole, pyrazole, thiazole, oxazole, isoxazole, isothiazole, triazole, oxadiazole, thiadiazole, tetrazole, pyridine, pyrazine, pyrimidine, pyridazine, indole, isoindole, benzofuran, benzothiophene, benzimidazole, benzothiazole, or benzoxazole, each substituted with one or two $R^x$ substituents independently selected from the group consisting of F, Cl, —$CF_3$, —$OCF_3$, cyano, —$CH_3$, —$OCH_3$, —NHC(O)$CH_3$, —$NHCH_2C(CH_3)_2OH$, morpholinyl, tetrahydrofuranyl, tetrahydropyranyl, pyrindinyl, and —$NHS(O)_2CH_3$.

In some embodiments, $R^1$ is —$(CR^eR^f)_o$-heterocycloalkyl, wherein $R^e$ and $R^f$ are each independently H, halo, or $C_{1-4}$alkyl, o is 0, 1, or 2, wherein the heterocycloalkyl is unsubstituted or substituted with one or two $R^x$ substituents. In some embodiments, $R^1$ is heterocycloalkyl, unsubstituted or substituted with one or two $R^x$ substituents. In some embodiments, $R^1$ is —$CH_2$-heterocycloalkyl, unsubstituted or substituted with one or two $R^x$ substituents. In some embodiments, $R^1$ is —$CH_2CH_2$-heterocycloalkyl, unsubstituted or substituted with one or two $R^x$ substituents. In some embodiments, $R^1$ is —$(CR^eR^f)_o$-heterocycloalkyl, wherein the heterocycloalkyl is monocyclic, and in some embodiments, the heterocycloalkyl is a 4- to 6-membered ring. In some embodiments, $R^1$ is —$(CR^eR^f)_o$-heterocycloalkyl, wherein the heterocycloalkyl is azetidine, tetrahydrofuran, pyrrolidine, tetrahydropyran, piperidine, piperazine, morpholine, thiomorpholine, 1,1-dioxothiomorpholine, azepine, or diazepine. In some embodiments, the heterocycloalkyl is attached to the remainder of the structure through a carbon atom (a C-linked heterocycloalkyl). In some embodiments, $R^1$ is —$CH_2$-heterocycloalkyl. or —$CH_2CH_2$-heterocycloalkyl, each unsubstituted or substituted with one or two $R^x$ substituents independently selected from the group consisting of halo, $C_{1-4}$alkyl, —$C_{1-2}$-haloalkyl, —OH, —$OC_{1-4}$alkyl, —O—$C_{1-2}$-haloalkyl, cyano, —$NR^qR^r$, and monocyclic heterocycloalkyl (optionally substituted with methyl, —C(O)$C_{1-4}$alkyl, or —$CO_2C_{1-4}$alkyl), wherein $R^q$ and $R^r$ are each independently H, $C_{1-4}$alkyl, —$C_{1-4}$alkyl-OH, —$C_{1-4}$ alkyl-O—$C_{1-4}$alkyl, —C(O)$C_{1-4}$alkyl, —$CO_2C_{1-4}$alkyl, or —$SO_2C_{1-4}$alkyl. In some embodiments, $R^1$ is azetidine, tetrahydrofuran, pyrrolidine, tetrahydropyran, piperidine, piperazine, morpholine, thiomorpholine, 1,1-dioxothiomorpholine, azepine, or diazepine. In some embodiments, $R^1$ is azetidine, tetrahydrofuran, pyrrolidine, tetrahydropyran, piperidine, piperazine, morpholine, thiomorpholine, 1,1-dioxothiomorpholine, azepine, or diazepine, each substituted with one or two $R^x$ substituents independently selected from the group consisting of F, Cl, —$CF_3$, —$OCF_3$, cyano, —$CH_3$, —$OCH_3$, —NHC(O)$CH_3$, —$NHCH_2C(CH_3)_2OH$, morpholinyl, tetrahydrofuranyl, tetrahydropyranyl, pyrindinyl, and —$NHS(O)_2CH_3$.

In some embodiments, $R^1$ is —$(CR^gR^h)_p$-cycloalkyl, wherein $R^g$ and $R^h$ are each independently H, halo, or $C_{1-4}$alkyl, and p is 0, 1, or 2, and wherein the cycloalkyl is unsubstituted or substituted with one or two $R^x$ substituents. In some embodiments, $R^1$ is cycloalkyl, unsubstituted or substituted with one or two $R^x$ substituents. In some embodiments, $R^1$ is —$CH_2$-cycloalkyl, unsubstituted or substituted with one or two $R^x$ substituents. In some embodiments, $R^1$ is —$CH_2CH_2$-cycloalkyl, unsubstituted or substituted with one or two $R^x$ substituents. In some embodiments, $R^1$ is —$(CR^gR^h)_p$-cycloalkyl, wherein the cycloalkyl is cyclopropyl, cyclobutyl, cyclopentyl, or cyclohexyl. In some embodiments, $R^1$ is cycloalkyl, —$CH_2$-cycloalkyl. or —$CH_2CH_2$-cycloalkyl, each unsubstituted or substituted with one or two $R^x$ substituents independently selected from the group consisting of halo, $C_{1-4}$alkyl, —$C_{1-2}$-haloalkyl, —OH, —$OC_{1-4}$alkyl, —O—$C_{1-2}$-haloalkyl, cyano, —$NR^qR^r$, and monocyclic heterocycloalkyl (optionally substituted with methyl, —C(O)$C_{1-4}$alkyl, or —$CO_2C_{1-4}$alkyl), wherein $R^q$ and $R^r$ are each independently H, $C_{1-4}$alkyl, —$C_{1-4}$alkyl-OH, —$C_{1-4}$alkyl-O—$C_{1-4}$alkyl, —C(O)$C_{1-4}$alkyl, —$CO_2C_{1-4}$alkyl, or —$SO_2C_{1-4}$alkyl. In some embodiments, $R^1$ is cyclopropyl, cyclobutyl, cyclopentyl, or cyclohexyl. In some embodiments, $R^1$ is cyclopropyl, cyclobutyl, cyclopentyl, or cyclohexyl, each substituted with one or two $R^x$ substituents independently selected from the group consisting of F, Cl, —$CF_3$, —$OCF_3$, cyano, —$CH_3$, —$OCH_3$, —NHC(O)$CH_3$, —$NHCH_2C(CH_3)_2OH$, morpholinyl, tetrahydrofuranyl, tetrahydropyranyl, pyrindinyl, and —NHS (O)$_2CH_3$.

In some embodiments, $R^1$ is phenyl, naphthyl, dihydrobenzofuran, benzofuran, benzyl, indolylmethyl, phenethyl, 1,1-difluoro(phenyl)methyl, imidazolylmethyl, benzimdazolylmethyl, pyridinylmethyl, cyclohexyl, cyclohexylmethyl, azetidine, tetrahydrofuran, tetrahydrofuranylmethyl, pyrrolidine, tetrahydropyran, tetrahydropyranylmethyl, or piperidine, each unsubstituted or substituted with one or two $R^x$ substituents.

In each instance, $R^1$ is unsubstituted or substituted with one or two $R^x$ substituents. In some embodiments, there is one $R^x$ substituent, and in others there are two $R^x$ substituents.

In some embodiments, each $R^x$ is independently halo, $C_{1-4}$alkyl, cycloalkyl, —$C_{1-2}$-haloalkyl, —OH, —$OC_{1-4}$alkyl, —O—$C_{1-2}$-haloalkyl, cyano, —C(O)$C_{1-4}$alkyl, —C(O)$NR^iR^j$, —$SO_2C_{1-4}$alkyl, —$SO_2NR^kR^l$, —$NR^qR^r$, —C(O)-cycloalkyl, —C(O)-aryl (optionally substituted with methyl or halo), —$CO_2C_{1-4}$alkyl, —C(O)$CH_2$-aryl (optionally substituted with methyl or halo), —$CH_2$-aryl (optionally substituted with methyl or halo), or monocyclic heterocycloalkyl (optionally substituted with methyl, —C(O)$C_{1-4}$alkyl, or —$CO_2C_{1-4}$alkyl). In some embodiments, each $R^x$ is independently halo, $C_{1-4}$alkyl, cycloalkyl, —$C_{1-2}$-haloalkyl, —OH, —$OC_{1-4}$alkyl, —O—$C_{1-2}$-haloalkyl, cyano, —C(O) $C_{1-4}$alkyl, —C(O)$NR^iR^j$, —$SO_2C_{1-4}$alkyl, —$SO_2NR^kR^l$, —$NR^qR^r$, —C(O)-cycloalkyl, —C(O)-aryl (optionally substituted with methyl or halo), —$CO_2C_{1-4}$alkyl, —$CO_2$aryl, —C(O)$CH_2$-aryl (optionally substituted with methyl or halo), —$CH_2$-aryl (optionally substituted with methyl or halo), or monocyclic heterocycloalkyl (optionally substituted with methyl, —C(O)$C_{1-4}$alkyl, or —$CO_2C_{1-4}$alkyl). In some embodiments, each $R^x$ is independently halo (such as fluoro, chloro, bromo), methyl, ethyl, propyl, isopropyl, —C(O)NH2, —C(O)$NHC_{1-4}$alkyl, —C(O)$NMe_2$, acetyl, —C(O)ethyl, —C(O)-isopropyl, —C(O)-tert-butyl, —C(O)-cyclopropyl, —$CO_2$-tert-butyl, —C(O)$CH_2$-phenyl, —C(O)phenyl, —C(O)$NHC_{1-2}$alkyl-$OCH_3$, Boc-piperidinyl, isopropyl, tetrahydropyranyl, cyano, morpholinyl, fluoro, chloro, —$CF_3$, methoxy, —$NHSO_2CH_3$, 2-hydroxy-2-methyl-1-aminopropyl, —NH-acetyl, or —$OCF_3$. In some embodiments, each $R^x$ is independently tetrahydrofuranyl, tetrahydropyranyl, or pyrindinyl, each optionally substituted. In each instance the aryl and heterocycloalkyl groups are optionally substituted as described above.

In some embodiments, $R^i$ and $R^j$ are each independently H, $C_{1-4}$alkyl, —$C_{1-4}$alkyl-OH, —$C_{1-4}$alkyl-O—$C_{1-4}$alkyl. In some embodiments, $R^i$ and $R^j$ are each independently H, methyl, ethyl, propyl, isopropyl, butyl, isobutyl, sec-butyl, tert-butyl, hydroxymethyl, hydroxyethyl, 2-hydroxy-2-methylpropyl, methoxymethyl, or methoxyethyl.

In some embodiments, $R^k$ and $R^l$ are each independently H, $C_{1-4}$alkyl, —$C_{1-4}$alkyl-OH, —$C_{1-4}$alkyl-O—$C_{1-4}$alkyl, —C(O)$C_{1-4}$alkyl, —$CO_2C_{1-4}$alkyl, or —$SO_2C_{1-4}$alkyl. In some embodiments, $R^k$ and $R^l$ are each independently H, methyl, ethyl, propyl, isopropyl, —$C_{1-4}$alkyl-OH, acetyl, or —$CO_2$-tert-butyl.

In some embodiments of Formula (III), $R^1$ is

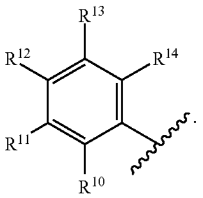

In some embodiments, $R^{10}$, $R^{11}$, $R^{12}$, $R^{13}$, and $R^{14}$ are each independently hydrogen, halogen, —OH, —CN, -alkyl, —Oalkyl, -haloalkyl, heterocycloalkyl, —O-haloalkyl, —$SO_2C_{1-4}$alkyl, or —$NR^{aa}R^{bb}$. In some embodiments, $R^{10}$ is taken together with $R^{11}$ and the atoms to which they are attached to form a heteroaryl or heterocyclic ring. In some embodiments, $R^{11}$ is taken together with $R^{12}$ and the atoms to which they are attached to form a heteroaryl or heterocyclic ring. In some embodiments, $R^{10}$ is taken together with $R^{11}$ to form a 5- or 6-membered heteroaryl or heterocyclic ring. In some embodiments, $R^{10}$ is taken together with $R^{11}$ to form a furanyl, pyridinyl, oxazoyl, oxadiazoyl, pyrrolidinyl, pyrazolidinyl, imidazolidinyl, tetrahydrofuranyl, 1,3-dioxolanyl, tetrahydrothiophenyl, oxathiolanyl, sulfolanyl, piperidinyl, piperazinyl, tetrahydropyranyl, dioxanyl, thianyl, dithianyl, trithianyl, morpholinyl, or thiomorpholinyl ring. In some embodiments, $R^{10}$ is taken together with $R^{11}$ to form a furanyl ring. In some embodiments, $R^{10}$ is taken together with $R^{11}$ to form a tetrahydrofuranyl ring.

In some embodiments, $R^{11}$ is taken together with $R^{12}$ to form a 5- or 6-membered heteroaryl or heterocyclic ring. In some embodiments, $R^{11}$ is taken together with $R^{12}$ to form a furanyl, pyridinyl, oxazoyl, oxadiazoyl, pyrrolidinyl, pyrazolidinyl, imidazolidinyl, tetrahydrofuranyl, 1,3-dioxolanyl, tetrahydrothiophenyl, oxathiolanyl, sulfolanyl, piperidinyl, piperazinyl, tetrahydropyranyl, dioxanyl, thianyl, dithianyl, trithianyl, morpholinyl, or thiomorpholinyl ring. In some embodiments, $R^{11}$ is taken together with $R^{12}$ to form a furanyl ring. In some embodiments, $R^{11}$ is taken together with $R^{12}$ to form a tetrahydrofuranyl ring.

In some embodiments of Formula (III), X is O. In some embodiments, X is S. In some embodiments, X is NH, N($CO_2C_{1-4}$alkyl), N($SO_2C_{1-4}$alkyl), or N($SO_2$cyclo-alkyl). In some embodiments, X is $CH_2$.

In some embodiments of Formula (III), $Y_1$, $Y_2$, and $Y_3$ are each CH. In some embodiments, $Y_1$, $Y_2$, and $Y_3$ are each N. In some embodiments, $Y_1$ is N, and $Y_2$ and $Y_3$ are each CH. In some embodiments, $Y_2$ is N, and $Y_1$ and $Y_3$ are each CH. In some embodiments, $Y_3$ is N, and $Y_1$ and $Y_2$ are each CH. In some embodiments, $Y_1$ and $Y_2$ are each N, and $Y_3$ is CH. In some embodiments, $Y_1$ and $Y_3$ are each N, and $Y_2$ is CH. In some embodiments, $Y_2$ and $Y_3$ are each N, and $Y_1$ is CH.

In some embodiments of Formula (III) or any variation thereof, L is absent, —$S(O)_2$—, —C(O)—, —$CH_2$—, —$CF_2$—, $C(CH_3)_2$, —C(=$CH_2$)—, or —$CR^sR^t$—; wherein $R^s$ and $R^t$ are independently H or alkyl, or $R^s$ and $R^t$ are taken together with the carbon atom to which they are attached to form a cycloalkyl ring; and $R^1$, $R^2$, $R^3$, $R^{4a}$, $R^{4b}$, $R^5$, $R^6$, $R^7$, $R^8$, X, $Y_1$, $Y_2$, $Y_3$, $G_2$, $G_3$, $G_4$, $G_5$, $G_6$, $R^a$, $R^b$, $R^c$, $R^d$, $R^e$, $R^f$, $R^g$, $R^h$, $R^i$, $R^j$, $R^k$, $R^l$, $R^q$, $R^r$, $R^u$, $R^v$, $R^w$, $R^x$, $R^y$, m, n, o, and p are as defined for Formula (III) or any variation or embodiment thereof.

In some embodiments of Formula (III), L is —$S(O)_2$—. In some embodiments, L is absent. In some embodiments, L is —C(O)—, —O—, —$CH_2$—, —$CF_2$—, $C(CH_3)_2$, —C(=$CH_2$)—, or —$CR^sR^t$—. In some embodiments, L is —C(O)—, —$CH_2$—, —$CF_2$—, $C(CH_3)_2$, —C(=$CH_2$)—, or —$CR^sR^t$—. In some embodiments, L is absent, —C(O)—, —$CH_2$—, —$CF_2$—, $C(CH_3)_2$, —C(=$CH_2$)—, or —$CR^sR^t$—; and $Y_2$ and $Y_3$ are each CH.

In some embodiments of Formula (II), $G_2$ is $CR^2$, $G_3$ is $CR^3$, $G_4$ is $CR^{4a}$, $G_5$ is $CR^5$, and $G_6$ is $CR^6$. In some embodiments, one of $G_2$, $G_3$, $G_4$, $G_5$, and $G_6$ is N. In some embodiments, one of $G_2$, $G_3$, $G_4$, $G_5$, and $G_6$ are N. In some embodiments, two of $G_2$, $G_3$, $G_4$, $G_5$, and $G_6$ are N. In some embodiments, $G_2$ is N, $G_3$ is $CR^3$, $G_4$ is $CR^{4a}$, $G_5$ is $CR^5$, and $G_6$ is $CR^6$. In some embodiments, $G_2$ is $CR^2$, $G_3$ is $CR^3$, $G_4$ is $CR^{4a}$, $G_5$ is N, and $G_6$ is $CR^6$. In some embodiments, $G_2$ and $G_4$ are each N, $G_3$ is $CR^3$, $G_5$ is $CR^5$, and $G_6$ is $CR^6$. In some embodiments, $G_4$ and $G_5$ are each N, $G_2$ is $CR^2$, $G_3$ is $CR^3$, and $G_6$ is $CR^6$.

In some embodiments wherein none of $G_2$, $G_3$, $G_5$, and $G_6$ are N, $G_4$ is not N or $NR^{4b}$, at least one of $R^2$, $R^3$, $R^{4a}$, $R^5$, and $R^6$ is not hydrogen. In some embodiments, $G_4$ is $NR^{4b}$. In some embodiments, $R^{4b}$ is taken together with $R^6$ and the atoms to which they are attached to form a heteroaryl or heterocyclic ring. In some embodiments, the heteroaryl ring comprising $R^{4b}$ and $R^6$ comprises no more than one N. In some embodiments, the heteroaryl ring comprising $R^{4b}$ and $R^6$ is optionally substituted with alkyl, and the heterocylic ring is optionally substituted with oxo, In some embodiments of Formula (III), $R^7$ and $R^8$ are each hydrogen. In some embodiments, one of $R^7$ and $R^8$ is hydrogen and the other is $C_{1-4}$alkyl. In some embodiments, both of $R^7$ and $R^1$ is $C_{1-4}$alkyl. In some embodiments, $R^7$ and $R^8$ are taken together to form —$CH_2CH_2$—.

In some embodiments of Formula (III), L is —$S(O)_2$— and $R^1$ is —$(CR^aR^b)_m$-aryl, wherein $R^a$ and $R^b$ are each independently H, halo, or $C_{1-4}$alkyl, and m is 0, 1, or 2, and wherein the aryl is unsubstituted or substituted with one or two $R^x$ substituents. In some embodiments, L is —$S(O)_2$— and $R^1$ is —$(CR^cR^d)_n$-heteroaryl, wherein $R^c$ and $R^d$ are each independently H, halo, or $C_{1-4}$alkyl, and n is 0, 1, or 2, and wherein the heteroaryl is unsubstituted or substituted with one or two $R^x$ substituents. In some embodiments, L is —$S(O)_2$— and $R^1$ is —$(CR^eR^f)_o$-heterocycloalkyl, wherein $R^e$ and $R^f$ are each independently H, halo, or $C_{1-4}$alkyl, and o is 0, 1, or 2, and wherein the heterocycloalkyl is unsubstituted or substituted with one or two $R^x$ substituents. In other embodiments, L is —$S(O)_2$— and $R^1$ is —$(CR^gR^h)_p$-cycloalkyl; wherein $R^g$ and $R^h$ are each independently H, halo, or $C_{1-4}$alkyl, and p is 0, 1, or 2, and wherein the cycloalkyl is unsubstituted or substituted with one or two $R^x$ substituents. In yet other embodiments, L is —$S(O)_2$— and $R^1$ is —CH═CH-aryl.

In some embodiments, L is —$S(O)_2$—, $R^1$ is —$(CR^aR^b)_m$-aryl or —CH═CH-aryl, and X is O. In some embodiments, L is —$S(O)_2$—, $R^1$ is —$(CR^cR^d)_n$-heteroaryl, and X is O. In some embodiments, L is —$S(O)_2$—, $R^1$ is —$(CR^eR^f)_o$-heterocycloalkyl, and X is O. In other embodiments, L is —$S(O)_2$—, $R^1$ is —$(CR^gR^h)_p$-cycloalkyl, and X is O.

In some embodiments, L is —$S(O)_2$—, $R^1$ is —$(CR^aR^b)_m$-aryl or —CH═CH-aryl, X is O, and none of $G_2$, $G_3$, $G_4$, $G_5$, and $G_6$ are N. In some embodiments, L is —$S(O)_2$—, $R^1$ is —$(CR^aR^b)_m$-aryl or —CH═CH-aryl, X is O, and one of $G_2$, $G_3$, $G_4$, $G_5$, and $G_6$ is N. In some embodiments, L is —$S(O)_2$—, $R^1$ is —$(CR^aR^b)_m$-aryl or —CH═CH-aryl, X is O, and two of $G_2$, $G_3$, $G_4$, $G_5$, and $G_6$ are N. In some embodiments, L is —$S(O)_2$—, $R^1$ is —$(CR^aR^b)_m$-aryl or —CH═CH-aryl, X is O, $G_2$ and $G_4$ are each N, $G_3$ is $CR^3$, $G_5$ is $CR^5$, and $G_6$ is $CR^6$.

In some embodiments, L is —$S(O)_2$—, $R^1$ is —$(CR^cR^d)_n$-heteroaryl, X is O, and none of $G_2$, $G_3$, $G_4$, $G_5$, and $G_6$ are N. In some embodiments, L is —$S(O)_2$—, $R^1$ is —$(CR^cR^d)_n$-heteroaryl, X is O, and one of $G_2$, $G_3$, $G_4$, $G_5$, and $G_6$ is N. In some embodiments, L is —$S(O)_2$—, $R^1$ is —$(CR^cR^d)_n$-heteroaryl, X is O, and two of $G_2$, $G_3$, $G_4$, $G_5$, and $G_6$ are N. In some embodiments, L is —$S(O)_2$—, $R^1$ is —$(CR^cR^d)_n$-heteroaryl, X is O, $G_2$ and $G_4$ are each N, $G_3$ is $CR^3$, $G_5$ is $CR^5$, and $G_6$ is $CR^6$. In some embodiments, L is —$S(O)_2$—, $R^1$ is —$(CR^eR^f)_o$-heterocycloalkyl, X is O, and none of $G_2$, $G_3$, $G_4$, $G_5$, and $G_6$ are N. In some embodiments, L is —$S(O)_2$—, $R^1$ is —$(CR^eR^f)_o$-heterocycloalkyl, X is O, and one of $G_2$, $G_3$, $G_4$, $G_5$, and $G_6$ is N. In some embodiments, L is —$S(O)_2$—, $R^1$ is —$(CR^eR^f)_o$-heterocycloalkyl, X is O, and two of $G_2$, $G_3$, $G_4$, $G_5$, and $G_6$ are N. In some embodiments, L is —$S(O)_2$—, $R^1$ is —$(CR^eR^f)_o$-heterocycloalkyl, X is O, $G_2$ and $G_4$ are each N, $G_3$ is $CR^3$, $G_5$ is $CR^5$, and $G_6$ is $CR^6$.

In some embodiments of Formula (I), L is —C(O)— and $R^1$ is —$(CR^aR^b)_m$-aryl, wherein $R^a$ and $R^b$ are each independently H, halo, or $C_{1-4}$alkyl, and m is 0, 1, or 2, and wherein the aryl is unsubstituted or substituted with one or two $R^x$ substituents. In some embodiments, L is —C(O)— and $R^1$ is —$(CR^cR^d)_n$-heteroaryl, wherein $R^c$ and $R^d$ are each independently H, halo, or $C_{1-4}$alkyl, and n is 0, 1, or 2, and wherein the heteroaryl is unsubstituted or substituted with one or two $R^x$ substituents. In some embodiments, L is —C(O)— and $R^1$ is —$(CR^eR^f)_o$-heterocycloalkyl, wherein $R^e$ and $R^f$ are each independently H, halo, or $C_{1-4}$alkyl, and o is 0, 1, or 2, and wherein the heterocycloalkyl is unsubstituted or substituted with one or two $R^x$ substituents. In other embodiments, L is —C(O)— and $R^1$ is —$(CR^gR^h)_p$-cycloalkyl; wherein $R^g$ and $R^h$ are each independently H, halo, or $C_{1-4}$alkyl, and p is 0, 1, or 2, and wherein the cycloalkyl is unsubstituted or substituted with one or two $R^x$ substituents. In yet other embodiments, L is —C(O)— and $R^1$ is —CH═CH-aryl.

In some embodiments, L is —C(O)—, $R^1$ is —$(CR^aR^b)_m$-aryl or —CH═CH-aryl, and X is O. In some embodiments, L is —C(O)—, $R^1$ is —$(CR^cR^d)_n$-heteroaryl, and X is O. In some embodiments, L is —C(O)—, $R^1$ is —$(CR^eR^f)_o$-heterocycloalkyl, and X is O. In other embodiments, L is —C(O)—, $R^1$ is —$(CR^gR^h)_p$-cycloalkyl, and X is O.

In some embodiments, L is —C(O)—, $R^1$ is —$(CR^aR^b)_m$-aryl or —CH═CH-aryl, X is O, and none of $G_2$, $G_3$, $G_4$, $G_5$, and $G_6$ are N. In some embodiments, L is —C(O)—, $R^1$ is —$(CR^aR^b)_m$-aryl or —CH═CH-aryl, X is O, and one of $G_2$, $G_3$, $G_4$, $G_5$, and $G_6$ is N. In some embodiments, L is —C(O)—, $R^1$ is —$(CR^aR^b)_m$-aryl or —CH═CH-aryl, X is O, and two of $G_2$, $G_3$, $G_4$, $G_5$, and $G_6$ are N. In some embodiments, L is —C(O)—, $R^1$ is —$(CR^aR^b)_m$-aryl or —CH═CH-aryl, X is O, $G_2$ and $G_4$ are each N, $G_3$ is $CR^3$, $G_5$ is $CR^5$, and $G_6$ is $CR^6$.

In some embodiments, L is —C(O)—, $R^1$ is —$(CR^cR^d)_n$-heteroaryl, X is O, and none of $G_2$, $G_3$, $G_4$, $G_5$, and $G_6$ are N. In some embodiments, L is —C(O)—, $R^1$ is —$(CR^cR^d)_n$-heteroaryl, X is O, and one of $G_2$, $G_3$, $G_4$, $G_5$, and $G_6$ is N. In some embodiments, L is —C(O)—, $R^1$ is —$(CR^cR^d)_n$-heteroaryl, X is O, and two of $G_2$, $G_3$, $G_4$, $G_5$, and $G_6$ are N. In some embodiments, L is —C(O)—, $R^1$ is —$(CR^cR^d)_n$-heteroaryl, X is O, $G_2$ and $G_4$ are each N, $G_3$ is $CR^3$, $G_5$ is $CR^5$, and $G_6$ is $CR^6$. In some embodiments, L is —C(O)—, $R^1$ is —$(CR^eR^f)_o$-heterocycloalkyl, X is O, and none of $G_2$, $G_3$, $G_4$, $G_5$, and $G_6$ are N. In some embodiments, L is —C(O)—, $R^1$ is —$(CR^eR^f)_o$-heterocycloalkyl, X is O, and one of $G_2$, $G_3$, $G_4$, $G_5$, and $G_6$ is N. In some embodiments, L is —C(O)—, $R^1$ is —$(CR^eR^f)_o$-heterocycloalkyl, X is O, and two of $G_2$, $G_3$, $G_4$, $G_5$, and $G_6$ are N. In some embodiments, L is —C(O)—, $R^1$ is —$(CR^eR^f)_o$-heterocycloalkyl, X is O, $G_2$ and $G_4$ are each N, $G_3$ is $CR^3$, $G_5$ is $CR^5$, and $G_6$ is $CR^6$.

In some embodiments of Formula (III), L is —O— and $R^1$ is —$(CR^aR^b)_m$-aryl, wherein $R^a$ and $R^b$ are each independently H, halo, or $C_{1-4}$alkyl, and m is 0, 1, or 2, and wherein the aryl is unsubstituted or substituted with one or two $R^x$ substituents. In some embodiments, L is —O— and $R^1$ is —$(CR^cR^d)_n$-heteroaryl, wherein $R^c$ and $R^d$ are each independently H, halo, or $C_{1-4}$alkyl, and n is 0, 1, or 2, and wherein the heteroaryl is unsubstituted or substituted with one or two $R^x$ substituents. In some embodiments, L is —O— and $R^1$ is —$(CR^eR^f)_o$-heterocycloalkyl, wherein $R^e$ and $R^1$ are each independently H, halo, or $C_{1-4}$alkyl, and o is 0, 1, or 2, and wherein the heterocycloalkyl is unsubstituted or substituted with one or two $R^x$ substituents. In other embodiments, L is —O— and $R^1$ is —$(CR^gR^h)_p$-cycloalkyl; wherein $R^g$ and $R^h$ are each independently H, halo, or $C_{1-4}$alkyl, and p is 0, 1, or 2, and wherein the cycloalkyl is unsubstituted or substituted with one or two $R^x$ substituents. In yet other embodiments, L is —O— and $R^1$ is —CH═CH-aryl.

In some embodiments, L is —O—, $R^1$ is —$(CR^aR^b)_m$-aryl or —CH═CH-aryl, and X is O. In some embodiments, L is —O—, $R^1$ is —$(CR^cR^d)_n$-heteroaryl, and X is O. In some embodiments, L is —O—, $R^1$ is —$(CR^eR^f)_o$-heterocycloalkyl, and X is O. In other embodiments, L is —O—, $R^1$ is —$(CR^gR^h)_p$-cycloalkyl, and X is O.

In some embodiments, L is —O—, $R^1$ is —$(CR^aR^b)_m$-aryl or —CH═CH-aryl, X is O, and none of $G_2$, $G_3$, $G_4$, $G_5$, and $G_6$ are N. In some embodiments, L is —O—, $R^1$ is —$(CR^aR^b)_m$-aryl or —CH═CH-aryl, X is O, and one of $G_2$, $G_3$, $G_4$, $G_5$, and $G_6$ is N. In some embodiments, L is —O—, $R^1$ is —$(CR^aR^b)_m$-aryl or —CH═CH-aryl, X is O, and two of $G_2$, $G_3$, $G_4$, $G_5$, and $G_6$ are N. In some embodiments, L is —O—, $R^1$ is —$(CR^aR^b)_m$-aryl or —CH═CH-aryl, X is O, $G_2$ and $G_4$ are each N, $G_3$ is $CR^3$, $G_5$ is $CR^5$, and $G_6$ is $CR^6$.

In some embodiments, L is —O—, $R^1$ is —$(CR^cR^d)_n$-heteroaryl, X is O, and none of $G_2$, $G_3$, $G_4$, $G_5$, and $G_6$ are N. In some embodiments, L is —O—, $R^1$ is —$(CR^cR^d)_n$-heteroaryl, X is O, and one of $G_2$, $G_3$, $G_4$, $G_5$, and $G_6$ is N. In some embodiments, L is —O—, $R^1$ is —$(CR^cR^d)_n$-heteroaryl, X is O, and two of $G_2$, $G_3$, $G_4$, $G_5$, and $G_6$ are N. In some embodiments, L is —O—, $R^1$ is —$(CR^cR^d)_n$-heteroaryl, X is O, $G_2$ and $G_4$ are each N, $G^3$ is $CR^3$, $G^5$ is $CR^5$, and $G^6$ is $CR^6$. In some embodiments, L is —O—, $R^1$ is —$(CR^eR^f)_o$-heterocycloalkyl, X is O, and none of $G_2$, $G_3$, $G_4$, $G_5$, and $G_6$ are N. In some embodiments, L is —O—, $R^1$ is —$(CR^eR^f)_o$-heterocycloalkyl, X is O, and one of $G_2$, $G_3$, $G_4$, $G_5$, and $G_6$ is N. In some embodiments, L is —O—, $R^1$ is —$(CR^eR^f)_o$-heterocycloalkyl, X is O, and two of $G_2$, $G_3$, $G_4$, $G_5$, and $G_6$ are N. In some embodiments, L is —O—, $R^1$ is —$(CR^eR^f)_o$-heterocycloalkyl, X is O, $G_2$ and $G_4$ are each N, $G_3$ is $CR^3$, $G_5$ is $CR^5$, and $G_6$ is $CR^6$.

In some embodiments of Formula (III), L is —$CH_2$—, —$CF_2$—, $C(CH_3)_2$, —C(=$CH_2$)—, or —$CR^sR^t$—, and $R^1$ is —$(CR^aR^b)_m$-aryl, wherein $R^a$ and $R^b$ are each independently H, halo, or $C_{1-4}$alkyl, and m is 0, 1, or 2, and wherein the aryl is unsubstituted or substituted with one or two $R^x$ substituents. In some embodiments, L is —$CH_2$—, —$CF_2$—, $C(CH_3)_2$, —C(=$CH_2$)—, or —$CR^sR^t$—, and $R^1$ is —$(CR^cR^d)_n$-heteroaryl, wherein $R^c$ and $R^d$ are each independently H, halo, or $C_{1-4}$alkyl, and n is 0, 1, or 2, and wherein the heteroaryl is unsubstituted or substituted with one or two $R^x$ substituents. In some embodiments, L is —$CH_2$—, —$CF_2$—, $C(CH_3)_2$, —C(=$CH_2$)—, or —$CR^sR^t$—, and $R^1$ is —$(CR^eR^f)_o$-heterocycloalkyl, wherein $R^e$ and $R^f$ are each independently H, halo, or $C_{1-4}$alkyl, and o is 0, 1, or 2, and wherein the heterocycloalkyl is unsubstituted or substituted with one or two $R^x$ substituents. In other embodiments, L is —$CH_2$—, —$CF_2$—, $C(CH_3)_2$, —C(=$CH_2$)—, or —$CR^sR^t$—, and $R^1$ is —$(CR^gR^h)_p$-cycloalkyl; wherein $R^g$ and $R^h$ are each independently H, halo, or $C_{1-4}$alkyl, and p is 0, 1, or 2, and wherein the cycloalkyl is unsubstituted or substituted with one or two $R^x$ substituents. In yet other embodiments, L is —$CH_2$—, —$CF_2$—, $C(CH_3)_2$, —C(=$CH_2$)—, or —$CR^sR^t$—, and $R^1$ is —CH=CH-aryl.

In some embodiments, L is —$CH_2$—, —$CF_2$—, $C(CH_3)_2$, —C(=$CH_2$)—, or —$CR^sR^t$—, $R^1$ is —$(CR^aR^b)_m$-aryl or —CH=CH-aryl, and X is O. In some embodiments, L is —$CH_2$—, —$CF_2$—, $C(CH_3)_2$, —C(=$CH_2$)—, or —$CR^sR^t$—, $R^1$ is —$(CR^cR^d)_n$-heteroaryl, and X is O. In some embodiments, L is —$CH_2$—, —$CF_2$—, $C(CH_3)_2$, —C(=$CH_2$)—, or —$CR^sR^t$—, $R^1$ is —$(CR^eR^f)_o$-heterocycloalkyl, and X is O. In other embodiments, L is —$CH_2$—, —$CF_2$—, $C(CH_3)_2$, —C(=$CH_2$)—, or —$CR^sR^t$—, $R^1$ is —$(CR^gR^h)_p$-cycloalkyl, and X is O.

In some embodiments, L is —$CH_2$—, —$CF_2$—, $C(CH_3)_2$, —C(=$CH_2$)—, or —$CR^sR^t$—, $R^1$ is —$(CR^aR^b)_m$-aryl or —CH=CH-aryl, X is O, and none of $G_2$, $G_3$, $G_4$, $G_5$, and $G_6$ are N. In some embodiments, L is —$CH_2$—, —$CF_2$—, $C(CH_3)_2$, —C(=$CH_2$)—, or —$CR^sR^t$—, $R^1$ is —$(CR^aR^b)_m$ aryl or —CH=CH-aryl, X is O, and one of $G_2$, $G_3$, $G_4$, $G_5$, and $G_6$ is N. In some embodiments, L is —$CH_2$—, —$CF_2$—, $C(CH_3)_2$, —C(=$CH_2$)—, or —$CR^sR^t$—, $R^1$ is —$(CR^aR^b)_m$-aryl or —CH=CH-aryl, X is O, and two of $G_2$, $G_3$, $G_4$, $G_5$, and $G_6$ are N. In some embodiments, L is —$CH_2$—, —$CF_2$—, $C(CH_3)_2$, —C(=$CH_2$)—, or —$CR^sR^t$—, $R^1$ is —$(CR^aR^b)_m$-aryl or —CH=CH-aryl, X is O, $G_2$ and $G_4$ are each N, $G_3$ is $CR^3$, $G_5$ is $CR^5$, and $G_6$ is $CR^6$.

In some embodiments, L is —$CH_2$—, —$CF_2$—, $C(CH_3)_2$, —C(=$CH_2$)—, or —$CR^sR^t$—, $R^1$ is —$(CR^cR^d)_n$-heteroaryl, X is O, and none of $G_2$, $G_3$, $G_4$, $G_5$, and $G_6$ are N. In some embodiments, L is —$CH_2$—, —$CF_2$—, $C(CH_3)_2$, —C(=$CH_2$)—, or —$CR^sR^t$—, $R^1$ is —$(CR^cR^d)_n$-heteroaryl, X is O, and one of $G_2$, $G_3$, $G_4$, $G_5$, and $G_6$ is N. In some embodiments, L is —$CH_2$—, —$CF_2$—, $C(CH_3)_2$, —C(=$CH_2$)—, or —$CR^sR^t$—, $R^1$ is —$(CR^cR^d)_n$-heteroaryl, X is O, and two of $G_2$, $G_3$, $G_4$, $G_5$, and $G_6$ are N. In some embodiments, L is —$CH_2$—, —$CF_2$—, $C(CH_3)_2$, —C(=$CH_2$)—, or —$CR^sR^t$—, $R^1$ is —$(CR^cR^d)_n$-heteroaryl, X is O, $G_2$ and $G_4$ are each N, $G_3$ is $CR^3$, $G_5$ is $CR^5$, and $G_6$ is $CR^6$. In some embodiments, L is —$CH_2$—, —$CF_2$—, $C(CH_3)_2$, —C(=$CH_2$)—, or —$CR^sR^t$—, $R^1$ is —$(CR^eR^f)_o$-heterocycloalkyl, X is O, and none of $G_2$, $G_3$, $G_4$, $G_5$, and $G_6$ are N. In some embodiments, L is —$CH_2$—, —$CF_2$—, $C(CH_3)_2$, —C(=$CH_2$)—, or —$CR^sR^t$—, $R^1$ is —$(CR^eR^f)_o$-heterocycloalkyl, X is O, and one of $G_2$, $G_3$, $G_4$, $G_5$, and $G_6$ is N. In some embodiments, L is —$CH_2$—, —$CF_2$—, $C(CH_3)_2$, —C(=$CH_2$)—, or —$CR^sR^t$—, $R^1$ is —$(CR^eR^f)_o$-heterocycloalkyl, X is O, and two of $G_2$, $G_3$, $G_4$, $G_5$, and $G_6$ are N. In some embodiments, L is —$CH_2$—, —$CF_2$—, $C(CH_3)_2$, —C(=$CH_2$)—, or —$CR^sR^t$—, $R^1$ is —$(CR^eR^f)_o$-heterocycloalkyl, X is O, $G_2$ and $G_4$ are each N, $G_3$ is $CR^3$, $G_5$ is $CR^5$, and $G_6$ is $CR^6$.

In some embodiments of Formula (III), L is absent and $R^1$ is —$(CR^aR^b)_m$-aryl, wherein $R^a$ and $R^b$ are each independently H, halo, or $C_{1-4}$alkyl, and m is 0, 1, or 2, and wherein the aryl is unsubstituted or substituted with one or two $R^x$ substituents. In some embodiments, L is absent and $R^1$ is —$(CR^cR^d)_n$-heteroaryl, wherein $R^c$ and $R^d$ are each independently H, halo, or $C_{1-4}$alkyl, and n is 0, 1, or 2, and wherein the heteroaryl is unsubstituted or substituted with one or two $R^x$ substituents. In some embodiments, L is absent and $R^1$ is —$(CR^eR^f)_o$-heterocycloalkyl, wherein $R^e$ and $R^f$ are each independently H, halo, or $C_{1-4}$alkyl, and o is 0, 1, or 2, and wherein the heterocycloalkyl is unsubstituted or substituted with one or two $R^x$ substituents. In other embodiments, L is absent and $R^1$ is —$(CR^gR^h)_p$-cycloalkyl; wherein $R^g$ and $R^h$ are each independently H, halo, or $C_{1-4}$alkyl, and p is 0, 1, or 2, and wherein the cycloalkyl is unsubstituted or substituted with one or two $R^x$ substituents. In yet other embodiments, L is absent and $R^1$ is —CH=CH-aryl.

In some embodiments, L is absent, $R^1$ is —$(CR^aR^b)_m$-aryl or —CH=CH-aryl, and X is O. In some embodiments, L is absent, $R^1$ is —$(CR^cR^d)_n$-heteroaryl, and X is O. In some embodiments, L is absent, $R^1$ is —$(CR^eR^f)_o$-heterocycloalkyl, and X is O. In other embodiments, L is absent, $R^1$ is —$(CR^gR^h)_p$-cycloalkyl, and X is O.

In some embodiments, L is absent, $R^1$ is —$(CR^aR^b)_m$-aryl or —CH=CH-aryl, X is O, and none of $G_2$, $G_3$, $G_4$, $G_5$, and $G_6$ are N. In some embodiments, L is absent, $R^1$ is —$(CR^aR^b)_m$-aryl or —CH=CH-aryl, X is O, and one of $G_2$, $G_3$, $G_4$, $G_5$, and $G_6$ is N. In some embodiments, L is absent, $R^1$ is —$(CR^aR^b)_m$-aryl or —CH=CH-aryl, X is O, and two of $G_2$, $G_3$, $G_4$, $G_5$, and $G_6$ are N. In some embodiments, L is absent, $R^1$ is —$(CR^aR^b)_m$-aryl or —CH=CH-aryl, X is O, $G_2$ and $G_4$ are each N, $G_3$ is $CR^3$, $G_5$ is $CR^5$, and $G_6$ is $CR^6$.

In some embodiments, L is absent, $R^1$ is —$(CR^cR^d)_n$-heteroaryl, X is O, and none of $G_2$, $G_3$, $G_4$, $G_5$, and $G_6$ are N. In some embodiments, L is absent, $R^1$ is —$(CR^cR^d)_n$-heteroaryl, X is O, and one of $G_2$, $G_3$, $G_4$, $G_5$, and $G_6$ is N. In some embodiments, L is absent, $R^1$ is —$(CR^cR^d)_n$-heteroaryl, X is O, and two of $G_2$, $G_3$, $G_4$, $G_5$, and $G_6$ are N. In some embodiments, L is absent, $R^1$ is —$(CR^cR^d)_n$-heteroaryl, X is O, $G_2$ and $G_4$ are each N, $G_3$ is $CR^3$, $G_5$ is $CR^5$, and $G_6$ is $CR^6$. In some embodiments, L is absent, $R^1$ is —$(CR^eR^f)_o$-heterocycloalkyl, X is O, and none of $G_2$, $G_3$, $G_4$, $G_5$, and $G_6$ are N. In some embodiments, L is absent, $R^1$ is —$(CR^eR^f)_o$-heterocycloalkyl, X is O, and one of $G_2$, $G_3$, $G_4$, $G_5$, and $G_6$ is N. In some embodiments, L is absent, $R^1$ is —$(CR^eR^f)_o$-heterocycloalkyl, X is O, and two of $G_2$, $G_3$, $G_4$, $G_5$, and $G_6$ are N. In some embodiments, L is absent, $R^1$ is —$(CR^eR^f)_o$-heterocycloalkyl, X is O, $G_2$ and $G_4$ are each N, $G_3$ is $CR^3$, $G_5$ is $CR^5$, and $G_6$ is $CR^6$.

Any variation or embodiment of $R^1$, $R^2$, $R^3$, $R^{4a}$, $R^{4b}$, $R^5$, $R^6$, $R^7$, $R^1$, L, X, $Y_1$, $Y_2$, $Y_3$, $G_2$, $G_3$, $G_4$, $G_5$, $G_6$, $R^a$, $R^b$, $R^c$, $R^d$, $R^e$, $R^f$, $R^g$, $R^h$, $R^i$, $R^j$, $R^k$, $R^l$, $R^q$, $R^r$, $R^s$, $R^t$, $R^u$, $R^v$, $R^w$, $R^x$, $R^y$, m, n, o, and p provided herein can be combined with every other variation or embodiment of $R^1$, $R^2$, $R^3$, $R^{4a}$, $R^{4b}$, $R^5$, $R^6$, $R^7$, $R^8$, L, X, $Y_1$, $Y_2$, $Y_3$, $G_2$, $G_3$, $G_4$, $G_5$, $G_6$, $R^a$, $R^b$, $R^c$, $R^d$, $R^e$, $R^f$, $R^g$, $R^h$, $R^i$, $R^j$, $R^k$, $R^l$, $R^q$, $R^r$, $R^s$, $R^t$, $R^u$, $R^v$, $R^w$, $R^x$, $R^y$, m, n, o, and p, as if each combination had been individually and specifically described.

It is understood that unless otherwise stated, any of the embodiments described herein, such as those described with respect to Formula (I), Formula (II), and Formula (III) are also intended to apply to any other formula described herein, including Formula (I), Formula (II), and Formula (III).

In some embodiments, provided herein are compounds and salts thereof described in Table 1.

| Cmpd # | Structure | Chemical Name |
|---|---|---|
| 1 | 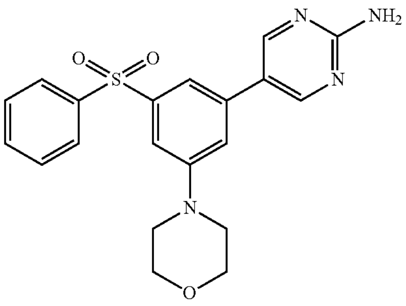 [SMILES: Nc1ncc(-c2cc(N3CCOCC3)cc(S(=O)(=O)c3ccccc3)c2)cn1] | 5-(3-morpholino-5-(phenylsulfonyl)phenyl)pyrimidin-2-amine |
| 2 | 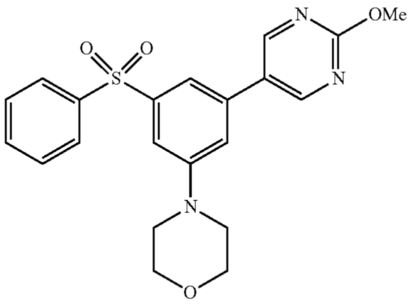 | 4-(3-(2-methoxypyrimidin-5-yl)-5-(phenylsulfonyl)phenyl)morpholine |
| 3 | 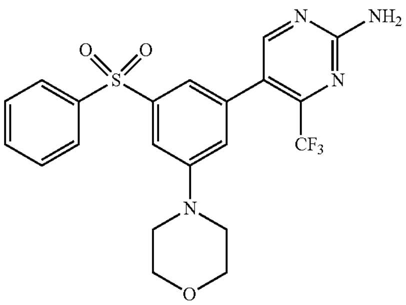 [SMILES: Nc1ncc(-c2cc(N3CCOCC3)cc(S(=O)(=O)c3ccccc3)c2)c(C(F)(F)F)n1] | 5-(3-morpholino-5-(phenylsulfonyl)phenyl)-4-(trifluoromethyl)pyrimidin-2-amine |
| 4 | 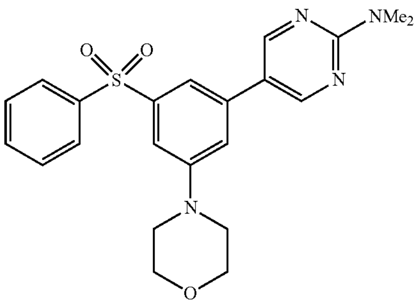 [SMILES: CN(C)c1ncc(-c2cc(N3CCOCC3)cc(S(=O)(=O)c3ccccc3)c2)cn1] | N,N-dimethyl-5-(3-morpholino-5-(phenylsulfonyl)phenyl)pyrimidin-2-amine |

-continued
| Cmpd # | Structure | Chemical Name |
| --- | --- | --- |
| 5 | 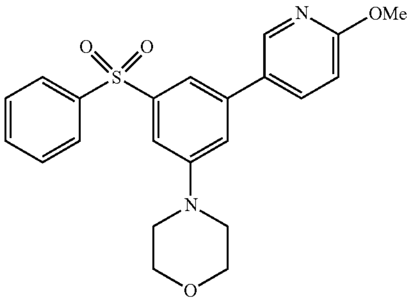 [SMILES: COc1ccc(-c2cc(N3CCOCC3)cc(S(=O)(=O)c3ccccc3)c2)cn1] | 4-(3-(6-methoxypyridin-3-yl)-5-(phenylsulfonyl)phenyl)morpholine |
| 6 | 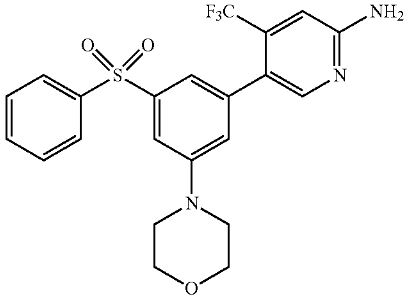 [SMILES: Nc1cc(C(F)(F)F)c(-c2cc(N3CCOCC3)cc(S(=O)(=O)c3ccccc3)c2)cn1] | 5-(3-morpholino-5-(phenylsulfonyl)phenyl)-4-(trifluoromethyl)pyridin-2-amine |
| 7 | 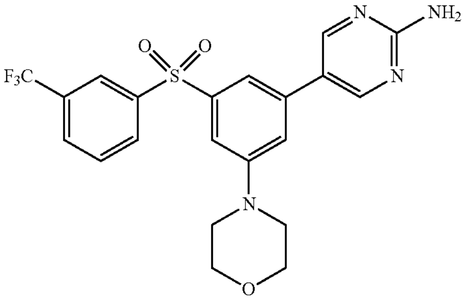 [SMILES: Nc1ncc(-c2cc(N3CCOCC3)cc(S(=O)(=O)c3cccc(C(F)(F)F)c3)c2)cn1] | 5-(3-morpholino-5-((3-(trifluoromethyl)phenyl)sulfonyl)phenyl) pyrimidin-2-amine |
| 8 | 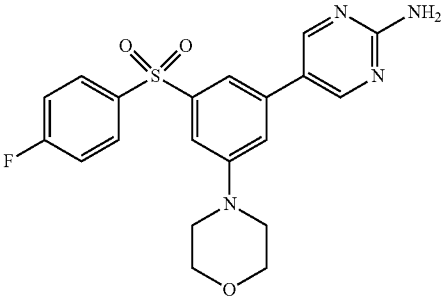 [SMILES: Nc1ncc(-c2cc(N3CCOCC3)cc(S(=O)(=O)c3ccc(F)cc3)c2)cn1] | 5-(3-((4-fluorophenyl)sulfonyl)-5-morpholinophenyl)pyrimidin-2-amine |
| 9 | 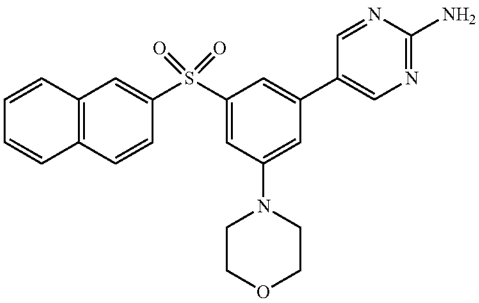 [SMILES: Nc1ncc(-c2cc(N3CCOCC3)cc(S(=O)(=O)c3ccc4ccccc4c3)c2)cn1] | 5-(3-morpholino-5-(naphthalen-2-ylsulfonyl)phenyl)pyrimidin-2-amine |

-continued
| Cmpd # | Structure | Chemical Name |
|---|---|---|
| 10 | 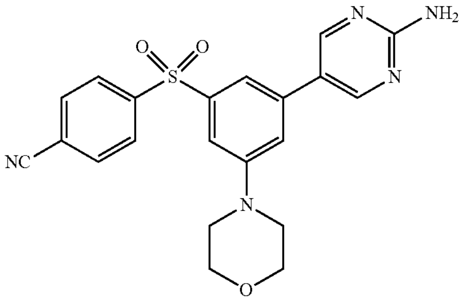 [SMILES: N#Cc1ccc(S(=O)(=O)c2cc(-c3cnc(N)nc3)cc(N3CCOCC3)c2)cc1] | 4-((3-(2-aminopyrimidin-5-yl)-5-morpholinophenyl)sulfonyl)benzonitrile |
| 11 | 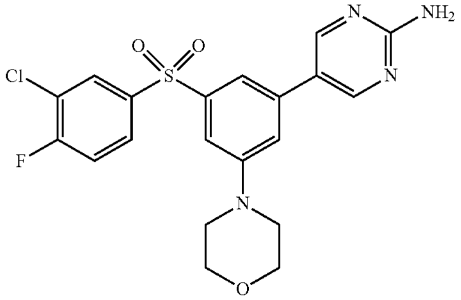 [SMILES: Nc1ncc(-c2cc(N3CCOCC3)cc(S(=O)(=O)c3ccc(F)c(Cl)c3)c2)cn1] | 5-(3-((3-chloro-4-fluorophenyl)sulfonyl)-5-morpholinophenyl)pyrimidin-2-amine |
| 12 | 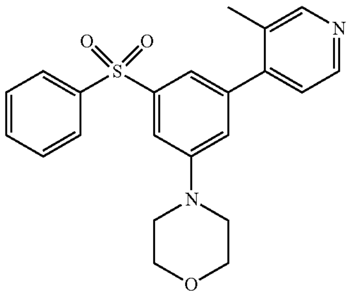 [SMILES: Cc1cnccc1-c1cc(N2CCOCC2)cc(S(=O)(=O)c2ccccc2)c1] | 4-(3-(3-methylpyridin-4-yl)-5-(phenylsulfonyl)phenyl)morpholine |
| 13 | 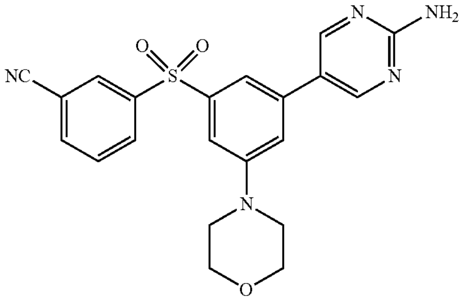 [SMILES: N#Cc1cccc(S(=O)(=O)c2cc(-c3cnc(N)nc3)cc(N3CCOCC3)c2)c1] | 3-((3-(2-aminopyrimidin-5-yl)-5-morpholinophenyl)sulfonyl)benzonitrile |
| 14 | 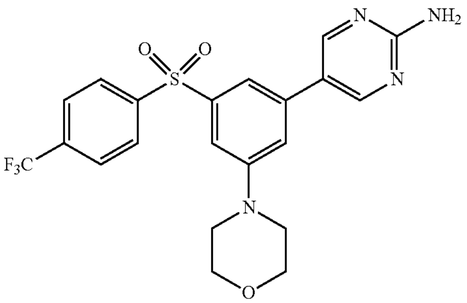 [SMILES: Nc1ncc(-c2cc(N3CCOCC3)cc(S(=O)(=O)c3ccc(C(F)(F)F)cc3)c2)cn1] | 5-(3-morpholino-5-((4-(trifluoromethyl)phenyl)sulfonyl)phenyl)pyrimidin-2-amine |

-continued

| Cmpd # | Structure | Chemical Name |
|---|---|---|
| 15 | 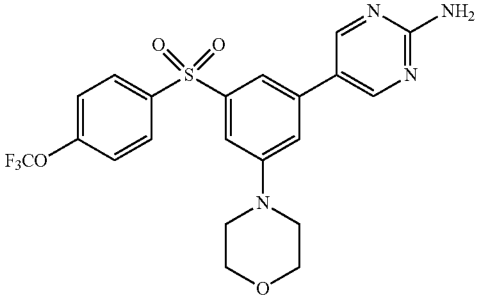 [SMILES: Nc1ncc(-c2cc(N3CCOCC3)cc(S(=O)(=O)c3ccc(OC(F)(F)F)cc3)c2)cn1] | 5-(3-morpholino-5-((4-(trifluoromethoxy)phenyl)sulfonyl)phenyl) pyrimidin-2-amine |
| 16 | 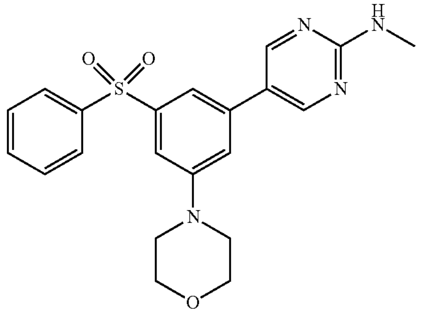 [SMILES: CNc1ncc(-c2cc(N3CCOCC3)cc(S(=O)(=O)c3ccccc3)c2)cn1] | N-methyl-5-(3-morpholino-5-(phenylsulfonyl)phenyl)pyrimidin-2-amine |
| 17 | 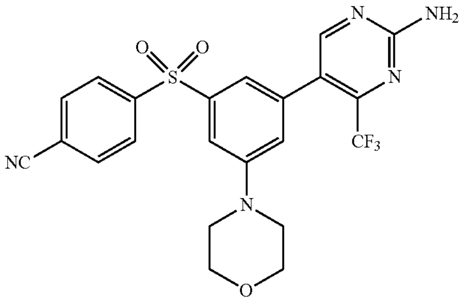 [SMILES: N#Cc1ccc(S(=O)(=O)c2cc(-c3cnc(N)nc3C(F)(F)F)cc(N3CCOCC3)c2)cc1] | 4-((3-(2-amino-4-(trifluoromethyl)pyrimidin-5-yl)-5-morpholinophenyl)sulfonyl)benzonitrile |
| 18 | 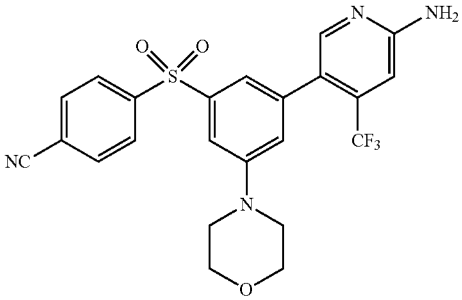 [SMILES: N#Cc1ccc(S(=O)(=O)c2cc(-c3cnc(N)cc3C(F)(F)F)cc(N3CCOCC3)c2)cc1] | 4-((3-(6-amino-4-(trifluoromethyl)pyridin-3-yl)-5-morpholinophenyl)sulfonyl)benzonitrile |
| 19 | 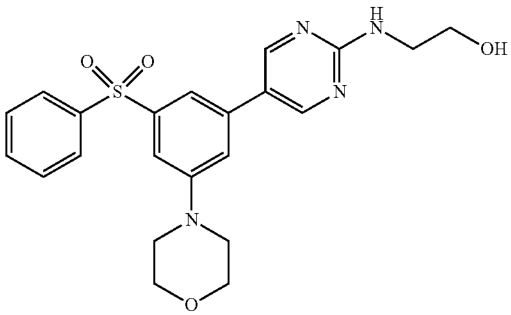 [SMILES: O=S(=O)(c1ccccc1)c1cc(-c2cnc(NCCO)nc2)cc(N2CCOCC2)c1] | 2-((5-(3-morpholino-5-(phenylsulfonyl)phenyl)pyrimidin-2-yl)amino)ethan-1-ol |

-continued
| Cmpd # | Structure | Chemical Name |
|---|---|---|
| 20 | 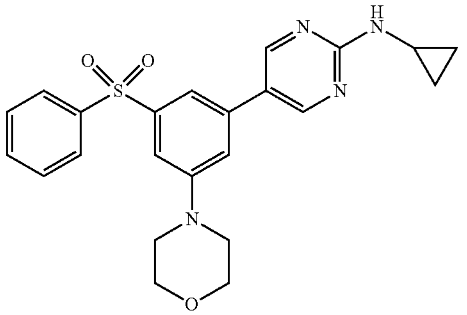 [SMILES: O=S(=O)(c1ccccc1)c1cc(-c2cnc(NC3CC3)nc2)cc(N2CCOCC2)c1] | N-cyclopropyl-5-(3-morpholino-5-(phenylsulfonyl)phenyl)pyrimidin-2-amine |
| 21 | 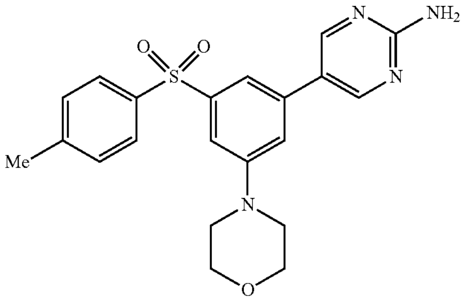 | 5-(3-morpholino-5-tosylphenyl)pyrimidin-2-amine |
| 22 | 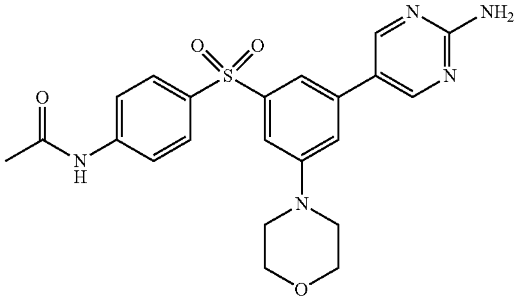 [SMILES: CC(=O)Nc1ccc(S(=O)(=O)c2cc(-c3cnc(N)nc3)cc(N3CCOCC3)c2)cc1] | N-(4-((3-(2-aminopyrimidin-5-yl)-5-morpholinophenyl)sulfonyl)phenyl) acetamide |
| 23 | 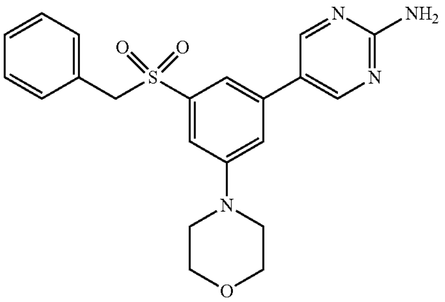 [SMILES: Nc1ncc(-c2cc(N3CCOCC3)cc(S(=O)(=O)Cc3ccccc3)c2)cn1] | 5-(3-(benzylsulfonyl)-5-morpholinophenyl)pyrimidin-2-amine |
| 24 | 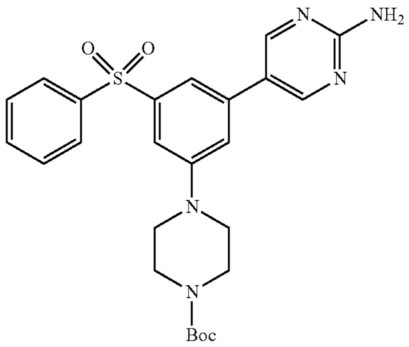 [SMILES: CC(C)(C)OC(=O)N1CCN(c2cc(-c3cnc(N)nc3)cc(S(=O)(=O)c3ccccc3)c2)CC1] | tert-butyl 4-(3-(2-aminopyrimidin-5-yl)-5-(phenylsulfonyl)phenyl)piperazine-1-carboxylate |

-continued
| Cmpd # | Structure | Chemical Name |
|---|---|---|
| 25 | 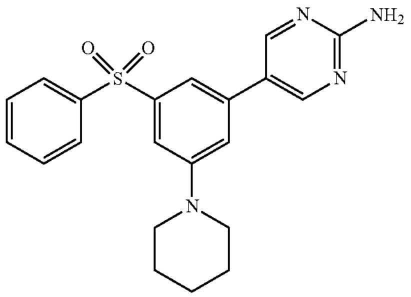 [SMILES: Nc1ncc(-c2cc(N3CCCCC3)cc(S(=O)(=O)c3ccccc3)c2)cn1] | 5-(3-(phenylsulfonyl)-5-(piperidin-1-yl)phenyl)pyrimidin-2-amine |
| 26 | 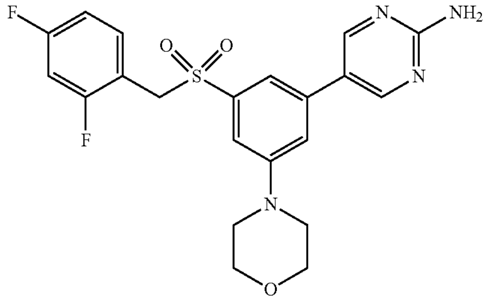 [SMILES: Nc1ncc(-c2cc(N3CCOCC3)cc(S(=O)(=O)Cc3ccc(F)cc3F)c2)cn1] | 5-(3-((2,4-difluorobenzyl)sulfonyl)-5-morpholinophenyl)pyrimidin-2-amine |
| 27 | 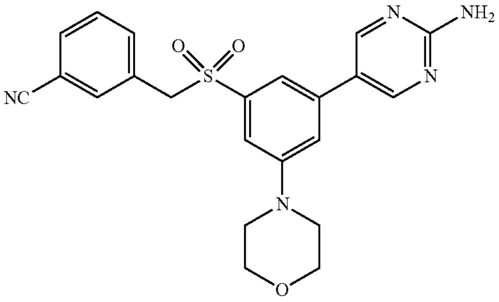 [SMILES: N#Cc1cccc(CS(=O)(=O)c2cc(-c3cnc(N)nc3)cc(N3CCOCC3)c2)c1] | 3-(((3-(2-aminopyrimidin-5-yl)-5-morpholinophenyl)sulfonyl)methyl) benzonitrile |
| 28 | 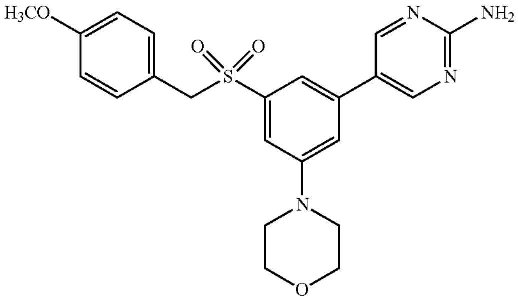 [SMILES: COc1ccc(CS(=O)(=O)c2cc(-c3cnc(N)nc3)cc(N3CCOCC3)c2)cc1] | 5-(3-((4-methoxybenzyl)sulfonyl)-5-morpholinophenyl)pyrimidin-2-amine |
| 29 | 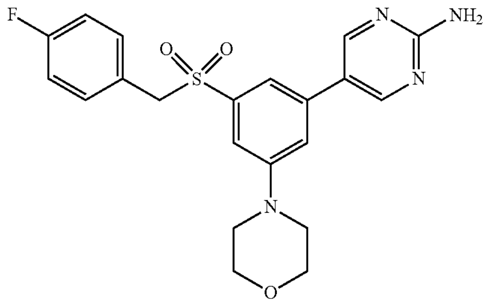 [SMILES: Nc1ncc(-c2cc(N3CCOCC3)cc(S(=O)(=O)Cc3ccc(F)cc3)c2)cn1] | 5-(3-((4-fluorobenzyl)sulfonyl)-5-morpholinophenyl)pyrimidin-2-amine |

-continued

| Cmpd # | Structure | Chemical Name |
| --- | --- | --- |
| 30 | 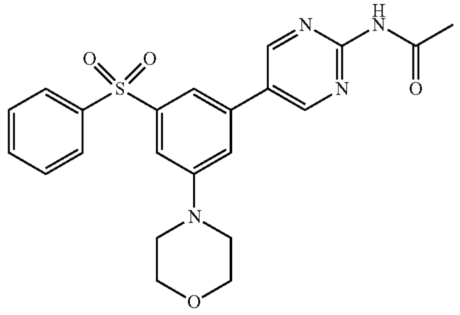 [SMILES: CC(=O)Nc1ncc(-c2cc(N3CCOCC3)cc(S(=O)(=O)c3ccccc3)c2)cn1] | N-(5-(3-morpholino-5-(phenylsulfonyl)phenyl)pyrimidin-2-yl)acetamide |
| 31 | 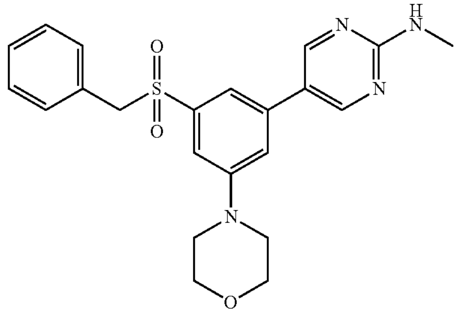 [SMILES: CNc1ncc(-c2cc(N3CCOCC3)cc(S(=O)(=O)Cc3ccccc3)c2)cn1] | 5-(3-(benzylsulfonyl)-5-morpholinophenyl)-N-methylpyrimidin-2-amine |
| 32 | 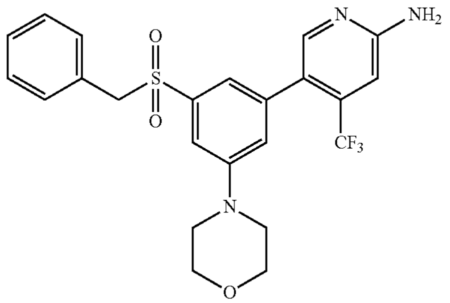 [SMILES: Nc1cc(C(F)(F)F)c(-c2cc(N3CCOCC3)cc(S(=O)(=O)Cc3ccccc3)c2)cn1] | 5-(3-(benzylsulfonyl)-5-morpholinophenyl)-4-(trifluoromethyl)pyridin-2-amine |
| 33 | 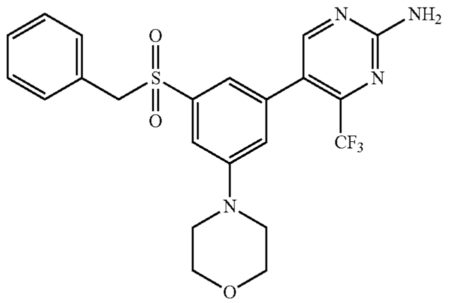 | 5-(3-(benzylsulfonyl)-5-morpholinophenyl)-4-(trifluoromethyl)pyrimidin-2-amine |
| 34 | 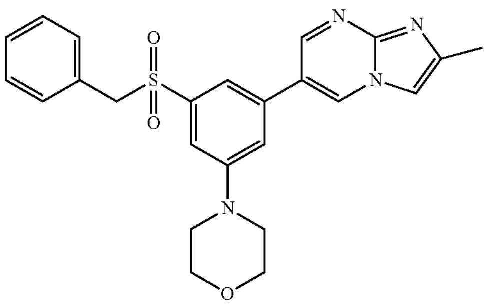 [SMILES: Cc1cn2cc(-c3cc(N4CCOCC4)cc(S(=O)(=O)Cc4ccccc4)c3)cnc2n1] | 4-(3-(benzylsulfonyl)-5-(2-methylimidazo[1,2-a]pyrimidin-6-yl)phenyl)morpholine |

-continued

| Cmpd # | Structure | Chemical Name |
|---|---|---|
| 35 | 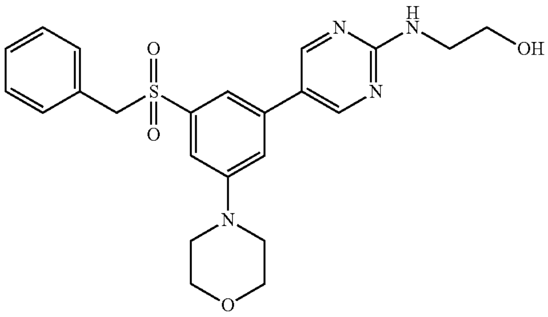 [SMILES: O=S(=O)(Cc1ccccc1)c1cc(-c2cnc(NCCO)nc2)cc(N2CCOCC2)c1] | 2-((5-(3-(benzylsulfonyl)-5-morpholinophenyl)pyrimidin-2-yl)amino)ethan-1-ol |
| 36 | 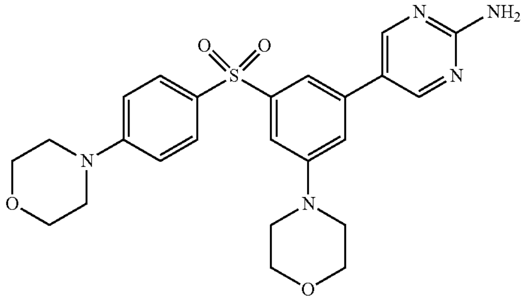 [SMILES: Nc1ncc(-c2cc(N3CCOCC3)cc(S(=O)(=O)c3ccc(N4CCOCC4)cc3)c2)cn1] | 5-(3-morpholino-5-((4-morpholinophenyl)sulfonyl)phenyl) pyrimidin-2-amine |
| 37 | 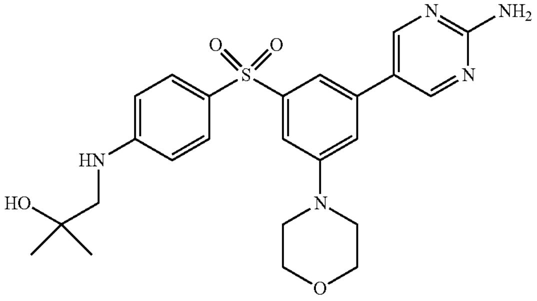 [SMILES: CC(C)(O)CNc1ccc(S(=O)(=O)c2cc(-c3cnc(N)nc3)cc(N3CCOCC3)c2)cc1] | 1-((4-((3-(2-aminopyrimidin-5-yl)-5-morpholinophenyl)sulfonyl)phenyl)amino)-2-methylpropan-2-ol |
| 38 | 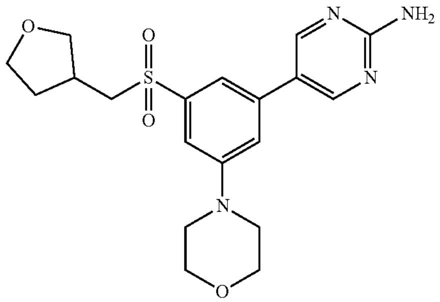 [SMILES: Nc1ncc(-c2cc(N3CCOCC3)cc(S(=O)(=O)CC3CCOC3)c2)cn1] | 5-(3-morpholino-5-(((tetrahydrofuran-3-yl)methyl)sulfonyl)phenyl)pyrimidin-2-amine |
| 39 | 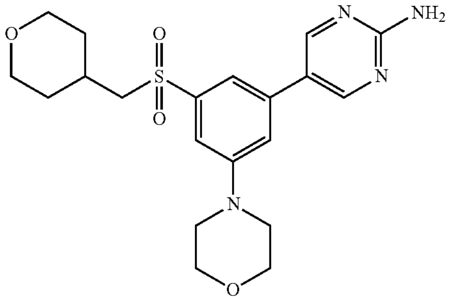 [SMILES: Nc1ncc(-c2cc(N3CCOCC3)cc(S(=O)(=O)CC3CCOCC3)c2)cn1] | 5-(3-morpholino-5-(((tetrahydro-2H-pyran-4-yl)methyl)sulfonyl)phenyl)pyrimidin-2-amine |

-continued
| Cmpd # | Structure | Chemical Name |
| --- | --- | --- |
| 40 | 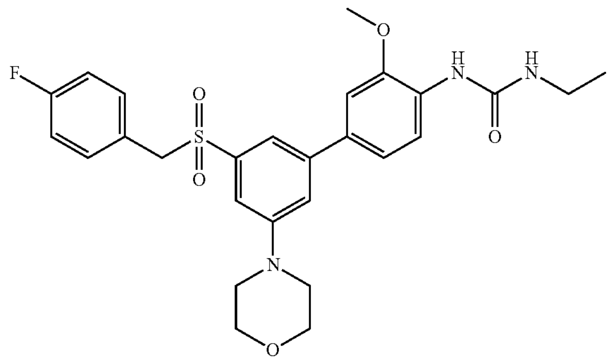 [SMILES: CCNC(=O)Nc1ccc(-c2cc(N3CCOCC3)cc(S(=O)(=O)Cc3ccc(F)cc3)c2)cc1OC] | 1-ethyl-3-(3'-((4-fluorobenzyl)sulfonyl)-3-methoxy-5'-morpholino-[1,1'-biphenyl]-4-yl)urea |
| 41 | 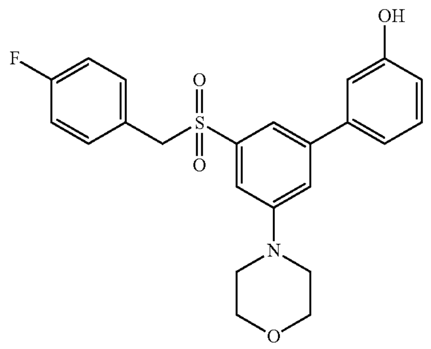 [SMILES: O=S(=O)(Cc1ccc(F)cc1)c1cc(-c2cccc(O)c2)cc(N2CCOCC2)c1] | 3'-((4-fluorobenzyl)sulfonyl)-5'-morpholino-[1,1'-biphenyl]-3-ol |
| 42 | 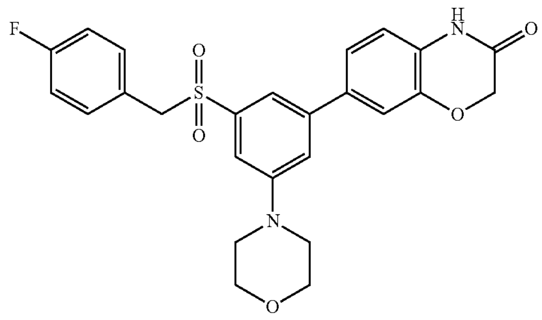 [SMILES: O=C1COc2cc(-c3cc(N4CCOCC4)cc(S(=O)(=O)Cc4ccc(F)cc4)c3)ccc2N1] | 7-(3-((4-fluorobenzyl)sulfonyl)-5-morpholinophenyl)-2H-benzo[b][1,4]oxazin-3(4H)-one |
| 43 | 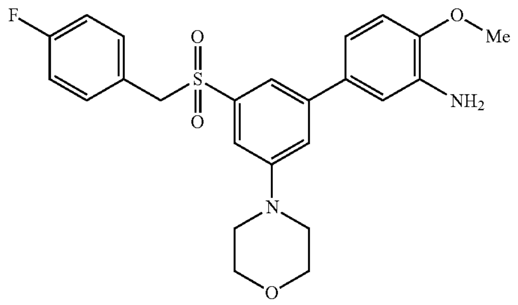 [SMILES: COc1ccc(-c2cc(N3CCOCC3)cc(S(=O)(=O)Cc3ccc(F)cc3)c2)cc1N] | 3'-((4-fluorobenzyl)sulfonyl)-4-methoxy-5'-morpholino-[1,1'-biphenyl]-3-amine |

-continued
| Cmpd # | Structure | Chemical Name |
| --- | --- | --- |
| 44 | 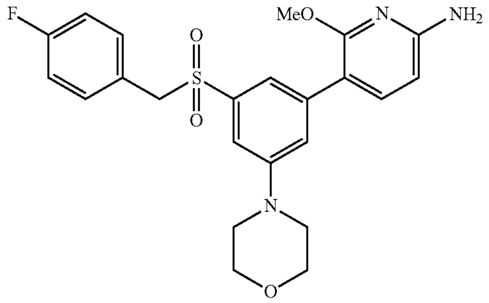 [SMILES: COc1nc(N)ccc1-c1cc(N2CCOCC2)cc(S(=O)(=O)Cc2ccc(F)cc2)c1] | 5-(3-((4-fluorobenzyl)sulfonyl)-5-morpholinophenyl)-6-methoxypyridin-2-amine |
| 45 | 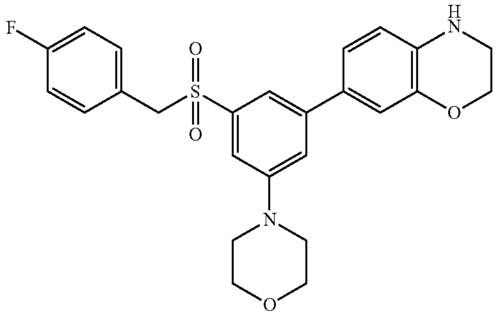 [SMILES: O=S(=O)(Cc1ccc(F)cc1)c1cc(-c2ccc3c(c2)OCCN3)cc(N2CCOCC2)c1] | 7-(3-((4-fluorobenzyl)sulfonyl)-5-morpholinophenyl)-3,4-dihydro-2H-benzo[b][1,4]oxazine |
| 46 | 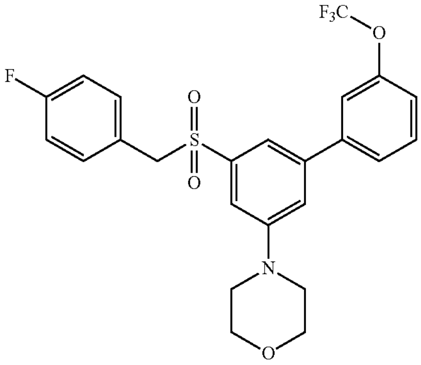 [SMILES: O=S(=O)(Cc1ccc(F)cc1)c1cc(-c2cccc(OC(F)(F)F)c2)cc(N2CCOCC2)c1] | 4-(5-((4-fluorobenzyl)sulfonyl)-3'-(trifluoromethoxy)-[1,1'-biphenyl]-3-yl)morpholine |
| 47 | 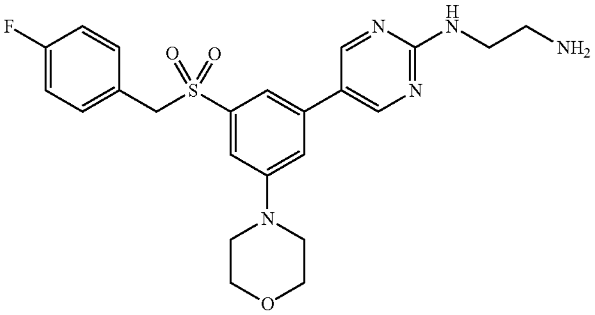 [SMILES: NCCNc1ncc(-c2cc(N3CCOCC3)cc(S(=O)(=O)Cc3ccc(F)cc3)c2)cn1] | N1-(5-(3-((4-fluorobenzyl)sulfonyl)-5-morpholinophenyl)pyrimidin-2-yl)ethane-1,2-diamine |

-continued
| Cmpd # | Structure | Chemical Name |
| --- | --- | --- |
| 48 | 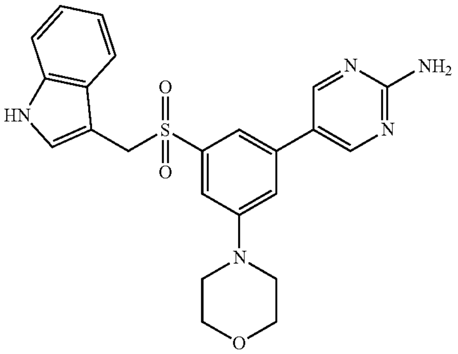 [SMILES: Nc1ncc(-c2cc(N3CCOCC3)cc(S(=O)(=O)Cc3c[nH]c4ccccc34)c2)cn1] | 5-(3-(((1H-indol-3-yl)methyl)sulfonyl)-5-morpholinophenyl)pyrimidin-2-amine |
| 49 | 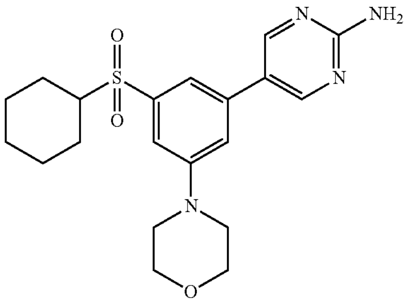 [SMILES: Nc1ncc(-c2cc(N3CCOCC3)cc(S(=O)(=O)C3CCCCC3)c2)cn1] | 5-(3-(cyclohexylsulfonyl)-5-morpholinophenyl)pyrimidin-2-amine |
| 50 | 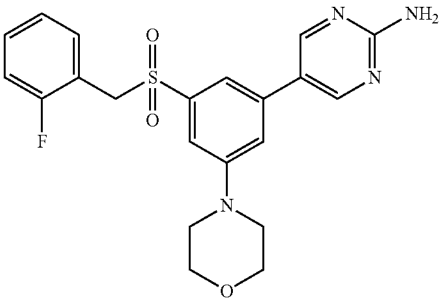 [SMILES: Nc1ncc(-c2cc(N3CCOCC3)cc(S(=O)(=O)Cc3ccccc3F)c2)cn1] | 5-(3-((2-fluorobenzyl)sulfonyl)-5-morpholinophenyl)pyrimidin-2-amine |
| 51 | 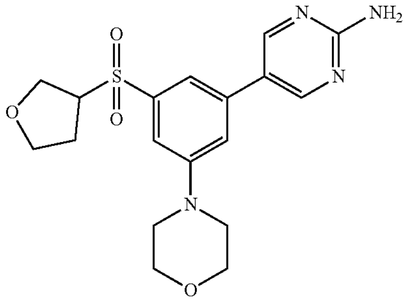 [SMILES: Nc1ncc(-c2cc(N3CCOCC3)cc(S(=O)(=O)C3CCOC3)c2)cn1] | 5-(3-morpholino-5-((tetrahydrofuran-3-yl)sulfonyl)phenyl)pyrimidin-2-amine |
| 52 | 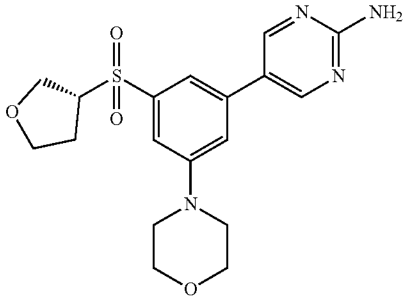 [SMILES: Nc1ncc(-c2cc(N3CCOCC3)cc(S(=O)(=O)[C@@H]3CCOC3)c2)cn1] | (R)-5-(3-morpholino-5-((tetrahydrofuran-3-yl)sulfonyl)phenyl)pyrimidin-2-amine |

-continued

| Cmpd # | Structure | Chemical Name |
|---|---|---|
| 53 | 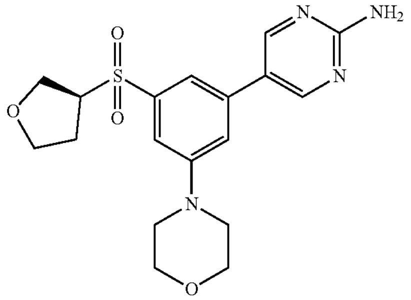 [SMILES: Nc1ncc(-c2cc(N3CCOCC3)cc(S(=O)(=O)[C@H]3CCOC3)c2)cn1] | (S)-5-(3-morpholino-5-((tetrahydrofuran-3-yl)sulfonyl)phenyl)pyrimidin-2-amine |
| 54 | 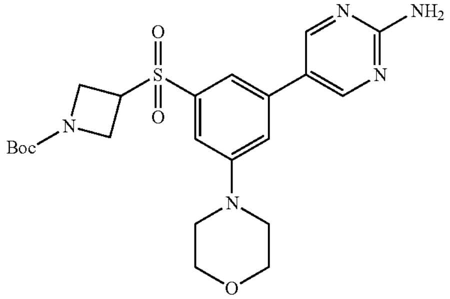 [SMILES: CC(C)(C)OC(=O)N1CC(S(=O)(=O)c2cc(-c3cnc(N)nc3)cc(N3CCOCC3)c2)C1] | tert-butyl 3-((3-(2-aminopyrimidin-5-yl)-5-morpholinophenyl)sulfonyl)azetidine-1-carboxylate |
| 55 | 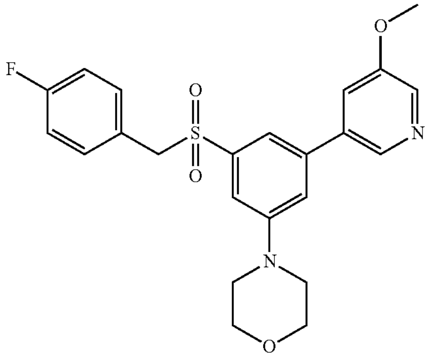 [SMILES: COc1cncc(-c2cc(N3CCOCC3)cc(S(=O)(=O)Cc3ccc(F)cc3)c2)c1] | 4-(3-((4-fluorobenzyl)sulfonyl)-5-(5-methoxypyridin-3-yl)phenyl)morpholine |
| 56 | 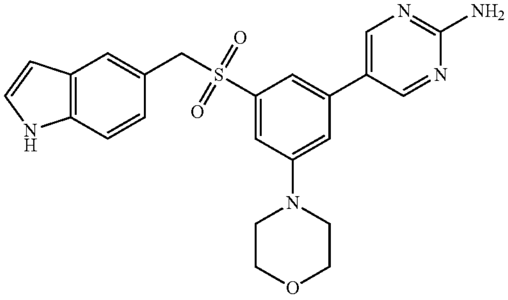 [SMILES: Nc1ncc(-c2cc(N3CCOCC3)cc(S(=O)(=O)Cc3ccc4[nH]ccc4c3)c2)cn1] | 5-(3-(((1H-indol-5-yl)methyl)sulfonyl)-5-morpholinophenyl)pyrimidin-2-amine |
| 57 | 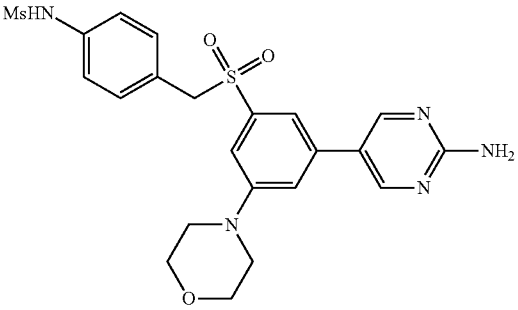 | N-(4-(((3-(2-aminopyrimidin-5-yl)-5-morpholinophenyl)sulfonyl)methyl)phenyl) methanesulfonamide |

-continued

| Cmpd # | Structure | Chemical Name |
| --- | --- | --- |
| 58 | 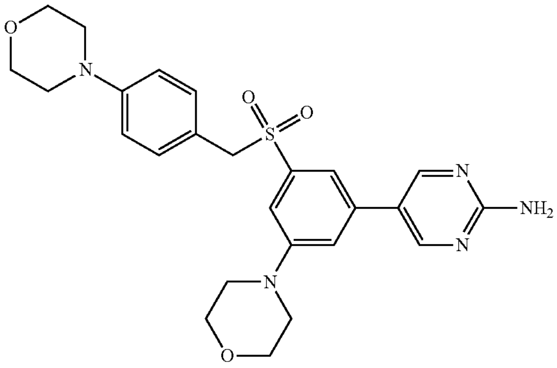 [SMILES: Nc1ncc(-c2cc(N3CCOCC3)cc(S(=O)(=O)Cc3ccc(N4CCOCC4)cc3)c2)cn1] | 5-(3-morpholino-5-((4-morpholinobenzyl)sulfonyl)phenyl) pyrimidin-2-amine |
| 59 | 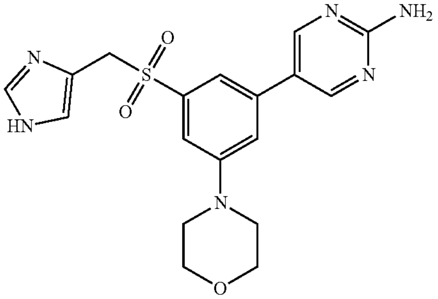 [SMILES: Nc1ncc(-c2cc(N3CCOCC3)cc(S(=O)(=O)Cc3c[nH]cn3)c2)cn1] | 5-(3-(((1H-imidazol-4-yl)methyl)sulfonyl)-5-morpholinophenyl)pyrimidin-2-amine |
| 60 | 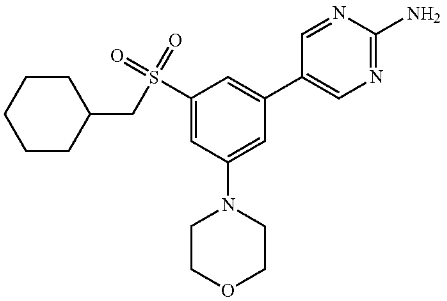 [SMILES: Nc1ncc(-c2cc(N3CCOCC3)cc(S(=O)(=O)CC3CCCCC3)c2)cn1] | 5-(3-((cyclohexylmethyl)sulfonyl)-5-morpholinophenyl)pyrimidin-2-amine |
| 61 | 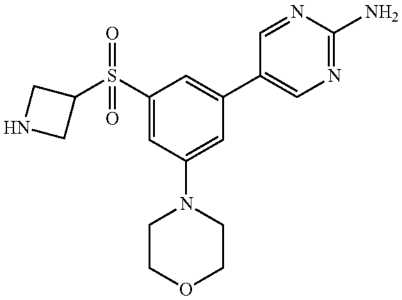 [SMILES: Nc1ncc(-c2cc(N3CCOCC3)cc(S(=O)(=O)C3CNC3)c2)cn1] | 5-(3-(azetidin-3-ylsulfonyl)-5-morpholinophenyl)pyrimidin-2-amine |
| 62 | 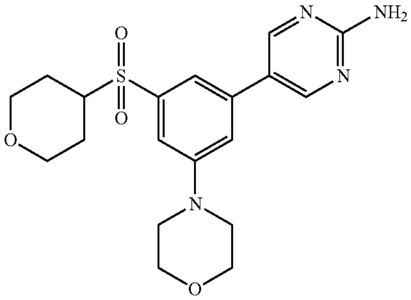 [SMILES: Nc1ncc(-c2cc(N3CCOCC3)cc(S(=O)(=O)C3CCOCC3)c2)cn1] | 5-(3-morpholino-5-((tetrahydro-2H-pyran-4-yl)sulfonyl)phenyl)pyrimidin-2-amine |

-continued

| Cmpd # | Structure | Chemical Name |
|---|---|---|
| 63 | 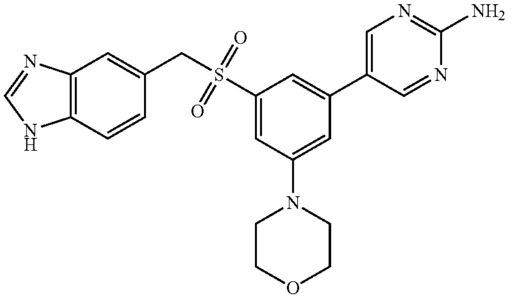 [SMILES: Nc1ncc(-c2cc(N3CCOCC3)cc(S(=O)(=O)Cc3ccc4[nH]cnc4c3)c2)cn1] | 5-(3-(((1H-benzo[d]imidazol-5-yl)methyl)sulfonyl)-5-morpholinophenyl)pyrimidin-2-amine |
| 64 | 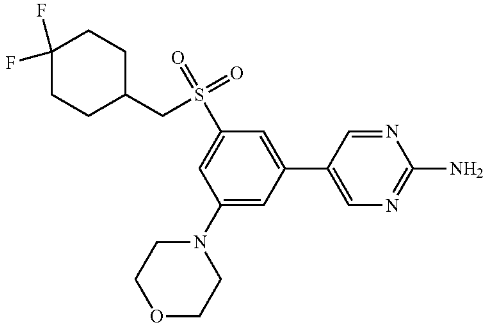 [SMILES: Nc1ncc(-c2cc(N3CCOCC3)cc(S(=O)(=O)CC3CCC(F)(F)CC3)c2)cn1] | 5-(3-(((4,4-difluorocyclohexyl)methyl)sulfonyl)-5-C21H26F2N4O3Smorpholinophenyl) pyrimidin-2-amine |
| 65 | 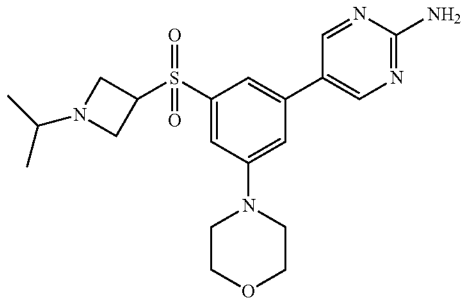 [SMILES: CC(C)N1CC(S(=O)(=O)c2cc(-c3cnc(N)nc3)cc(N3CCOCC3)c2)C1] | 5-(3-((1-isopropylazetidin-3-yl)sulfonyl)-5-morpholinophenyl)pyrimidin-2-amine |
| 66 | 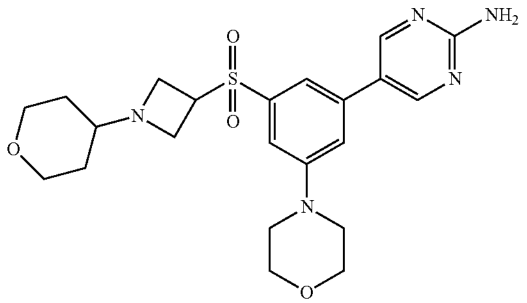 [SMILES: Nc1ncc(-c2cc(N3CCOCC3)cc(S(=O)(=O)C3CN(C4CCOCC4)C3)c2)cn1] | 5-(3-morpholino-5-((1-(tetrahydro-2H-pyran-4-yl)azetidin-3-yl)sulfonyl)phenyl)pyrimidin-2-amine |
| 67 | 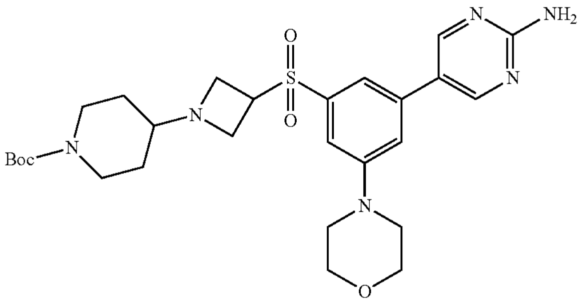 [SMILES: CC(C)(C)OC(=O)N1CCC(N2CC(S(=O)(=O)c3cc(-c4cnc(N)nc4)cc(N4CCOCC4)c3)C2)CC1] | tert-butyl 4-(3-((3-(2-aminopyrimidin-5-yl)-5-morpholinophenyl)sulfonyl)azetidin-1-yl)piperidine-1-carboxylate |

-continued

| Cmpd # | Structure | Chemical Name |
| --- | --- | --- |
| 68 | 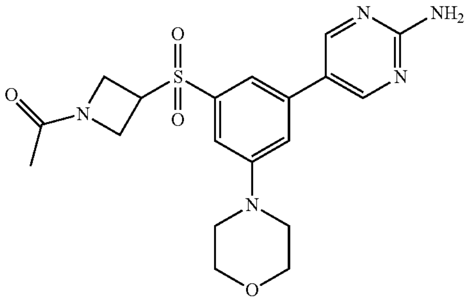 [SMILES: CC(=O)N1CC(S(=O)(=O)c2cc(-c3cnc(N)nc3)cc(N3CCOCC3)c2)C1] | 1-(3-((3-(2-aminopyrimidin-5-yl)-5-morpholinophenyl)sulfonyl)azetidin-1-yl)ethan-1-one |
| 69 | 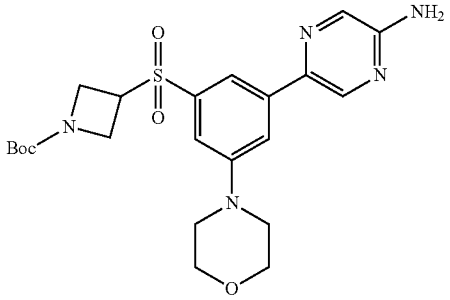 [SMILES: CC(C)(C)OC(=O)N1CC(S(=O)(=O)c2cc(-c3cnc(N)cn3)cc(N3CCOCC3)c2)C1] | tert-butyl 3-((3-(5-aminopyrazin-2-yl)-5-morpholinophenyl)sulfonyl)azetidine-1-carboxylate |
| 70 | 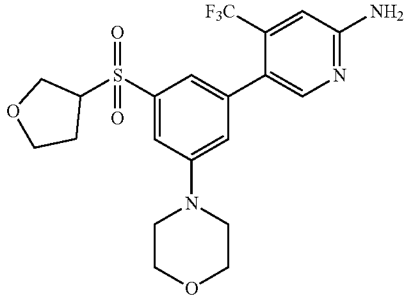 [SMILES: Nc1cc(C(F)(F)F)c(-c2cc(N3CCOCC3)cc(S(=O)(=O)[C@@H]3CCOC3)c2)cn1] | 5-(3-morpholino-5-((tetrahydrofuran-3-yl)sulfonyl)phenyl)-4-(trifluoromethyl)pyridin-2-amine |
| 71 | 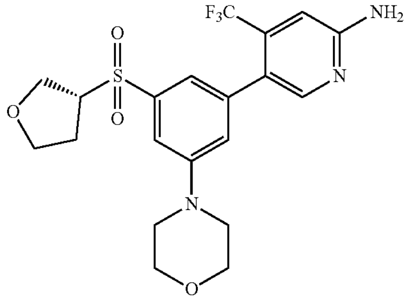 | (R)-5-(3-morpholino-5-((tetrahydrofuran-3-yl)sulfonyl)phenyl)-4-(trifluoromethyl)pyridin-2-amine |
| 72 | 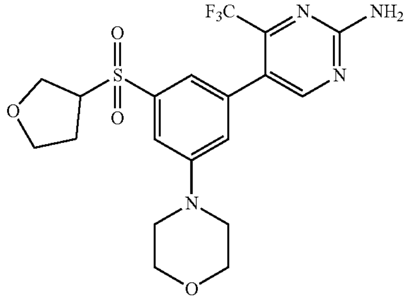 [SMILES: Nc1ncc(-c2cc(N3CCOCC3)cc(S(=O)(=O)C3CCOC3)c2)c(C(F)(F)F)n1] | 5-(3-morpholino-5-((tetrahydrofuran-3-yl)sulfonyl)phenyl)-4-(trifluoromethyl)pyrimidin-2-amine |

-continued

| Cmpd # | Structure | Chemical Name |
| --- | --- | --- |
| 73 | 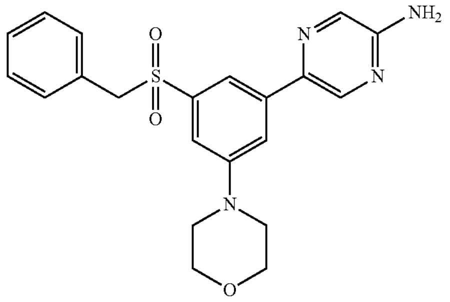 [SMILES: Nc1cnc(-c2cc(N3CCOCC3)cc(S(=O)(=O)Cc3ccccc3)c2)cn1] | 5-(3-(benzylsulfonyl)-5-morpholinophenyl)pyrazin-2-amine |
| 74 | 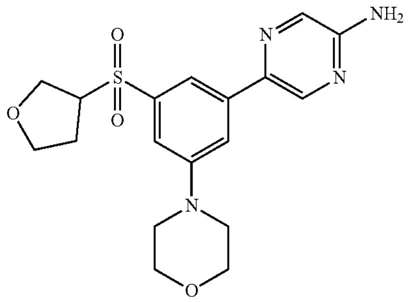 [SMILES: Nc1cnc(-c2cc(N3CCOCC3)cc(S(=O)(=O)C3CCOC3)c2)cn1] | 5-(3-morpholino-5-((tetrahydrofuran-3-yl)sulfonyl)phenyl)pyrazin-2-amine |
| 75 | 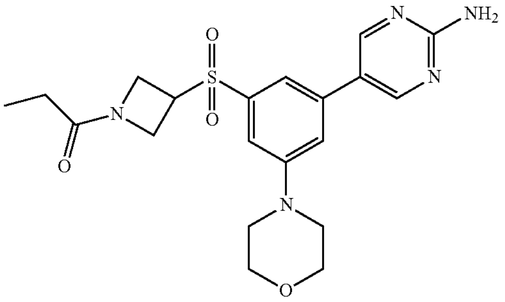 [SMILES: CCC(=O)N1CC(S(=O)(=O)c2cc(-c3cnc(N)nc3)cc(N3CCOCC3)c2)C1] | 1-(3-((3-(2-aminopyrimidin-5-yl)-5-morpholinophenyl)sulfonyl)azetidin-1-yl)propan-1-one |
| 76 | 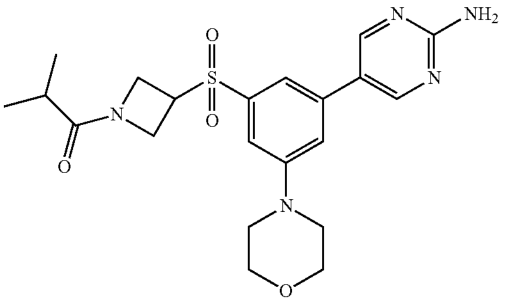 [SMILES: CC(C)C(=O)N1CC(S(=O)(=O)c2cc(-c3cnc(N)nc3)cc(N3CCOCC3)c2)C1] | 1-(3-((3-(2-aminopyrimidin-5-yl)-5-morpholinophenyl)sulfonyl)azetidin-1-yl)-2-methylpropan-1-one |
| 77 | 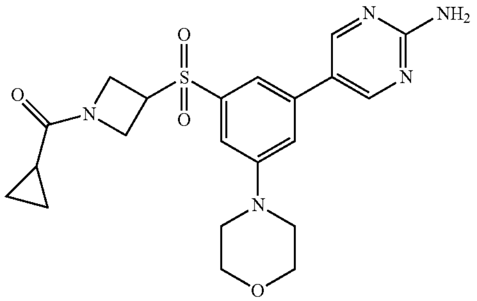 [SMILES: Nc1ncc(-c2cc(N3CCOCC3)cc(S(=O)(=O)C3CN(C(=O)C4CC4)C3)c2)cn1] | (3-((3-(2-aminopyrimidin-5-yl)-5-morpholinophenyl)sulfonyl)azetidin-1-yl)(cyclopropyl)methanone |

-continued

| Cmpd # | Structure | Chemical Name |
|---|---|---|
| 78 | 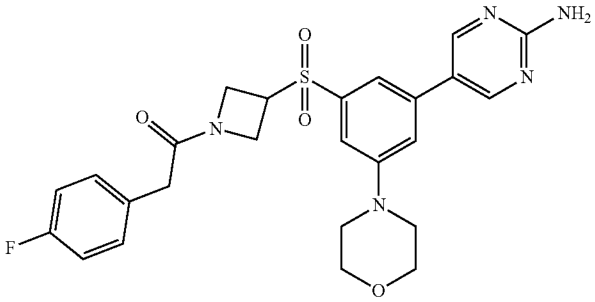 [SMILES: Nc1ncc(-c2cc(N3CCOCC3)cc(S(=O)(=O)C3CN(C(=O)Cc4ccc(F)cc4)C3)c2)cn1] | 1-(3-((3-(2-aminopyrimidin-5-yl)-5-morpholinophenyl)sulfonyl)azetidin-1-yl)-2-(4-fluorophenyl)ethan-1-one |
| 79 | 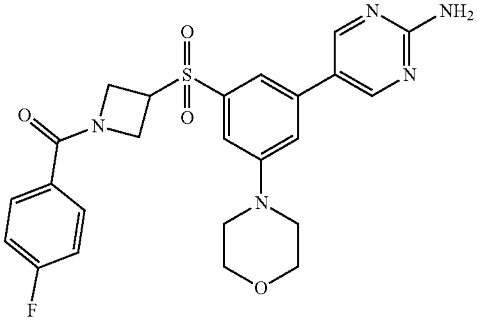 [SMILES: Nc1ncc(-c2cc(N3CCOCC3)cc(S(=O)(=O)C3CN(C(=O)c4ccc(F)cc4)C3)c2)cn1] | (3-((3-(2-aminopyrimidin-5-yl)-5-morpholinophenyl)sulfonyl)azetidin-1-yl)(4-fluorophenyl)methanone |
| 80 | 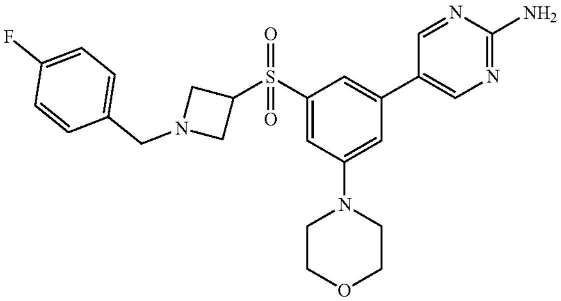 [SMILES: Nc1ncc(-c2cc(N3CCOCC3)cc(S(=O)(=O)C3CN(Cc4ccc(F)cc4)C3)c2)cn1] | 5-(3-((1-(4-fluorobenzyl)azetidin-3-yl)sulfonyl)-5-morpholinophenyl)pyrimidin-2-amine |
| 81 | 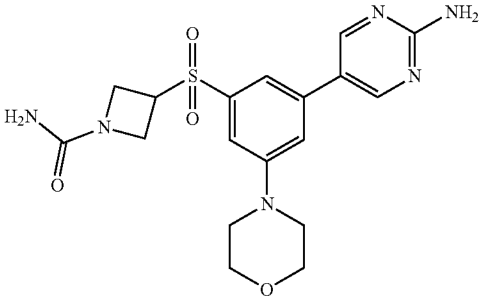 [SMILES: NC(=O)N1CC(S(=O)(=O)c2cc(-c3cnc(N)nc3)cc(N3CCOCC3)c2)C1] | 3-((3-(2-aminopyrimidin-5-yl)-5-morpholinophenyl)sulfonyl)azetidine-1-carboxamide |
| 82 | 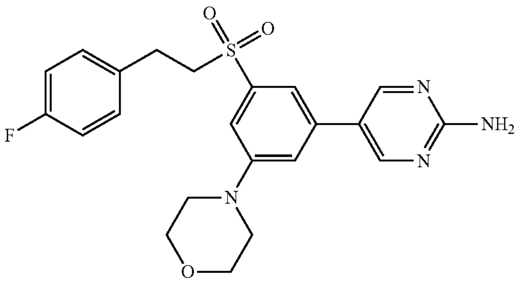 [SMILES: Nc1ncc(-c2cc(N3CCOCC3)cc(S(=O)(=O)CCc3ccc(F)cc3)c2)cn1] | 5-(3-((4-fluorophenethyl)sulfonyl)-5-morpholinophenyl)pyrimidin-2-amine |

-continued

| Cmpd # | Structure | Chemical Name |
| --- | --- | --- |
| 83 | 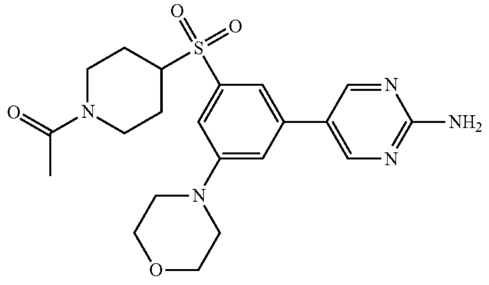 [SMILES: CC(=O)N1CCC(S(=O)(=O)c2cc(-c3cnc(N)nc3)cc(N3CCOCC3)c2)CC1] | 1-(4-((3-(2-aminopyrimidin-5-yl)-5-morpholinophenyl)sulfonyl)piperidin-1-yl)ethan-1-one |
| 84 | 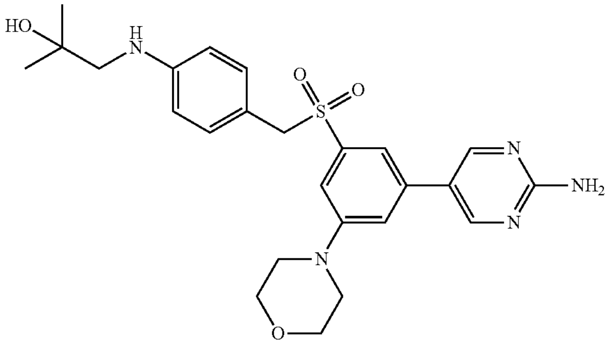 [SMILES: CC(C)(O)CNc1ccc(CS(=O)(=O)c2cc(-c3cnc(N)nc3)cc(N3CCOCC3)c2)cc1] | 1-((4-(((3-(2-aminopyrimidin-5-yl)-5-morpholinophenyl)sulfonyl)methyl)phenyl)amino)-2-methylpropan-2-ol |
| 85 | 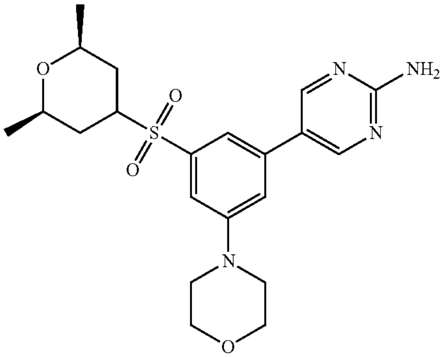 [SMILES: C[C@@H]1CC(S(=O)(=O)c2cc(-c3cnc(N)nc3)cc(N3CCOCC3)c2)C[C@H](C)O1] | 5-(3-(((2R,6S)-2,6-dimethyltetrahydro-2H-pyran-4-yl)sulfonyl)-5-morpholinophenyl)pyrimidin-2-amine |
| 86 | 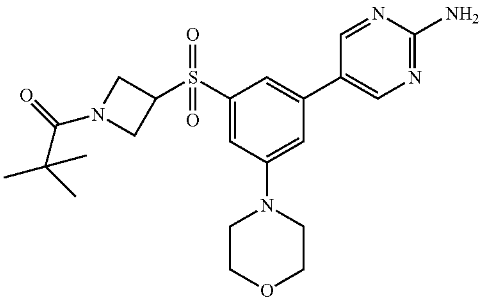 [SMILES: CC(C)(C)C(=O)N1CC(S(=O)(=O)c2cc(-c3cnc(N)nc3)cc(N3CCOCC3)c2)C1] | 1-(3-((3-(2-aminopyrimidin-5-yl)-5-morpholinophenyl)sulfonyl)azetidin-1-yl)-2,2-dimethylpropan-1-one |
| 87 | 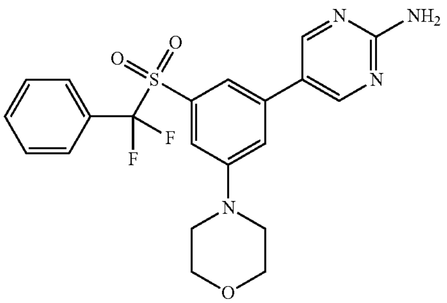 [SMILES: Nc1ncc(-c2cc(N3CCOCC3)cc(S(=O)(=O)C(F)(F)c3ccccc3)c2)cn1] | 5-(3-((difluoro(phenyl)methyl)sulfonyl)-5-morpholinophenyl)pyrimidin-2-amine |

-continued
| Cmpd # | Structure | Chemical Name |
| --- | --- | --- |
| 88 | 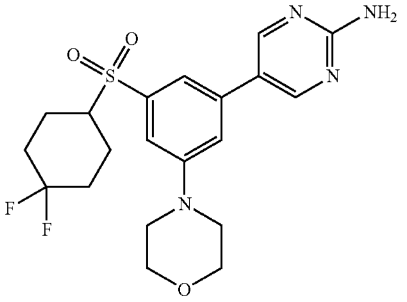 [SMILES: Nc1ncc(-c2cc(N3CCOCC3)cc(S(=O)(=O)C3CCC(F)(F)CC3)c2)cn1] | 5-(3-((4,4-difluorocyclohexyl)sulfonyl)-5-morpholinophenyl)pyrimidin-2-amine |
| 89 | 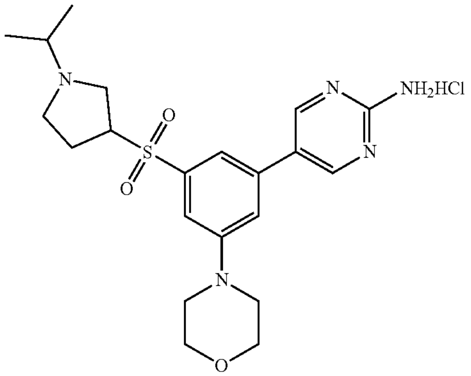 | 5-(3-((1-isopropylpyrrolidin-3-yl)sulfonyl)-5-morpholinophenyl)pyrimidin-2-amine hydrochloride |
| 90 | 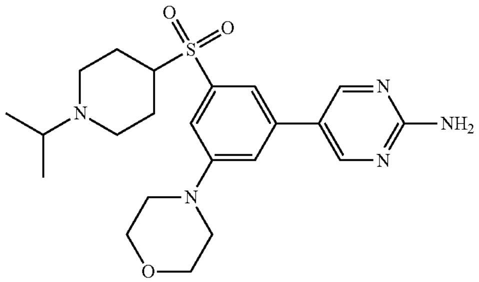 [SMILES: CC(C)N1CCC(S(=O)(=O)c2cc(-c3cnc(N)nc3)cc(N3CCOCC3)c2)CC1] | 5-(3-((1-isopropylpiperidin-4-yl)sulfonyl)-5-morpholinophenyl)pyrimidin-2-amine |
| 91 | 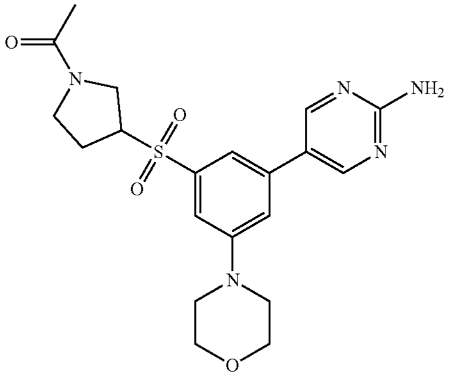 [SMILES: CC(=O)N1CCC(S(=O)(=O)c2cc(-c3cnc(N)nc3)cc(N3CCOCC3)c2)C1] | 1-(3-((3-(2-aminopyrimidin-5-yl)-5-morpholinophenyl)sulfonyl)pyrrolidin-1-yl)ethan-1-one |

-continued

| Cmpd # | Structure | Chemical Name |
|---|---|---|
| 92 | 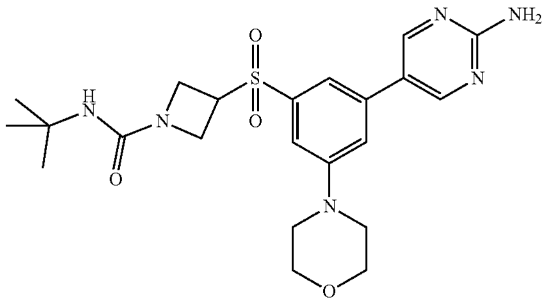 [SMILES: CC(C)(C)NC(=O)N1CC(S(=O)(=O)c2cc(-c3cnc(N)nc3)cc(N3CCOCC3)c2)C1] | 3-((3-(2-aminopyrimidin-5-yl)-5-morpholinophenyl)sulfonyl)-N-(tert-butyl)azetidine-1-carboxamide |
| 93 | 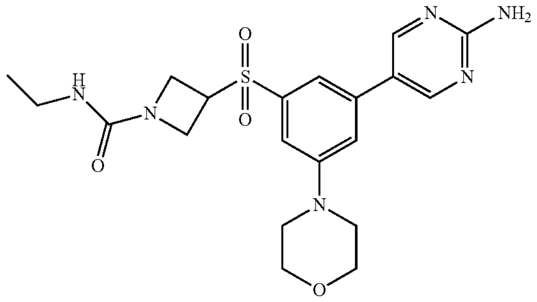 [SMILES: CCNC(=O)N1CC(S(=O)(=O)c2cc(-c3cnc(N)nc3)cc(N3CCOCC3)c2)C1] | 3-((3-(2-aminopyrimidin-5-yl)-5-morpholinophenyl)sulfonyl)-N-ethylazetidine-1-carboxamide |
| 94 | 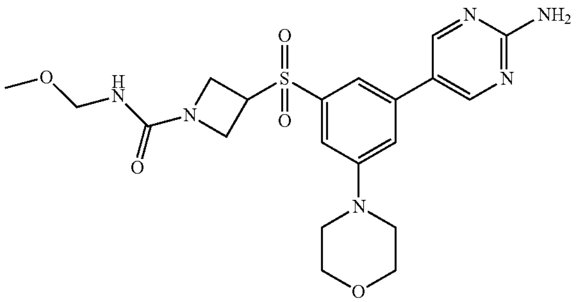 [SMILES: COCNC(=O)N1CC(S(=O)(=O)c2cc(-c3cnc(N)nc3)cc(N3CCOCC3)c2)C1] | 3-((3-(2-aminopyrimidin-5-yl)-5-morpholinophenyl)sulfonyl)-N-(methoxymethyl)azetidine-1-carboxamide |
| 95 | 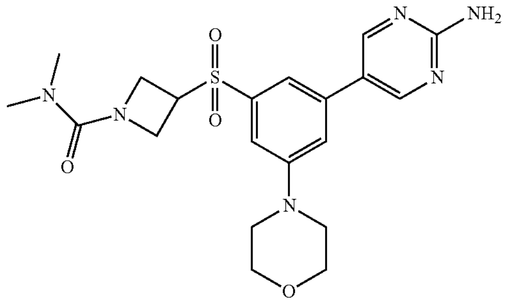 | 3-((3-(2-aminopyrimidin-5-yl)-5-morpholinophenyl)sulfonyl)-N,N-dimethylazetidine-1-carboxamide |
| 96 | 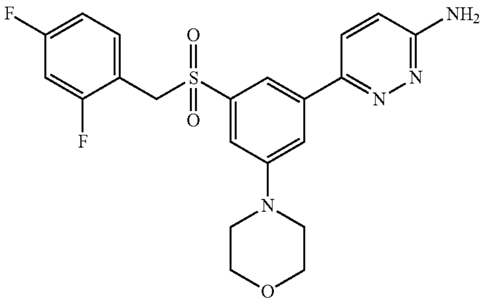 [SMILES: Nc1ccc(-c2cc(N3CCOCC3)cc(S(=O)(=O)Cc3ccc(F)cc3F)c2)nn1] | 6-(3-((2,4-difluorobenzyl)sulfonyl)-5-morpholinophenyl)pyridazin-3-amine |

-continued

| Cmpd # | Structure | Chemical Name |
|---|---|---|
| 97 | 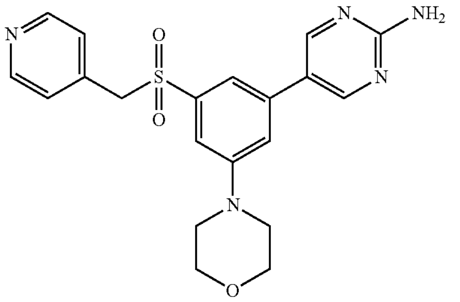 [SMILES: Nc1ncc(-c2cc(N3CCOCC3)cc(S(=O)(=O)Cc3ccncc3)c2)cn1] | 5-(3-morpholino-5-((pyridin-4-ylmethyl)sulfonyl)phenyl)pyrimidin-2-amine |
| 98 | 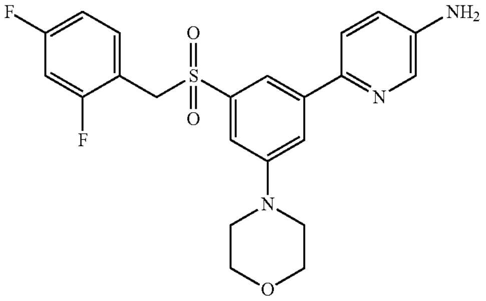 [SMILES: Nc1ccc(-c2cc(N3CCOCC3)cc(S(=O)(=O)Cc3ccc(F)cc3F)c2)nc1] | -(3-((2,4-difluorobenzyl)sulfonyl)-5-morpholinophenyl)pyridin-3-amine |
| 99 | 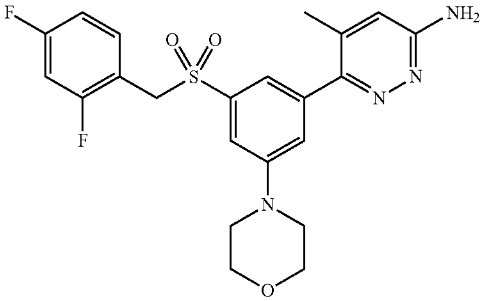 [SMILES: Cc1cc(N)nnc1-c1cc(N2CCOCC2)cc(S(=O)(=O)Cc2ccc(F)cc2F)c1] | 6-(3-((2,4-difluorobenzyl)sulfonyl)-5-morpholinophenyl)-5-methylpyridazin-3-amine |
| 100 | 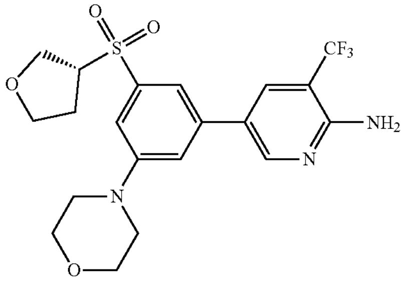 [SMILES: Nc1ncc(-c2cc(N3CCOCC3)cc(S(=O)(=O)[C@@H]3CCOC3)c2)cc1C(F)(F)F] | (R)-5-(3-morpholino-5-((tetrahydrofuran-3-yl)sulfonyl)phenyl)-3-(trifluoromethyl)pyridin-2-amine |
| 101 | 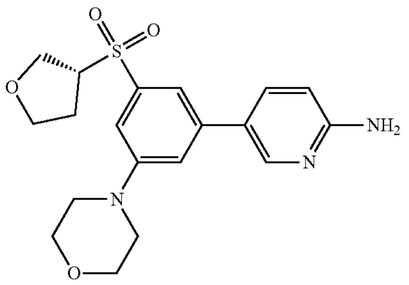 [SMILES: Nc1ccc(-c2cc(N3CCOCC3)cc(S(=O)(=O)[C@@H]3CCOC3)c2)cn1] | (R)-5-(3-morpholino-5-((tetrahydrofuran-3-yl)sulfonyl)phenyl)pyridin-2-amine |

-continued

| Cmpd # | Structure | Chemical Name |
|---|---|---|
| 102 | 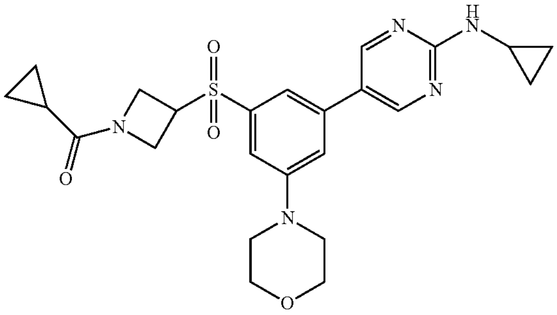 [SMILES: O=C(C1CC1)N1CC(S(=O)(=O)c2cc(-c3cnc(NC4CC4)nc3)cc(N3CCOCC3)c2)C1] | cyclopropyl(3-((3-(2-(cyclopropylamino)pyrimidin-5-yl)-5-morpholinophenyl)sulfonyl)azetidin-1-yl)methanone |
| 103 | 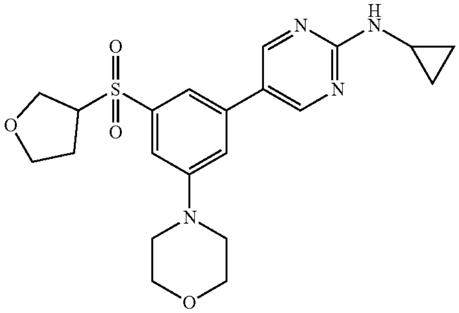 [SMILES: O=S(=O)(c1cc(-c2cnc(NC3CC3)nc2)cc(N2CCOCC2)c1)C1CCOC1] | N-cyclopropyl-5-(3-morpholino-5-((tetrahydrofuran-3-yl)sulfonyl)phenyl)pyrimidin-2-amine |
| 104 | 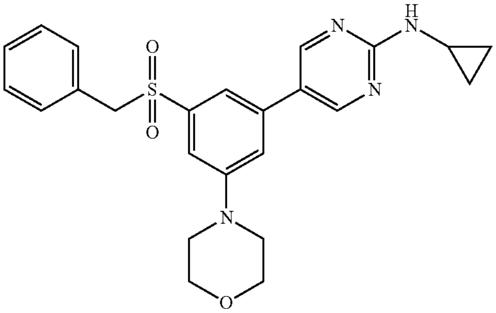 [SMILES: O=S(=O)(Cc1ccccc1)c1cc(-c2cnc(NC3CC3)nc2)cc(N2CCOCC2)c1] | 5-(3-(benzylsulfonyl)-5-morpholinophenyl)-N-cyclopropylpyrimidin-2-amine |
| 105 | 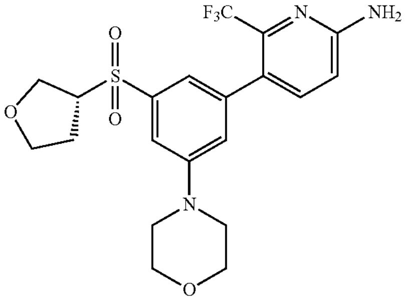 [SMILES: Nc1ccc(-c2cc(N3CCOCC3)cc(S(=O)(=O)[C@@H]3CCOC3)c2)c(C(F)(F)F)n1] | (R)-5-(3-morpholino-5-((tetrahydrofuran-3-yl)sulfonyl)phenyl)-6-(trifluoromethyl)pyridin-2-amine |
| 106 | 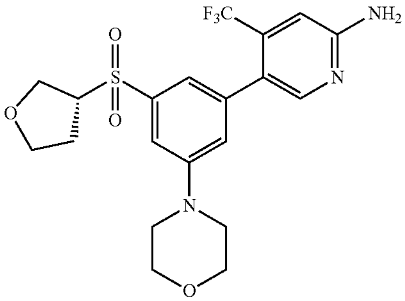 [SMILES: Nc1cc(C(F)(F)F)c(-c2cc(N3CCOCC3)cc(S(=O)(=O)[C@@H]3CCOC3)c2)cn1] | (R)-4-fluoro-5-(3-morpholino-5-((tetrahydrofuran-3-yl)sulfonyl)phenyl)pyridin-2-amine |

-continued

| Cmpd # | Structure | Chemical Name |
|---|---|---|
| 107 | 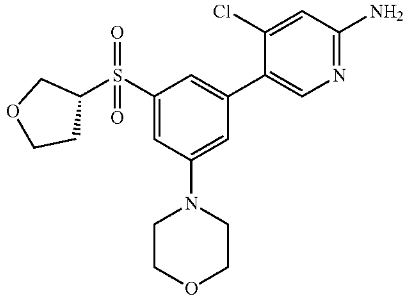 [SMILES: Nc1cc(Cl)c(-c2cc(N3CCOCC3)cc(S(=O)(=O)[C@@H]3CCOC3)c2)cn1] | (R)-4-chloro-5-(3-morpholino-5-((tetrahydrofuran-3-yl)sulfonyl)phenyl)pyridin-2-amine |
| 108 | 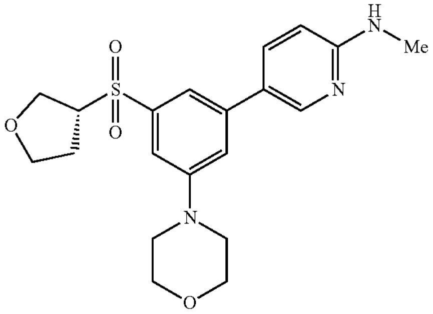 [SMILES: CNc1ccc(-c2cc(N3CCOCC3)cc(S(=O)(=O)[C@@H]3CCOC3)c2)cn1] | (R)-N-methyl-5-(3-morpholino-5-((tetrahydrofuran-3-yl)sulfonyl)phenyl)pyridin-2-amine |
| 109 | 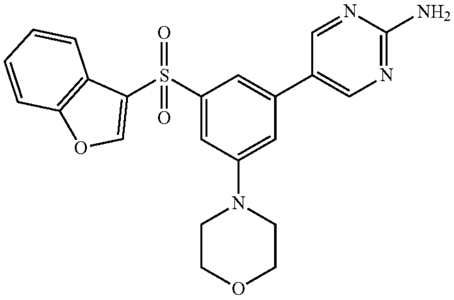 [SMILES: Nc1ncc(-c2cc(N3CCOCC3)cc(S(=O)(=O)c3coc4ccccc34)c2)cn1] | 5-(3-(benzofuran-3-ylsulfonyl)-5-morpholinophenyl)pyrimidin-2-amine |
| 110 | 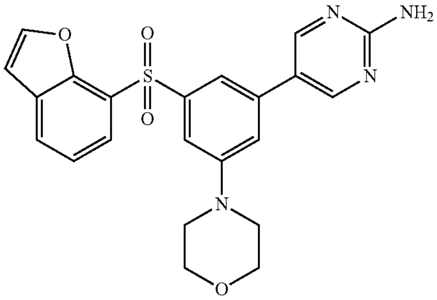 [SMILES: Nc1ncc(-c2cc(N3CCOCC3)cc(S(=O)(=O)c3cccc4ccoc34)c2)cn1] | 5-(3-(benzofuran-7-ylsulfonyl)-5-morpholinophenyl)pyrimidin-2-amine |
| 111 | 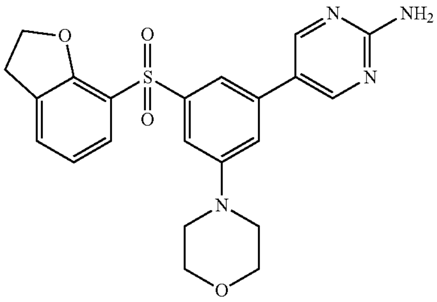 [SMILES: Nc1ncc(-c2cc(N3CCOCC3)cc(S(=O)(=O)c3cccc4c3OCC4)c2)cn1] | 5-(3-((2,3-dihydrobenzofuran-7-yl)sulfonyl)-5-morpholinophenyl)pyrimidin-2-amine |

-continued
| Cmpd # | Structure | Chemical Name |
|---|---|---|
| 112 | 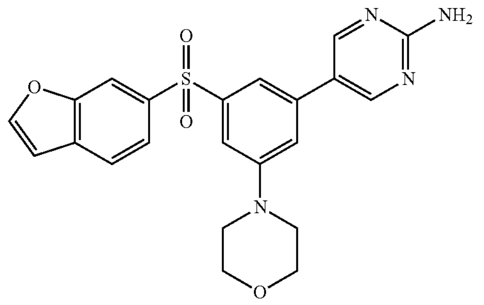 [SMILES: Nc1ncc(-c2cc(N3CCOCC3)cc(S(=O)(=O)c3ccc4ccoc4c3)c2)cn1] | 5-(3-(benzofuran-6-ylsulfonyl)-5-morpholinophenyl)pyrimidin-2-amine |
| 113 | 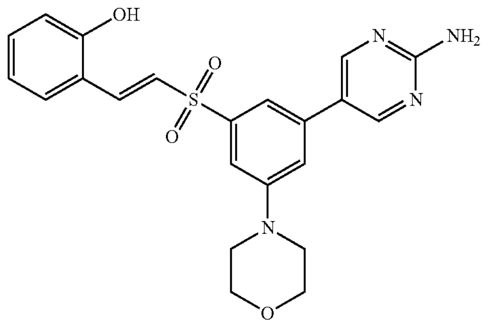 [SMILES: Nc1ncc(-c2cc(N3CCOCC3)cc(S(=O)(=O)/C=C/c3ccccc3O)c2)cn1] | (E)-2-(2-((3-(2-aminopyrimidin-5-yl)-5-morpholinophenyl)sulfonyl)vinyl)phenol |
| 114 | 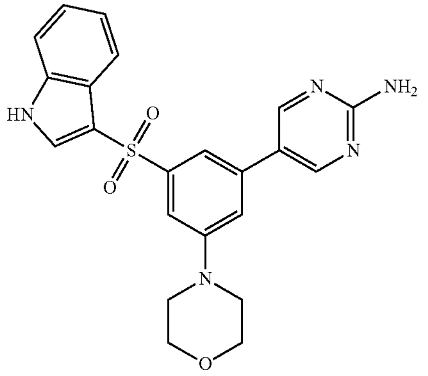 [SMILES: Nc1ncc(-c2cc(N3CCOCC3)cc(S(=O)(=O)c3c[nH]c4ccccc34)c2)cn1] | 5-(3-((1H-indol-3-yl)sulfonyl)-5-morpholinophenyl)pyrimidin-2-amine |
| 115 | 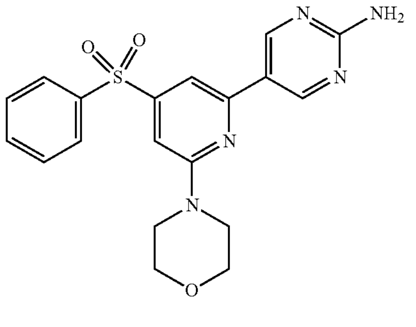 [SMILES: Nc1ncc(-c2cc(S(=O)(=O)c3ccccc3)cc(N3CCOCC3)n2)cn1] | 5-(6-morpholino-4-(phenylsulfonyl)pyridin-2-yl)pyrimidin-2-amine |

-continued
| Cmpd # | Structure | Chemical Name |
|---|---|---|
| 116 | 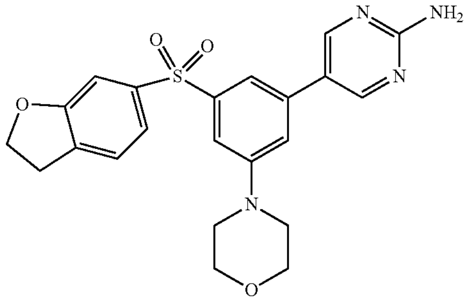 [SMILES: Nc1ncc(-c2cc(N3CCOCC3)cc(S(=O)(=O)c3ccc4c(c3)OCC4)c2)cn1] | 5-(3-((2,3-dihydrobenzofuran-6-yl)sulfonyl)-5-morpholinophenyl)pyrimidin-2-amine |
| 117 | 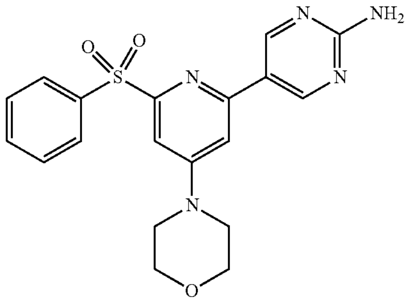 [SMILES: Nc1ncc(-c2cc(N3CCOCC3)cc(S(=O)(=O)c3ccccc3)n2)cn1] | 5-(4-morpholino-6-(phenylsulfonyl)pyridin-2-yl)pyrimidin-2-amine |
| 118 | 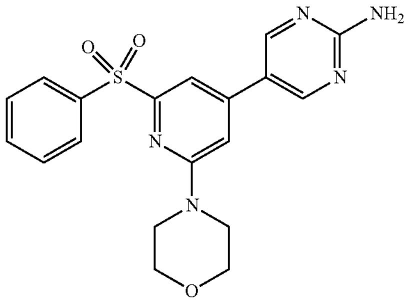 [SMILES: Nc1ncc(-c2cc(N3CCOCC3)nc(S(=O)(=O)c3ccccc3)c2)cn1] | 5-(2-morpholino-6-(phenylsulfonyl)pyridin-4-yl)pyrimidin-2-amine |
| 119 | 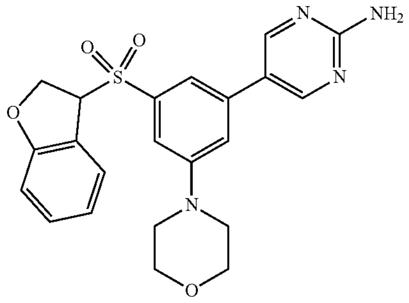 [SMILES: Nc1ncc(-c2cc(N3CCOCC3)cc(S(=O)(=O)C3COc4ccccc43)c2)cn1] | 5-(3-((2,3-dihydrobenzofuran-3-yl)sulfonyl)-5-morpholinophenyl)pyrimidin-2-amine |
| 120 | 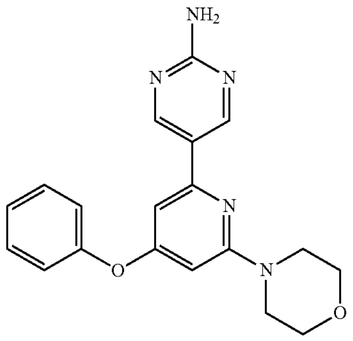 [SMILES: Nc1ncc(-c2cc(Oc3ccccc3)cc(N3CCOCC3)n2)cn1] | 5-(6-morpholino-4-phenoxypyridin-2-yl)pyrimidin-2-amine |

-continued
| Cmpd # | Structure | Chemical Name |
| --- | --- | --- |
| 121 | 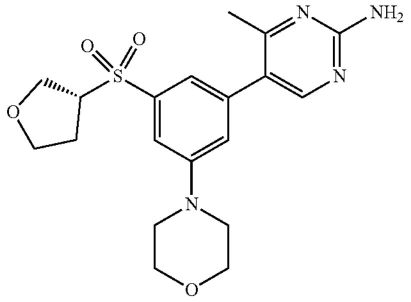 [SMILES: Cc1nc(N)ncc1-c1cc(N2CCOCC2)cc(S(=O)(=O)[C@@H]2CCOC2)c1] | (R)-4-methyl-5-(3-morpholino-5-((tetrahydrofuran-3-yl)sulfonyl)phenyl)pyrimidin-2-amine |
| 122 | 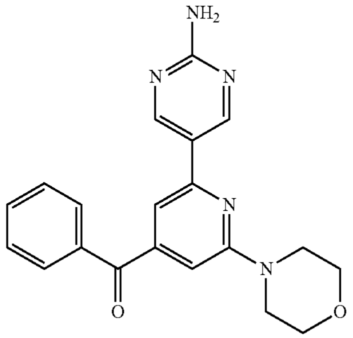 [SMILES: Nc1ncc(-c2cc(C(=O)c3ccccc3)cc(N3CCOCC3)n2)cn1] | (2-(2-aminopyrimidin-5-yl)-6-morpholinopyridin-4-yl)(phenyl)methanone |
| 123 | 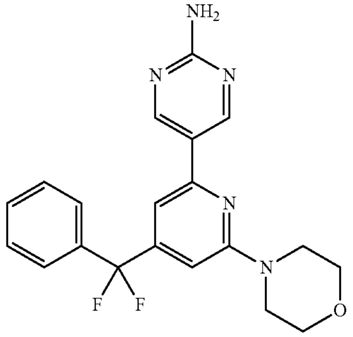 [SMILES: Nc1ncc(-c2cc(C(F)(F)c3ccccc3)cc(N3CCOCC3)n2)cn1] | 5-(4-(difluoro(phenyl)methyl)-6-morpholinopyridin-2-yl)pyrimidin-2-amine |
| 124 | 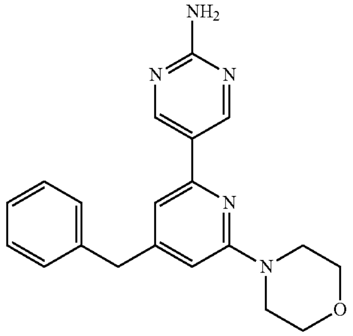 [SMILES: Nc1ncc(-c2cc(Cc3ccccc3)cc(N3CCOCC3)n2)cn1] | 5-(4-benzyl-6-morpholinopyridin-2-yl)pyrimidin-2-amine |

-continued
| Cmpd # | Structure | Chemical Name |
|---|---|---|
| 125 | 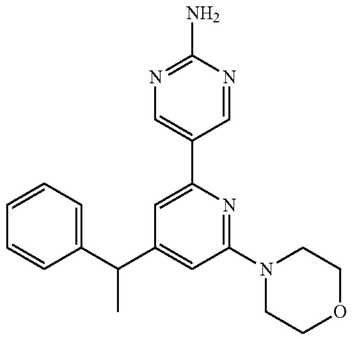 [SMILES: CC(c1ccccc1)c1cc(-c2cnc(N)nc2)nc(N2CCOCC2)c1] | 5-(6-morpholino-4-(1-phenylethyl)pyridin-2-yl)pyrimidin-2-amine |
| 126 | 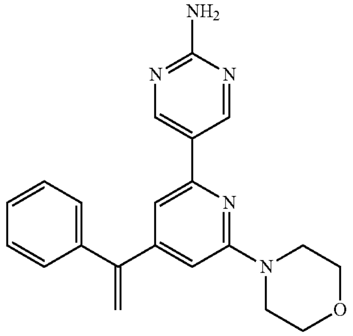 [SMILES: C=C(c1ccccc1)c1cc(-c2cnc(N)nc2)nc(N2CCOCC2)c1] | 5-(6-morpholino-4-(1-phenylvinyl)pyridin-2-yl)pyrimidin-2-amine |
| 127 | 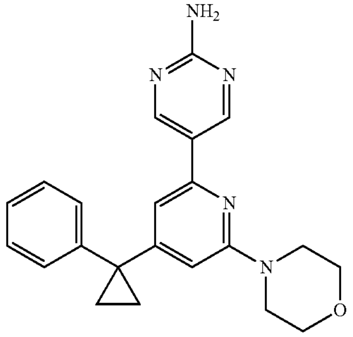 [SMILES: Nc1ncc(-c2cc(C3(c4ccccc4)CC3)cc(N3CCOCC3)n2)cn1] | 5-(6-morpholino-4-(1-phenylcyclopropyl)pyridin-2-yl)pyrimidin-2-amine |
| 128 | 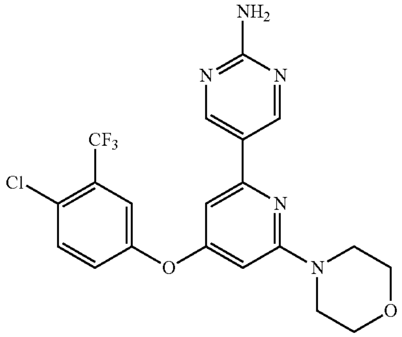 [SMILES: Nc1ncc(-c2cc(Oc3ccc(Cl)c(C(F)(F)F)c3)cc(N3CCOCC3)n2)cn1] | 5-(4-(4-chloro-3-(trifluoromethyl)phenoxy)-6-morpholinopyridin-2-yl)pyrimidin-2-amine |

-continued

| Cmpd # | Structure | Chemical Name |
| --- | --- | --- |
| 129 | 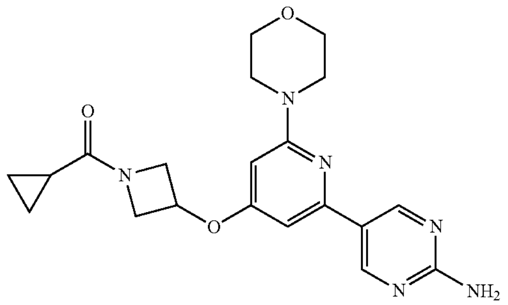 [SMILES: Nc1ncc(-c2cc(OC3CN(C(=O)C4CC4)C3)cc(N3CCOCC3)n2)cn1] | (3-((2-(2-aminopyrimidin-5-yl)-6-morpholinopyridin-4-yl)oxy)azetidin-1-yl)(cyclopropyl)methanone |
| 130 | 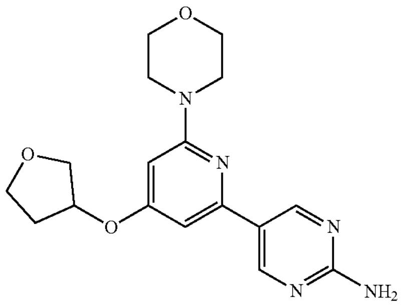 [SMILES: Nc1ncc(-c2cc(OC3CCOC3)cc(N3CCOCC3)n2)cn1] | 5-(6-morpholino-4-((tetrahydrofuran-3-yl)oxy)pyridin-2-yl)pyrimidin-2-amine |
| 131 | 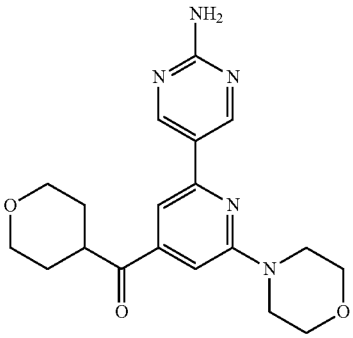 [SMILES: Nc1ncc(-c2cc(C(=O)C3CCOCC3)cc(N3CCOCC3)n2)cn1] | (2-(2-aminopyrimidin-5-yl)-6-morpholinopyridin-4-yl)(tetrahydro-2H-pyran-4-yl)methanone |
| 132 | 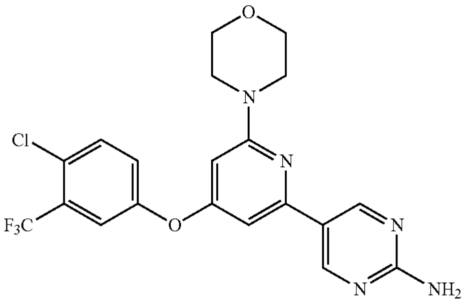 [SMILES: Nc1ncc(-c2cc(Oc3ccc(Cl)c(C(F)(F)F)c3)cc(N3CCOCC3)n2)cn1] | 5-(4-(4-chloro-3-(trifluoromethyl)phenoxy)-6-morpholinopyridin-2-yl)pyrimidin-2-amine |
| 133 | 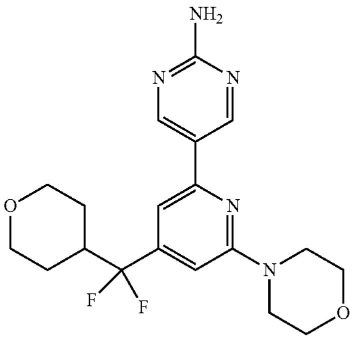 [SMILES: Nc1ncc(-c2cc(C(F)(F)C3CCOCC3)cc(N3CCOCC3)n2)cn1] | 5-(4-(difluoro(tetrahydro-2H-pyran-4-yl)methyl)-6-morpholinopyridin-2-yl)pyrimidin-2-amine |

-continued
| Cmpd # | Structure | Chemical Name |
| --- | --- | --- |
| 134 | 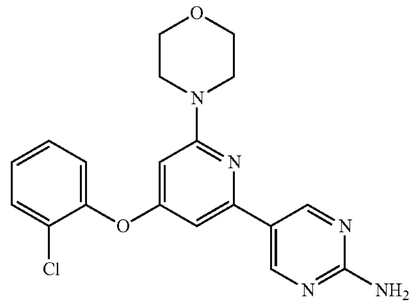 [SMILES: Nc1ncc(-c2cc(Oc3ccccc3Cl)cc(N3CCOCC3)n2)cn1] | 5-(4-(2-chlorophenoxy)-6-morpholinopyridin-2-yl)pyrimidin-2-amine |
| 135 | 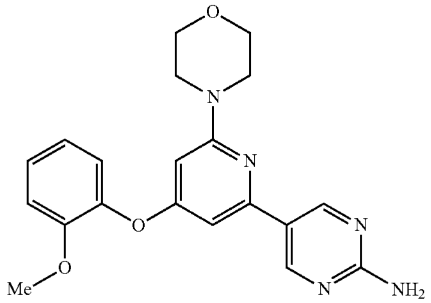 [SMILES: COc1ccccc1Oc1cc(-c2cnc(N)nc2)nc(N2CCOCC2)c1] | 5-(4-(2-methoxyphenoxy)-6-morpholinopyridin-2-yl)pyrimidin-2-amine |
| 136 | 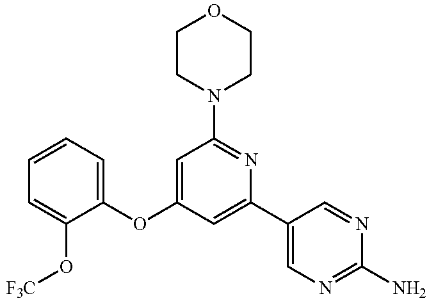 [SMILES: Nc1ncc(-c2cc(Oc3ccccc3OC(F)(F)F)cc(N3CCOCC3)n2)cn1] | 5-(6-morpholino-4-(2-(trifluoromethoxy)phenoxy)pyridin-2-yl)pyrimidin-2-amine |
| 137 | 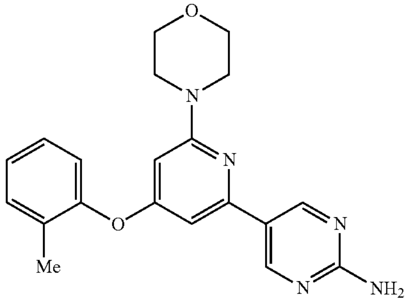 [SMILES: Cc1ccccc1Oc1cc(-c2cnc(N)nc2)nc(N2CCOCC2)c1] | 5-(6-morpholino-4-(o-tolyloxy)pyridin-2-yl)pyrimidin-2-amine |
| 138 | 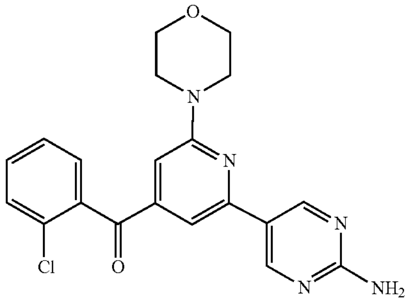 [SMILES: Nc1ncc(-c2cc(C(=O)c3ccccc3Cl)cc(N3CCOCC3)n2)cn1] | (2-(2-aminopyrimidin-5-yl)-6-morpholinopyridin-4-yl)(2-chlorophenyl)methanone |

-continued
| Cmpd # | Structure | Chemical Name |
|---|---|---|
| 139 | 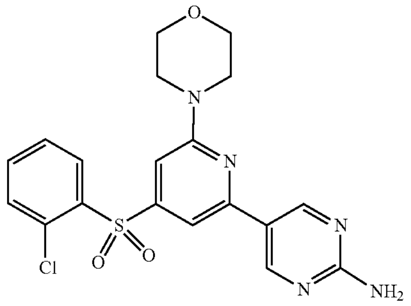 [SMILES: Nc1ncc(-c2cc(S(=O)(=O)c3ccccc3Cl)cc(N3CCOCC3)n2)cn1] | 5-(4-((2-chlorophenyl)sulfonyl)-6-morpholinopyridin-2-yl)pyrimidin-2-amine |
| 140 | 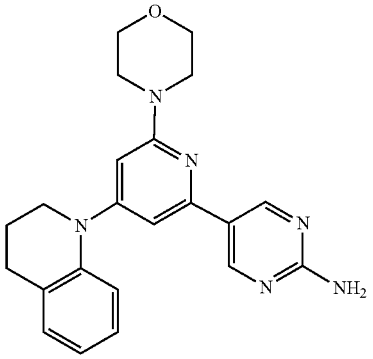 [SMILES: Nc1ncc(-c2cc(N3CCCc4ccccc43)cc(N3CCOCC3)n2)cn1] | 5-(4-(3,4-dihydroquinolin-1(2H)-yl)-6-morpholinopyridin-2-yl)pyrimidin-2-amine |
| 141 | 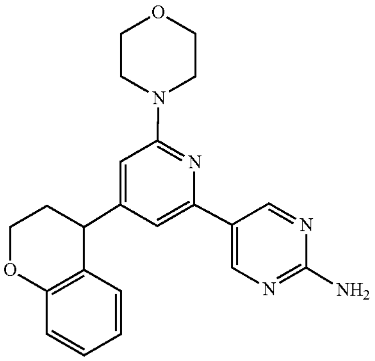 [SMILES: Nc1ncc(-c2cc(C3CCOc4ccccc43)cc(N3CCOCC3)n2)cn1] | 5-(4-(chroman-4-yl)-6-morpholinopyridin-2-yl)pyrimidin-2-amine |
| 142a | 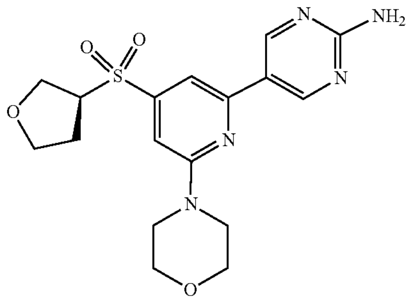 [SMILES: Nc1ncc(-c2cc(S(=O)(=O)[C@H]3CCOC3)cc(N3CCOCC3)n2)cn1] | (S)-5-(6-morpholino-4-((tetrahydrofuran-3-yl)sulfonyl)pyridin-2-yl)pyrimidin-2-amine |

-continued

| Cmpd # | Structure | Chemical Name |
| --- | --- | --- |
| 142b | 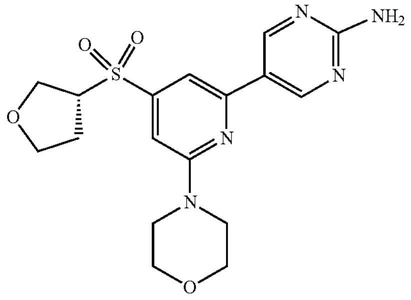 [SMILES: Nc1ncc(-c2cc(S(=O)(=O)[C@@H]3CCOC3)cc(N3CCOCC3)n2)cn1] | (R)-5-(6-morpholino-4-((tetrahydrofuran-3-yl)sulfonyl)pyridin-2-yl)pyrimidin-2-amine |
| 143 | 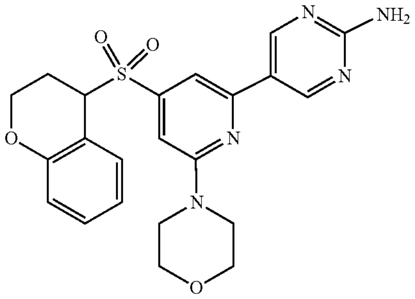 [SMILES: Nc1ncc(-c2cc(S(=O)(=O)C3CCOc4ccccc43)cc(N3CCOCC3)n2)cn1] | 5-(4-(chroman-4-ylsulfonyl)-6-morpholinopyridin-2-yl)pyrimidin-2-amine |
| 144 | 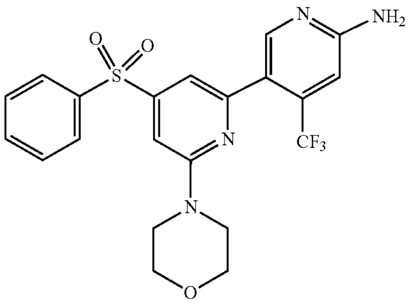 [SMILES: Nc1cc(C(F)(F)F)c(-c2cc(S(=O)(=O)c3ccccc3)cc(N3CCOCC3)n2)cn1] | 6-morpholino-4-(phenylsulfonyl)-4'-(trifluoromethyl)-[2,3'-bipyridin]-6'-amine |
| 145 | 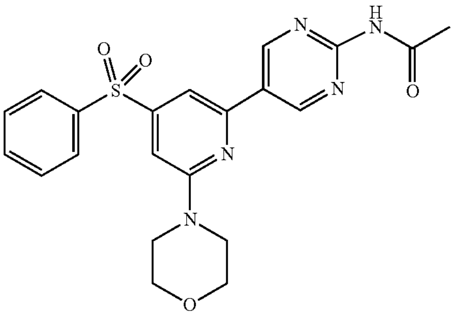 [SMILES: CC(=O)Nc1ncc(-c2cc(S(=O)(=O)c3ccccc3)cc(N3CCOCC3)n2)cn1] | N-(5-(6-morpholino-4-(phenylsulfonyl)pyridin-2-yl)pyrimidin-2-yl)acetamide |
| 146 | 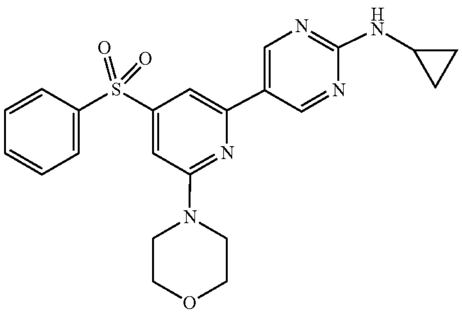 [SMILES: O=S(=O)(c1ccccc1)c1cc(-c2cnc(NC3CC3)nc2)nc(N2CCOCC2)c1] | N-cyclopropyl-5-(6-morpholino-4-(phenylsulfonyl)pyridin-2-yl)pyrimidin-2-amine |

-continued

| Cmpd # | Structure | Chemical Name |
|---|---|---|
| 147 | 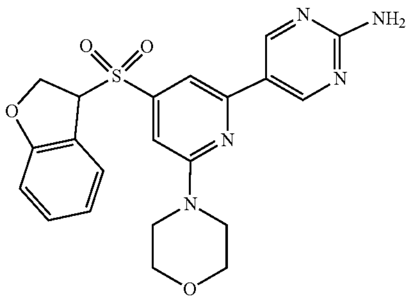 [SMILES: Nc1ncc(-c2cc(S(=O)(=O)C3COc4ccccc43)cc(N3CCOCC3)n2)cn1] | 5-(4-((2,3-dihydrobenzofuran-3-yl)sulfonyl)-6-morpholinopyridin-2-yl)pyrimidin-2-amine |
| 148 | 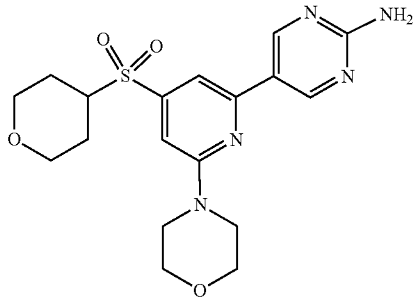 [SMILES: Nc1ncc(-c2cc(S(=O)(=O)C3CCOCC3)cc(N3CCOCC3)n2)cn1] | 5-(6-morpholino-4-((tetrahydro-2H-pyran-4-yl)sulfonyl)pyridin-2-yl)pyrimidin-2-amine |
| 149 | 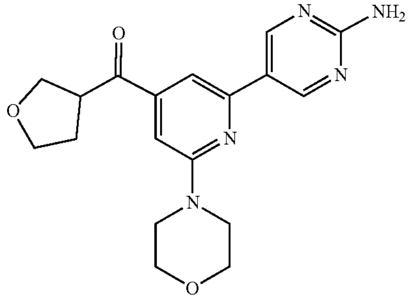 [SMILES: Nc1ncc(-c2cc(C(=O)C3CCOC3)cc(N3CCOCC3)n2)cn1] | (2-(2-aminopyrimidin-5-yl)-6-morpholinopyridin-4-yl)(tetrahydrofuran-3-yl)methanone |
| 150 | 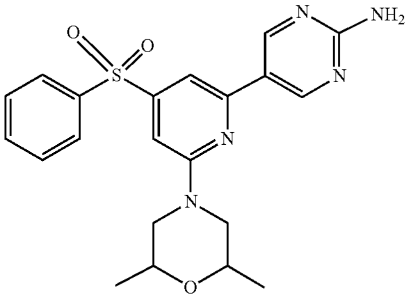 [SMILES: CC1CN(c2cc(S(=O)(=O)c3ccccc3)cc(-c3cnc(N)nc3)n2)CC(C)O1] | 5-(6-(2,6-dimethylmorpholino)-4-(phenylsulfonyl)pyridin-2-yl)pyrimidin-2-amine |
| 151 | 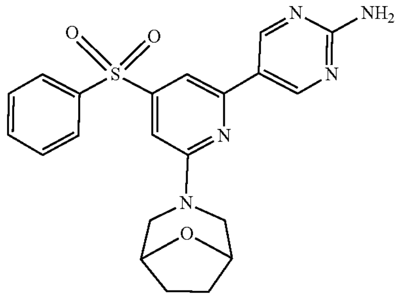 [SMILES: Nc1ncc(-c2cc(S(=O)(=O)c3ccccc3)cc(N3CC4CCC(C3)O4)n2)cn1] | 5-(6-(8-oxa-3-azabicyclo[3.2.1]octan-3-yl)-4-(phenylsulfonyl)pyridin-2-yl)pyrimidin-2-amine |

and pharmaceutically acceptable salts thereof.

Any formula or compound given herein, such as Formula (I), (II), or (III), or compounds of Tables 1, is intended to represent compounds having structures depicted by the structural formula as well as certain variations or forms. In particular, compounds of any formula given herein may have asymmetric centers and therefore exist in different enantiomeric or diastereomeric forms. All optical isomers and stereoisomers of the compounds of the general formula, and mixtures thereof in any ratio, are considered within the scope of the formula. Thus, any formula given herein is intended to represent a racemate, one or more enantiomeric forms, one or more diastereomeric forms, one or more atropisomeric forms, and mixtures thereof in any ratio. Where a compound of Table 1 is depicted with a particular stereochemical configuration, also provided herein is any alternative stereochemical configuration of the compound, as well as a mixture of stereoisomers of the compound in any ratio. For example, where a compound of Table 1 has a stereocenter that is in an “S” stereochemical configuration, also provided herein is enantiomer of the compound wherein that stereocenter is in an “R” stereochemical configuration. Likewise, when a compound of Table 1 has a stereocenter that is in an “R” configuration, also provided herein is enantiomer of the compound in an “S” stereochemical configuration. Also provided are mixtures of the compound with both the “S” and the “R” stereochemical configuration. Additionally, if a compound of Table 1 has two or more stereocenters, also provided are any enantiomer or diastereomer of the compound. For example, if a compound of Table 1 contains a first stereocenter and a second stereocenter with “R” and “R” stereochemical configurations, respectively, also provided are stereoisomers of the compound having first and second stereocenters with “S” and “S” stereochemical configurations, respectively, “S” and “R” stereochemical configurations, respectively, and “R” and “S” stereochemical configurations, respectively. If a compound of Table 1 contains a first stereocenter and a second stereocenter with “S” and “S” stereochemical configurations, respectively, also provided are stereoisomers of the compound having first and second stereocenters with “R” and “R” stereochemical configurations, respectively, “S” and “R” stereochemical configurations, respectively, and “R” and “S” stereochemical configurations, respectively. If a compound of Table 1 contains a first stereocenter and a second stereocenter with “S” and “R” stereochemical configurations, respectively, also provided are stereoisomers of the compound having first and second stereocenters with “R” and “S” stereochemical configurations, respectively, “R” and “R” stereochemical configurations, respectively, and “S” and “S” stereochemical configurations, respectively. Similarly, if a compound of Table 1 contains a first stereocenter and a second stereocenter with “R” and “S” stereochemical configurations, respectively, also provided are stereoisomers of the compound having first and second stereocenters with “S” and “R” stereochemical configurations, respectively, “R” and “R” stereochemical configurations, respectively, and “S” and “S” stereochemical configurations, respectively. Furthermore, certain structures may exist as geometric isomers (i.e., cis and trans isomers), as tautomers, or as atropisomers. Additionally, any compound of Table 1 is intended to represent a racemate, one or more enantiomeric forms, one or more diastereomeric forms, one or more atropisomeric forms, and mixtures thereof in any ratio. Furthermore, certain structures may exist as geometric isomers (i.e., cis and trans isomers), as tautomers, or as atropisomers. Additionally, any formula given herein, such as Formula (I), (II), or (III), is intended to refer to hydrates, solvates, and amorphous forms of such compounds, and mixtures thereof, even if such forms are not listed explicitly. In some embodiments, the solvent is water and the solvates are hydrates.

The compounds of Formula (I), (II), or (III) may be prepared and/or formulated as pharmaceutically acceptable salts. Pharmaceutically acceptable salts are non-toxic salts of a free base form of a compound that possesses the desired pharmacological activity of the free base. In some embodiments, pharmaceutically acceptable salts include acid addition salts formed with inorganic acids such as hydrochloric acid, hydrobromic acid, sulfuric acid, nitric acid, phosphoric acid, and the like; or formed with organic acids such as acetic acid, oxalic acid, propionic acid, succinic acid, maleic acid, tartaric acid and the like. Non-limiting examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, methylsulfonates, propylsulfonates, besylates, tosylates, xylenesulfonates, naphthalene-1-sulfonates, naphthalene-2-sulfonates, edisylates, phenylacetates, phenylpropionates, phenylbutyrates, citrates, lactates, γ-hydroxybutyrates, glycolates, tartrates, and mandelates. In some embodiments, pharmaceutically acceptable salts are formed when an acidic proton present in the parent compound either is replaced by a metal ion, e.g., an alkali metal ion, an alkaline earth ion, or an aluminum ion; or coordinates with an organic base. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, tromethamine, trimethamine, dicyclohexylamine, caffeine, procaine, hydrabamine, choline, betaine, ethylenediamine, glucosamine, N-ethylglucamine, N-methylglucamine, theobromine, purines, piperazine, piperidine, N-ethylpiperidine, polyamine resins, amino acids such as lysine, arginine, histidine, and the like. Examples of pharmaceutically acceptable base addition salts include those derived from inorganic bases such as sodium, potassium, lithium, ammonium, calcium, magnesium, iron, zinc, copper, manganese, aluminum salts and the like. In some embodiments, the organic non-toxic bases are L-amino acids, such as L-lysine and L-arginine, tromethamine, N-ethylglucamine and N-methylglucamine. Acceptable inorganic bases include aluminum hydroxide, calcium hydroxide, potassium hydroxide, sodium carbonate, sodium hydroxide, and the like. Lists of other suitable pharmaceutically acceptable salts are found in Remington's Pharmaceutical Sciences, 17th Edition, Mack Publishing Company, Easton, Pa., 1985.

For a compound described herein that contains a basic nitrogen, a pharmaceutically acceptable salt may be prepared by any suitable method available in the art, for example, treatment of the free base with an inorganic acid, such as hydrochloric acid, hydrobromic acid, sulfuric acid, sulfamic acid, nitric acid, boric acid, phosphoric acid, and the like, or with an organic acid, such as acetic acid, phenylacetic acid, propionic acid, stearic acid, lactic acid, ascorbic acid, maleic acid, hydroxymaleic acid, isethionic acid, succinic acid, valeric acid, fumaric acid, malonic acid, pyruvic acid, oxalic acid, glycolic acid, salicylic acid, oleic acid, palmitic acid, lauric acid, a pyranosidyl acid, such as glucuronic acid or galacturonic acid, an alpha-hydroxy acid, such as mandelic acid, citric acid, or tartaric acid, an amino acid, such as aspartic acid or glutamic acid, an aromatic acid, such as benzoic acid, 2-acetoxybenzoic acid, naphthoic acid, or cinnamic acid, a sulfonic acid, such as laurylsulfonic acid, p-toluenesulfonic acid, methanesulfonic acid, benzenesulfonic acid, ethanesulfonic acid, or ethanedisulfonic acid, or any compatible mixture of acids such as those given as examples herein, and any other acid and mixture thereof that are regarded as equivalents or acceptable substitutes in light of the ordinary level of skill in this technology.

The embodiments also relate to pharmaceutically acceptable prodrugs of the compounds described herein, and treatment methods employing such pharmaceutically acceptable prodrugs. The term "prodrug" means a precursor of a designated compound that, following administration to a subject, yields the compound in vivo via a chemical or physiological process such as solvolysis or enzymatic cleavage, or under physiological conditions (e.g., a prodrug on being brought to physiological pH is converted to the compound of Formula (I)). A "pharmaceutically acceptable prodrug" is a prodrug that is non-toxic, biologically tolerable, and otherwise biologically suitable for administration to the subject. Illustrative procedures for the selection and preparation of suitable prodrug derivatives are described, for example, in "Design of Prodrugs", ed. H. Bundgaard, Elsevier, 1985.

The embodiments also relate to pharmaceutically active metabolites of compounds described herein, and uses of such metabolites in the methods provided herein. A "pharmaceutically active metabolite" means a pharmacologically active product of metabolism in the body of a compound described herein or salt thereof. Prodrugs and active metabolites of a compound may be determined using routine techniques known or available in the art. See, e.g., Bertolini et al., *J. Med. Chem.* 1997, 40, 2011-2016; Shan et al., *J. Pharm. Sci.* 1997, 86 (7), 765-767; Bagshawe, *Drug Dev. Res.* 1995, 34, 220-230; Bodor, *Adv. Drug Res.* 1984, 13, 255-331; Bundgaard, Design of Prodrugs (Elsevier Press, 1985); and Larsen, Design and Application of Prodrugs, Drug Design and Development (Krogsgaard-Larsen et al., eds., Harwood Academic Publishers, 1991).

Pharmaceutical Compositions

For treatment purposes, a pharmaceutical composition according to the present disclosure comprises at least one compound of Formula (I), or a pharmaceutically acceptable salt thereof. The pharmaceutical compositions may further comprise one or more pharmaceutically-acceptable excipients. A pharmaceutically-acceptable excipient is a substance that is non-toxic and otherwise biologically suitable for administration to a subject. Such excipients facilitate administration of the compounds described herein and are compatible with the active ingredient. Examples of pharmaceutically-acceptable excipients include stabilizers, lubricants, surfactants, diluents, anti-oxidants, binders, coloring agents, bulking agents, emulsifiers, or taste-modifying agents. In certain embodiments, pharmaceutical compositions according to the embodiments are sterile compositions. Pharmaceutical compositions may be prepared using compounding techniques known or that become available to those skilled in the art.

Sterile compositions are also contemplated by the embodiments, including compositions that are in accord with national and local regulations governing such compositions.

The pharmaceutical compositions and compounds described herein may be formulated as solutions, emulsions, suspensions, dispersions, or inclusion complexes such as cyclodextrins in suitable pharmaceutical solvents or carriers, or as pills, tablets, lozenges, suppositories, sachets, dragees, granules, powders, powders for reconstitution, or capsules along with solid carriers according to conventional methods known in the art for preparation of various dosage forms. Pharmaceutical compositions of the embodiments may be administered by a suitable route of delivery, such as oral, parenteral, rectal, nasal, topical, or ocular routes, or by inhalation. In some embodiments, the compositions are formulated for intravenous or oral administration.

For oral administration, the compounds the embodiments may be provided in a solid form, such as a tablet or capsule, or as a solution, emulsion, or suspension. To prepare the oral compositions, the compounds of the embodiments may be formulated to yield a dosage of, e.g., from about 0.01 to about 50 mg/kg daily, or from about 0.05 to about 20 mg/kg daily, or from about 0.1 to about 10 mg/kg daily. Oral tablets may include the active ingredient(s) mixed with compatible pharmaceutically acceptable excipients such as diluents, disintegrating agents, binding agents, lubricating agents, sweetening agents, flavoring agents, coloring agents and preservative agents. Suitable inert fillers include sodium and calcium carbonate, sodium and calcium phosphate, lactose, starch, sugar, glucose, methyl cellulose, magnesium stearate, mannitol, sorbitol, and the like. Exemplary liquid oral excipients include ethanol, glycerol, water, and the like. Starch, polyvinyl-pyrrolidone (PVP), sodium starch glycolate, microcrystalline cellulose, and alginic acid are exemplary disintegrating agents. Binding agents may include starch and gelatin. The lubricating agent, if present, may be magnesium stearate, stearic acid, or talc. If desired, the tablets may be coated with a material such as glyceryl monostearate or glyceryl distearate to delay absorption in the gastrointestinal tract, or may be coated with an enteric coating.

Capsules for oral administration include hard and soft gelatin capsules. To prepare hard gelatin capsules, active ingredient(s) may be mixed with a solid, semi-solid, or liquid diluent. Soft gelatin capsules may be prepared by mixing the active ingredient with water, an oil such as peanut oil or olive oil, liquid paraffin, a mixture of mono and di-glycerides of short chain fatty acids, polyethylene glycol 400, or propylene glycol.

Liquids for oral administration may be in the form of suspensions, solutions, emulsions, or syrups, or may be lyophilized or presented as a dry product for reconstitution with water or other suitable vehicle before use. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

The inventive compositions may be formulated for rectal administration as a suppository. For parenteral use, including intravenous, intramuscular, intraperitoneal, intranasal, or subcutaneous routes, the agents of the embodiments may be provided in sterile aqueous solutions or suspensions, buffered to an appropriate pH and isotonicity or in parenterally acceptable oil. Suitable aqueous vehicles include Ringer's solution and isotonic sodium chloride. Such forms may be presented in unit-dose form such as ampoules or disposable injection devices, in multi-dose forms such as vials from which the appropriate dose may be withdrawn, or in a solid form or pre-concentrate that can be used to prepare an injectable formulation. Illustrative infusion doses range from about 1 to 1000 μg/kg/minute of agent admixed with a pharmaceutical carrier over a period ranging from several minutes to several days.

For nasal, inhaled, or oral administration, the inventive pharmaceutical compositions may be administered using, for example, a spray formulation also containing a suitable carrier.

For topical applications, the compounds of the present embodiments are preferably formulated as creams or ointments or a similar vehicle suitable for topical administration. For topical administration, the inventive compounds may be mixed with a pharmaceutical carrier at a concentration of about 0.1% to about 10% of drug to vehicle. Another mode of administering the agents of the embodiments may utilize a patch formulation to effect transdermal delivery.

As used herein, the terms "treat" or "treatment" encompass both "preventative" and "curative" treatment. "Preventative" treatment is meant to indicate a postponement of development of a disease, a symptom of a disease, or medical condition, suppressing symptoms that may appear, slowing the worsening or progression of a disease, disorder, or symptom, or reducing the risk of developing or recurrence of a disease or symptom. "Curative" treatment includes reducing the severity of or suppressing the worsening of an existing disease, symptom, or condition. Thus, treatment includes ameliorating or preventing the worsening of existing disease symptoms, preventing additional symptoms from occurring, ameliorating or preventing the underlying systemic causes of symptoms, inhibiting the disorder or disease, e.g., arresting the development of the disorder or disease, relieving the disorder or disease, causing regression of the disorder or disease, relieving a condition caused by the disease or disorder, or stopping the symptoms of the disease or disorder.

The term "subject" refers to a mammalian patient in need of such treatment, such as a human.

Exemplary neurodegenerative diseases that may be therapeutic targets for modulators of the PI3K-AKT-mTOR pathway include Alzheimer's disease, Parkinson's disease, fronto-temporal dementia, dementia with Lewy bodies, PD Dementia, multiple system atrophy, Huntington's disease and amyotrophic lateral sclerosis. In addition to neurodegenerative disorders, compounds that modulate the PI3K-AKT-mTOR pathway may also have utility in the treatment of cancer (particularly, prostate, colon, pancreatic and renal), infections, Crohn's disease, heart disease, and aging.

In one aspect, the compounds and pharmaceutical compositions of the present disclosure specifically target PI3K, AKT and/or mTOR. Thus, these compounds and pharmaceutical compositions can, by preventing, reversing, slowing, or inhibiting the P13K-AKT-mTOR pathway, treat degenerative neurological diseases related to or caused by mis-regulation of autophagy, e.g., such as inadequate clearance of protein aggregates and/or damaged organelles, insufficient activation of a survival pattern of gene expression, and/or deficiencies in cell energetics. Preferably, the methods of the present disclosure target neurodegenerative diseases associated with the P13K-AKT-mTOR pathway. In preferred embodiments, methods of treatment target Parkinson's disease, Alzheimer's disease, Lewy body disease, multiple system atrophy, or Huntington's disease. In other embodiments, the methods of the present disclosure target peripheral degenerative disorders associated with the P13K-AKT-mTOR pathway. In some embodiments, methods of treatment target Paget's disease, Charcot-Marie-Tooth Disease, macular degeneration or cardiomyopathy. The compounds, compositions, and method of the present disclosure are also used to mitigate deleterious effects that inhibit autophagy, such as impaired clearance of protein aggregates or damaged organelles. While the disclosure is not limited by any particular mechanism of action, dysregulation of autophagy is thought to be caused by alpha synuclein and/or beta amyloid.

In the methods of the embodiments, an "effective amount" of a PI3K-AKT-MTOR modulator means an amount sufficient to alter the phosphorylation of constituents of the PI3K-AKT-MTOR pathway, alter expression of survival genes regulated by this pathway, improve cellular energetics, increase markers of autophagy and/or decrease the accumulation of protein aggregates. Measuring one or more of these markers of modulation of the PI3I-AKT-MTOR pathway may be performed by routine analytical methods such as those described below and is useful in a variety of settings, including in vitro assays.

In treatment methods according to the embodiments, an "effective amount" means an amount or dose sufficient to generally bring about the desired therapeutic benefit in subjects needing such treatment. Effective amounts or doses of the compounds of the embodiments may be ascertained by routine methods, such as modeling, dose escalation, or clinical trials, taking into account routine factors, e.g., the mode or route of administration or drug delivery, the pharmacokinetics of the agent, the severity and course of the infection, the subject's health status, condition, and weight, and the judgment of the treating physician. An exemplary dose is in the range of about 1 μg to 2 mg of active agent per kilogram of subject's body weight per day, preferably about 0.05 to 100 mg/kg/day, or about 1 to 35 mg/kg/day, or about 0.1 to 10 mg/kg/day. The total dosage may be given in single or divided dosage units (e.g., BID, TID, QID).

Once improvement of the patient's disease has occurred, the dose may be adjusted for preventative or maintenance treatment. For example, the dosage or the frequency of administration, or both, may be reduced as a function of the symptoms, to a level at which the desired therapeutic or prophylactic effect is maintained. Of course, if symptoms have been alleviated to an appropriate level, treatment may cease. Patients may, however, require intermittent treatment on a long-term basis upon any recurrence of symptoms. Patients may also require chronic treatment on a long-term basis.

Drug Combinations

The inventive compounds described herein may be used in pharmaceutical compositions or methods in combination with one or more additional active ingredients in the treatment of neurodegenerative disorders. For example, additional active ingredients are those that are known or discovered to be effective in treating neurodegenerative disorders, including those active against another target associated with the disease, such as but not limited to, a) compounds that address protein misfolding (such as drugs which reduce the production of these proteins, which increase their clearance or which alter their aggregation and/or propagation); b) compounds that treat symptoms of such disorders (e.g., dopamine replacement therapies, cholinesterase inhibitors and precognitive glutamatergic drugs); and c) drugs that act as neuroprotectants by complementary mechanisms (e.g., those targeting autophagy, those that are anti-oxidants, and those acting by other mechanisms such as adenosine A2A antagonists).

For example, additional active ingredients are those that are known or discovered to be effective in treating neurodegenerative disorders, including those active against another target associated with the disease, such as but not limited to, a) compounds that target different mechanisms of protein misfolding (such as aggregation and/or propagation); b) compounds that treat symptoms of such disorders (e.g., dopamine replacement therapies); and c) drugs that act as neuroprotectants by complementary mechanisms (e.g., those targeting autophagy, anti-oxidants, and adenosine A2A antagonists).

For example, compositions and formulations of the embodiments, as well as methods of treatment, can further comprise other drugs or pharmaceuticals, e.g., other active agents useful for treating or palliative for a degenerative neurological disease related to or caused by protein aggregation, e.g., synuclein, beta-amyloid and/or tau protein aggregation, e.g., Parkinson's disease, Alzheimer's Disease (AD), Lewy body disease (LBD) and multiple system atrophy (MSA), or related symptoms or conditions. In this regard, compositions and formulations of the generic and specific compounds described herein are useful in methods of treatment for Alzheimer's Disease, Parkinson's Disease, fronto-temporal dementia, dementia with Lewy Bodies, PD dementia, multiple system atrophy, Huntington's disease, Amyotrophic lateral sclerosis, cancer, infection, Crohn's disease, heart disease, Paget's disease, Charcot-Marie-Tooth Disease, macular degeneration, cardiomyopathy, and aging. The pharmaceutical compositions of the embodiments may additional comprise one or more of such active agents, and methods of treatment may additionally comprise administering an effective amount of one or more of such active agents. In certain embodiments, additional active agents may be antibiotics (e.g., antibacterial or bacteriostatic peptides or proteins), e.g., those effective against gram positive or negative bacteria, fluids, cytokines, immunoregulatory agents, anti-inflammatory agents, complement activating agents, such as peptides or proteins comprising collagen-like domains or fibrinogen-like domains (e.g., a ficolin), carbohydrate-binding domains, and the like and combinations thereof. Additional active agents include those useful in such compositions and methods include dopamine therapy drugs, catechol-O-methyl transferase (COMT) inhibitors, monamine oxidase inhibitors, cognition enhancers (such as acetylcholinesterase inhibitors or memantine), adenosine 2A receptor antagonists, beta-secretase inhibitors, or gamma-secretase inhibitors. In particular embodiments, at least one compound of the present embodiments may be combined in a pharmaceutical composition or a method of treatment with one or more drugs selected from the group consisting of: tacrine (Cognex), donepezil (Aricept), rivastigmine (Exelon) galantamine (Reminyl), physostigmine, neostigmine, Icopezil (CP-118954, 5,7-dihydro-3-[2-[1-(phenylmethyl)-4-piperidinyl]ethyl]-6H-pyrrolo-[4,5-f-]-1,2-benzisoxazol-6-one maleate), ER-127528 (4-[(5,6-dimethoxy-2-fluoro-1-indanon)-2-yl]methyl-1-(3-fluorobenzyl) piperidine hydrochloride), zanapezil (TAK-147; 3-[1-(phenylmethyl)piperidin-4-yl]-1-(2,3,4,5-tetrahydro-1H-1-benzazepin-8-yl)-1-propane fumarate), Metrifonate (T-588; (−)—R-alpha-[[2-(dimethylamino)ethoxy]methyl]benzo[b] thiophene-5-methanol hydrochloride), FK-960 (N-(4-acetyl-1-piperazinyl)-p-fluorobenzamide-hydrate), TCH-346 (N-methyl-N-2-pyropinyldibenz[b,f]oxepine-10-methanamine), SDZ-220-581 ((S)-alpha-amino-5-(phosphonomethyl)-[1,1'-biphenyl]-3-propionic acid), memantine (Namenda/Exiba) and 1,3,3,5,5-pentamethylcyclohexan-1-amine (Neramexane), tarenflurbil (Flurizan), tramiprosate (Alzhemed), clioquinol, PBT-2 (an 8-hydroxyquinilone derivative), 1-(2-(2-Naphthyl)ethyl)-4-(3-trifluoromethylphenyl)-1,2,3,6-tetrahydropyr-idine, Huperzine A, posatirelin, leuprolide or derivatives thereof, ispronicline, (3-aminopropyl)(n-butyl)phosphinic acid (SGS-742), N-methyl-5-(3-(5-isopropoxypyridinyl))-4-penten-2-amine (ispronicline), 1-decanaminium, N-(2-hydroxy-3-sulfopropyl)-N-methyl-N-octyl-, inner salt (zt-1), salicylates, aspirin, amoxiprin, benorilate, choline magnesium salicylate, diflunisal, faislamine, methyl salicylate, magnesium salicylate, salicyl salicylate, diclofenac, aceclofenac, acemetacin, bromfenac, etodolac, indometacin, nabumetone, sulindac, tolmetin, ibuprofen, carprofen, fenbufen, fenoprofen, flurbiprofen, ketoprofen, ketorolac, loxoprofen, naproxen, tiaprofenic acid, suprofen, mefenamic acid, meclofenamic acid, phenylbutazone, azapropazone, metamizole, oxyphenbutazone, sulfinprazone, piroxicam, lornoxicam, meloxicam, tenoxicam, celecoxib, etoricoxib, lumiracoxib, parecoxib, rofecoxib, valdecoxib, nimesulide, arylalkanoic acids, 2-arylpropionic acids (profens), N-arylanthranilic acids (fenamic acids), pyrazolidine derivatives, oxicams, COX-2 inhibitors, sulphonanilides, essential fatty acids, and Minozac (2-(4-(4-methyl-6-phenylpyridazin-3-yl)piperazin-1-yl)pyrimidine dihydrochloride hydrate). Such a combination may serve to increase efficacy, ameliorate other disease symptoms, decrease one or more side effects, or decrease the required dose of an inventive compound. The additional active ingredients may be administered in a separate pharmaceutical composition from a compound of the embodiments or may be included with a compound of the embodiments in a single pharmaceutical composition. The additional active ingredients may be administered simultaneously with, prior to, or after administration of a compound of Formula (I).

Methods of Use

The compounds and pharmaceutical compositions herein may be used to treat or prevent a disease or condition in an individual. In some embodiments, provided are methods of treating a disease or condition associated with autophagy or the PI3K-AKT-MTOR pathway, comprising administering to the individual in need thereof a compound of Formula (I), (II), or (III), or a compound of Table 1, or a pharmaceutically acceptable salt of any of the foregoing. In some embodiments, provided are methods of treating a disease or condition associated with autophagy or the PI3K-AKT-MTOR pathway comprising administering to the subject a therapeutically effective amount of at least one chemical entity as described herein.

In some embodiments, provided are compositions containing one or more compounds of Formula (I), (II), or (III), or a compound of Table 1, or a pharmaceutically acceptable salt of any of the foregoing, for use in the treatment of a disease or condition associated with autophagy or the PI3K-AKT-MTOR pathway. In some embodiments, provided are compositions containing at least one chemical entity as described herein for use in the treatment of a disease or condition associated with autophagy or the PI3K-AKT-MTOR pathway. In some embodiments, the disease or medical condition is a neurodegenerative disorder. In other embodiments, the disease or medical condition is a peripheral degenerative disorder. In some embodiments, the disease or medical condition is Alzheimer's Disease, Parkinson's Disease, fronto-temporal dementia, dementia with Lewy Bodies, PD dementia, multiple system atrophy, Huntington's disease, Amyotrophic lateral sclerosis, cancer, infection, Crohn's disease, heart disease, Paget's disease, Charcot-Marie-Tooth Disease, macular degeneration, cardiomyopathy, or aging.

Also provided herein is the use of a compound of Formula (I), (II), or (III), or a compound of Table 1, or a pharmaceutically acceptable salt thereof in the manufacture of a medicament for treatment of a disease or condition associated with autophagy or the PI3K-AKT-MTOR pathway. In some embodiments, provided is the use of at least one chemical entity as described herein in the manufacture of a medicament for treatment of a disease or condition associated with autophagy or the PI3K-AKT-MTOR pathway.

In some embodiments, the disease or medical condition is a neurodegenerative disorder. In other embodiments, the disease or medical condition is a peripheral degenerative disorder. In some embodiments, the disease or condition is selected from Alzheimer's Disease, Parkinson's Disease, fronto-temporal dementia, dementia with Lewy Bodies, PD dementia, multiple system atrophy, Huntington's disease, Amyotrophic lateral sclerosis, cancer, infection, Crohn's disease, heart disease, Paget's disease, Charcot-Marie-Tooth Disease, macular degeneration, cardiomyopathy, and aging.

Also provided are methods for interfering with the PI3K-AKT-MTOR pathway in a cell, or modulating, preventing, slowing, reversing, or inhibiting the PI3K-AKT-MTOR pathway in a cell which involves contacting the cell with an effective amount of at least one compound of Formula (I), (II), or (III), or a compound of Table 1, or a pharmaceutically acceptable salt thereof. In some embodiments, provided are methods for interfering with the PI3K-AKT-MTOR pathway in a cell, or modulating, preventing, slowing, reversing, or inhibiting the PI3K-AKT-MTOR pathway in a cell which involves contacting the cell with an effective amount of at least one chemical entity as described herein.

Also provided herein are compositions containing one or more compounds of Formula (I), (II), or (III), or a compound of Table 1, or a pharmaceutically acceptable salt of any of the foregoing, for use in interfering with the PI3K-AKT-MTOR pathway in a cell, or modulating, preventing, slowing, reversing, or inhibiting the PI3K-AKT-MTOR pathway in a cell. In some embodiments, provided are compositions containing at least one chemical entity as described herein for use in interfering with the PI3K-AKT-MTOR pathway in a cell, or modulating, preventing, slowing, reversing, or inhibiting the PI3K-AKT-MTOR pathway in a cell.

Additionally provided herein is the use of at least one chemical entity as described herein, such as a compound of Formula (I), (I), or (III), or a compound of Table 1, or a pharmaceutically acceptable salt of any of the foregoing in the manufacture of a medicament for interfering with the PI3K-AKT-MTOR pathway, or modulating, preventing, slowing, reversing, or inhibiting the PI3K-AKT-MTOR pathway.

Kits

Also provided are articles of manufacture and kits containing any of the compounds or pharmaceutical compositions provided herein. The article of manufacture may comprise a container with a label. Suitable containers include, for example, bottles, vials, and test tubes. The containers may be formed from a variety of materials such as glass or plastic. The container may hold a pharmaceutical composition provided herein. The label on the container may indicate that the pharmaceutical composition is used for preventing, treating or suppressing a condition described herein, and may also indicate directions for either in vivo or in vitro use.

In one aspect, provided herein are kits containing a compound or composition described herein and instructions for use. The kits may contain instructions for use in the treatment of a disease or condition associated with the PI3K-AKT-MTOR pathway in an individual in need thereof. A kit may additionally contain any materials or equipment that may be used in the administration of the compound or composition, such as vials, syringes, or IV bags. A kit may also contain sterile packaging.

Chemical Synthesis

The embodiments are also directed to processes and intermediates useful for preparing subject compounds or a salt or solvate or stereoisomer thereof.

Many general references providing commonly known chemical synthetic schemes and conditions useful for synthesizing the disclosed compounds are available (see, e.g., Smith and March, March's Advanced Organic Chemistry: Reactions, Mechanisms, and Structure, Fifth Edition, Wiley-Interscience, 2001.)

Compounds as described herein can be purified by any of the means known in the art, including chromatographic means, such as high performance liquid chromatography (HPLC), preparative thin layer chromatography, flash column chromatography and ion exchange chromatography. Any suitable stationary phase can be used, including normal and reversed phases as well as ionic resins. Most typically the disclosed compounds are purified via silica gel and/or alumina chromatography. See, e.g., Introduction to Modern Liquid Chromatography, 2nd ed., ed. L. R. Snyder and J. J. Kirkland, John Wiley and Sons, 1979; and Thin Layer Chromatography, E. Stahl (ed.), Springer-Verlag, New York, 1969.

During any of the processes for preparation of the subject compounds, it may be necessary and/or desirable to protect sensitive or reactive groups on any of the molecules concerned. This may be achieved by means of conventional protecting groups as described in standard works, such as T. W. Greene and P. G. M. Wuts, "Protective Groups in Organic Synthesis," $4^{th}$ ed., Wiley, New York 2006. The protecting groups may be removed at a convenient subsequent stage using methods known from the art.

Exemplary chemical entities useful in methods of the embodiments will now be described by reference to illustrative synthetic schemes for their general preparation herein and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Furthermore, one of skill in the art will recognize that the transformations shown in the schemes below may be performed in any order that is compatible with the functionality of the particular pendant groups. Each of the reactions depicted in the general schemes is preferably run at a temperature from about 0° C. to the reflux temperature of the organic solvent used. Unless otherwise specified, the variables are as defined above in reference to Formula (I). Isotopically labeled compounds as described herein are prepared according to the methods described below, using suitably labeled starting materials. Such materials are generally available from commercial suppliers of radiolabeled chemical reagents.

Representative syntheses for compounds of Formula (I) are described in Schemes 1-3 and A-Q, and the particular examples that follow.

In some embodiments, compounds provided herein may be synthesized according to Scheme 1.

Scheme 1

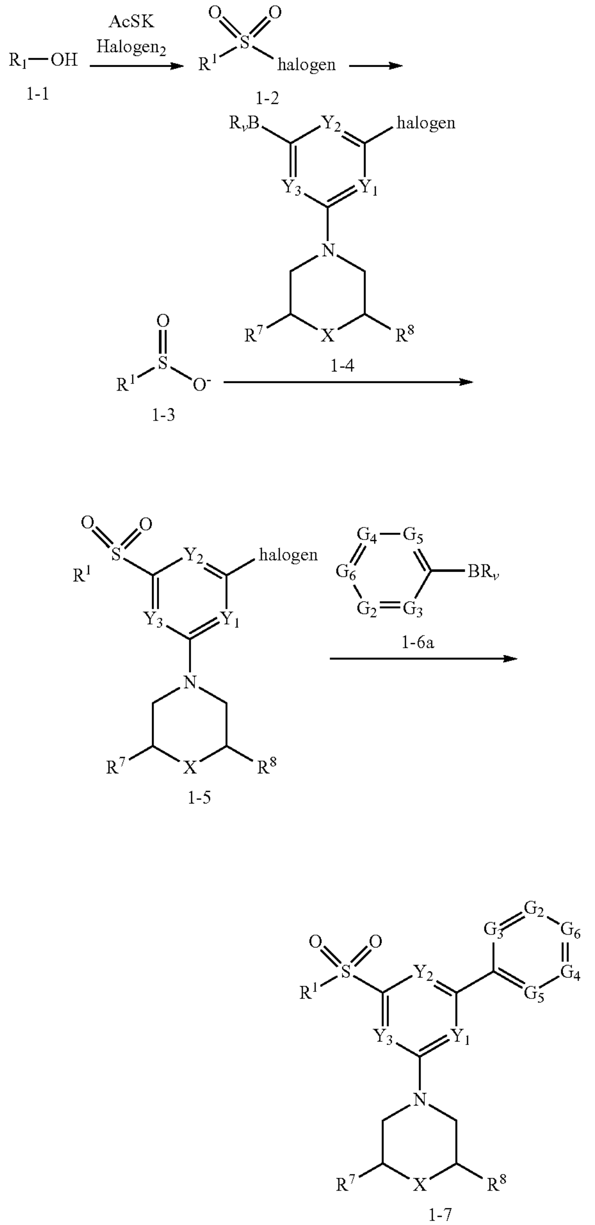

wherein $R^1$, $R^7$, $R^8$, $Y_1$, $Y_2$, $Y_3$, $G_2$, $G_3$, $G_4$, $G_5$, $G_6$, and X are as defined for Formula (I), (II), (III), or any variation thereof detailed herein, v is 2 or 3, and R is —OH, —Oalkyl, or halogen, or —$BR_v$ is

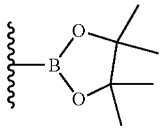

or

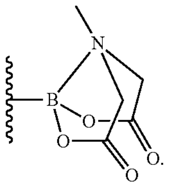

In some embodiments, compounds provided herein may be synthesized according to Scheme A.

Scheme A

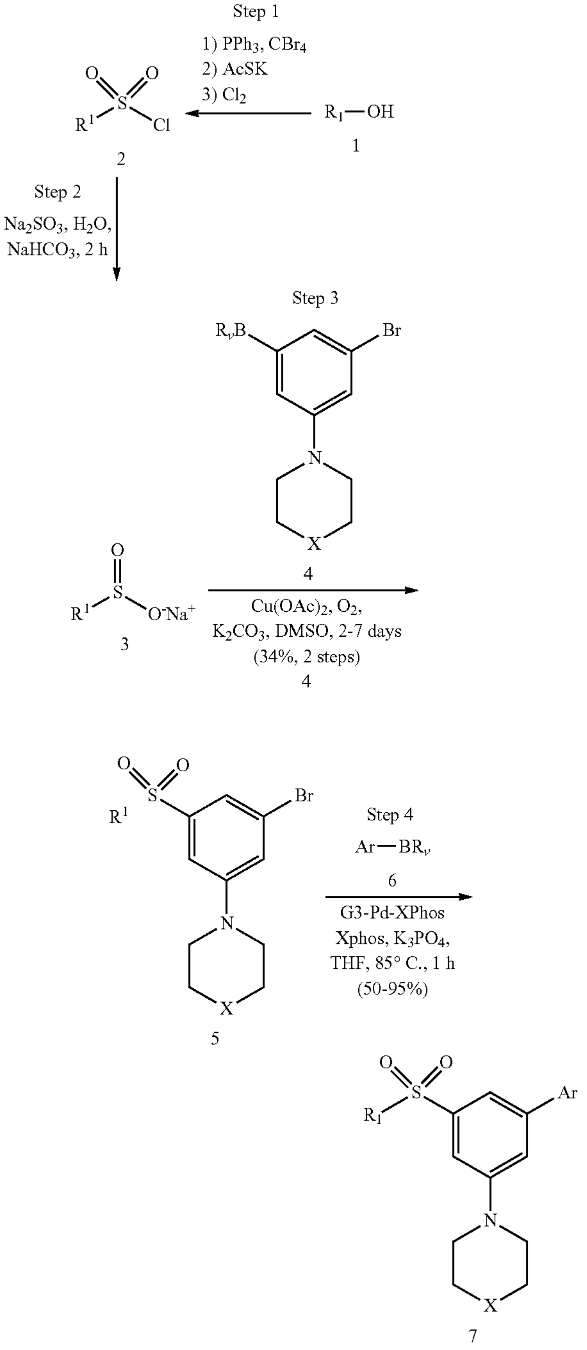

wherein Ar is

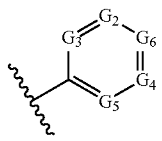

and $R^1$, $G_2$, $G_3$, $G_4$, $G_5$, $G_6$, and X are as defined Formula (I), (II), (III), or any variation thereof detailed herein, v is 2 or 3, and R is —OH, —Oalkyl, or halogen, or —$BR_v$ is

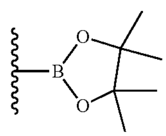

or

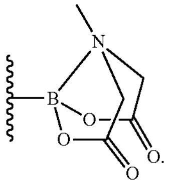

In some embodiments, compounds provided herein may be synthesized according to Scheme B.

wherein Ar is

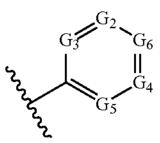

and $R^1$, $G_2$, $G_3$, $G_4$, $G_5$, $G_6$, X, and $R^x$ are as defined for Formula (I), (II), (III), or any variation thereof detailed herein, v is 2 or 3, and R is —OH, —Oalkyl, or halogen, or —$BR_v$ is

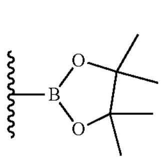

or

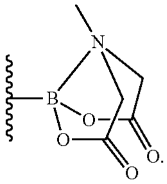

Scheme B.

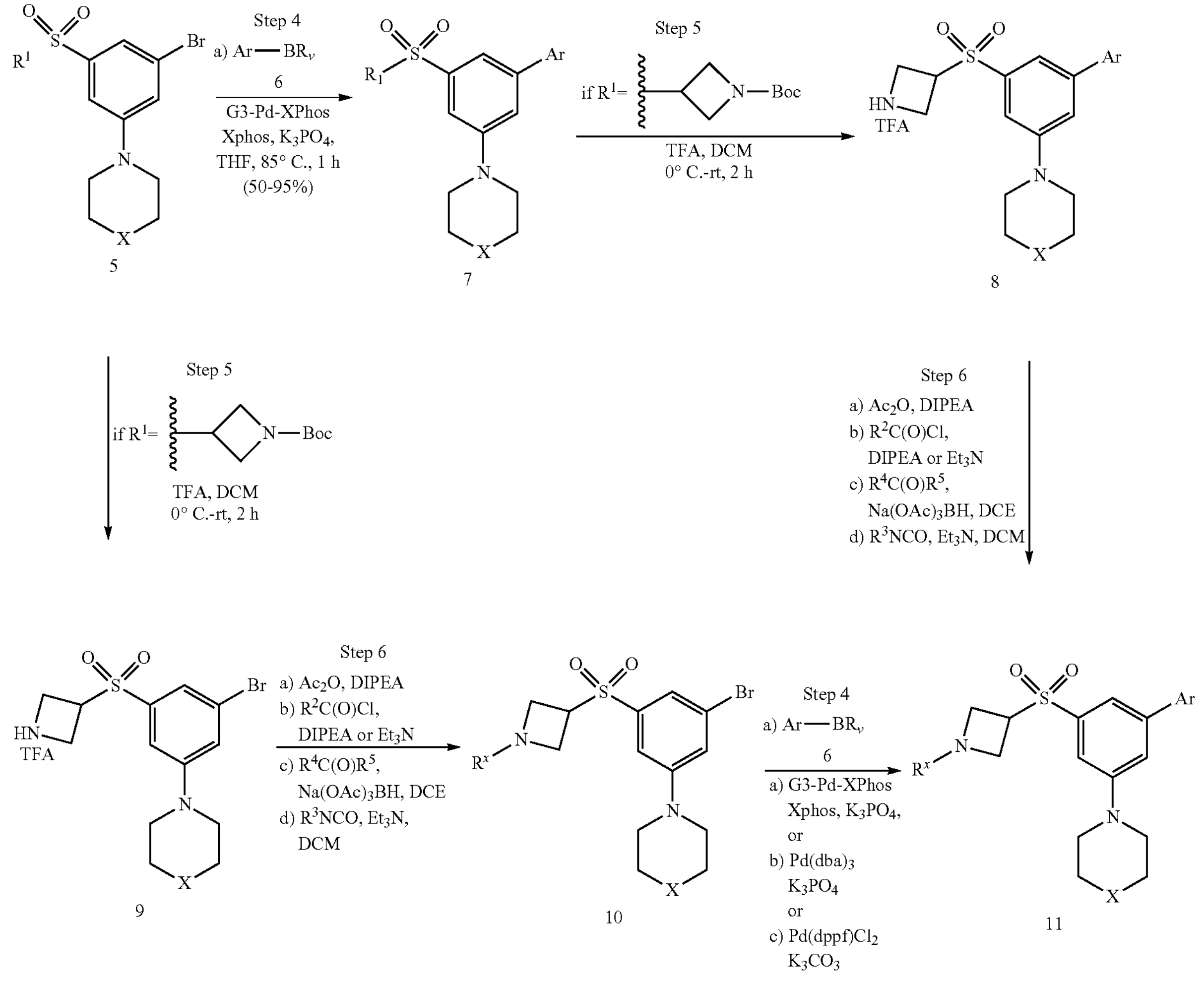

In some embodiments, compounds provided herein may be synthesized according to Scheme C.

Scheme C

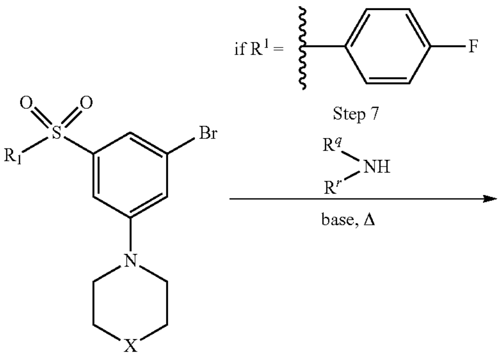

5

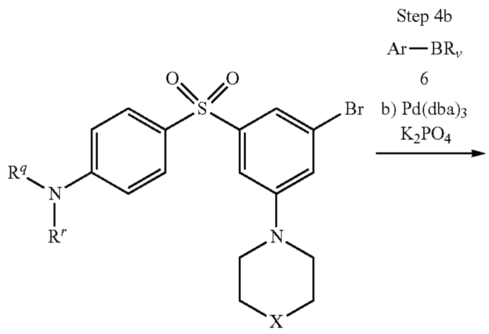

12

-continued

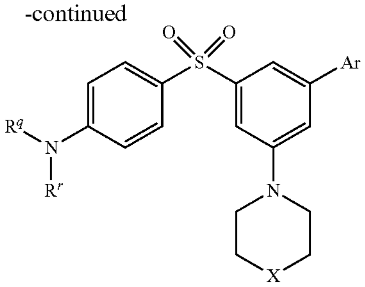

13 wherein Ar is

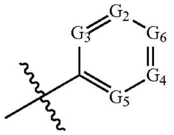

and $R^1$, $R^q$, R, $G_2$, $G_3$, $G_4$, $G_5$, $G_6$, and X are as defined for Formula (I), (II), (III), or any variation thereof detailed herein, v is 2 or 3, and R is —OH, —Oalkyl, or halogen, or $—BR_v$ is

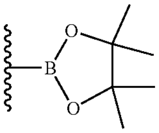

or

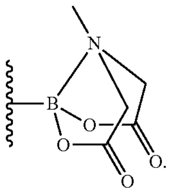

In some embodiments, compounds provided herein may be synthesized according to Scheme D.

Scheme D

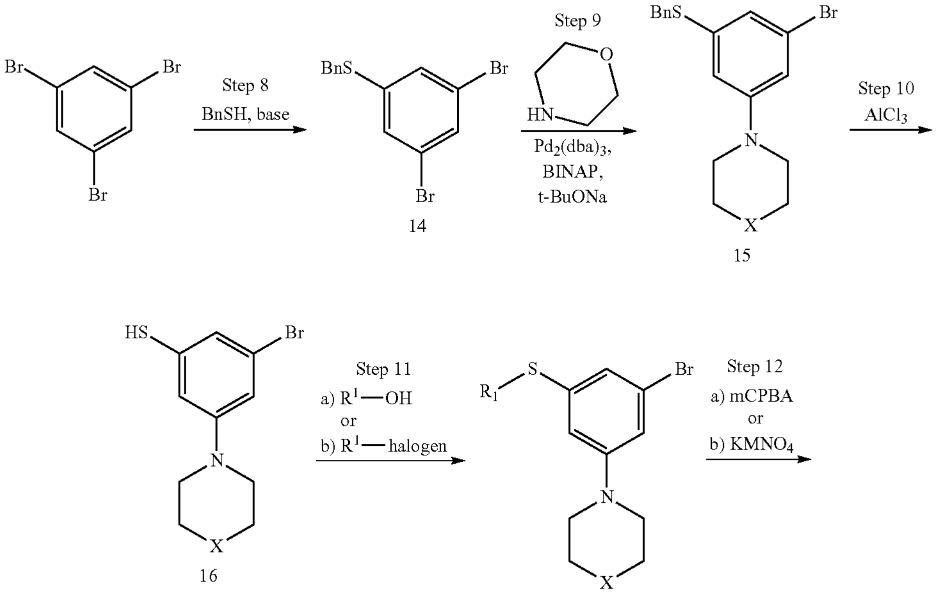

17

-continued
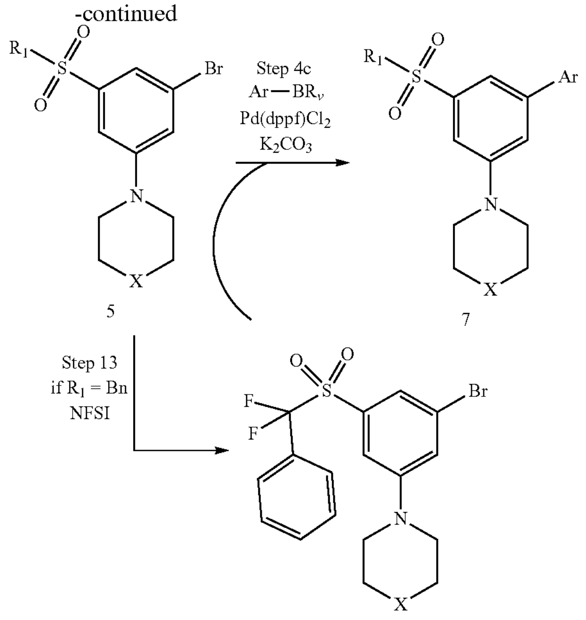
5 7 18
wherein Ar is
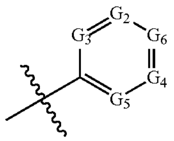
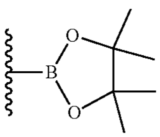
or
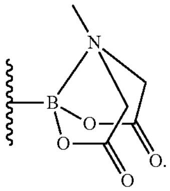
and R[1], $G_2$, $G_3$, $G_4$, $G_5$, $G_6$, and X are as defined for Formula (I), (II), (III), or any variation thereof detailed herein, v is 2 or 3, and R is —OH, —Oalkyl, or halogen, or —BR$_v$ is
In some embodiments, compounds provided herein may be synthesized according to Scheme E.
Scheme E
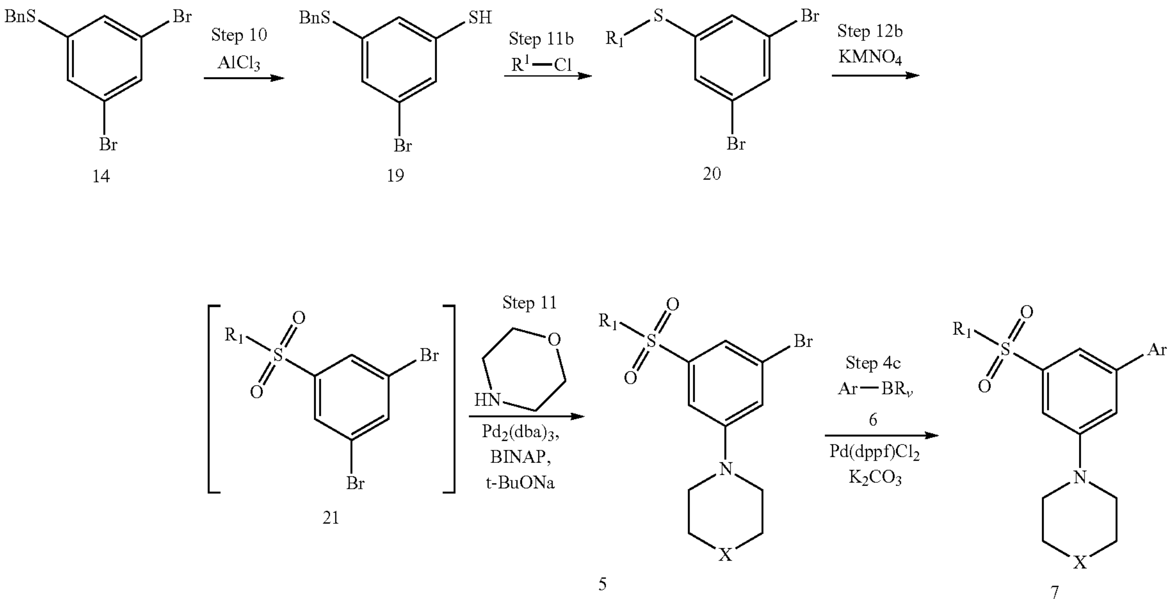
14 19 20 21 5 7

-continued

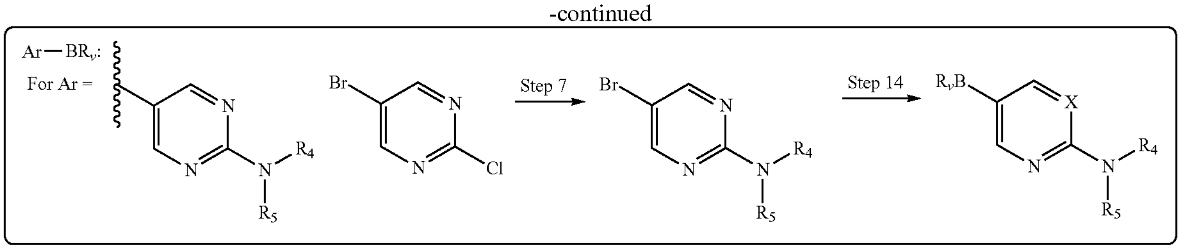

wherein Ar is

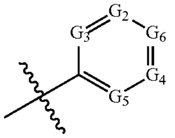

and $R^1$, $G_2$, $G_3$, $G_4$, $G_5$, and $G_6$ are as defined for Formula (I), (II), (III), or any variation thereof detailed herein, v is 2 or 3, and R is —OH, —Oalkyl, or halogen, or —$BR_v$ is

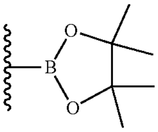

or

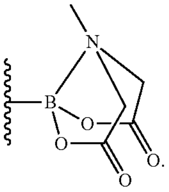

In some embodiments, compounds provided herein may be synthesized according to Scheme F.

Scheme F

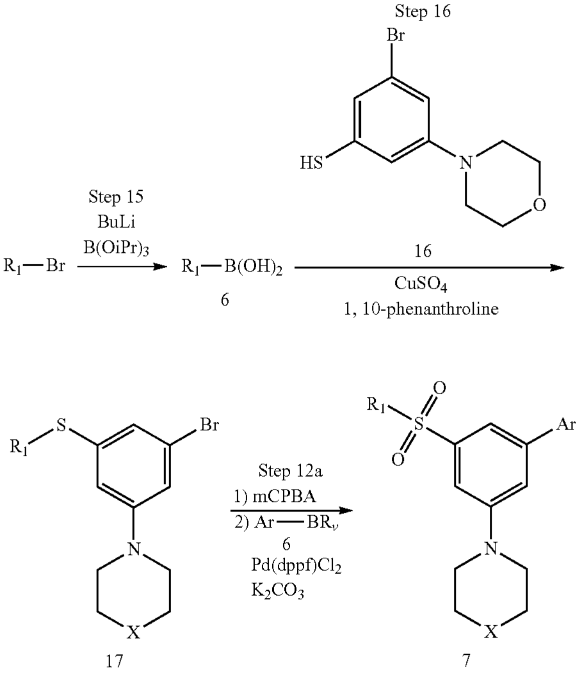

wherein Ar is

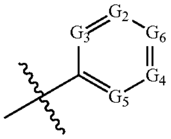

and $R^1$, $G_2$, $G_3$, $G_4$, $G_5$, and $G_6$ are as defined for Formula (I), (II), (III), or any variation thereof detailed herein, v is 2 or 3, and R is —OH, —Oalkyl, or halogen, or —$BR_v$ is

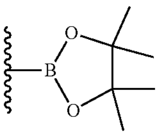

or

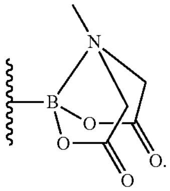

In some embodiments, compounds provided herein may be synthesized according to Scheme G.

Scheme G

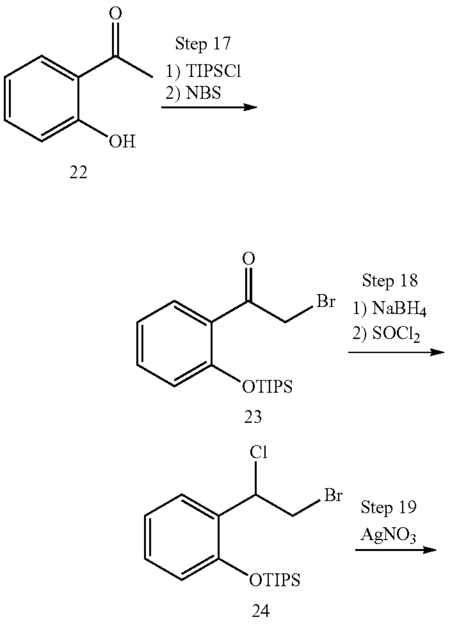

-continued
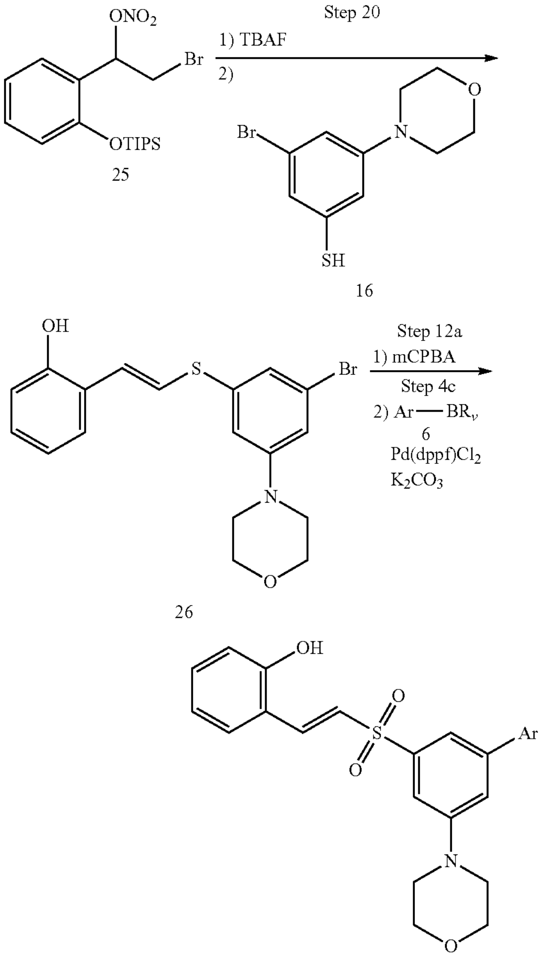
25
16
26
27
wherein Ar is
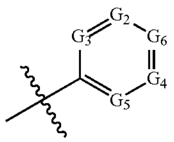
and $G_2$, $G_3$, $G_4$, $G_5$, and $G_6$ are as defined for Formula (I), (II), or (III), or any variation thereof detailed herein, v is 2 or 3, and R is —OH, —Oalkyl, or halogen, or —$BR_v$ is
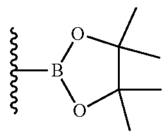
or
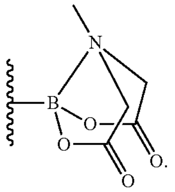
In some embodiments, compounds provided herein may be synthesized according to Scheme H.
Scheme H
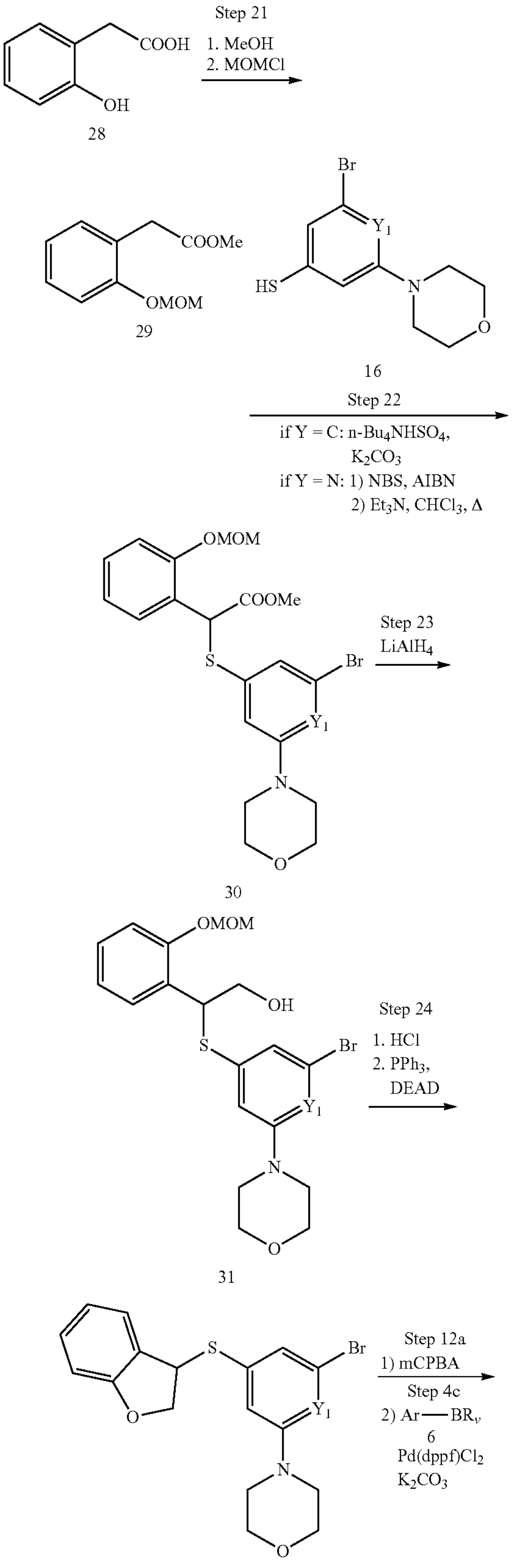
28
29
16
30
31
32

-continued

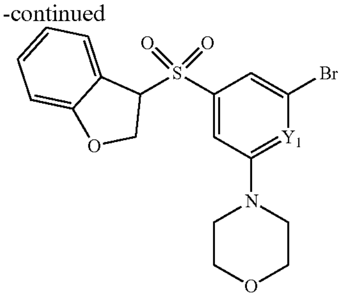

33 wherein Ar is

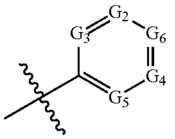

and $R^1$, $G_2$, $G_3$, $G_4$, $G_5$, $G_6$, and $Y_1$ are as defined for Formula (I), (II), or (III), or any variation thereof detailed herein, v is 2 or 3, and R is —OH, —Oalkyl, or halogen, or —$BR_v$ is

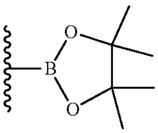

or

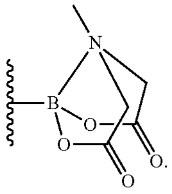

In some embodiments, compounds provided herein may be synthesized according to Scheme I.

Scheme I

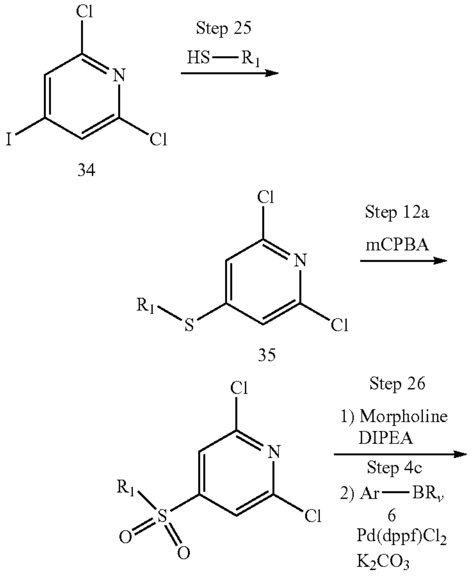

-continued

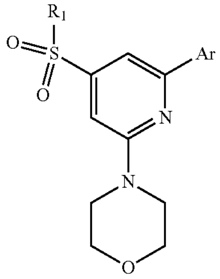

37 wherein Ar is

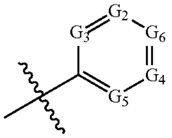

and $R^1$, $G_2$, $G_3$, $G_4$, $G_5$, and $G_6$ are as defined for Formula (I), (II), or (III), or any variation thereof detailed herein, v is 2 or 3, and R is —OH, —Oalkyl, or halogen, or —$BR_v$ is

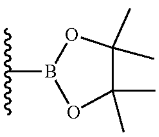

or

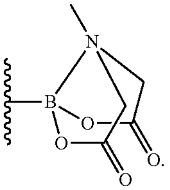

In some embodiments, compounds provided herein may be synthesized according to Scheme J.

Scheme J

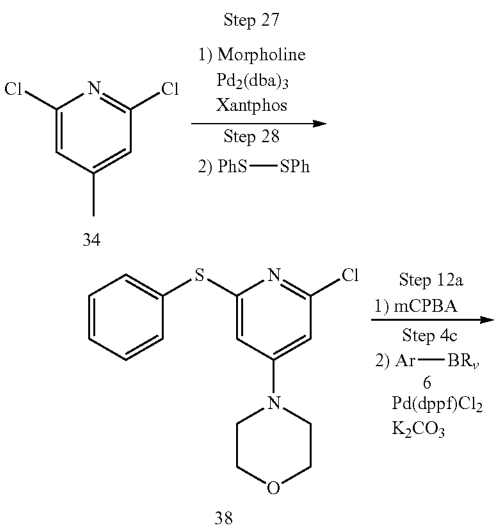

-continued

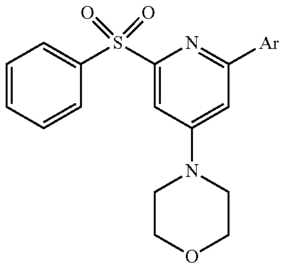

39 wherein Ar is

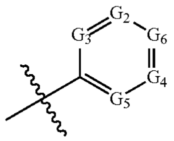

and $G_2$, $G_3$, $G_4$, $G_5$, and $G_6$ are as defined for Formula (I), (II), or (III), or any variation thereof detailed herein, v is 2 or 3, and R is —OH, —Oalkyl, or halogen, or —$BR_v$ is

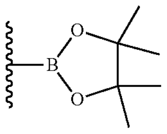

or

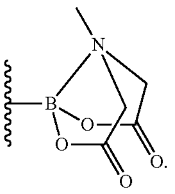

In some embodiments, compounds provided herein may be synthesized according to Scheme K.

Scheme K

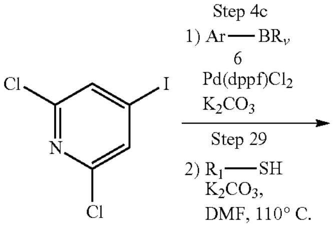

34

-continued

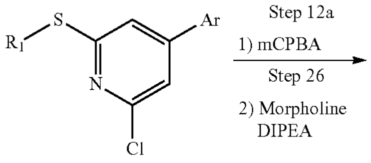

40

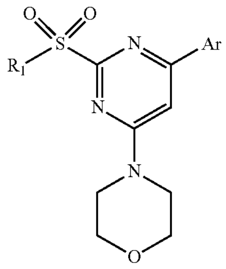

41 wherein Ar is

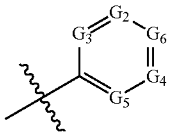

and $G_2$, $G_3$, $G_4$, $G_5$, $G_6$, and $R^1$ are as defined for Formula (I), (II), or (III), or any variation thereof detailed herein, v is 2 or 3, and R is —OH, —Oalkyl, or halogen, or —$BR_v$ is

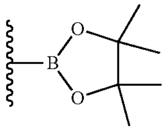

or

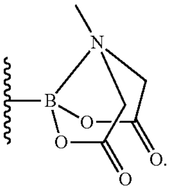

In some embodiments, compounds provided herein may be synthesized according to Scheme L.

Scheme L
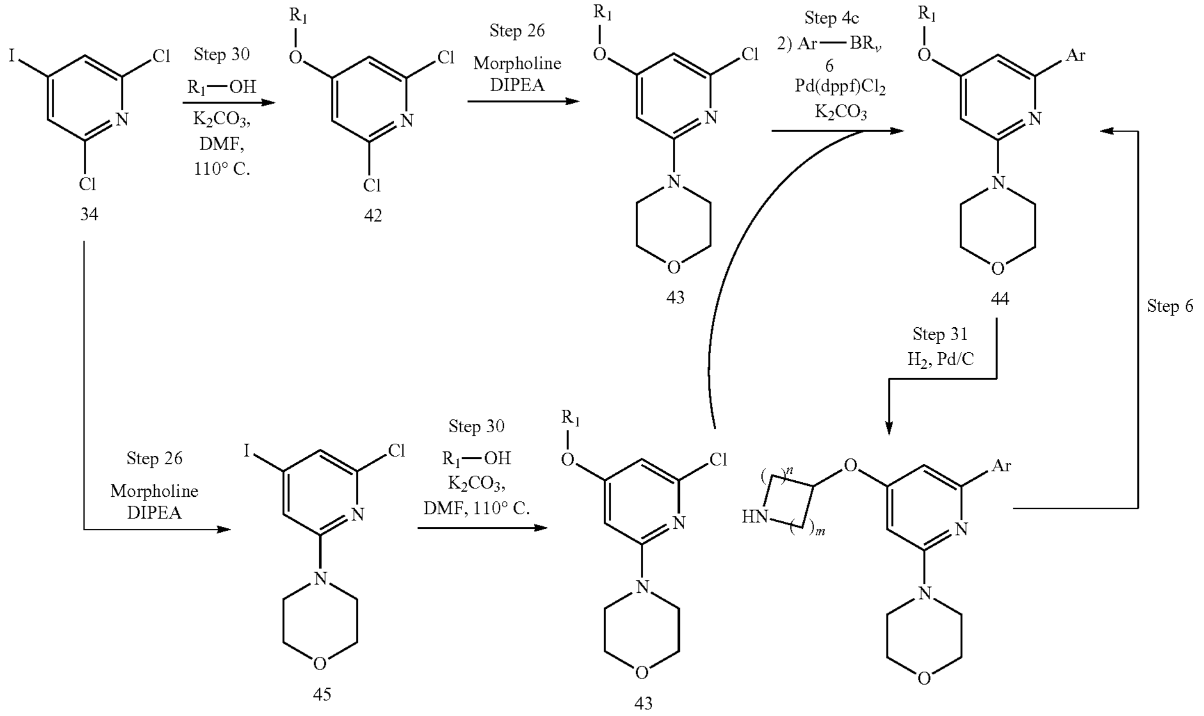
wherein Ar is
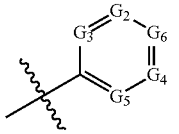
and $R^1$, $G_2$, $G_3$, $G_4$, $G_5$, and $G_6$ are as defined for Formula (I), (II), or (III), or any variation thereof detailed herein, n and m are each independently 0, 1, 2, 3, or 4, v is 2 or 3, and R is —OH, —Oalkyl, or halogen, or —$BR_v$ is
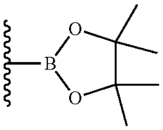
or
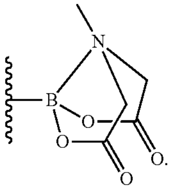
In some embodiments, compounds provided herein may be synthesized according to Scheme M.
Scheme M
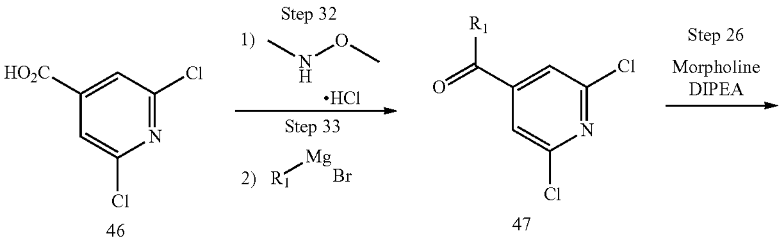

-continued
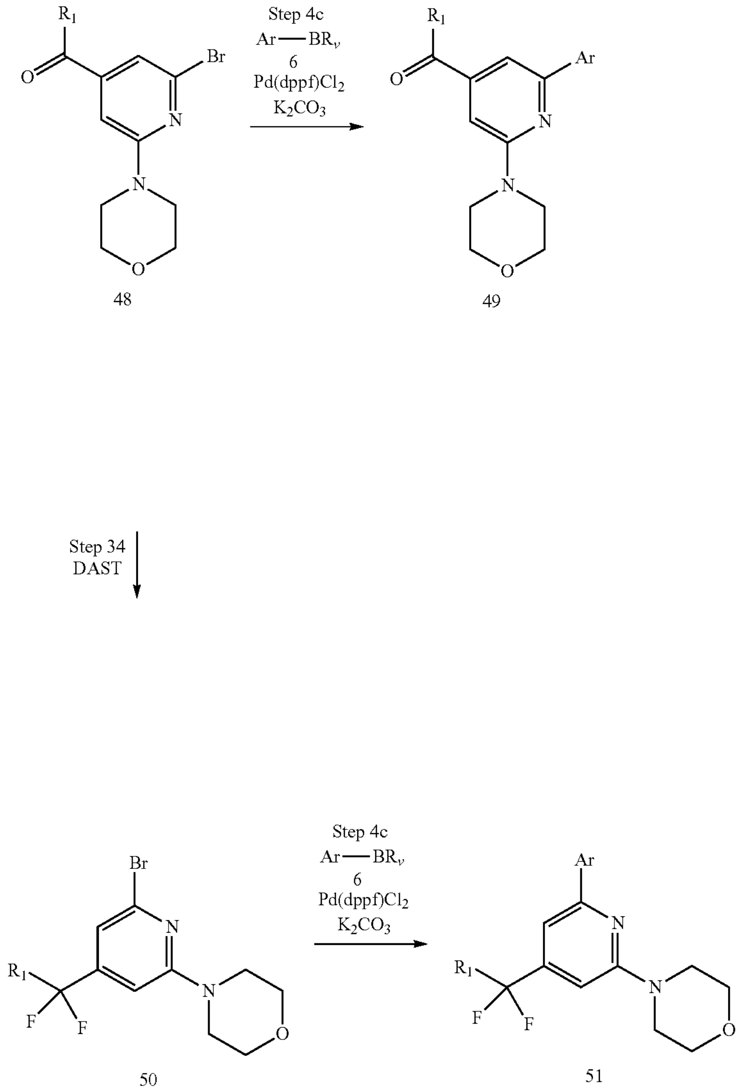
wherein Ar is
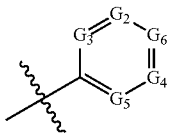
and $R^1$, $G_2$, $G_3$, $G_4$, $G_5$, and $G_6$ are as defined for Formula (I), (II), or (III), or any variation thereof detailed herein, v is 2 or 3, and R is —OH, —Oalkyl, or halogen, or —$BR_v$ is
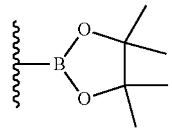
or
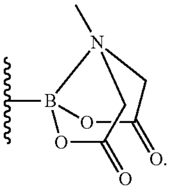
In some embodiments, compounds provided herein may be synthesized according to Scheme N.

Scheme N
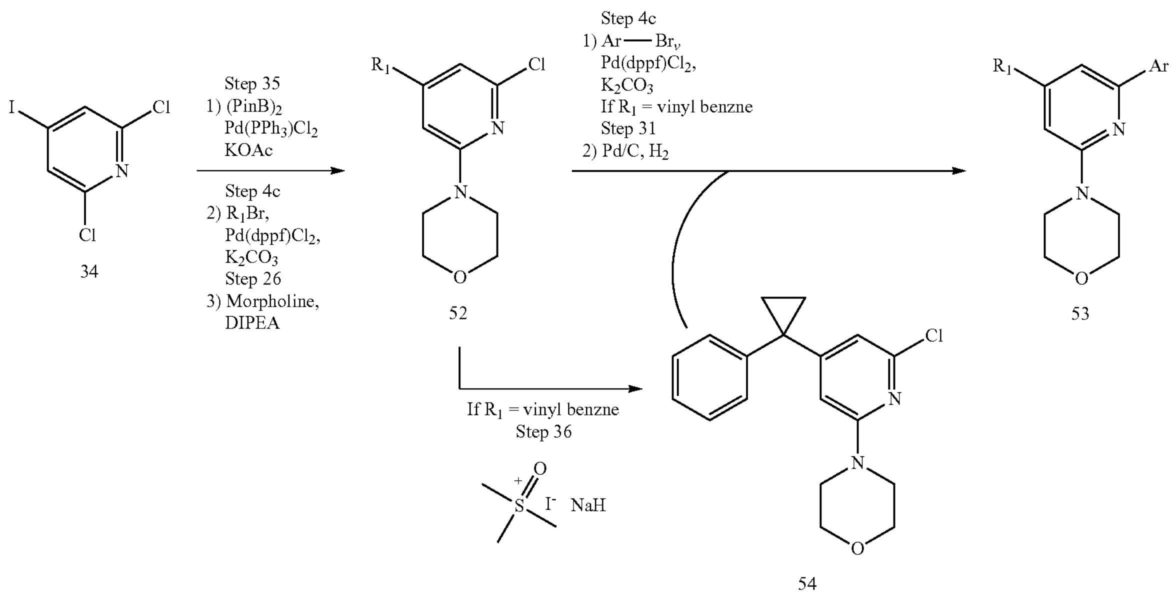
34 52 53 54
wherein Ar is
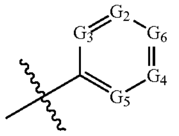
and $G_2$, $G_3$, $G_4$, $G_5$, and $G_6$ are as defined for Formula (I), (II), or (III), or any variation thereof detailed herein, v is 2 or 3, and R is —OH, —Oalkyl, or halogen, or —$BR_v$ is
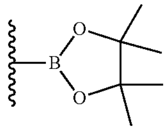
or
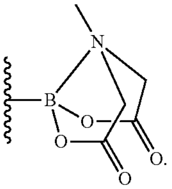
In some embodiments, compounds provided herein may be synthesized according to Scheme O.
Scheme O
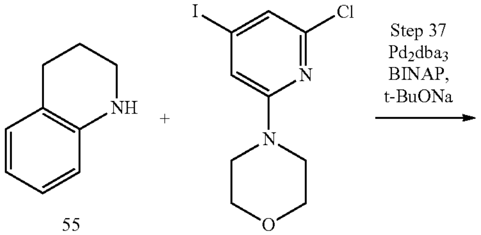
55 44
-continued
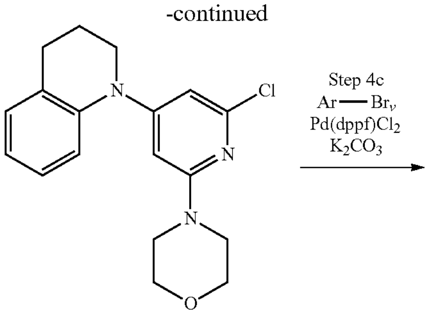
56
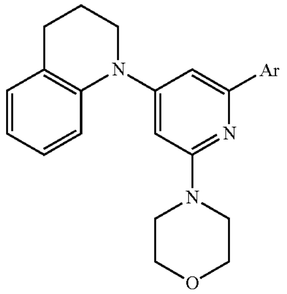
57
wherein Ar is
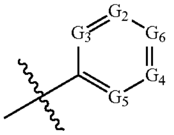

and $G_2$, $G_3$, $G_4$, $G_5$, and $G_6$ are as defined for Formula (I), (II), or (III), or any variation thereof detailed herein, v is 2 or 3, and R is —OH, —Oalkyl, or halogen, or —$BR_v$ is

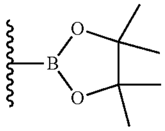

or

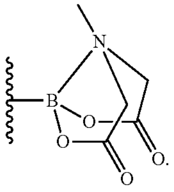

In some embodiments, compounds provided herein may be synthesized according to Scheme P.

Scheme P

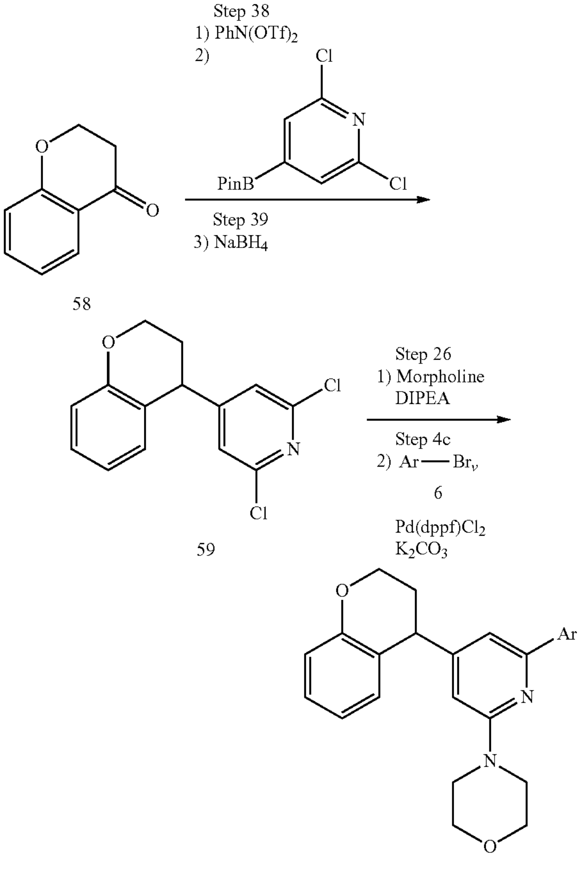

58

59

60 wherein Ar is

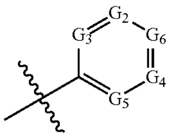

and $G_2$, $G_3$, $G_4$, $G_5$, and $G_6$ are as defined for Formula (I), (II), or (III), or any variation thereof detailed herein, v is 2 or 3, and R is —OH, —Oalkyl, or halogen, or —$BR_v$ is

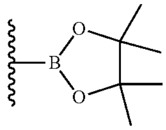

or

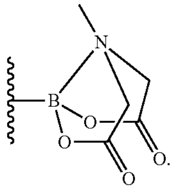

In some embodiments, compounds provided herein may be synthesized according to Scheme Q.

Scheme Q

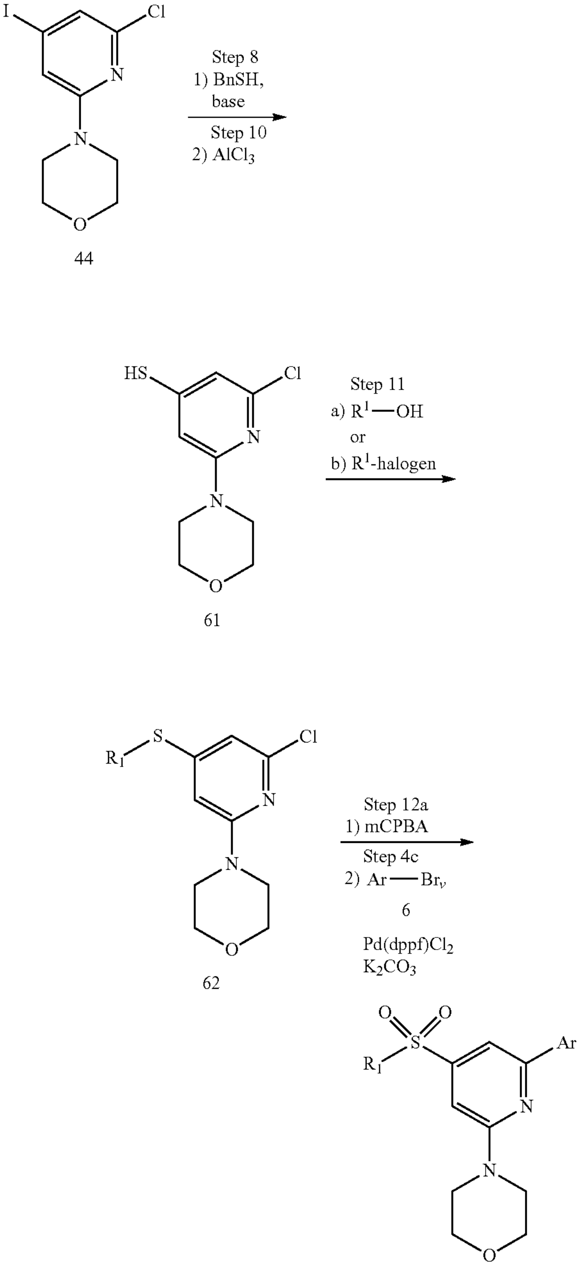

44

61

62

63 wherein Ar is

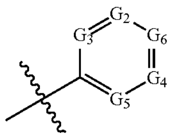

and $R^1$, $G_2$, $G_3$, $G_4$, $G_5$, and $G_6$ are as defined for Formula (I), (II), or (III), or any variation thereof detailed herein, v is 2 or 3, and R is —OH, —Oalkyl, or halogen, or —$BR_v$ is

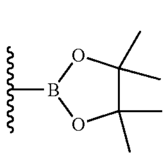

or

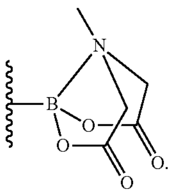

In some embodiments, the above processes described in Schemes 1 or A-Q further include the step of forming a salt, including a pharmaceutically acceptable salt, of a compound of the present disclosure. Salt forms may be prepared using standard salt formation procedures known in the art.

Embodiments are directed to the other processes described herein; and to the product prepared by any of the processes described herein. Particular non-limiting examples are provided in the Example section below.

EXAMPLES

The following examples are offered to illustrate but not to limit the compositions, uses, and methods provided herein. The compounds are prepared using the general methods described above.

The following chemical abbreviations are used throughout the Examples: AcSK (potassium thioacetate), BINAP (2,2'-bis(diphenylphosphino)-1,1'-binaphthyl), CDI (1,1'-Carbonyldiimidazole), DAST (Diethylaminosulfur trifluoride), DBU (1,8-Diazabicyclo[5.4.0]undec-7-ene), DCE (dichloroethane), DCM (dichloromethane), DEAD (Diethyl azodicarboxylate), DMAP (4-dimethylaminopyridine), DMF (N,N-dimethylformamide), DMSO (dimethyl sulfoxide), DIPEA (N,N-Diisopropylethylamine), EA (Ethyl acetate), EtOH (ethanol), iPrOH (propan-2-ol), mCPBA (meta-Chloroperoxybenzoic acid), MeOH (methanol), MOMCl (Chloromethyl methyl ether), NaHMDS (Sodium bis(trimethylsilyl)amide), NBS (N-bromosuccinimide), PTSA (p-toluenesulfonic acid), SNAr (nucleophilic aromatic substitution), TEA (trimethylamine), TFA (trifluoroacetic acid), THF (tetrahydrofuran), TIPS (triisopropylsilane), and TIPSCl (triisopropylsilyl chloride).

Example 1: 5-(3-morpholino-5-(phenylsulfonyl)phenyl)pyrimidin-2-amine (Compound 1)

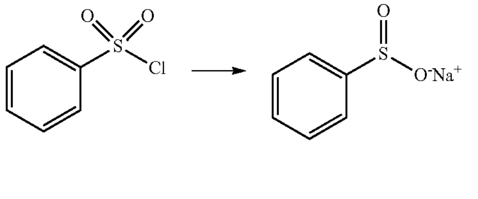

Step 1 (see Scheme A, Step 2): Synthesis of sodium benzenesulfinate from benzenesulfonyl chloride. (Adapted from PCT Int. Appl., 2012031199, 8 Mar. 2012; sodium benzenesulfinate is also available from commercial sources).

Sodium sulfite (10.7 g, 85 mmol) was added to 23 mL of water. After complete dissolution, the solution was cooled to 0° C. and 5 g of benzenesulfonyl chloride (28.3 mmol) was added dropwise. Sodium bicarbonate ($NaHCO_3$) was added portion-wise to keep the solution basic (~5.0 g). Reaction was warmed to room temperature and stirred 2 hours. Water on was removed via rotary evaporator and any remaining water was lyophilized overnight. Solid was taken up in methanol and filtered. The filtrate was concentrated under reduced pressure. The resultant solid was taken up in methanol and filtered, evaporated, and dried under high vacuum and used as is in next reaction.

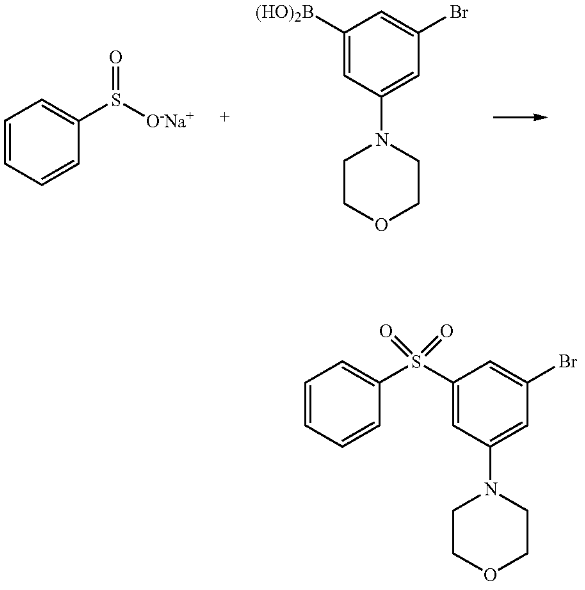

Step 2 (see Scheme A, Step 3): Synthesis of 4-(3-bromo-5-(phenylsulfonyl)phenyl)morpholine. (*Tetrahedron Letters,* 2004, 45 (16), 3233.)

To a round bottom flask equipped with an air drying tube (filled with drierite) was added 3-bromo-5-morpholinophenyl boronic acid (3.5 g, 12.3 mmol, 1 equiv.), 1.1 equiv. of $Cu(OAc)_2$ (2.5 g, 13.5 mmol), 2.3 equiv. of sodium phenyl sulfinate (28.3 mmol), 2 equiv. of $K_2CO_3$ (7.82 g, 56.6 mmol), and 4 Å MS (7 g, 200% wt/wt). DMSO (50 mL, 0.25 M) was added and the mixture was stirred for 72 h at rt and then filtered on a Celite pad eluted with dichloromethane. The filtrate was diluted with dichloromethane and aqueous saturated ammonium chloride and the aqueous layers were extracted with DCM. The combined organic layers were washed with brine, dried over $Na_2SO_4$, filtered, and concentrated. The residue was purified by flash column chromatography (0-5% (0.5M $NH_3$/MeOH)/DCM) to afford the desired product (1.58 g, 4.13 mmol, 34% yield). ESMS+: 404.1, 406.1 $(M+Na)^+$, $C_{16}H_{16}BrNO_3S$. $^1H$ NMR ($CDCl_3$, 500 MHz) δ: 7.93 (dd, J=7.5, 1.5 Hz, 2H), 7.59-7.59 (td, J=7.5, 2 Hz, 1H), 7.53 (td, J=7.5, 1.5 Hz, 2H), 7.45 (t, J=1.5 Hz, 1H), 7.36 (t, J=2 Hz, 1H), 7.21 (t, J=2.0 Hz, 1H), 3.85-3.83 (m, 4H), 3.20 (dd, J=4.5, 4.5 Hz, 4H).

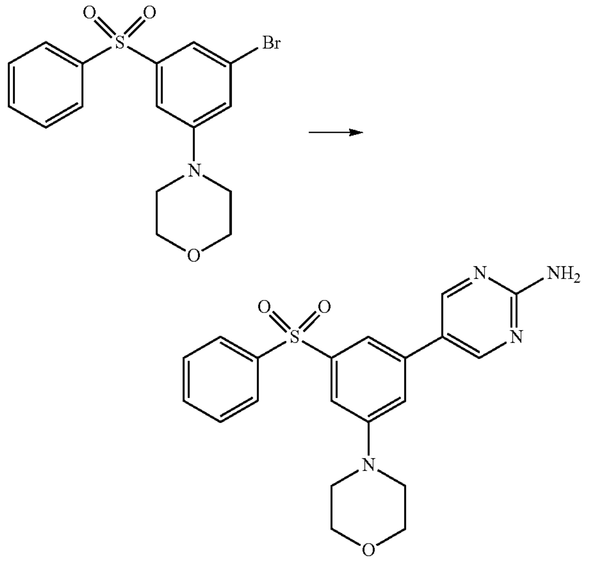

Compound 1

Step 3 (see Scheme A, Step 4): Synthesis of 5-(3-morpholino-5-(phenylsulfonyl)phenyl)pyrimidin-2-amine (*Chem. Sci.,* 2013, 4, 916.)

A vial, equipped with a magnetic stir bar, was charged with Xphos (59 mg, 0.12 mmol), G-3 Xphos precatalyst (105 mg, 0.12 mmol), 4-(3-bromo-5-(phenylsulfonyl)phenyl)morpholine (1.58 g, 4.12 mmol) and (2-aminopyrimidin-5-yl)boronic acid (0.86 g, 6.2 mmol). The vessel was sealed with a screw-cap septum, and then evacuated and backfilled with argon. Degassed THF (8.24 mL) and degassed 0.5 M aqueous $K_3PO_4$ solution (16.5 mL) were added via syringe, and the reaction was stirred at 75° C. for 2.5 h. The reaction was cooled, then DCM (40 mL) and water (40 mL) were added to the mixture, and the aqueous phase was extracted with DCM (3×40 mL). The combined organic phase was dried over $Na_2SO_4$, concentrated in vacuo, and purified via column chromatography (0-7% (0.5 M $NH_3$/MeOH)/DCM) to afford the desired product (Compound 1) (1.15 g, 2.9 mmol, 70% yield). ESMS+: 397.5 (M+H), 419.3 (M+Na), $C_{16}H_{16}BrNO_3S$. $^1H$ NMR (DMSO, 500 MHz) δ: 8.61 (s, 2H), 8.09-8.01 (m, 2H), 7.71-7.64 (m, 1H), 7.64-7.56 (m, 2H), 7.52 (t, J=1.5 Hz, 1H), 7.38 (t, J=2.0 Hz, 1H), 7.32 (t, J=2.0 Hz, 1H), 6.88 (s, 2H), 3.74 (dd, J=6.1, 3.7 Hz, 4H), 3.27-3.23 (m, 4H).

The following compounds were prepared by methods analogous to the method described for Compound 1 and as described in Scheme A:

| Cmpd # | MS | $^1H$ NMR |
|---|---|---|
| 2 | 412.5 (M + H), 434.3 (M + Na) | ($CDCl_3$, 500 MHz) δ: 8.66 (s, 2H), 7.99-7.95 (m, 2H), 7.61-7.57 (m, 1H), 7.55-7.50 (m, 2H), 7.49-7.46 (m, 2H), 7.10 (dd, J = 2.4, 1.5 Hz, 1H), 4.07 (s, 3H), 3.90-3.86 (m, 4H), 3.28 (dd, J = 4.3, 2.6 Hz, 4H). |
| 3 | 465.5 (M + H), 487.4 (M + Na) | ($CDCl_3$, 500 MHz) δ: 8.33 (s, 1H), 7.95-7.91 (m, 2H), 7.61-7.56 (m, 1H), 7.54-7.49 (m, 2H), 7.47 (dd, J = 2.5, 1.6 Hz, 1H), 7.30-7.28 (m, 1H), 6.90 (t, |

-continued

| Cmpd # | MS | $^1H$ NMR |
|---|---|---|
| | | J = 1.9 Hz, 1H), 5.42 (bs, 2H), 3.88-3.82 (m, 4H), 3.26-3.19 (m, 4H). |
| 4 | 425.5 (M + H), 447.3 (M + Na) | ($CDCl_3$, 500 MHz) δ:8.48 (s, 2H), 7.99-7.92 (m, 2H), 7.60-7.54 (m, 1H), 7.55-7.47 (m, 2H), 7.45-7.37 (m, 2H), 7.05 (dd, J = 2.4, 1.5 Hz, 1H), 3.89-3.85 (m, 4H), 3.27-3.21 (m, 10H). |
| 5 | 411.4 (M + H), 433.3 (M + Na), 449.4 (M + K) | ($CDCl_3$, 500 MHz) δ: 8.32 (dd, J = 4.0, 2.5 Hz, 1H), 7.99-7.94 (m, 2H), 7.73 (ddd, J = 8.4, 5.8, 2.5 Hz, 1H), 7.60-7.54 (m, 1H), 7.53-7.47 (m, 3H), 7.43 (dd, J = 2.4, 1.5 Hz, 1H), 7.12 (dd, J = 2.5, 1.5 Hz, 1H), 6.82 (d, J = 8.7 Hz, 1H), 3.98 (s, 3H), 3.89-3.84 (m, 4H), 3.29-3.23 (m, 4H). |
| 6 | 464.5 (M + H), 486.3 (M + Na), 502.6 (M + K) | ($CDCl_3$, 500 MHz) δ: 8.01 (s, 1H), 7.95-7.91 (m, 2H), 7.59-7.55 (m, 1H), 7.53-7.48 (m, 2H), 7.45 (dd, J = 2.5, 1.6 Hz, 1H), 7.31 (s, 1H), 6.93 (d, J = 2.0 Hz, 1H), 6.79 (s, 1H), 5.16 (s, 2H), 3.88-3.81 (m, 4H), 3.24-3.18 (m, 4H). |
| 7 | 465.2 (M + H), 487.3 (M + Na) | ($CDCl_3$, 500 MHz) δ: 8.48 (s, 2H), 8.33 (d, J = 4.9 Hz, 1H), 8.23 (d, J = 1.8 Hz, 1H), 8.15 (d, J = 7.9 Hz, 1H), 7.84 (d, J = 7.8 Hz, 1H), 7.68 (t, J = 8.0 Hz, 1H), 7.44 (t, J = 1.5 Hz, 1H), 7.09 (dd, J = 2.4, 1.5 Hz, 1H), 5.21 (s, 2H), 3.92-3.84 (m, 4H), 3.31-3.24 (m, 4H). |
| 8 | 437.4 (M + Na) | (DMSO-d6, 500 MHz) δ: 8.62 (s, 2H), 8.18-8.11 (m, 2H), 7.53 (d, J = 1.5 Hz, 1H), 7.47-7.41 (m, 2H), 7.38 (t, J = 1.9 Hz, 1H), 7.33 (t, J = 1.9 Hz, 1H), 6.90 (s, 2H), 3.74 (dd, J = 6.0, 3.7 Hz, 4H), 3.27 (dd, J = 6.0, 3.8 Hz, 4H). |
| 9 | 469.4 (M + Na) | (CDCl3, 500 MHz) δ: 8.58 (d, J = 1.8 Hz, 1H), 8.48 (s, 2H), 8.01-7.97 (m, 1H), 7.95 (d, J = 8.7 Hz, 1H), 7.90-7.84 (m, 2H), 7.67-7.58 (m, 2H), 7.49 (dt, J = 6.1, 1.6 Hz, 2H), 7.04 (dd, J = 2.5, 1.5 Hz, 1H), 6.37 (s, 2H), 3.90-3.84 (m, 4H), 3.29-3.24 (m, 4H). |
| 10 | 422.3 (M + H), 444.2 (M + Na) | (CDCl3, 500 MHz) δ: 8.48 (s, 2H), 8.10-8.03 (m, 2H), 7.85-7.77 (m, 2H), 7.42 (t, J = 1.5 Hz, 1H), 7.39 (t, J = 2.0 Hz, 1H), 7.09 (t, J = 1.9 Hz, 1H), 5.31 (s, 2H), 3.90-3.85 (m, 4H), 3.29-3.25 (m, 4H). |
| 11 | 449.1 (M + H), 471.8 (M + Na) | (CDCl3, 500 MHz) δ: 8.65 (s, 2H), 8.36 (dd, J = 6.9, 2.4 Hz, 1H), 8.12 (ddd, J = 8.8, 4.5, 2.4 Hz, 1H), 7.65 (t, J = 8.9 Hz, 1H), 7.60 (t, J = 1.4 Hz, 1H), 7.39 (dt, J = 14.9, 2.0 Hz, 2H), 6.89 (s, 2H), 3.75 (t, J = 4.9 Hz, 4H), 3.28 (m, 4H). |
| 12 | 395.5 (M + H), 417.5 (M + Na), 433.5 (M + K) | (CDCl3, 500 MHz) δ: 8 8.52 (d, J = 20.9 Hz, 2H), 7.99-7.89 (m, 2H), 7.61-7.55 (m, 1H), 7.55-7.46 (m, 3H), 7.31-7.27 (m, 1H), 7.19 (d, J = 5.1 Hz, 1H), 6.92 (t, J = 2.0 Hz, 1H), 3.90-3.81 (m, 4H), 3.30-3.23 (m, 4H). |
| 13 | 422.1(M + H) | (DMSO-d6, 500 MHz) δ: 8.65 (s, 2H), 8.61 (t, J = 1.8 Hz, 1H), 8.38 (dt, J = 8.3, 1.4 Hz, 1H), 8.15 |

-continued

| Cmpd # | MS | $^1$H NMR |
|---|---|---|
| | | (dt, J = 7.8, 1.3 Hz, 1H), 7.81 (t, J = 7.9 Hz, 1H), 7.64-7.58 (m, 1H), 7.41 (d, J = 1.8 Hz, 1H), 7.38 (t, J = 2.0 Hz, 1H), 6.91 (s, 2H), 3.79-3.68 (m, 4H), 3.29 (t, J = 4.9 Hz, 4H). |
| 14 | 465.1 (M + H) | (DMSO-d6, 500 MHz) δ: 8.63 (s, 2H), 8.29 (d, J = 8.3 Hz, 2H), 7.98 (d, J = 8.3 Hz, 2H), 7.57 (d, J = 1.6 Hz, 1H), 7.42 (t, J = 2.0 Hz, 1H), 7.36 (t, J = 2.0 Hz, 1H), 6.91 (s, 2H), 3.74 (t, J = 4.8 Hz, 4H), 3.28 (t, J = 4.9 Hz, 4H). |
| 15 | 481.1 (M + H) | (DMSO-d6, 500 MHz) δ: 8.63 (s, 2H), 8.23-8.19 (m, 2H), 7.59 (dt, J = 7.8, 1.1 Hz, 2H), 7.57-7.55 (m, 1H), 7.41 (t, J = 1.9 Hz, 1H), 7.35 (t, J = 1.9 Hz, 1H), 6.91 (s, 2H), 3.77-3.70 (m, 4H), 3.30-3.25 (m, 4H). |
| 16 | 411.1 (M + H) | (DMSO-d6, 500 MHz) δ: 8.65 (s, 2H), 8.08-8.02 (m, 2H), 7.71-7.65 (m, 1H), 7.61 (dd, J = 8.5, 7.0 Hz, 2H), 7.52 (t, J = 1.5 Hz, 1H), 7.40-7.35 (m, 2H), 7.32 (t, J = 2.0 Hz, 1H), 3.74 (dd, J = 5.9, 3.8 Hz, 4H), 3.26 (dd, J = 5.9, 3.9 Hz, 4H), 2.84 (d, J = 4.8 Hz, 3H). |
| 17 | 490.1 (M + H) | (DMSO-d6, 500 MHz) δ: 8.41 (s, 1H), 8.17 (d, J = 8.5 Hz, 2H), 8.10 (d, J = 8.5 Hz, 2H), 7.44 (m, 3H), 7.28 (s, 1H), 7.21 (t, J = 1.9 Hz, 1H), 3.73 (dd, J = 6.0, 3.8 Hz, 4H), 3.24 (dd, J = 5.9, 3.9 Hz, 4H). |
| 18 | 489.1(M + H) | (DMSO-d6, 500 MHz) δ: 8.19-8.14 (m, 2H), 8.11-8.07 (m, 2H), 7.96 (s, 1H), 7.42 (t, J = 2.0 Hz, 1H), 7.22 (s, 1H), 7.14 (t, J = 1.9 Hz, 1H), 6.81 (s, 1H), 6.68 (s, 2H), 3.72 (dd, J = 6.1, 3.6 Hz, 4H), 3.23 (dd, J = 5.8, 3.9 Hz, 4H). |
| 19 | 441.2 (M + H) | (DMSO-d6, 500 MHz) δ: 8.64 (s, 2H), 8.07-8.03 (m, 2H), 7.71-7.65 (m, 1H), 7.61 (dd, J = 8.4, 7.0 Hz, 2H), 7.52 (t, J = 1.4 Hz, 1H), 7.38 (t, J = 2.0 Hz, 1H), 7.35-7.30 (m, 2H), 4.68 (t, J = 5.6 Hz, 1H), 3.74 (dd, J = 5.9, 3.7 Hz, 4H), 3.53 (q, J = 6.1 Hz, 2H), 3.39 (q, J = 6.2 Hz, 2H), 3.28-3.23 (m, 4H). |
| 20 | 437.1 (M + H) | (DMSO-d6, 500 MHz) δ: 8.67 (s, 2H), 8.07-8.03 (m, 2H), 7.70-7.64 (m, 2H), 7.61 (dd, J = 8.4, 7.0 Hz, 2H), 7.53 (t, J = 1.4 Hz, 1H), 7.39 (t, J = 1.9 Hz, 1H), 7.33 (t, J = 2.0 Hz, 1H), 3.74 (dd, J = 6.0, 3.8 Hz, 4H), 3.28-3.24 (m, 4H), 2.75 (tq, J = 7.3, 3.8 Hz, 1H), 0.69 (td, J = 6.9, 4.6 Hz, 2H), 0.51-0.47 (m, 2H). |
| 21 | 411.1(M + H) | (DMSO-d6, 500 MHz) δ: 8.60 (s, 2H), 7.95-7.89 (m, 2H), 7.51-7.48 (m, 1H), 7.40 (d, J = 8.1 Hz, 2H), 7.36 (t, J = 1.9 Hz, 1H), 7.30 (t, J = 1.9 Hz, 1H), 6.89 (s, 2H), 3.74 (dd, J = 6.0, 3.8 Hz, 4H), 3.29-3.22 (m, 4H), 2.36 (s, 3H). |
| 22 | 454.2 (M + H) | (DMSO-d6, 500 MHz) δ: 10.35 (s, 1H), 8.60 (s, 2H), 7.99-7.93 (m, 2H), 7.82-7.71 (m, 2H), 7.47 (t, J = 1.5 Hz, 1H), 7.36 (t, J = 1.9 Hz, 1H), 7.28 (t, J = 1.9 Hz, 1H), 6.89 (s, 2H), 3.74 (dd, J = 6.0, 3.8 Hz, 4H), 3.25 (dd, J = 5.9, 3.7 Hz, 4H), 2.07 (s, 3H). |
| 23 | 411.1 (M + H) | (DMSO-d6, 500 MHz) δ: 8.56 (s, 2H), 7.42 (d, J = 2.1 Hz, 1H), 7.35-7.27 (m, 3H), 7.25 (d, J = 1.5 Hz, 1H), 7.21 (dd, J = 7.2, 2.3 Hz, 2H), 7.03 (t, J = 1.9 Hz, 1H), 6.89 (s, 2H), 4.69 (s, 2H), 3.74 (t, J = 4.8 Hz, 4H), 3.22-3.16 (m, 4H). |
| 24 | 496.2(M + H) | (DMSO-d6, 500 MHz) δ: 8.61 (s, 2H), 8.09-8.02 (m, 2H), 7.71-7.65 (m, 1H), 7.61 (dd, J = 8.4, 7.0 Hz, 2H), 7.52 (t, J = 1.4 Hz, 1H), 7.38 (t, J = 1.9 Hz, 1H), 7.34 (t, J = 1.9 Hz, 1H), 6.90 (s, 2H), 3.46 (t, J = 5.1 Hz, 4H), 3.28 (dd, J = 6.4, 4.0 Hz, 4H), 1.42 (s, 9H). |
| 25 | 395.1 (M + H) | (DMSO-d6, 500 MHz) δ: 8.59 (s, 2H), 8.07-8.02 (m, 2H), 7.71-7.64 (m, 1H), 7.63-7.57 (m, 2H), 7.43 (t, J = 1.5 Hz, 1H), 7.34 (t, J = 1.9 Hz, 1H), 7.28 (t, J = 1.9 Hz, 1H), 6.87 (s, 2H), 3.29 (t, J = 5.3 Hz, 4H), 1.61 (dd, J = 7.5, 4.0 Hz, 4H), 1.56 (q, J = 7.3, 5.9 Hz, 2H). |
| 26 | 447.1 (M + H) | (DMSO-d6, 500 MHz) δ: 8.58 (s, 2H), 7.46 (t, J = 2.0 Hz, 1H), 7.33-7.27 (m, 2H), 7.24 (td, J = 9.6, 2.5 Hz, 1H), 7.10 (td, J = 8.5, 2.6 Hz, 1H), 7.04 (t, J = 2.0 Hz, 1H), 6.90 (s, 2H), 4.72 (s, 2H), 3.81-3.68 (m, 4H), 3.23-3.15 (m, 4H). |
| 27 | 436.2 (M + H) | (DMSO-d6, 500 MHz) δ: 8.59 (s, 2H), 7.82 (qd, J = 4.4, 3.9, 1.8 Hz, 1H), 7.57 (ddd, J = 5.2, 3.5, 1.4 Hz, 3H), 7.46 (t, J = 1.9 Hz, 1H), 7.28 (d, J = 1.5 Hz, 1H), 7.00 (t, J = 2.0 Hz, 1H), 6.91 (s, 2H), 4.82 (s, 2H), 3.74 (t, J = 4.8 Hz, 4H), 3.28-3.00 (m, 4H). |
| 28 | 441.2 (M + H) | (DMSO-d6, 500 MHz) δ: 8.56 (s, 2H), 7.42 (t, J = 1.9 Hz, 1H), 7.24 (d, J = 1.5 Hz, 1H), 7.14-7.08 (m, 2H), 7.00 (t, J = 1.9 Hz, 1H), 6.92-6.83 (m, 4H), 4.60 (s, 2H), 3.74 (d, J = 5.0 Hz, 4H), 3.72 (s, 3H), 3.21-3.14 (m, 4H). |
| 29 | 429.1 (M + H) | (DMSO-d6, 500 MHz) δ: 8.58 (s, 2H), 7.43 (t, J = 1.9 Hz, 1H), 7.27 (t, J = 1.4 Hz, 1H), 7.26-7.21 (m, 2H), 7.19-7.12 (m, 2H), 7.02 (t, J = 1.9 Hz, 1H), 6.91 (s, 2H), 4.71 (s, 2H), 3.74 (t, J = 4.8 Hz, 4H), 3.23-3.16 (m, 4H). |
| 30 | 439.2(M + H) | (DMSO-d6, 500 MHz) δ: 10.71 (s, 1H), 9.01 (s, 2H), 8.09-8.04 (m, 2H), 7.72-7.64 (m, 2H), 7.61 (dd, J = 8.4, 7.0 Hz, 2H), 7.52 (t, J = 2.0 Hz, 1H), 7.42 (t, J = 1.9 Hz, 1H), 3.79-3.70 (m, 4H), 3.31-3.28 (m, 4H), 2.21 (s, 3H). |
| 31 | 425.1 (M + H) | (DMSO-d6, 500 MHz) δ: 8.60 (s, 2H), 7.42 (t, J = 1.9 Hz, 1H), 7.38-7.28 (m, 4H), 7.28-7.23 (m, 1H), 7.23-7.17 (m, 2H), 7.03 (t, J = 1.9 Hz, 1H), 4.69 (s, 2H), 3.74 (t, J = 4.8 Hz, 4H), 3.22-3.15 (m, 4H), 2.85 (d, J = 4.8 Hz, 3H). |

-continued

| Cmpd # | MS | $^1$H NMR |
|---|---|---|
| 32 | 478.2 (M + H) | (DMSO-d6, 500 MHz) δ: 7.86 (s, 1H), 7.33-7.25 (m, 3H), 7.16-7.10 (m, 4H), 6.92 (q, J = 2.0, 1.3 Hz, 1H), 6.80 (s, 1H), 6.66 (s, 2H), 4.65 (s, 2H), 3.72 (dd, J = 5.9, 3.8 Hz, 4H), 3.17-3.08 (m, 4H). |
| 33 | 479.2 (M + H) | (DMSO-d6, 500 MHz) δ: 8.33 (s, 1H), 7.43 (s, 2H), 7.34-7.24 (m, 4H), 7.18 (t, J = 1.9 Hz, 1H), 7.16-7.10 (m, 3H), 6.97 (t, J = 1.4 Hz, 1H), 4.66 (s, 2H), 3.72 (dd, J = 6.0, 3.7 Hz, 4H), 3.18-3.09 (m, 4H). |
| 34 | 449.2 (M + H) | (DMSO-d6, 500 MHz) δ: 9.28 (d, J = 2.5 Hz, 1H), 8.80 (d, J = 2.5 Hz, 1H), 7.69 (d, J = 1.2 Hz, 1H), 7.58 (t, J = 2.0 Hz, 1H), 7.48-7.44 (m, 1H), 7.37-7.29 (m, 3H), 7.26-7.19 (m, 2H), 7.11 (t, J = 1.9 Hz, 1H), 4.73 (s, 2H), 3.79-3.72 (m, 4H), 3.23 (dd, J = 5.9, 3.8 Hz, 4H), 2.40 (s, 3H). |
| 35 | 455.4 (M + H), 477.4 (M + Na), 493.6 (M + K) | (DMSO-d6, 500 MHz) δ: 8.59 (s, 2H), 7.42 (t, J = 1.9 Hz, 1H), 7.35-7.28 (m, 4H), 7.27 (d, J = 1.4 Hz, 1H), 7.21 (dd, J = 7.2, 2.3 Hz, 2H), 7.03 (t, J = 1.7 Hz, 1H), 4.69 (d, J = 2.1 Hz, 3H), 3.74 (t, J = 4.9 Hz, 4H), 3.53 (q, J = 6.1 Hz, 2H), 3.39 (q, J = 6.2 Hz, 2H), 3.20 (t, J = 4.8 Hz, 4H). |
| 39 | 419.4 (M + H) | (DMSO-d6, 400 MHz) δ: 8.67 (s, 2H), 7.47 (s, 1H), 7.45 (s, 1H), 7.27 (s, 1H), 6.92 (s, 2H), 3.77 (m, 6H), 3.36 (m, 2H), 3.28 (m, 6H), 2.09 (m, 1H), 1.71 (m, 2H), 1.34 (m, 2H). |
| 40 | 528.6 (M + H) | (DMSO-d6, 500 MHz) δ: 8.19 (d, J = 8.8 Hz, 1H), 7.97 (s, 1H), 7.42 (t, J = 1.9 Hz, 1H), 7.27-7.21 (m, 3H), 7.20-7.09 (m, 4H), 7.06 (t, J = 2.0 Hz, 1H), 6.88 (t, J = 5.4 Hz, 1H), 4.71 (s, 2H), 3.94 (s, 3H), 3.76 (dd, J = 5.9, 3.9 Hz, 4H), 3.22 (dd, J = 5.8, 4.1 Hz, 4H), 3.11 (qd, J = 7.1, 5.1 Hz, 2H), 1.08-1.04 (m, 3H). |
| 41 | 428.4 (M + H) | (DMSO-d6, 500 MHz) δ: 9.56 (d, J = 1.4 Hz, 1H), 7.40 (t, J = 2.0 Hz, 1H), 7.29-7.20 (m, 4H), 7.18-7.12 (m, 2H), 7.10 (t, J = 1.9 Hz, 1H), 7.05 (dt, J = 7.7, 1.2 Hz, 1H), 7.02 (t, J = 2.1 Hz, 1H), 6.81 (ddd, J = 8.1, 2.5, 0.9 Hz, 1H), 4.72 (s, 2H), 3.80-3.69 (m, 4H), 3.24-3.16 (m, 4H). |
| 42 | 483.4(M + H) | (DMSO-d6, 500 MHz) δ:10.81 (s, 1H), 7.41 (t, J = 1.9 Hz, 1H), 7.30 (d, J = 2.0 Hz, 1H), 7.28-7.20 (m, 4H), 7.19-7.12 (m, 2H), 7.06 (t, J = 1.9 Hz, 1H), 6.97 (d, J = 8.2 Hz, 1H), 4.71 (s, 2H), 4.63 (s, 2H), 3.78-3.69 (m, 4H), 3.24-3.16 (m, 4H). |
| 43 | 457.2 (M + H) | (DMSO-d6, 500 MHz) δ: 7.33 (t, J = 1.9 Hz, 1H), 7.26-7.22 (m, 3H), 7.18-7.12 (m, 2H), 7.04 (t, J = 2.0 Hz, 1H), 6.94 (d, J = 2.3 Hz, 1H), 6.86 (d, J = 8.4 Hz, 1H), 6.82 (dd, J = 8.2, 2.2 Hz, 1H), 4.81 (s, 2H), 4.69 (s, 2H), 3.80 (s, 3H), 3.78-3.71 (m, 5H), 3.23-3.17 (m, 4H). |
| 44 | 458.2 (M + H) | (DMSO-d6, 500 MHz) δ: 7.41 (d, J = 8.1 Hz, 1H), 7.29 (t, J = 1.9 Hz, 1H), 7.25-7.19 (m, 3H), 7.18-7.11 (m, 2H), 6.99 (t, J = 2.0 Hz, 1H), 6.14-6.08 (m, 3H), 4.64 (s, 2H), 3.77 (s, 3H), 3.74 (dd, J = 6.0, 3.7 Hz, 4H), 3.16-3.09 (m, 4H). |
| 45 | 469.1(M + H) | (DMSO-d6, 500 MHz) δ: 7.34-7.30 (m, 1H), 7.27-7.21 (m, 2H), 7.20 (t, J = 1.5 Hz, 1H), 7.18-7.12 (m, 2H), 7.00-6.96 (m, 3H), 6.66-6.59 (m, 1H), 6.03 (d, J = 2.6 Hz, 1H), 4.69 (s, 2H), 4.14 (dd, J = 5.0, 3.7 Hz, 2H), 3.79-3.68 (m, 4H), 3.34-3.32 (m, 2H), 3.21-3.12 (m, 4H). |
| 46 | 496.2 (M + H) | (DMSO-d6, 500 MHz) δ: 7.72 (dt, J = 7.9, 1.2 Hz, 1H), 7.65-7.59 (m, 2H), 7.50 (t, J = 2.0 Hz, 1H), 7.42 (ddt, J = 8.2, 2.4, 1.2 Hz, 1H), 7.28 (t, J = 1.4 Hz, 1H), 7.27-7.21 (m, 2H), 7.19-7.12 (m, 3H), 4.74 (s, 2H), 3.79-3.72 (m, 4H), 3.26-3.20 (m, 4H). |
| 49 | 403.2(M + H) | (DMSO-d6, 500 MHz) δ: 8.64 (s, 2H), 7.45 (d, J = 1.9 Hz, 1H), 7.37 (d, J = 1.5 Hz, 1H), 7.19 (t, J = 1.8 Hz, 1H), 6.88 (d, J = 4.3 Hz, 2H), 3.76 (dt, J = 8.7, 4.6 Hz, 4H), 3.31-3.27 (m, 4H), 3.18 (dd, J = 5.9, 3.8 Hz, 1H), 1.93-1.81 (m, 2H), 1.76 (dt, J = 12.9, 3.4 Hz, 2H), 1.36-1.04 (m, 6H). |
| 50 | 429.2(M + H) | (DMSO-d6, 500 MHz) δ: 8.56 (s, 2H), 7.45 (t, J = 1.9 Hz, 1H), 7.40 (tdd, J = 7.7, 5.3, 1.8 Hz, 1H), 7.30-7.22 (m, 2H), 7.21-7.12 (m, 2H), 7.03 (t, J = 1.9 Hz, 1H), 6.90 (s, 2H), 4.72 (s, 2H), 3.75-3.72 (m, 4H), 3.21-3.18 (m, 4H). |
| 51 | 391.1 (M + H) | (DMSO-d6, 500 MHz) δ: 8.66 (s, 2H), 7.46 (d, J = 1.9 Hz, 2H), 7.27 (t, J = 2.0 Hz, 1H), 6.90 (s, 2H), 4.31 (tt, J = 8.6, 5.1 Hz, 1H), 4.03 (dd, J = 10.0, 4.8 Hz, 1H), 3.86-3.73 (m, 6H), 3.66 (dt, J = 8.4, 6.9 Hz, 1H), 3.32-3.28 (m, 4H), 2.23-2.14 (m, 1H), 2.09 (dddd, J = 13.1, 9.3, 7.1, 5.8 Hz, 1H). |
| 55 | 443.2 (M + H) | (DMSO-d6, 500 MHz) δ:8.46 (d, J = 1.9 Hz, 1H), 8.34 (d, J = 2.7 Hz, 1H), 7.59 (t, J = 2.3 Hz, 1H), 7.53 (t, J = 1.9 Hz, 1H), 7.35 (d, J = 1.5 Hz, 1H), 7.28-7.20 (m, 2H), 7.19-7.09 (m, 3H), 4.74 (s, 2H), 3.92 (s, 3H), 3.75 (dd, J = 5.9, 3.7 Hz, 4H), 3.25-3.18 (m, 4H). |
| 60 | 417.3 (M + H) | (CDCl3, 400 MHz) δ: 8.54 (s, 2H), 7.44 (s, 1H), 7.37 (s, 1H), 7.14 (s, 1H), 5.30 (br, 2H), 3.89 (m, 4H), 3.29 (m, 4H), 3.01 (d, J = 5.6 Hz, 2H), 2.07 (m, 1H), 1.90 (m, 2H), 1.63 (m, 2H), 1.36-1.03 (m, 6H). |
| 62 | 405.2 (M + H) | (DMSO-d6, 500 MHz) δ: 8.65 (s, 2H), 7.48 (t, J = 1.9 Hz, 1H), 7.39 (t, J = 1.3 Hz, 1H), 7.20 (t, J = 1.9 Hz, 1H), 6.90 (s, 2H), 3.91 (ddd, J = 11.7, 4.7, 1.6 Hz, 2H), 3.79-3.73 (m, 4H), 3.64 (tt, J = 12.0, 3.8 Hz, 1H), |

-continued

| Cmpd # | MS | $^1$H NMR |
|---|---|---|
| | | 3.31-3.24 (m, 6H), 1.73 (ddd, J = 12.6, 4.0, 1.8 Hz, 2H), 1.59 (qd, J = 12.2, 4.7 Hz, 2H). |
| 64 | 453.4 (M + H) | (CDCl3, 400 MHz) δ: 8.54 (s, 2H), 7.43 (s, 1H), 7.36 (s, 1H), 7.15 (s, 1H), 5.37 (br, 2H), 3.90 (m, 4H), 3.31 (m, 4H), 3.05 (d, J = 6.0 Hz, 2H), 2.22 (m, 1H), 2.07 (m, 4H), 1.77 (m, 2H), 1.46 (m, 2H) |
| 69 | 476.3 (M + H) | (DMSO-d6, 500 MHz) δ: 8.67 (d, J = 1.6 Hz, 1H), 7.98 (d, J = 1.5 Hz, 1H), 7.85-7.80 (m, 1H), 7.79 (t, J = 1.9 Hz, 1H), 7.27 (t, J = 1.9 Hz, 1H), 6.74 (s, 2H), 4.49 (tt, J = 8.2, 5.3 Hz, 1H), 4.05 (d, J = 29.5 Hz, 4H), 3.77 (t, J = 4.9 Hz, 4H), 3.33-3.23 (m, 4H), 1.36 (s, 9H). |
| 70 | 458.2 (M + H) | (DMSO-d6, 500 MHz) δ: 8.00 (s, 1H), 7.34 (t, J = 2.0 Hz, 1H), 7.18 (t, J = 1.8 Hz, 1H), 7.14 (s, 1H), 6.83 (s, 1H), 6.67 (s, 2H), 4.24 (tt, J = 8.6, 5.3 Hz, 1H), 3.98 (dd, J = 10.1, 4.9 Hz, 1H), 3.82 (dd, J = 10.0, 8.1 Hz, 1H), 3.79-3.71 (m, 5H), 3.65 (dt, J = 8.4, 6.9 Hz, 1H), 3.28-3.21 (m, 4H), 2.18-2.03 (m, 2H). |
| 72 | 459.1 (M + H) | (DMSO-d6, 500 MHz) δ: 8.46 (s, 1H), 7.44 (s, 2H), 7.36 (t, J = 2.0 Hz, 1H), 7.25 (t, J = 1.9 Hz, 1H), 7.19 (d, J = 1.8 Hz, 1H), 4.24 (tt, J = 9.8, 5.2 Hz, 1H), 4.04-3.96 (m, 1H), 3.82 (dd, J = 10.0, 8.1 Hz, 1H), 3.75 (dt, J = 5.8, 3.9 Hz, 5H), 3.65 (dt, J = 8.3, 6.8 Hz, 1H), 3.26 (t, J = 4.9 Hz, 4H), 2.20-2.05 (m, 2H). |
| 73 | 411.2 (M + H) | (DMSO-d6, 500 MHz) δ: 8.57 (d, J = 1.5 Hz, 1H), 7.96 (d, J = 1.5 Hz, 1H), 7.73 (t, J = 2.0 Hz, 1H), 7.69 (d, J = 1.6 Hz, 1H), 7.31 (dd, J = 5.1, 2.0 Hz, 3H), 7.21 (dd, J = 6.3, 2.7 Hz, 2H), 7.02 (t, J = 1.9 Hz, 1H), 6.70 (s, 2H), 4.67 (s, 2H), 3.75 (t, J = 4.8 Hz, 4H), 3.18 (t, J = 4.9 Hz, 4H). |
| 74 | 391.2 (M + H) | (DMSO-d6, 500 MHz) δ:8.66 (d, J = 1.6 Hz, 1H), 7.99 (d, J = 1.5 Hz, 1H), 7.82 (d, J = 1.6 Hz, 1H), 7.77 (t, J = 1.9 Hz, 1H), 7.27 (t, J = 2.0 Hz, 1H), 6.74 (bs, 2H), 4.27 (tt, J = 9.6, 5.2 Hz, 1H), 4.01 (dd, J = 10.0, 4.8 Hz, 1H), 3.87-3.80 (m, 1H), 3.78 (q, J = 5.0 Hz, 5H), 3.69-3.62 (m, 1H), 3.29 (dd, J = 5.9, 3.8 Hz, 4H), 2.24-1.99 (m, 2H). |
| 85 | 433.16 (M + H) | (CDCl3, 400 MHz) δ: 8.55 (br, 2H), 7.38 (s, 1H), 7.31 (s, 1H), 7.17 (s, 1H), 5.31 (br, 2H), 3.91 (m, 4H), 3.43 (m, 2H), 3.30 (m, 4H), 3.23 (m, 1H), 1.91 (m, 2H), 1.42 (m, 2H), 1.23 (d, J = 6.0 Hz, 6H). |
| 88 | 438.7 (M + H) | (DMSO-d6, 400 MHz) δ: 8.66 (s, 2H), 7.49 (s, 1H), 7.39 (s, 1H), 7.21 (s, 1H), 6.94 (s, 2H), 3.77 (m, 4H), 3.57 (m, 1H), 3.29 (m, 4H), 2.11 (m, 2H), 1.95 (m, 2H), 1.83 (m, 2H), 1.61 (m, 2H). |
| 94 | 463.1 (M + H) | (DMSO-d6, 500 MHz) δ: 8.66 (s, 2H), 7.49 (t, J = 1.9 Hz, 1H), 7.45 (d, J = 1.6 Hz, 1H), 7.41 (t, J = 6.6 Hz, 1H), 7.26 (t, J = 1.9 Hz, 1H), 6.90 (s, 2H), 4.58-4.48 (m, 1H), 4.40 (d, J = 6.6 Hz, 2H), 4.08-3.98 (m, 4H), 3.76 (dd, J = 6.0, 3.6 Hz, 4H), 3.30 (d, J = 5.9 Hz, 4H), 3.13 (s, 3H). |
| 95 | 447.1 (M + H) | (DMSO-d6, 500 MHz) δ: 8.66 (s, 2H), 7.47 (dt, J = 6.3, 1.7 Hz, 2H), 7.26 (t, J = 1.9 Hz, 1H), 6.89 (s, 2H), 4.56 (tt, J = 8.5, 5.7 Hz, 1H), 4.19-3.97 (m, 4H), 3.76 (dd, J = 6.0, 3.7 Hz, 4H), 3.30 (d, J = 6.1 Hz, 4H), 2.73 (s, 6H). |
| 96 | 446.83 (M + H) | (DMSO-d6, 400 MHz) δ: 7.91 (d, J = 9.6 Hz, 1H), 7.79 (m, 1H), 7.76 (s, 1H), 7.34 (m, 1H), 7.25 (m, 1H), 7.11 (m, 2H), 6.85 (d, J = 9.6 Hz, 1H), 6.65 (s, 2H), 4.73 (s, 2H), 3.77 (m, 4H), 3.22 (m, 4H). |
| 103 | 431.2 (M + H) | (DMSO-d6, 500 MHz) δ: 8.72 (s, 2H), 7.65 (d, J = 3.6 Hz, 1H), 7.47 (q, J = 1.9 Hz, 2H), 7.28 (t, J = 2.0 Hz, 1H), 4.38-4.17 (m, 1H), 4.03 (dd, J = 10.0, 4.8 Hz, 1H), 3.87-3.71 (m, 6H), 3.66 (dt, J = 8.2, 6.8 Hz, 1H), 3.34-3.27 (m, 4H), 2.83-2.71 (m, 1H), 2.24-2.16 (m, 1H), 2.15-2.05 (m, 1H), 0.72-0.67 (m, 2H), 0.54-0.46 (m, 2H). |
| 104 | 451.2 (M + H) | (DMSO-d6, 500 MHz) δ: 8.62 (s, 2H), 7.63 (d, J = 3.8 Hz, 1H), 7.43 (dd, J = 2.4, 1.5 Hz, 1H), 7.34-7.26 (m, 4H), 7.23-7.19 (m, 2H), 7.04 (dd, J = 2.4, 1.5 Hz, 1H), 4.69 (s, 2H), 3.77-3.73 (m, 4H), 3.23-3.16 (m, 4H), 2.80-2.71 (m, 1H), 0.72-0.66 (m, 2H), 0.53-0.47 (m, 2H). |

Example 2: 5-(3-morpholino-5-(((tetrahydrofuran-3-yl)methyl)sulfonyl)phenyl)pyrimidin-2-amine;(tetrahydrofuran-3-yl)methanesulfonyl chloride (Compound 38)

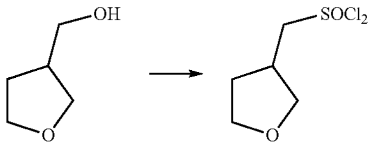

Step 1: Triphenylphosphine (7.7 g, 29.4 mmol) was added to a solution of (tetrahydrofuran-3-yl)methanol (2 g, 19.6 mmol) and carbon tetrabromide (7.7 g, 23.5 mmol) in DCM (30 mL) at 0° C. The reaction was stirred for 2 hours at room temperature. The mixture was poured into water (50 mL) and extracted with dichloromethane (50 mL×3). The organic extracts were combined, dried over anhydrous sodium sulfate, and concentrated. The residue was purified by silica gel column chromatography to give 3-(bromomethyl)tetrahydrofuran (2.0 g, 62% yield).

Step 2: A solution of 3-(bromomethyl)tetrahydrofuran (2 g, 12.2 mmol) and AcSK (2.7 g, 24.4 mmol) in DMF (10 mL) was stirred overnight at rt. The mixture was poured into water (50 mL) and extracted with dichloromethane (50 mL×3). The organic extracts were combined, dried over anhydrous sodium sulfate, and concentrated to give crude S-(tetrahydrofuran-3-yl)methyl ethanethioate (2.0 g, quantative yield), which was used for next reaction without further purification. The compound was confirmed with LC-MS only: 161.27 $(M+H)^+$, $C_7H_{12}O_2S$.

Step 3: $Cl_2$ gas was bubbled into a mixture of S-(tetrahydrofuran-3-yl)methyl ethanethioate (2.0 g, 12.5 mmol) in DCM/water (20 mL/20 mL) at 0-5° C. for 20 min. The DCM layer was separated and the water phase was extracted with DCM (20 mL×2). The organic extracts were combined and concentrated to give crude (tetrahydrofuran-3-yl)methanesulfonyl chloride (1.7 g, 75% yield), which was used for next reaction without further purification.

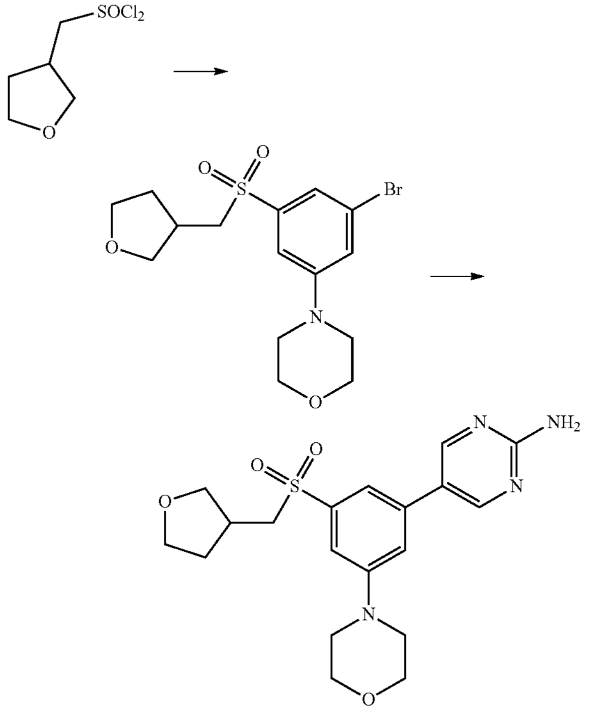

Compound 38

Step 4: Synthesis of 5-(3-morpholino-5-(((tetrahydrofuran-3-yl)methyl)sulfonyl)phenyl)pyrimidin-2-amine 4-(3-bromo-5-((tetrahydrofuran-3-yl)methylsulfonyl)phenyl)morpholine was synthesized using methods analogous to the methods described in Example 1 from crude (tetrahydrofuran-3-yl)methanesulfonyl chloride (0.9 g, 17% yield). The compound was confirmed with LC-MS only: 389.90 (M+H)+, $C_{15}H_{20}BrNO_4S$.

Step 5 (see Scheme B, Step 4b): A solution of 4-(3-bromo-5-(((tetrahydrofuran-3-yl)methyl)sulfonyl)phenyl)morpholine (300 mg, 0.77 mmol), 5-(4,4,5,5-tetramethyl-1,3,2-dioxaborolan-2-yl)pyrimidin-2-amine (170 mg, 0.77 mmol), and potassium phosphate aqueous solution (20 mL, 0.5 M) in THF (20 mL) was purged with nitrogen for three times. $Pd_2(dba)_3$ (100 mg) was added and the reaction was heated at 70-80° C. for 2 h under $N_2$ protection. The solvent was removed in vacuo and the residue was partitioned in ethyl acetate (30 mL) and water (30 mL). The organic layer was separated and the water phase was re-extracted with ethyl acetate (20 mL×2). The organic extracts were combined, washed with brine (20 mL), dried over anhydrous sodium sulfate, and concentrated. The residue was purified by silica gel column chromatography to afford 5-(3-morpholino-5-(((tetrahydrofuran-3-yl)methyl)sulfonyl)phenyl)pyrimidin-2-amine (72 mg, 23% yield). ESMS+: 404.97 (M+H). $^1H$ NMR ($CDCl_3$, 400 MHz) δ: 8.54 (s, 2H), 7.44 (s, 1H), 7.36 (s, 1H), 7.16 (s, 1H), 5.33 (br, 2H), 3.96 (m, 1H), 3.88 (m, 4H), 3.85 (m, 1H), 3.76 (m, 1H), 3.54 (m, 1H), 3.31 (m, 4H), 3.22 (m, 2H), 2.77 (m, 1H), 2.22 (m, 1H), 1.73 (m, 1H).

Example 3: tert-butyl 3-((3-(2-aminopyrimidin-5-yl)-5-morpholinophenyl)sulfonyl) azetidine-1-carboxylate (Compound 54)

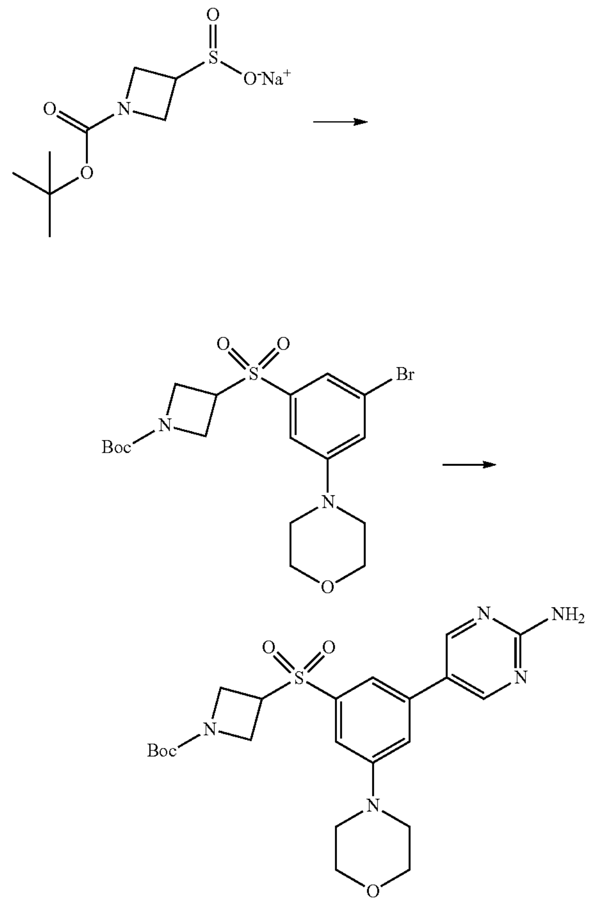

Compound 54

The synthesis of tert-butyl 3-((3-(2-aminopyrimidin-5-yl)-5-morpholinophenyl)sulfonyl) azetidine-1-carboxylate from commercially available sodium 1-(tert-butoxycarbonyl)azetidine-3-sulfinate was accomplished using methods analogous to the methods as previously described in Example 1 for Compound 1 (130 mg, 42% yield, 2 steps). ESMS+: 476.3 (M+H). $^1H$ NMR (DMSO-d6, 500 MHz) δ: 8.66 (s, 2H), 7.57-7.42 (m, 2H), 7.27 (t, J=1.9 Hz, 1H), 6.90 (s, 2H), 4.53 (tt, J=8.2, 5.5 Hz, 1H), 4.23-3.91 (m, 4H), 3.76 (dd, J=6.0, 3.8 Hz, 4H), 3.32-3.29 (m, 4H), 1.36 (s, 9H).

Example 4: 5-(3-(azetidin-3-ylsulfonyl)-5-morpholinophenyl)pyrimidin-2-amine (Compound 61)

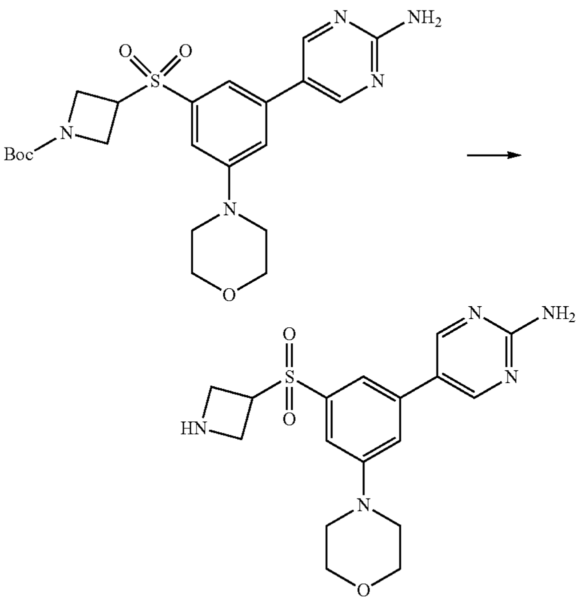

Compound 61

(See Scheme B, Step 5): A round bottom flask, equipped with a magnetic stir bar and 5-(3-morpholino-5-(phenylsulfonyl)phenyl)pyrimidin-2-amine (313 mg, 0.67 mmol) in 3 mL of DCM was cooled to 0° C. under an atmosphere of argon. Trifluoroacetic acid (1 mL, 13.6 mmol) was added dropwise and the mixture was allowed to come to room temperature and stir until no starting material was visible by TLC. The solvent and excess trifluoroacetic acid was removed in vacuo. The crude material was carried forward as the TFA salt. Alternatively, the crude material could be purified via column chromatography (0-10% (0.5M $NH_3$/MeOH)/DCM) to afford the free amine. ESMS+: 376.3 (M+H). $^1$H NMR (DMSO-d6, 500 MHz) δ: 8.64 (d, J=2.5 Hz, 2H), 7.45 (t, J=2.0 Hz, 1H), 7.40 (d, J=1.7 Hz, 1H), 7.22 (d, J=1.9 Hz, 1H), 6.89 (s, 2H), 4.66-4.57 (m, 1H), 3.82-3.72 (m, 6H), 3.51 (t, J=8.6 Hz, 2H), 3.30-3.26 (m, 4H), 1.24 (bs, 1H).

Example 5: 1-(3-((3-(2-aminopyrimidin-5-yl)-5-morpholinophenyl)sulfonyl)azetidin-1-yl)ethan-1-one (Compound 68)

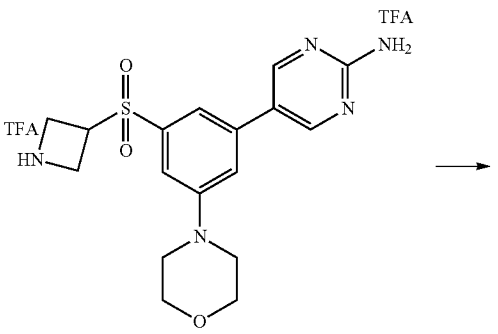

-continued

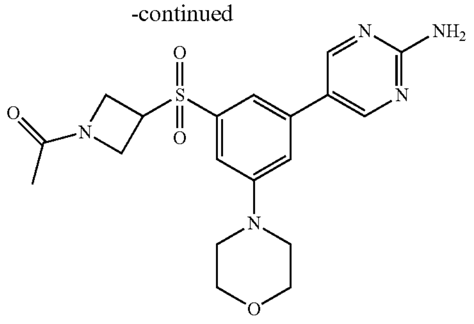

Compound 68

(See Scheme B, Step 6a): To a round bottom flask equipped with a stir bar under argon atmosphere was added 5-(3-(azetidin-3-ylsulfonyl)-5-morpholinophenyl)pyrimidin-2-amine-TFA salt (182.2 mg, 0.30 mmol), DCM (3 mL) and N,N-diisopropylethylamine (0.157 mL, 0.9 mmol). Acetic anhydride (0.028 mL, 0.3 mmol) was added dropwise. The reaction was stirred for 2 hrs under argon. No starting material was visible by TLC. The compound was taken up in DCM, added saturated sodium bicarbonate and extracted 3 times with DCM.). The combined organic phase was washed with brine, dried over $Na_2SO_4$, concentrated in vacuo, and purified via column chromatography (0-10% (0.5 M $NH_3$/MeOH)/DCM) to afford the desired product (76.7 mg, 0.184 mmol, 61% yield). ESMS+: 418.2 (M+H). $^1$H NMR (DMSO-d6, 500 MHz) δ: 8.67 (s, 2H), 7.48 (p, J=1.5 Hz, 2H), 7.28 (t, J=1.8 Hz, 1H), 6.90 (s, 2H), 4.55 (ddd, J=13.8, 7.6, 6.0 Hz, 1H), 4.38-4.30 (m, 2H), 4.05 (d, J=6.9 Hz, 2H), 3.76 (t, J=4.8 Hz, 4H), 3.30 (m, 4H), 1.77 (s, 3H).

Example 6: 1-(3-((3-(2-aminopyrimidin-5-yl)-5-morpholinophenyl)sulfonyl)azetidin-1-yl)-2,2-dimethylpropan-1-one (Compound 86)

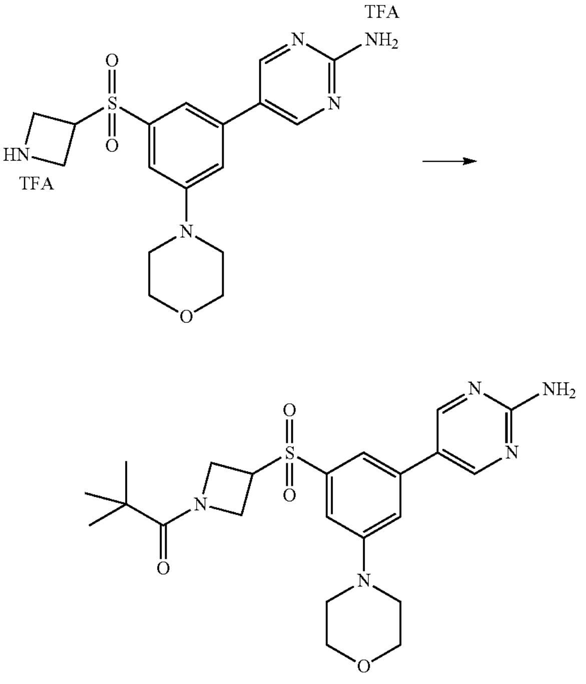

Compound 86

(See Scheme B, Step 6b): To a vial equipped with a stir bar under argon atmosphere was added 5-(3-(azetidin-3-ylsulfonyl)-5-morpholinophenyl)pyrimidin-2-amine-TFA salt (54 mg, 0.093 mmol), DCM (1.2 mL) and triethylamine (0.036 mL, 0.26 mmol). Pivaloyl chloride (0.012 mL, 0.1 mmol) was added dropwise. The reaction was stirred for overnight under argon. The compound was taken up in DCM, saturated sodium bicarbonate was added and the organic layer was separated. The aqueous layer was extracted 2 more times with DCM. The combined organic phase was washed with brine, dried over $Na_2SO_4$, concentrated in vacuo, and purified via column chromatography (0-7% (0.5M $NH_3$/MeOH)/DCM) to afford the desired product (35.9 mg, 0.084 mmol, 90% yield). ESMS+: 460.2 (M+H). $^1$H NMR (DMSO-d6, 500 MHz) δ: 8.66 (s, 2H), 7.54-7.42 (m, 2H), 7.28 (t, J=2.0 Hz, 1H), 6.90 (s, 2H), 5.75 (s, 1H), 4.55 (p, J=7.3, 6.7 Hz, 2H), 4.02 (s, 2H), 3.76 (dd, J=5.9, 3.8 Hz, 4H), 3.31-3.26 (m, 4H), 1.06 (s, 9H).

Example 7: 5-(3-((1-isopropylazetidin-3-yl)sulfonyl)-5-morpholinophenyl)pyrimidin-2-amine (Compound 65)

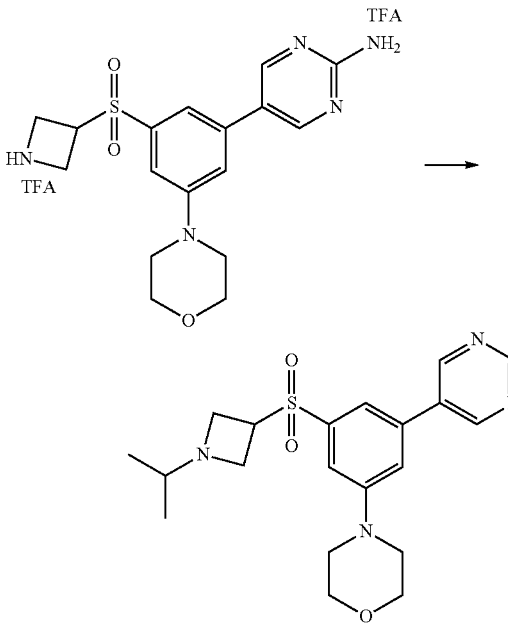

Compound 65

(See Scheme B, Step 6c): To a vial equipped with a stir bar under argon atmosphere was added 5-(3-(azetidin-3-ylsulfonyl)-5-morpholinophenyl)pyrimidin-2-amine-TFA salt (34 mg, 0.06 mmol), sodium triacetoxyborohydride (22 mg) acetone (0.076 mL) and DCE (1 mL). The reaction was stirred overnight at room temperature. The reaction was diluted with DCM and saturated sodium bicarbonate was added. After separating the organic layer, the aqueous layer was extracted 2 times with DCM. The combined organic phase was washed with brine, dried over $Na_2SO_4$, concentrated in vacuo, and purified via column chromatography (0-10% (0.5M $NH_3$/MeOH)/DCM) to afford the desired product (16.8 mg, 0.040 mmol, 67% yield). ESMS+: 418.1 (M+H). $^1$H NMR (DMSO-d6, 500 MHz) δ: 8.65 (s, 2H), 7.45 (t, J=2.0 Hz, 1H), 7.40 (d, J=1.7 Hz, 1H), 7.22 (t, J=2.0 Hz, 1H), 6.89 (s, 2H), 4.36 (p, J=7.3 Hz, 1H), 3.76 (t, J=4.9 Hz, 4H), 3.36 (t, J=7.9 Hz, 2H), 3.30-3.25 (m, 6H), 2.31 (p, J=6.2 Hz, 1H), 0.82 (d, J=6.2 Hz, 6H).

Example 8: (3-((3-(2-aminopyrimidin-5-yl)-5-morpholinophenyl)sulfonyl)azetidin-1-yl)(cyclopropyl)methanone (Compound 77)

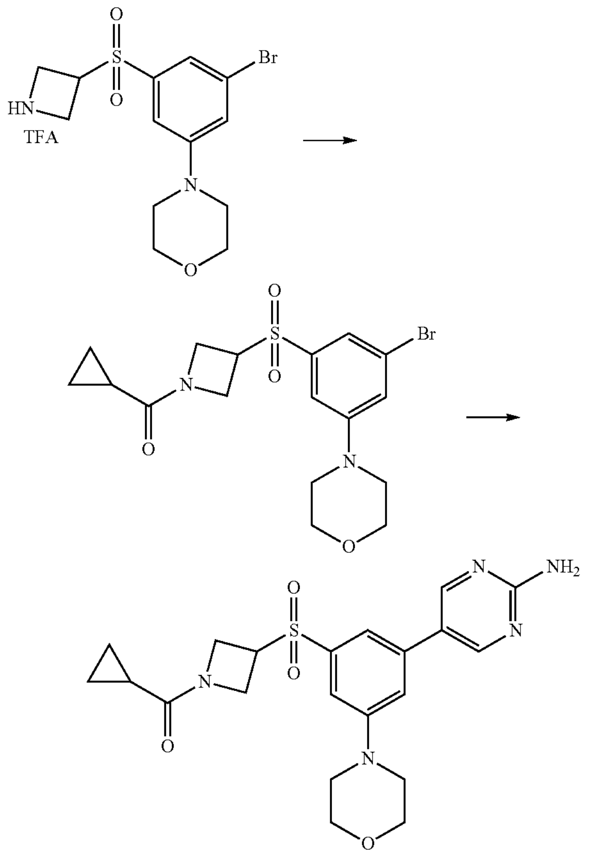

Compound 77

Step 1 (See Scheme B, Step 5): Tert-butyl 3-((3-bromo-5-morpholinophenyl)sulfonyl)azetidine-1-carboxylate, which was synthesized as described in Example 3, was deprotected with TFA in DCM I using similar methods as those described in Example 4. The TFA salt was used crude after drying under vacuum overnight.

Step 2 (See Scheme B, Step 6b): To a round bottom flask equipped with a stir bar under argon atmosphere was added 4-(3-(azetidin-3-ylsulfonyl)-5-bromophenyl)morpholine-TFA salt (376 mg, 0.65 mmol), DCM (6.5 mL) and triethylamine (0.292 mL, 2.15 mmol). Cyclopropanecarbonyl chloride (0.088 mL, 0.975 mmol) was added dropwise. The reaction was stirred for overnight under argon. The compound was taken up in DCM, saturated sodium bicarbonate was added and the mixture was separated. The aqueous layer was extracted 2 more times with DCM. The combined organic phases were washed with brine, dried over $Na_2SO_4$, concentrated in vacuo, and purified via column chromatography (0-7% (0.5M $NH_3$/MeOH)/DCM) to afford (3-((3-bromo-5-morpholinophenyl)sulfonyl)azetidin-1-yl)(cyclopropyl)methanone (267.1 mg, 0.62 mmol, 96%). ESMS+: 429.1, 431.1.

Step 3 (See Scheme B, Step 4a): This step was accomplished by using the procedure for Suzuki coupling as previously described in Example 1, Step 3, starting from 303 mg (0.705 mmol) of (3-((3-bromo-5-morpholinophenyl)sulfonyl)azetidin-1-yl)(cyclopropyl)methanone to obtain 128.9 mg (0.289 mmol) of (3-((3-(2-aminopyrimidin-5-yl)-5-morpholinophenyl)sulfonyl)azetidin-1-yl)(cyclopropyl)methanone in 41% yield. ESMS+: 445.3 (M+H). $^1$H NMR ($CDCl_3$, 500 MHz) δ:8.51 (s, 2H), 7.41 (s, 1H), 7.33 (d, J=2.0 Hz, 1H), 7.17 (t, J=1.8 Hz, 1H), 5.29 (s, 2H), 4.69 (dd, J=9.1, 4.6 Hz, 1H), 4.47 (t, J=8.4 Hz, 1H), 4.29 (dd, J=9.2, 4.3 Hz, 1H), 4.20-4.04 (m, 2H), 3.89 (t, J=4.8 Hz, 4H), 3.30 (dd, J=5.9, 3.8 Hz, 4H), 1.36 (tt, J=8.2, 4.6 Hz, 1H), 0.97 (q, J=3.9, 3.4 Hz, 2H), 0.79 (tt, J=7.7, 3.2 Hz, 2H).

Example 9: 3-((3-(2-aminopyrimidin-5-yl)-5-morpholinophenyl)sulfonyl)-N-ethylazetidine-1-carboxamide (Compound 93)

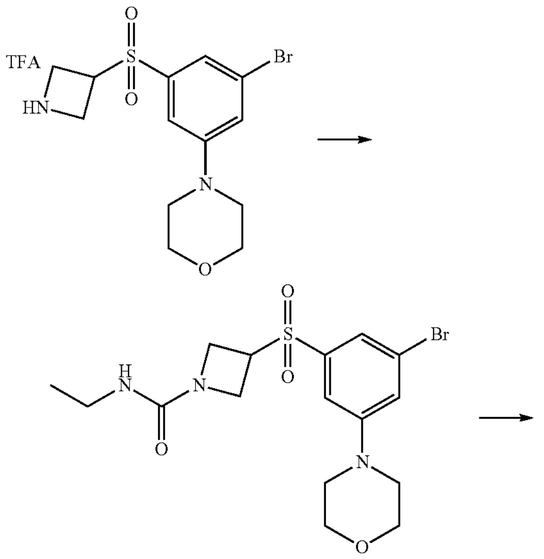

-continued

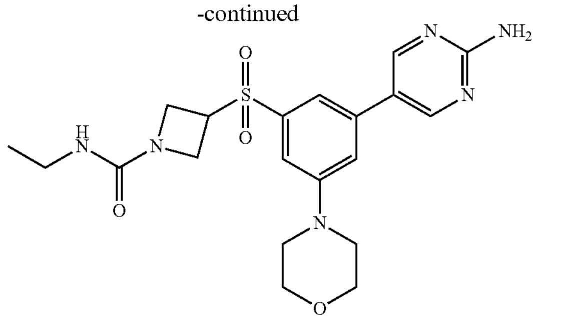

Compound 93

Step 1 (See Scheme B, Step 6d): To a vial equipped with a stir bar under argon atmosphere was added 4-(3-(azetidin-3-ylsulfonyl)-5-bromophenyl)morpholine TFA salt (64 mg, 0.11 mmol), DCM (1.4 mL) and triethylamine (0.031 mL). Ethyl isocyanate (0.0163 mL, 0.206 mmol) was added dropwise. The reaction was stirred for 2 hours at room temperature until no starting material was visible by TLC. The compound was taken up in DCM, water and saturated sodium bicarbonate was added and separated. The aqueous layer was extracted two more times with DCM. The combined organic phase was washed with brine, dried over $Na_2SO_4$, concentrated in vacuo, and purified via column chromatography (0-5% (0.5M $NH_3$/MeOH)/DCM) to afford 3-((3-bromo-5-morpholinophenyl)sulfonyl)-N-ethylazetidine-1-carboxamide (32.4 mg, 0.075 mmol, 68% yield). ESMS+: 432.1, 434.1.

Step 2: This step was accomplished by using the procedure for Suzuki coupling as previously described in Example 1, Step 3, starting from 3-((3-bromo-5-morpholinophenyl)sulfonyl)-N-ethylazetidine-1-carboxamide (32.4 mg, 0.075 mmol) to obtain 23.3 mg (0.052 mmol) of 3-((3-(2-aminopyrimidin-5-yl)-5-morpholinophenyl)sulfonyl)-N-ethylazetidine-1-carboxamide in 69% yield. ESMS+: 447.1, 448.1, 449.0. $^1$H NMR (DMSO-d6, 500 MHz) δ: 8.66 (s, 2H), 7.48 (t, J=1.9 Hz, 1H), 7.44 (d, J=1.5 Hz, 1H), 7.25 (t, J=1.9 Hz, 1H), 6.90 (s, 2H), 6.45 (d, J=5.6 Hz, 1H), 4.51 (tt, J=8.1, 5.5 Hz, 1H), 4.06-3.87 (m, 4H), 3.76 (dd, J=6.0, 3.7 Hz, 4H), 3.30 (s, 4H), 2.99 (qd, J=7.1, 5.4 Hz, 2H), 0.98 (t, J=7.1 Hz, 3H).

The following compounds were prepared by methods analogous to the method described for Compounds 54, 61, 68, 65, 77, and 93, and as described in Scheme B:

| Cmpd # | MS | $^1$H NMR |
|---|---|---|
| 66 | 460.3 (M + H) | (DMSO-d6, 500 MHz) δ: 8.65 (s, 2H), 7.45 (d, J = 2.2 Hz, 1H), 7.41 (d, J = 1.6 Hz, 1H), 7.23 (t, J = 2.1 Hz, 1H), 6.89 (s, 2H), 4.42 (p, J = 7.4 Hz, 1H), 3.82-3.65 (m, 6H), 3.37 (m, 4H), 3.30-3.21 (m, 6H), 2.27 (m, 1H), 1.64-1.42 (m, 2H), 1.07 (m, 2H). |
| 67 | 559.3 (M + H) | (DMSO-d6, 500 MHz) δ: 8.64 (s, 2H), 7.43 (dt, J = 6.2, 1.7 Hz, 2H), 7.24 (t, J = 2.0 Hz, 1H), 6.89 (s, 2H), 4.37 (q, J = 7.0 Hz, 1H), 3.80-3.69 (m, 4H), 3.45 (dt, J = 12.8, 4.9 Hz, 2H), 3.37 (d, J = 7.3 Hz, 4H), 3.30-3.26 (m, 4H), 2.90 (s, 2H), 2.23 (d, J = 8.7 Hz, 1H), 1.52 (dd, J = 10.9, 5.6 Hz, 2H), 1.37 (s, 9H), 1.04-0.93 (m, 2H) . |
| 75 | 432.2 (M + H) | ($CDCl_3$, 500 MHz) δ: 8.52 (s, 2H), 7.40 (d, J = 1.5 Hz, 1H), 7.32 (t, J = 2.0 Hz, 1H), 7.17 (t, J = 1.8 Hz, 1H), 5.31 (s, 2H), 4.54 (dd, J = 9.3, 5.2 Hz, 1H), 4.37-4.25 (m, 2H), 4.16-4.00 (m, 2H), 3.93-3.83 (m, 4H), 3.30 (dd, J = 5.9, 3.9 Hz, 4H), 2.11 (dq, J = 11.1, 7.7 Hz, 2H), 1.11 (t, J = 7.5 Hz, 3H). |
| 76 | 446.15 (M + H) | ($CDCl_3$, 500 MHz) δ: 8.51 (s, 2H), 7.40 (d, J = 1.5 Hz, 1H), 7.33 (t, J = 2.0 Hz, 1H), 7.17 (t, J = 1.9 Hz, 1H), 5.22 (s, 2H), 4.58 (dd, J = 9.4, 5.0 Hz, 1H), 4.37 (t, J = 8.7 Hz, 1H), 4.27 (dd, J = 10.2, 5.1 Hz, 1H), 4.14-4.00 (m, 2H), 3.93-3.85 (m, 4H), 3.30 (dd, J = 5.8, 3.9 Hz, 4H), 2.41 (p, J = 6.8 Hz, 1H), 1.09 (dd, J = 12.2, 6.8 Hz, 6H). |

-continued

| Cmpd # | MS | $^1$H NMR |
|---|---|---|
| 78 | 512.2 (M + H) | (DMSO-d6, 500 MHz) δ: 8.67 (s, 2H), 7.49 (dt, J = 6.6, 1.7 Hz, 2H), 7.29-7.20 (m, 3H), 7.16-7.05 (m, 2H), 6.91 (s, 2H), 4.59 (p, J = 6.9 Hz, 1H), 4.43 (d, J = 6.8 Hz, 2H), 4.08 (d, J = 6.8 Hz, 2H), 3.76 (t, J = 4.8 Hz, 4H), 3.45 (s, 2H), 3.31-3.28 (m, 4H). |
| 79 | 498.2 (M + H) | (DMSO-d6, 500 MHz) δ: 8.65 (s, 2H), 7.76-7.61 (m, 2H), 7.49 (dt, J = 8.0, 1.6 Hz, 2H), 7.36-7.18 (m, 3H), 6.90 (s, 2H), 4.72-4.59 (m, 2H), 4.48 (s, 1H), 4.28 (s, 2H), 3.75 (t, J = 4.8 Hz, 4H), 3.29 (dd, J = 7.1, 4.4 Hz, 4H). |
| 80 | 484.2 (M + H) | (DMSO-d6, 500 MHz) δ: 8.64 (s, 2H), 7.46 (t, J = 1.9 Hz, 1H), 7.42 (t, J = 1.4 Hz, 1H), 7.27-7.21 (m, 3H), 7.11-7.05 (m, 2H), 6.89 (s, 2H), 4.45 (p, J = 7.2 Hz, 1H), 3.76 (t, J = 4.8 Hz, 4H), 3.56 (s, 2H), 3.42 (d, J = 7.2 Hz, 4H), 3.28 (t, J = 4.9 Hz, 4H). |
| 81 | 419.1 (M + H) | (DMSO-d6, 500 MHz) δ: 8.66 (s, 2H), 7.48 (t, J = 1.9 Hz, 1H), 7.46-7.42 (m, 1H), 7.25 (t, J = 1.9 Hz, 1H), 6.90 (s, 2H), 6.04 (s, 2H), 4.51 (tt, J = 8.4, 5.4 Hz, 1H), 4.02-3.93 (m, 4H), 3.76 (dd, J = 5.8, 3.8 Hz, 4H), 3.32-3.22 (m, 4H). |
| 92 | 475.2 (M + H) | (DMSO-d6, 500 MHz) δ: 8.66 (s, 2H), 7.48 (t, J = 2.0 Hz, 1H), 7.44 (t, J = 1.5 Hz, 1H), 7.25 (t, J = 1.9 Hz, 1H), 6.90 (s, 2H), 5.84 (s, 1H), 4.49 (tt, J = 8.4, 5.4 Hz, 1H), 4.01-3.87 (m, 4H), 3.81-3.74 (m, 4H), 3.31-3.28 (m, 4H), 1.21 (s, 9H). |
| 102 | 484.2 (M + H) | (DMSO-d6, 500 MHz) δ: 8.73 (s, 2H), 7.65 (d, J = 3.5 Hz, 1H), 7.50 (d, J = 1.8 Hz, 2H), 7.30 (t, J = 1.9 Hz, 1H), 4.65-4.53 (m, 1H), 4.53-4.42 (m, 2H), 4.07 (d, J = 6.8 Hz, 2H), 3.76 (dd, J = 6.0, 3.8 Hz, 4H), 3.34-3.30 (m, 4H), 2.76 (tq, J = 7.2, 3.8 Hz, 1H), 1.60-1.53 (m, 1H), 0.76-0.60 (m, 6H), 0.53-0.47 (m, 2H). |

Example 10: 5-(3-morpholino-5-((4-morpholinophenyl)sulfonyl)phenyl)pyrimidin-2-amine (Compound 36)

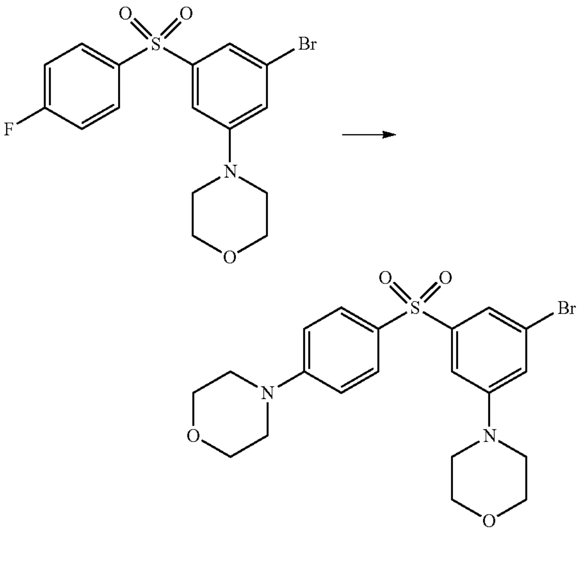

Step 1 (See Scheme C, Step 7): Synthesis of 4-(3-bromo-5-(4-morpholinophenylsulfonyl)phenyl)morpholine Morpholine (1.25 g, 14.4 mmol) and $Cs_2CO_3$ (2.93 g, 9.0 mmol) were added successively to a stirred solution of 4-(3-bromo-5-((4-fluorophenyl)sulfonyl)phenyl)morpholine (1.2 g, 3.0 mmol) in DMF (10 mL). The reaction was heated at 110-120° C. overnight. The reaction mixture was poured into water (30 mL) and extracted with ethyl acetate (20 mL×3). The organic extracts were combined, washed with brine (15 mL×2), dried over anhydrous sodium sulfate, and concentrated to give crude 4-(3-bromo-5-(4-morpholinophenylsulfonyl)phenyl)morpholine (0.9 g, 64% yield), which was used for next reaction without further purification. The compound was confirmed with LC-MS only: 467.27 $(M+H)^+$, $C_{20}H_{23}BrN_2O_4S$.

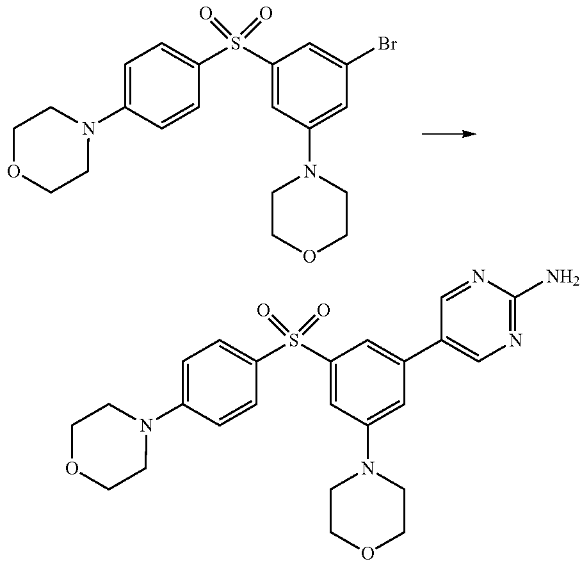

Compound 36

Step 2 (See Scheme C, Step 4b): 5-(3-morpholino-5-((4-morpholinophenyl)sulfonyl)phenyl)pyrimidin-2-amine was synthesized as described for Compound 38 in Example 2 (45 mg, 4.8% yield). ESMS+: 482.5 (M+H). $^1$H NMR ($CDCl_3$, 400 MHz) δ: 8.48 (s, 2H), 7.81 (d, J=9.2 Hz, 2H), 7.42 (s, 1H), 7.39 (s, 1H), 7.02 (s, 1H), 6.88 (d, J=9.2 Hz, 2H), 5.31 (br, 2H), 3.87 (m, 4H), 3.83 (m, 4H), 3.27 (m, 8H).

The following compounds were prepared by methods analogous to the method described for Compound 36, and as described in Scheme C:

| Cmpd # | MS | $^1$H NMR |
|---|---|---|
| 37 | 484.4 (M + H) | (DMSO-d6, 400 MHz) δ: 8.59 (s, 2H), 7.64 (d, J = 8.8 Hz, 2H), 7.41 (s, 1H), 7.31 (s, 1H), 7.23 (s, 1H), 6.90 (s, 2H), 6.72 (d, J = 8.8 Hz, 2H), 6.52 (t, J = 5.6 Hz, 1H), 4.51 (s, 1H), 3.74 (m, 4H), 3.24 (m, 4H), 2.99 (d, J = 6.0 Hz, 2H), 1.12 (s, 6H). |

Example 11: (R)-5-(3-morpholino-5-((tetrahydrofuran-3-yl)sulfonyl)phenyl)pyrimidin-2-amine (Compound 52)

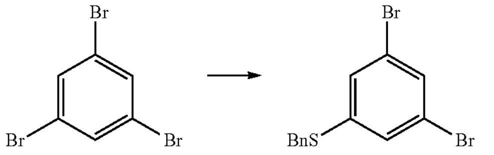

Step 1 (See Scheme D, Step 8): Synthesis of benzyl(3,5-dibromophenyl)sulfane

Phenylmethanethiol (19.8 g, 0.16 mol) was added to a solution of sodium hydride (7.04 g, 0.18 mol, 60% purity in mineral oil) in DMF (300 mL) at 0° C. The reaction was stirred for 15 min at rt and 1,3,5-tribromobenzene (50 g, 0.16 mol) was added. The reaction was stirred for another 2 h at rt. The solution was poured into ice-water (500 mL) and extracted with ethyl acetate (300 mL×3). The organic extracts were combined, washed with brine (300 mL×2), dried over anhydrous sodium sulfate, and concentrated. The residue was purified by silica gel column chromatography (petroleum ether) to give benzyl(3,5-dibromophenyl)sulfane. (50.1 g, 88% yield). The compound was confirmed with LC-MS only: 379.10 $(M+Na)^+$, $C_{13}H_{10}Br_2S$.

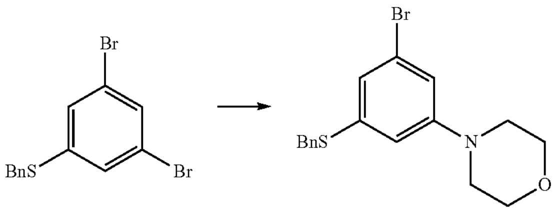

Step 2 (See Scheme D, Step 9): Synthesis of 4-(3-(benzylthio)-5-bromophenyl)morpholine $Pd_2dba_3$ (5 g) was added to a mixture of benzyl(3,5-dibromophenyl)sulfane (50 g, 0.14 mmol), BINAP (7.9 g, 12.6 mmol), t-BuONa (20.16 g, 0.21 mol), DBU (19.2 g, 0.126 mol), and morpholine (12.2 g, 0.14 mol) in toluene (400 mL) under nitrogen protection. The reaction was heated at 95° C. for 2 h. The mixture was cooled to rt and poured into water (500 mL). The mixture was extracted with ethyl acetate (300 mL×3). The organic extracts were combined, washed with brine (200 m L×2), dried over anhydrous sodium sulfate, and concentrated. The residue was purified by silica gel column chromatography (petroleum ether/ethyl acetate=30:1) to give 4-(3-(benzylthio)-5-bromophenyl) morpholine (21.3 g, 42% yield) as yellow solid. The compound was confirmed with LC-MS only: 364.30 $(M+H)^+$, $C_{17}H_{18}BrNOS$.

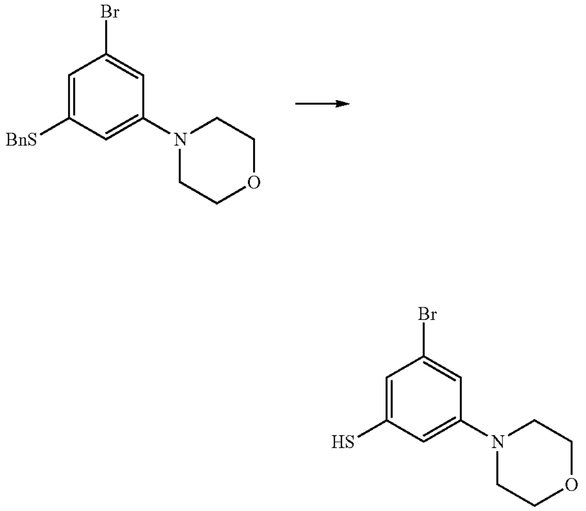

Step 3 (See Scheme D, Step 10): Synthesis of 3-bromo-5-morpholinobenzenethiol

Anhydrous $AlCl_3$ (60.7 g, 0.45 mol) was added to a solution of 4-(3-(benzylthio)-5-bromophenyl)morpholine (33 g, 0.09 mol) in toluene (500 mL). The reaction was heated at 50° C. for 2 h. The mixture was quenched with ice-water (500 mL) carefully and extracted with ethyl acetate (500 mL×3). The organic extracts were combined, washed with brine (300 mL×2), dried over anhydrous sodium sulfate, and concentrated. The residue was purified by silica gel column chromatography (petroleum ether/ethyl acetate=10:1) to give crude 3-bromo-5-morpholinobenzenethiol (21.6 g, 87% yield), which was used for next reaction without further purification. The compound was confirmed with LC-MS only: 276.22 $(M+H)^+$, $C_{10}H_{12}BrNOS$.

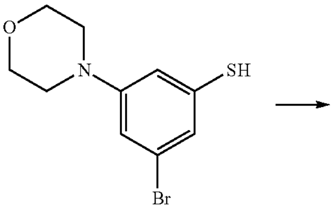

-continued

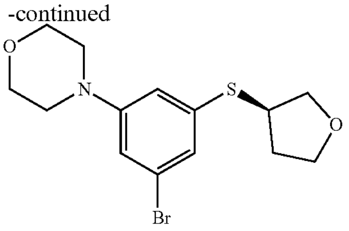

Step 4 (See Scheme D, Step 11a): Synthesis of 4-[3-bromo-5-[(3R)-tetrahydrofuran-3-yl]sulfanyl-phenyl]morpholine DEAD (9.88 g, 56.7 mmol) was added to a solution of $PPh_3$ (14.9 g, 56.7 mmol) in toluene (100 mL) at 0° C. The solution was stirred for 0.5 h at 0° C. and a solution of (S)-tetrahydrofuran-3-ol (5.0 g, 56.7 mmol) in toluene (10 mL) was added. After stirring for another 0.5 h at 0° C., a solution of 3-bromo-5-morpholino-benzenethiol (15.56 g, 56.75 mmol, in toluene (20 mL) was added. The reaction was further stirred for 1 hour at room temperature. The reaction solution was poured into water (200 mL) and extracted with ethyl acetate (200 mL×3). The combined organics were washed with brine (200 mL), dried over sodium sulfate, and concentrated to give a yellow solid. The crude was purified by silica gel column chromatography (petroleum ether/ethyl acetate=5:1) to give 4-[3-bromo-5-[(3R)-tetrahydrofuran-3-yl]sulfanyl-phenyl]morpholine (11.6 g, 59% yield) as a pale yellow oil. The compound was confirmed with LC-MS: 344.35 $(M+H)^+$, $C_{14}H_{18}O_2SBrN$.

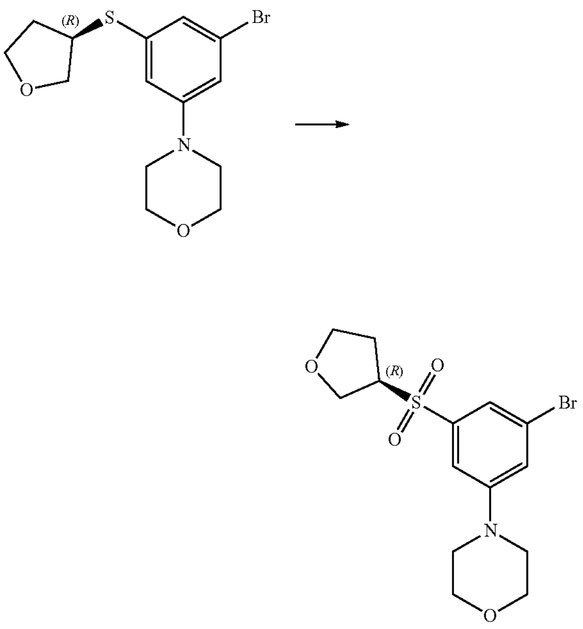

Step 5 (See Scheme D, Step 12a): Synthesis of 4-[3-bromo-5-[(3R)-tetrahydrofuran-3-yl]sulfonyl-phenyl]morpholine mCPBA (23.3 g, 0.13 mol) was added in portions to a solution of 4-[3-bromo-5-[(3R)-tetrahydrofuran-3-yl]sulfanyl-phenyl]morpholine (11.6 g, 33.7 mmol) in dichloromethane (250 mL). The mixture was stirred at rt for 2 h. 4,4,4',4',5,5,5',5'-Octamethyl-2,2'-bi(1,3,2-dioxaborolane) (34.2 g, 0.13 mol) was added and the resulting mixture was stirred for 0.5 h at rt. The reaction mixture was washed with sat. $Na_2CO_3$ (200 mL×3), brine (100 mL), dried over sodium sulfate, and concentrated. The crude was purified by silica gel column chromatography (petroleum ether/ethyl acetate=1:1) to give the compound 4-[3-bromo-5-[(3R)-tetrahydrofuran-3-yl]sulfonyl-phenyl]morpholine (5.0 g, 39% yield) as a colorless oil. The compound was confirmed with LC-MS: 376.53 $(M+H)^+$, $C_{14}H_{18}NO_4SBr$.

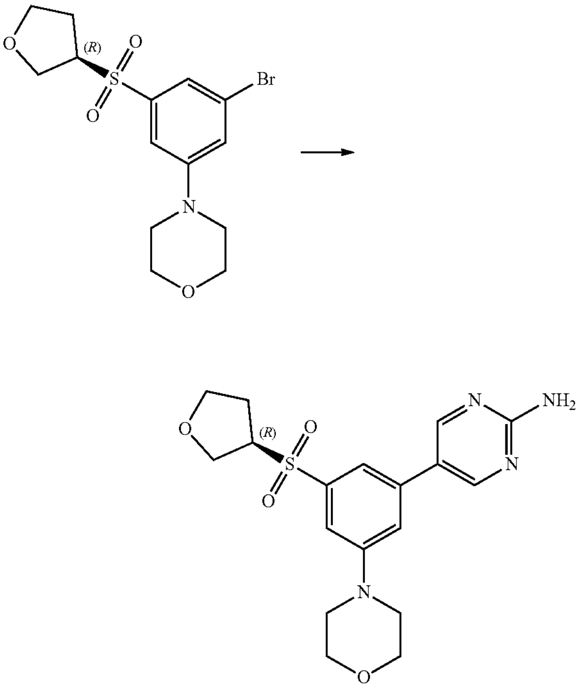

Compound 52

Step 6 (See Scheme D, Step 4c): A mixture of 4-[3-bromo-5-[(3R)-tetrahydrofuran-3-yl]sulfonyl-phenyl]morpholine (3.0 g, 8.0 mmol), 5-(4,4,5,5-tetramethyl-1,3,2-dioxaborolan-2-yl)pyrimidin-2-amine (3.53 g, 16.0 mmol, $K_2CO_3$ (2.20 g, 16.0 mmol), and $Pd(dppf)Cl_2$ (651 mg, 0.8 mmol) in 1,4-dioxane (15 mL) and $H_2O$ (5 mL) was stirred at 95° C. for 1 h under $N_2$. The mixture was poured into water (50 mL) and extracted with ethyl acetate (50 mL×3). The combined organics were washed with brine (30 mL), dried over sodium sulfate, and concentrated. The crude was purified by silica gel column chromatography (dichloromethane/methanol=50:1) to afford (R)-5-(3-morpholino-5-((tetrahydrofuran-3-yl)sulfonyl)phenyl)pyrimidin-2-amine (Compound 52) (1.65 g, 53% yield) as an off-white solid. ESMS+: 391.5 (M+H). $^1H$ NMR (DMSO-d6, 400 MHz) δ: 8.67 (s, 2H), 7.46 (s, 2H), 7.27 (s, 1H), 6.92 (s, 2H), 4.33 (m, 1H), 4.04 (m, 1H), 3.80 (m, 2H), 3.77 (m, 4H), 3.68 (m, 1H), 3.31 (m, 4H), 2.18 (m, 1H), 2.09 (m, 1H).

The following compounds were prepared by methods analogous to the method described for Compound 52, and as described in Scheme D:

| Cmpd # | MS | $^1$H NMR |
|---|---|---|
| 48 (as a TFA salt) | 450.3 (M + H) | (DMSO-d6, 400 MHz) δ: 11.19 (br, 1H), 8.55 (s, 2H), 7.41 (d, J = 7.6 Hz, 1H), 7.35 (m, 2H), 7.27 (s, 1H), 7.21 (d, J = 2.4 Hz, 1H), 7.03 (m,2H), 6.89 (m, 1H), 4.815 (s, 2H), 3.71 (m, 4H), 3.11 (m, 4H). |
| 53 | 390.82 (M + H) | (DMSO-d6, 400 MHz) δ: 8.67 (s, 2H), 7.47 (s, 2H), 7.27 (s, 1H), 6.93 (s, 2H), 4.31 (m, 1H), 4.02 (m, 1H), 3.73-3.87 (m, 6H), 3.66 (m, 1H), 3.30 (m, 4H), 2.17 (m, 1H), 2.09 (m, 1H). |
| 56 | 450.2 (M + H) | (MeOD, 400 MHz) δ: 8.35 (s, 2H), 7.27 (m, 4H), 7.12 (s, 1H), 6.94 (m, 1H), 6.77 (d, J = 1.2 Hz, 1H), 6.37 (d, J = 2.8 Hz, 1H), 4.55 (s, 2H), 3.72 (m, 4H), 2.96 (m, 4H). |
| 57 (as a TFA salt) | 503.6 (M + H) | (DMSO-d6, 400 MHz) δ: 9.86 (s, 1H), 8.66 (s, 2H), 7.45 (s, 1H), 7.31 (s, 1H), 7.13 (m, 5H), 7.02 (s, 1H), 4.64 (s, 2H), 3.74 (m, 4H), 3.20 (m, 4H), 2.98 (s, 3H). |
| 58 | 495.53 (M + H) | (DMSO-d6, 400 MHz) δ: 8.56 (s, 2H), 7.41 (s, 1H), 7.22 (s, 1H), 7.02 (d, J = 8.8 Hz, 2H), 6.95 (s, 1H), 6.91 (s, 2H), 6.85 (d, J = 8.8 Hz, 2H), 4.54 (s, 2H), 3.72 (m, 8H), 3.17 (m, 4H), 3.07 (m, 4H). |
| 59 (as a TFA salt) | 401.3 (M + H) | (MeOD, 400 MHz) δ: 8.95 (s, 1H), 8.70 (s, 2H), 7.46 (s, 1H), 7.42 (m, 2H), 7.27 (s, 1H), 4.80 (s, 2H), 3.84 (m, 4H), 3.29 (m, 4H). |
| 63 | 450.9 (M + H) | (MeOD, 400 MHz) δ: 8.37 (s, 2H), 8.19 (s, 1H), 7.52 (d, J = 8.4 Hz, 1H), 7.34 (s, 1H), 7.29 (m, 1H), 7.12 (m, 2H), 6.86 (s, 1H), 4.63 (s, 2H), 3.72 (m, 4H), 3.01 (m, 4H). |
| 71 | 458.2 (M + H) | ($CDCl_3$, 500 MHz) δ: 8.08 (s, 1H), 7.39 (d, J = 1.9 Hz, 1H), 7.28 (s, 1H), 7.03 (s, 1H), 6.86 (s, 1H), 5.01 (s, 2H), 4.16 (dd, J = 10.1, 5.8 Hz, 1H), 3.96 (dd, J = 10.1, 7.9 Hz, 1H), 3.92-3.75 (m, 6H), 3.26 (dd, J = 5.9, 3.8 Hz, 4H), 2.41 (dq, J = 13.1, 6.1 Hz, 1H), 2.18 (ddd, J = 13.2, 9.3, 6.7 Hz, 1H), 1.97-1.86 (m, 1H). |
| 82 | 442.86 (M + H) | (DMSO-d6, 400 MHz) δ: 8.66 (s, 2H), 7.43 (d, J = 9.2 Hz, 2H), 7.25 (m, 3H), 7.05 (m, 2H), 6.92 (s, 2H), 3.76 (m, 4H), 3.71 (m, 2H), 3.29 (m, 4H), 2.92 (d, J = 8.0 Hz, 2H). |
| 83 | 446.4 (M + H) | ($CDCl_3$, 400 MHz) δ: 8.54 (s, 2H), 7.38 (s, 1H), 7.29 (s, 1H), 7.17 (s, 1H), 5.38 (br, 2H), 4.75 (m, 2H), 3.97 (m, 1H), 3.90 (m, 4H), 3.30 (m, 4H), 3.14 (m, 1H), 3.07 (m, 1H), 2.50 (m, 1H), 2.15 (m, 1H), 2.08 (s, 3H), 1.99 (m, 1H), 1.89 (m, 2H), 1.65 (m, 2H). |
| 84 | 497.8 (M + H) | ($CDCl_3$, 400 MHz) δ: 8.22 (s, 2H), 7.21 (s, 1H), 7.06 (s, 1H), 6.91 (d, J = 8.0 Hz, 2H), 6.64 (s, 1H), 6.56 (d, J = 8.0 Hz, 2H), 4.23 (s, 2H), 3.89 (m, 4H), 3.76 (m, 2H), 3.40 (s, 1H), 3.24 (m, 4H), 3.08 (s, 2H), 2.01 (m, 1H), 1.32 (s, 6H). |
| 89 | 432.3 (M + H) | (DMSO-d6, 400 MHz) δ: 12.04 (br, 1H), 9.07 (br, 2H), 7.62 (br, 2H), 7.36 (m, 1H), 4.48 (br, 1H), 3.78 (m, 5H), 3.46 (m, 3H), 3.34 (m, 4H), 3.11 (m, 1H), 2.26 (m, 2H), 1.27 (m, 6H). |
| 90 | 446.6 (M + H) | (DMSO-d6, 400 MHz) δ: 8.66 (s, 2H), 7.51 (s, 1H), 7.38 (s, 1H), 7.19 (s, 1H), 6.95 (s, 2H), 3.77 (m, 4H), 3.36 (m, 3H), 3.30 (m, 4H), 2.93 (br, 2H), 1.73-2.21 (br, 5H), 0.82-1.39 (br, 6H). |
| 91 | 431.90 (M + H) | (DMSO-d6, 400 MHz) δ: 8.74 (s, 2H), 7.54 (m, 2H), 7.32 (m, 1H), 7.01 (s, 2H), 4.36 (m, 1H), 3.83 (m, 4H), 3.79 (m, 1H), 3.52 (m, 2H), 3.37 (m, 5H), 2.32 (m, 2H), 1.92 (m, 3H). |
| 97 | 412.01 (M + H) | (DMSO-d6, 400 MHz) δ: 8.59 (s, 2H), 8.52 (m, 2H), 7.46 (s, 1H), 7.32 (s, 1H), 7.22 (m, 2H), 7.05 (s, 1H), 6.94 (s, 2H), 4.82 (s, 2H), 3.74 (m, 4H), 3.21 (m, 4H). |
| 98 | 446.5 (M + H) | ($CDCl_3$, 400 MHz) δ: 8.54 (s, 2H), 7.38 (s, 1H), 7.29 (s, 1H), 7.17 (s, 1H), 5.38 (br, 2H), 4.75 (m, 1H), 3.97 (m, 1H), 3.90 (m, 4H), 3.30 (m, 4H), 3.14 (m, 1H), 3.07 (m, 1H), 2.50 (m, 1H), 2.15 (m, 1H), 2.08 (s, 3H), 1.99 (m, 1H), 1.65 (m, 2H). |
| 99 | 461.6 (M + H) | (DMSO-d6, 400 MHz) δ: 7.37 (s, 1H), 7.34 (m, 1H), 7.22 (m, 1H), 7.17 (s, 2H), 7.08 (m, 1H), 6.66 (s, 1H), 6.41 (s, 2H), 4.73 (s, 2H), 3.75 (m, 4H), 3.18 (m, 4H), 2.09 (s, 3H). |
| 100 | 458.35 (M + H) | (DMSO-d6, 400 MHz) δ: 8.62 (s, 1H), 8.09 (s, 1H), 7.50 (s, 2H), 7.27 (s, 1H), 6.73 (s, 2H), 4.34 (m, 1H), 4.03 (m, 1H), 3.75-3.85 (m, 6H), 3.67 (m, 1H), 3.30 (m, 4H), 2.11-2.19 (m, 2H). |
| 101 | 390.4 (M + H) | (DMSO-d6, 400 MHz) δ: 8.33 (s, 1H), 7.79 (m, 1H), 7.40 (m, 2H), 7.23 (s, 1H), 6.53 (d, J-8.4 Hz, 1H), 6.22 (s, 2H), 4.31 (m, 1H), 4.02 (m, 1H), 3.84 (m, 2H), 3.76 (m, 4H), 3.65 (m, 1H), 3.30 (m, 4H), 2.15 (m, 2H). |
| 105 | 458.43 (M + H) | (DMSO-d6, 400 MHz) δ: 7.50 (d, 1H), 7.33 (s, 1H), 7.16 (s, 1H), 7.11 (s, 1H), 6.73 (d, 1H), 6.66 (s, 2H), 4.24 (m, 1H), 3.97 (m, 1H), 3.81 (m, 1H), 3.75 (m, 5H), 3.64 (m, 1H), 3.25 (m, 4H), 2.13 (m, 2H). |
| 106 | 408.6 (M + H) | ($CDCl_3$, 400 MHz) δ: 8.13 (d, J = 10.4 Hz, 1H), 7.43 (s, 1H), 7.35 (s, 1H), 7.19 (s, 1H), 6.31 (d, J = 12.0 Hz, 1H), 4.89 (br, 2H), 4.20 (m, 1H), 3.77-4.03 (m, 8H), 3.28 (m, 4H), 2.44 (m, 1H), 2.20 (m, 1H). |

-continued

| Cmpd # | MS | $^{1}$H NMR |
|---|---|---|
| 107 | 424.37 (M + H) | ($CDCl_3$, 400 MHz) δ: 8.00 (s, 1H), 7.37 (m, 2H), 7.12 (s, 1H), 6.66 (s, 1H), 4.81 (s, 2H), 4.18 (m, 1H), 3.80-4.00 (m, 8H), 3.29 (m, 4H), 2.44 (m, 1H), 2.20 (m, 1H). |
| 108 | 404.7 (M + H) | (DMSO-d6, 400 MHz) δ: 8.31 (s, 1H), 7.70 (m, 1H), 7.45 (s, 1H), 7.29 (m, 1H), 7.21 (s, 1H), 6.50 (d, J-8.8 Hz, 1H), 6.26 (br, 1H), 4.19 (m, 1H), 3.77-3.98 (m, 8H), 3.29 (m, 4H), 2.98 (s, 3H), 2.44 (m, 1H), 2.19 (m, 1H). |
| 114 | 436.5 (M + H) | (DMSO-d6, 400 MHz) δ: 12.25 (br, 1H), 8.56 (s, 2H), 8.23 (s, 1H), 7.87 (dd, J = 6.8 Hz, 2.0 Hz, 1H), 7.53 (s, 1H), 7.49 (m, 1H), 7.38 (s, 1H), 7.26 (s, 1H), 7.21 (m, 2H), 6.89 (s, 2H), 3.73 (m, 4H), 3.23 (m, 4H). |
| 121 | 404.7 (M + H) | ($CDCl_3$, 500 MHz) δ: 8.11 (s, 1H), 7.35 (dd, J = 2.5, 1.6 Hz, 1H), 7.25 (t, J = 1.5 Hz, 1H), 6.98 (dd, J = 2.5, 1.4 Hz, 1H), 5.20 (s, 2H), 4.18 (dd, J = 10.1, 5.7 Hz, 1H), 3.99-3.90 (m, 2H), 3.90-3.86 (m, 4H), 3.86-3.78 (m, 2H), 3.27 (dd, J = 5.9, 4.0 Hz, 4H), 2.46-2.39 (m, 1H), 2.33 (d, J = 1.8 Hz, 3H), 2.20 (m, 1H). |

Example 12: 5-(3-((difluoro(phenyl)methyl)sulfonyl)-5-morpholinophenyl)pyrimidin-2-amine (Compound 87)

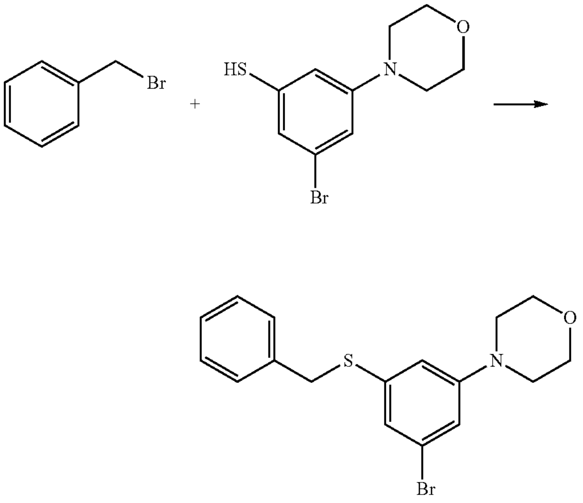

Step 1 (See Scheme D, Step 11b): Synthesis of 4-(3-(benzylthio)-5-bromophenyl)morpholine (Bromomethyl)benzene (1.25 g, 7.33 mmol) was mixed with 3-bromo-5-morpholinobenzenethiol (2 g, 7.33 mmol) and $Cs_2CO_3$ (4.8 g, 14.66 mmol) in acetonitrile (30 mL). The reaction was stirred for 1 h at rt. The insoluable precipitate was filtered and washed with acetonitrile (20 mL). The filtrate and wash were combined and concentrated. The residue was purified by silica gel column chromatography (petroleum ether/ethyl acetate=1:1) to give 4-(3-(benzylthio)-5-bromophenyl)morpholine (1.2 g, 45% yield) as an off-white solid. The compound was confirmed with LC-MS only: 366.14 $(M+H)^+$, $C_{17}H_{18}BrNOS$.

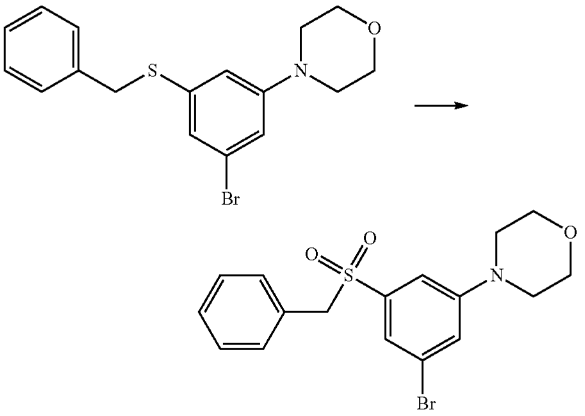

Step 2 (See Scheme D, Step 12a): Synthesis of 4-(3-(benzylsulfonyl)-5-bromophenyl)morpholine 4-(3-(benzylthio)-5-bromophenyl)morpholine (1.2 g, 3.3 mmol) was oxidized with mCPBA as described for Example 11 for Compound 52 to give 4-(3-(benzylsulfonyl)-5-bromophenyl)morpholine (0.6 g, 46% yield) as a white solid. The compound was confirmed with LC-MS only: 397.50 $(M+H)^+$, $C_{17}H_{16}BrF_2NO_3S$.

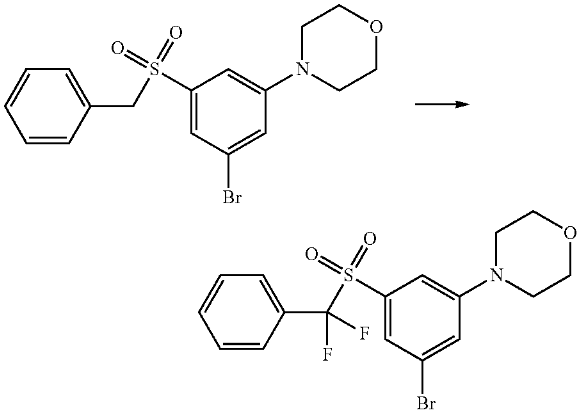

Step 3 (See Scheme D, Step 13): Synthesis of 4-(3-Bromo-5-(difluoro(phenyl)methylsulfonyl)phenyl) morpholine NaHMDS (2.68 mL, 5.36 mmol, 2 M in THF) was added to a solution of 4-(3-(benzylsulfonyl)-5-bromophenyl)morpholine (0.53 g, 1.34 mmol) in THF (50 mL) at 0° C. The reaction was stirred for 1 h at 0° C. N-fluoro-N-(phenylsulfonyl)benzenesulfonamide (1.69 g, 5.36 mmol) was added and the reaction was stirred for another 1 h at 0° C. The mixture was poured into ice-water (200 mL) and extracted with ethyl acetate (200 mL×3). The organic extracts were combined, washed with sat. sodium carbonate (100 mL×2). The organic layer was separated, dried over anhydrous sodium sulfate, and concentrated. The residue was purified by silica gel column chromatography (petroleum ether/ethyl acetate=3:1) to give 4-(3-bromo-5-((difluoro(phenyl)methyl)sulfonyl)phenyl)morpholine (0.22 g, 38% yield) as an off-white solid. The compound was confirmed with LC-MS only: 434.23 $(M+H)^+$, $C_{17}H_{16}BrF_2NO_3S$.

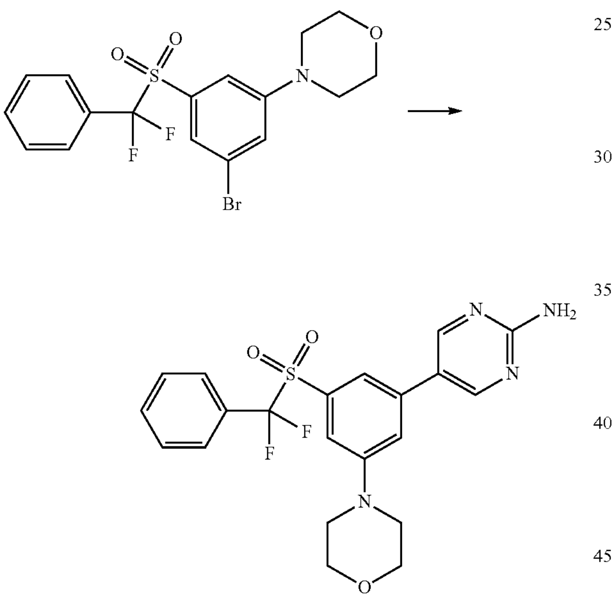

Compound 87

Step 4 (See Scheme D, Step 4c): Synthesis of 5-(3-((difluoro(phenyl)methyl)sulfonyl)-5-morpholinophenyl)pyrimidin-2-amine A Suzuki reaction of 4-(3-bromo-5-((difluoro(phenyl)methyl)sulfonyl)phenyl)morpholine (220 mg, 0.51 mmol) and 5-(4,4,5,5-tetramethyl-1,3,2-dioxaborolan-2-yl)pyrimidin-2-amine (110 mg, 0.51 mmol) as described in Example 11 for Compound 52 provided 5-(3-((difluoro(phenyl)methyl)sulfonyl)-5-morpholinophenyl)pyrimidin-2-amine (93 mg, 41% yield) as an off-white solid. ESMS+: 447.2 (M+H). $^1H$ NMR (DMSO-d6, 400 MHz) δ: 8.59 (s, 2H), 7.71 (m, 1H), 7.61 (m, 5H), 7.37 (s, 1H), 7.17 (s, 1H), 6.99 (s, 2H), 3.77 (m, 4H), 3.28 (m, 4H).

Example 13: N[1]-(5-(3-((4-fluorobenzyl)sulfonyl)-5-morpholinophenyl)pyrimidin-2-yl)ethane-1,2-diamine (Compound 47)

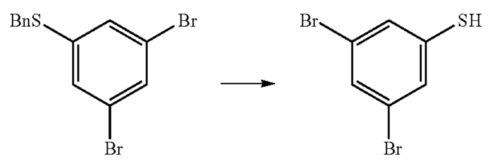

Step 1 (See Scheme E, Step 10): Synthesis of 3,5-dibromobenzenethiol

Debenzylation of benzyl(3,5-dibromophenyl)sulfane (26 g, 73.0 mmol) with anhydrous $AlCl_3$ (48 g, 0.36 mol) was completed as described in Example 11 for Compound 52 to give 3,5-dibromobenzenethiol (10.7 g, 55% yield), which was used for next reaction without further purification. The compound was confirmed with LC-MS only: 266.82 $(M-H)^-$, $C_6H_4Br_2S$.

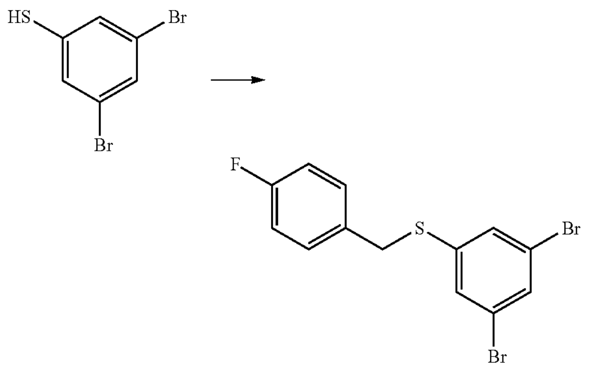

Step 2 (See Scheme E, Step 11b): Synthesis of (3,5-dibromophenyl)(4-fluorobenzyl)sulfane 3,5-Dibromobenzenethiol (5 g, 18.8 mmol) was treated with 4-fluorobenzyl chloride (3.0 g, 20.7 mmol) and $Cs_2CO_3$ (12.3 g, 37.6 mmol) in acetonitrile (300 mL). The reaction was stirred for 1 h at rt. The reaction was filtered and washed with acetonitrile (20 mL). The filtrate and wash were combined and concentrated to give crude (3,5-dibromophenyl)(4-fluorobenzyl)sulfane (6.9 g, 98% yield) as a colorless oil, which was used for next reaction without further purification. GC-MS: 376. $^1H$NMR ($CDCl_3$, 400 MHz) δ: 7.45 (s, 1H), 7.31 (s, 2H), 7.27 (m, 2H), 7.00 (m, 2H), 4.09 (s, 2H).

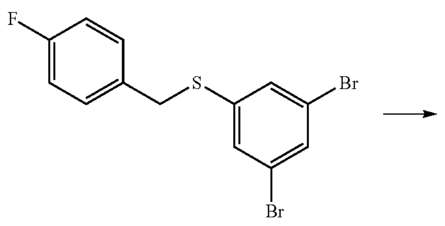

-continued

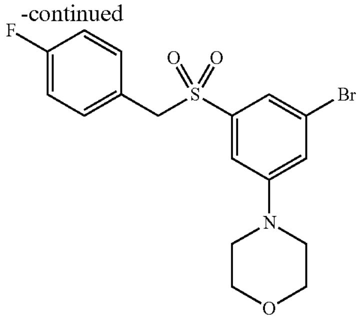

Step 3 (See Scheme E, Step 12b and Step 11): Synthesis of 4-(3-bromo-5-(4-fluorobenzylsulfonyl) phenyl)morpholine A solution of $KMnO_4$ (3.79 g, 24.0 mmol) in water (225 mL) was added to a solution of (3,5-dibromophenyl)(4-fluorobenzyl)sulfane (6 g, 16.0 mmol) in acetic acid (350 mL). The reaction was stirred for 1 h. 10% $Na_2SO_3$ solution (30 mL) was added. The resulting precipitate was filtered and washed with water (50 mL). The cake was dissolved in ethyl acetate (100 mL) and washed with sat. sodium bicarbonate (30 mL). The organic layer was separated, dried over anhydrous sodium sulfate, and concentrated to give crude intermediate (6.5 g, quantative yield). The crude intermediate (6.5 g, 16.0 mmol) was dissolved in toluene (200 mL). $Pd_2dba_3$ (0.5 g), BINAP (0.1 g, 0.18 mmol), t-BuONa (2.3 g, 24.0 mol), DBU (2.2 g, 14.4 mol), and morpholine (1.4 g, 16.0 mol) were added under nitrogen protection. The reaction was heated at 95° C. for 5 h. The mixture was cooled to rt and poured into water (500 mL). The mixture was extracted with ethyl acetate (300 mL×3). The organic extracts were combined, washed with brine (200 mL×2), dried over anhydrous sodium sulfate, and concentrated. The residue was purified by silica gel column chromatography (petroleum ether/ethyl acetate=6:1) to give 4-(3-bromo-5-((4-fluorobenzyl)sulfonyl)phenyl)morpholine (0.7 g, 11% yield) as a yellow solid. The compound was confirmed with LC-MS only: 415.75 $(M+H)^+$, $C_{17}H_{17}BrFNO_3S$.

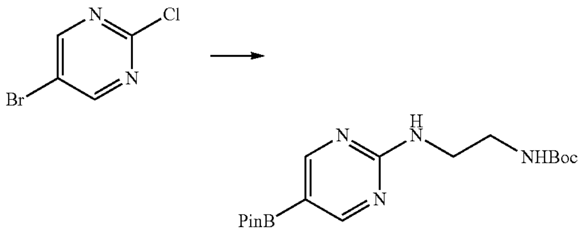

Step 4 (See Scheme E, Step 7): Synthesis of tert-butyl-2-(5-(4,4,5,5-tetramethyl-1,3,2-dioxaborolan-2-yl)pyrimidin-2-ylamino)ethylcarbamate A solution of 5-bromo-2-chloropyrimidine (0.84 g, 4.4 mmol), tert-butyl 2-aminoethylcarbamate (0.7 g, 4.4 mmol), and DIPEA (1.1 g, 8.8 mmol) in isopropyl alcohol (30 mL) was heated at 80° C. for 3 h. iPrOH was removed in vacuo. The residue was suspended in water (30 mL) and extracted with ethyl acetate (30 mL×3). The organic extracts were combined, dried over anhydrous sodium sulfate, and concentrated to give crude tert-butyl (2-((5-bromopyrimidin-2-yl)amino)ethyl)carbamate (0.75 g, 54% yield), which was used for next reaction without further purification. tert-butyl 2-(5-bromopyrimidin-2-ylamino)ethylcarbamate was confirmed with LC-MS only: 317.16 $(M+H)^+$, $C_{11}H_{17}BrN_4O_2$.

(See Scheme E, Step 14): A mixture of tert-butyl (2-((5-bromopyrimidin-2-yl)amino)ethyl)carbamate (0.75 g, 2.4 mmol), 4,4,4',4',5,5,5',5'-octamethyl-2,2'-bi(1,3,2-dioxaborolane) (0.67 g, 2.6 mmol), potassium acetate (0.46 g, 4.7 mol), and $Pd(dppf)Cl_2$ (0.2 g, 0.24 mmol) in 1,4-dioxane (30 mL) was heated at 115° C. for 3 h. The mixture was cooled to rt and diluted with ethyl acetate (50 mL). The insolubles were filtered and washed with ethyl acetate (5 mL). The filtrate and wash were combined, washed with water (30 mL×2), brine (30 mL), dried over anhydrous sodium sulfate, and concentrated. The residue was washed with a combination of petroleum ether/ethyl acetate (40 mL, 20:1) to give crude tert-butyl-2-(5-(4,4,5,5-tetramethyl-1,3,2-dioxaborolan-2-yl)pyrimidin-2-ylamino)ethylcarbamate (0.93 g, quantative yield), which was used for next reaction without further purification. The compound was confirmed with LC-MS only: 365.00 $(M+H)^+$, $C_{17}H_{29}BN_4O_4$.

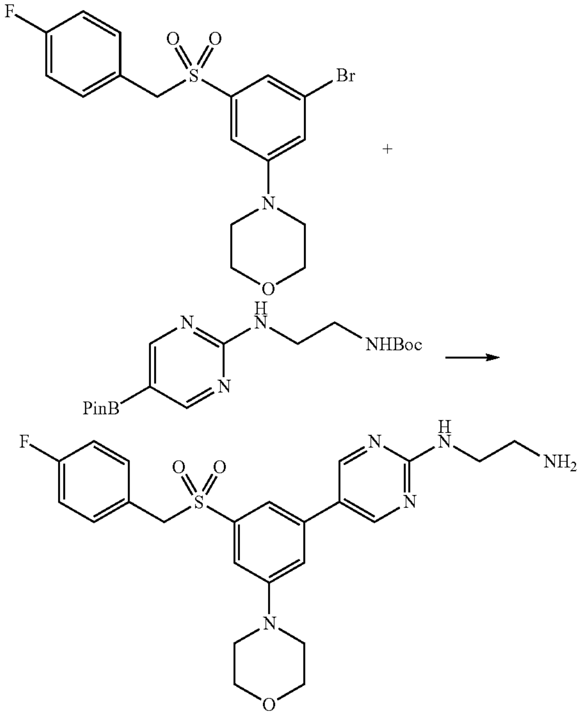

Compound 47

Step 5 (See Scheme E, Step 4c): The Suzuki reaction of 4-(3-bromo-5-(4-fluorobenzylsulfonyl)phenyl)morpholine (200 mg, 0.48 mmol) and tert-butyl-2-(5-(4,4,5,5-tetramethyl-1,3,2-dioxaborolan-2-yl)pyrimidin-2-ylamino)ethylcarbamate as described in Example 11 for Compound 52 provided tert-butyl (2-((5-(3-((4-fluorobenzyl)sulfonyl)-5-morpholinophenyl)pyrimidin-2-yl)amino)ethyl)carbamate (130 mg, 47% yield) as a white solid. The compound was confirmed with LC-MS only: 572.47 $(M+H)^+$, $C_{28}H_{34}FN_5O_5S$.

3 N HCl (gas)/EA (15 mL) was added to as solution of tert-butyl (2-((5-(3-((4-fluorobenzyl)sulfonyl)-5-morpholinophenyl)pyrimidin-2-yl)amino)ethyl)carbamate (130 mg, 0.23 mmol) in methanol (15 mL). The reaction was stirred for 1 h at rt. The solvent was removed in vacuo and the residue was washed with methanol (1 mL×3) to afford $N^1$-(5-(3-((4-fluorobenzyl)sulfonyl)-5-morpholinophenyl)pyrimidin-2-yl)ethane-1,2-diamine hydrochloride (Compound 47 hydrochloride) (79 mg, 68% yield) as a yellow solid. ESMS+: 472.4 (M+H). $^1H$ NMR (DMSO-d6, 400 MHz) δ: 8.76 (s, 2H), 8.07 (br, 3H), 7.69 (br, 1H), 7.47 (s, 1H), 7.31 (s, 1H), 7.24 (m, 2H), 7.17 (m, 2H), 7.07 (s, 1H), 4.74 (s, 2H), 3.75 (m, 4H), 3.60 (m, 2H), 3.22 (m, 4H), 3.072 (m, 2H).

Example 14: 5-(3-(benzofuran-3-ylsulfonyl)-5-morpholinophenyl)pyrimidin-2-amine (Compound 109)

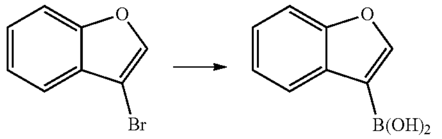 [SMILES: Brc1coc2ccccc12 ; OB(O)c1coc2ccccc12]

Step 1 (See Scheme F, Step 15): Synthesis of benzofuran-3-ylboronic acid n-BuLi (8.12 mmol) was added dropwise to a solution of 3-bromobenzofuran (800 mg, 4.06 mmol) and triisopropyl borate (2.29 g, 12.2 mmol) in THF (15 mL) at −78° C. under $N_2$. The reaction was stirred for 1 h at −78° C. The reaction was quenched with sat. $NH_4Cl$ and extracted ethyl acetate (20 mL×3). The combined organics were washed with brine (20 mL), dried over sodium sulfate, and concentrated to give benzofuran-3-ylboronic acid (657 mg, quantative yield) as a pale yellow solid, which was used for next reaction without further purification. The compound was confirmed with LC-MS only: 162.90 $(M+H)^+$, $C_8H_7O_3B$.

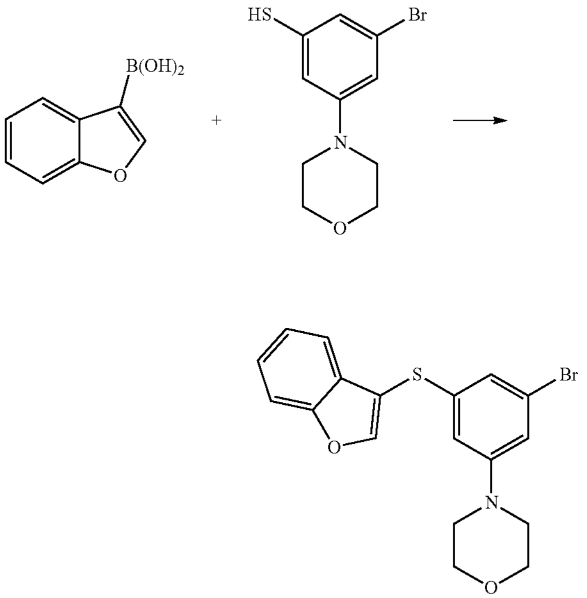 [SMILES: OB(O)c1coc2ccccc12 ; Sc1cc(Br)cc(N2CCOCC2)c1 ; Brc1cc(Sc2coc3ccccc23)cc(N2CCOCC2)c1]

Step 2 (See Scheme F, Step 16): Synthesis of 4-[3-(benzofuran-3-ylsulfanyl)-5-bromo-phenyl]morpholine A solution of benzofuran-3-ylboronic acid (660 mg, 4.08 mmol), 3-bromo-5-morpholino-benzenethiol (1.57 g, 5.71 mmol), $CuSO_4 \cdot 5H_2O$ (51 mg, 0.20 mmol), 1,10-phenanthroline monohydrate (40 mg, 0.20 mmol) and n-$Bu_4NOH$ in EtOH (12 mL) was stirred overnight at rt under $O_2$. The reaction mixture was poured into water (20 mL) and extracted with ethyl acetate (20 mL×3). The combined organics were washed with brine (20 mL), dried over sodium sulfate, and concentrated. The crude was purified by silica gel column chromatography (petroleum ether/ethyl acetate=10:1) to give 4-[3-(benzofuran-3-ylsulfanyl)-5-bromo-phenyl]morpholine (520 mg, 33% yield) as a yellow oil. The compound was confirmed with LC-MS only: 390.25 $(M+H)^+$, $C_{18}H_{16}O_2NSBr$.

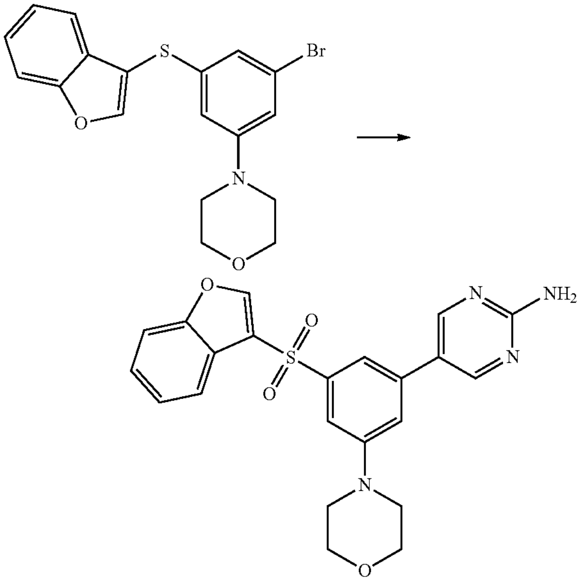

Compound 109

Step 3 (See Scheme F, Step 12a): Synthesis of 4-[3-(benzofuran-3-ylsulfonyl)-5-bromo-phenyl]morpholine Oxidation of 4-[3-(benzofuran-3-ylsulfanyl)-5-bromo-phenyl]morpholine (520 mg, 1.33 mmol) was accomplished as described in Example 11 for Compound 52 to give 4-[3-(benzofuran-3-ylsulfonyl)-5-bromo-phenyl]morpholine (500 mg, 89% yield) as pale yellow solid. The compound was confirmed with LC-MS only: 422.34 $(M+H)^+$, $C_{18}H_{16}BrNO_4S$.

Step 4 (See Scheme F, Step 4c): The reaction of 4-[3-(benzofuran-3-ylsulfonyl)-5-bromo-phenyl]morpholine (300 mg, 0.71 mmol) and 5-(4,4,5,5-tetramethyl-1,3,2-dioxaborolan-2-yl)pyrimidin-2-amine (157 mg, 0.71 mmol) was completed as described in Example 11 for Compound 52 to afford 5-(3-(benzofuran-3-ylsulfonyl)-5-morpholinophenyl)pyrimidin-2-amine (Compound 109) (150 mg, 48% yield) as an off-white solid. ESMS+: 437.34 (M+H). $^1H$ NMR (DMSO-d6, 400 MHz) δ: 8.94 (s, 1H), 8.61 (s, 2H), 7.90 (d, 1H), 7.75 (d, 1H), 7.63 (s, 1H), 7.4-7.49 (m, 4H), 6.91 (s, 2H), 3.75 (m, 4H), 3.25 (m, 4H).

The following compounds were prepared by methods analogous to the method described for Compound 109 and as described in Scheme F:

| Cmpd # | MS | $^1$H NMR |
|---|---|---|
| 110 | 437.44 (M + H) | (DMSO-d6, 400 MHz) δ: 8.58 (s, 2H), 8.25 (s, 1H), 8.03 (d, 1H), 7.96 (d, 1H), 7.58 (s, 1H), 7.49 (d, 2H), 7.41 (s, 1H), 7.12 (d, 1H), 6.91 (s, 2H), 3.75 (m, 4H), 3.25 (m, 4H). |
| 111 | 439.6 (M + H) | (DMSO-d6, 400 MHz) δ: 8.57 (s, 2H), 7.65(d, J = 7.6 Hz, 1H), 7.52 (d, J = 7.2 Hz, 1H), 7.47 (s, 1H), 7.40 (s, 1H), 7.37 (s, 1H), 7.00 (t, J = 7.6 Hz, 1H), 6.89 (s, 2H), 4.68 (t, J = 8.8 Hz, 2H), 3.76 (m, 4H), 3.25 (m, 6H). |
| 112 | 437.6 (M + H) | (DMSO-d6, 400 MHz) δ 8.63 (s, 2H), 8.42-8.38 (m, 1H), 8.28 (d, J = 2.2 Hz, 1H), 7.92 (dd, J = 8.2, 1.6 Hz, 1H), 7.87 (d, J = 8.2 Hz, 1H), 7.59 (d, J = 1.5 Hz, 1H), 7.40-7.35 (m, 2H), 7.11 (dd, J = 2.2, 1.0 Hz, 1H), 6.91 (s, 2H), 3.74 (dd, J = 6.0, 3.7 Hz, 4H), 3.27 (t, J = 4.9 Hz, 4H). |

Example 15: (E)-2-(2-((3-(2-aminopyrimidin-5-yl)-5-morpholinophenyl) sulfonyl)vinyl)phenol (Compound 113)

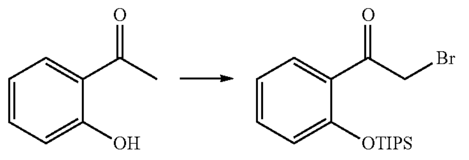

Step 1 (See Scheme G, Step 17): Synthesis of 2-bromo-1-(2-(triisopropylsilyloxy)phenyl)ethanone TIPSCl (33.8 g, 0.18 mol) was added dropwise to a solution of 1-(2-hydroxyphenyl)ethanone (20 g, 0.15 mmol), DIPEA (32.8 g, 0.32 mol), and DMAP (36.2 g, 0.29 mmol) in dichloromethane (300 mL) at 0° C. The reaction was stirred for 2 h at rt. The solution was poured into water (500 mL) and pH of water phase was adjusted to 4-5 with citric acid. The mixture was extracted with dichloromethane (300 mL×3). The organic extracts were combined, dried over anhydrous sodium sulfate, and concentrated. The crude was purified by silica gel column chromatography (petroleum ether/ethyl acetate=100:1) to give TIPS-protected ketone (29.1 g, 67% yield). The TIPS-protected ketone (20 g, 68.5 mmol) was mixed with PTSA (1.3 g, 6.9 mmol). NBS (12.1 g, 68.5 mmol) was added in portions with stirring. The mixed solid was stirred overnight. The solid was suspended in water (200 mL) and extracted with dichloromethane (200 mL×3). The organic extracts were combined, dried over anhydrous sodium sulfate, and concentrated. The residue was purified by silica gel column chromatography (petroleum ether/ethyl acetate=200:1) to give 2-bromo-1-(2-(triisopropylsilyloxy)phenyl)ethanone (14.2 g, 55% yield) as a colorless oil. The compound was confirmed with LC-MS only: 373.64 $(M+H)^+$, $C_{17}H_{27}BrO_2Si$.

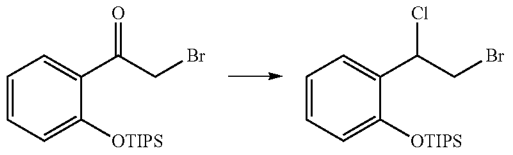

Step 2 (See Scheme G, Step 18): Synthesis of (2-(2-bromo-1-chloroethyl)phenoxy)triisopropylsilane A solution of 2-bromo-1-(2-(triisopropylsilyloxy)phenyl) ethanone (14 g, 37.8 mmol) in THF (50 mL) was added to a solution of sodium borohydride (1.73 g, 45.5 mmol) in THF (200 mL). The reaction was stirred for 2 h at 50° C. The mixture was cooled to rt, diluted with water (300 mL), and then extracted with ethyl acetate (300 mL×3). The organic extracts were combined, washed with brine (300 mL), dried over anhydrous sodium sulfate, and concentrated. The residue was purified by silica gel column chromatography (petroleum ether/ethyl acetate=50:1) to give alcohol (10 g, 71% yield) as a colorless oil. The alcohol (10 g, 26.9 mmol) was dissolved in thionyl chloride (50 mL) and refluxed for 1 h. The solvent was removed in vacuo and co-evaporated with dichloromethane two times to give (2-(2-bromo-1-chloroethyl)phenoxy)triisopropylsilane (10.3 g, quantative yield).

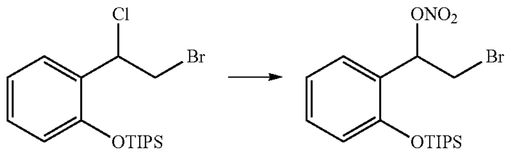

Step 3 (See Scheme G, Step 19): Synthesis of 2-bromo-1-(2-(triisopropylsilyloxy)phenyl)ethyl nitrate $AgNO_3$ (9.57 g, 56.4 mmol) was added to a solution of (2-(2-bromo-1-chloroethyl)phenoxy)triisopropylsilane (10 g, 25.6 mmol) in acetonitrile (50 mL). The reaction mixture was stirred overnight at rt. The solvent was removed in vacuo. The residue was suspended in water (100 mL) and extracted with dichloromethane (100 mL×3). The organic extracts were combined, dried over anhydrous sodium sulfate, and concentrated to give crude 2-bromo-1-(2-(triisopropylsilyloxy)phenyl)ethyl nitrate (9.3 g, 94% yield).

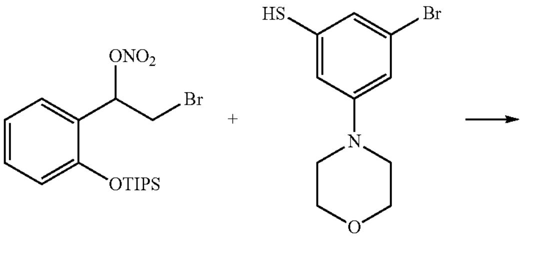

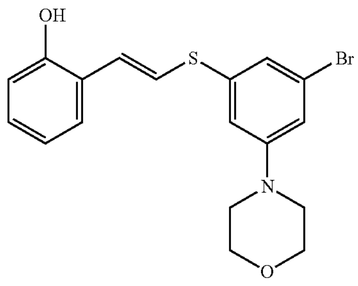

Step 4 (See Scheme G, Step 20): Synthesis of (E)-2-(2-(3-bromo-5-morpholinophenylthio)vinyl)phenol A solution of 3-bromo-5-morpholino-benzenethiol (0.8 g, 2.9 mmol) and TBAF-THF solution (4.8 mL, 1 M in THF) were added successively to a solution of bromo-1-(2-(triisopropylsilyloxy)phenyl)ethyl nitrate (2 g, 4.8 mmol) in THF (100 mL) at −78° C. The reaction was stirred for 1 h at rt. The reaction mixture was poured into water (200 mL) and extracted with ethyl acetate (200 mL×3). The combined organics were washed with brine (50 mL×2), dried over sodium sulfate, and concentrated. The crude was purified by silica gel column chromatography (petroleum ether/ethyl acetate=10:1) to give (E)-2-(2-(3-bromo-5-morpholinophenylthio)vinyl)phenol (0.47 g, 25% yield). The compound was confirmed by LC-MS only: 394.87 $(M+H)^+$, $C_{18}H_{18}BrNO_2S$.

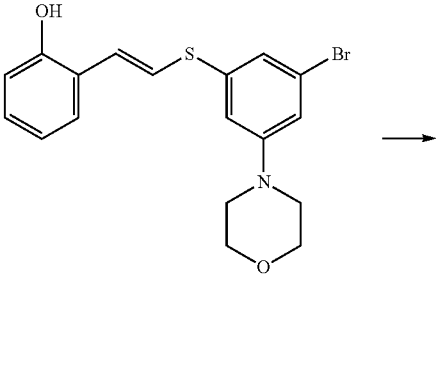

-continued

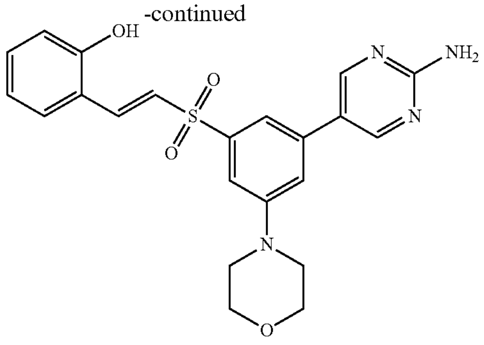

Compound 113

Step 5 (See Scheme G, Step 12a): Synthesis of (E)-2-(2-((3-(2-aminopyrimidin-5-yl)-5-morpholinophenyl)sulfonyl)vinyl)phenol Oxidation with mCPBA was completed as described in Example 11 for Compound 52 to give (E)-2-(2-(3-bromo-5-morpholinophenylsulfonyl)vinyl)phenol (270 mg, 55% yield). LC-MS: 426.29 $(M+H)^+$, $C_{18}H_{18}BrNO_4S$. $^1H$ NMR (DMSO-d6, 400 MHz) δ: 7.83 (d, J=15.2 Hz, 1H), 7.53 (m, 1H), 7.39 (m, 2H), 7.29 (m, 2H), 7.14 (d, J=15.6 Hz, 1H), 6.94 (m, 1H), 6.84 (m, 1H), 3.88 (m, 4H), 3.24 (m, 4H).

Step 6 (See Scheme G, Step 4c): A mixture of (E)-2-(2-(3-bromo-5-morpholinophenylsulfonyl)vinyl)phenol (270 mg, 0.64 mmol), 5-(4,4,5,5-tetramethyl-1,3,2-dioxaborolan-2-yl)pyrimidin-2-amine (282 mg, 1.28 mmol), $K_2CO_3$ (176 mg, 1.28 mmol), and $Pd(dppf)Cl_2$ (52 mg, 0.06 mmol) in 1,4-dioxane (9 mL) and $H_2O$ (3 mL) was stirred at 95° C. for 2 h under $N_2$. The reaction mixture was poured into water (50 mL) and extracted with dichloromethane (50 mL×3). The combined organics were washed with brine (30 mL), dried over sodium sulfate, and concentrated. The crude was purified by silica gel column chromatography (dichloromethane/methanol=50:1) to afford (E)-2-(2-((3-(2-aminopyrimidin-5-yl)-5-morpholinophenyl)sulfonyl)vinyl)phenol (120 mg, 43% yield). ESMS+: 439.1 (M+H). $^1H$ NMR (DMSO-d6, 400 MHz) δ:10.46 (s, 1H), 8.64 (s, 2H), 7.79 (d, J=15.6 Hz, 1H), 7.41-7.65 (m, 4H), 7.29 (m, 2H), 6.90 (m, 3H), 6.84 (m, 1H), 3.76 (m, 4H), 3.28 (m, 4H).

Example 16: 5-(3-((2,3-dihydrobenzofuran-3-yl)sulfonyl)-5-morpholinophenyl)pyrimidin-2-amine (Compound 119)

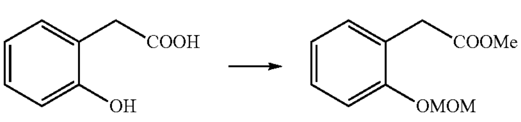

Step 1 (See Scheme H, Step 21): Synthesis of methyl 2-(2-(methoxymethoxy)phenyl)acetate Conc. $H_2SO_4$ (1.32 mL) was added to a solution of 2-(2-hydroxyphenyl)acetic acid (10 g, 65.8 mmol) in methanol (132 mL). The reaction was heated at 90° C. for 1.5 h. The solvent was removed and the residue was poured into ice-water (100 mL). The resulting mixture was extracted with ethyl acetate (100 mL×2). The organic extracts were combined, dried over anhydrous sodium sulfate, and concentrated to give crude methyl ester (12.9 g, quantative yield). Partial of the crude ester (3.6 g, 21.7 mmol) was dissolved in acetone (15 mL). Potassium carbonate (12 g, 87.0 mmol) was added, and the mixture was stirred for 10 min at rt. The mixture was then cooled to 0° C. and MOMCl (10 mL, 0.13 mol) was added dropwise. The reaction was stirred overnight at rt. Potassium carbonate was filtered and washed with acetone. The filtrate and wash were combined and concentrated in vacuo. The residue was dissolved in ethyl acetate (100 mL) and washed with water (50 mL) and brine (50 mL) successively. The organic phase was dried over anhydrous sodium sulfate and concentrated. The crude was purified by silica gel column chromatography (petroleum ether/ethyl acetate=50:1) to give methyl 2-(2-(methoxymethoxy)phenyl)acetate (2.8 g, 62% yield). $C_{11}H_{14}O_4$. $^1H$ NMR ($CDCl_3$, 400 MHz) δ: 7.23 (m, 2H), 7.09 (d, J=8.0 Hz, 1H), 6.97 (m, 1H), 5.19 (s, 2H), 3.68 (s, 3H), 3.63 (s, 2H), 3.45 (s, 3H).

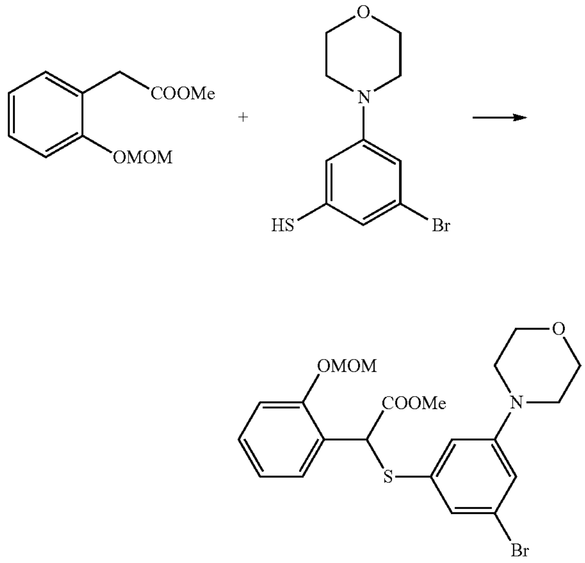

Step 2 (See Scheme H, Step 22): Synthesis of methyl 2-(3-bromo-5-morpholinophenylthio)-2-(2-(methoxymethoxy)phenyl)acetate A solution of methyl 2-(2-(methoxymethoxy)phenyl)acetate (1.73 g, 8.2 mmol), 3-bromo-5-morpholino-benzenethiol (4.5 g, 16.4 mmol), potassium carbonate (1.36 g, 9.9 mmol), and n-$Bu_4NHSO_4$ (0.56 g, 1.6 mmol) in DMSO (30 mL) was stirred overnight at 60° C. under $O_2$. The reaction mixture was poured into water (100 mL) and extracted with ethyl acetate (60 mL×3). The combined organics were washed with brine (50 mL×2), dried over sodium sulfate, and concentrated. The crude was purified by silica gel column chromatography (petroleum ether/ethyl acetate=20:1) to give methyl 2-((3-bromo-5-morpholinophenyl)thio)-2-(2-(methoxymethoxy)phenyl)acetate (2.6 g, 66% yield). The compound was confirmed with LC-MS only: 484.21 $(M+H)^+$, $C_{21}H_{24}BrNO_5S$.

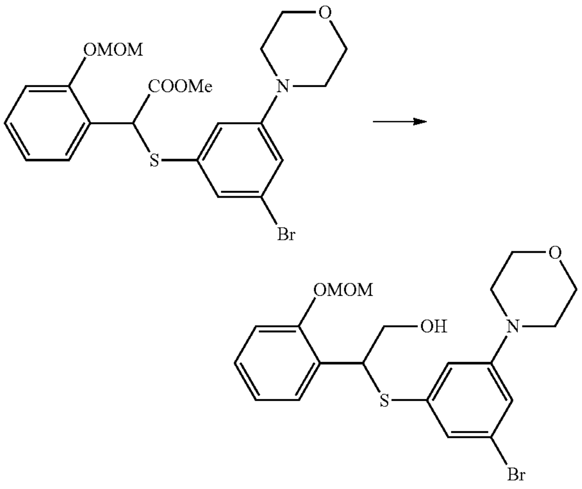

Step 3 (See Scheme H, Step 23): Synthesis of 2-(3-bromo-5-morpholinophenylthio)-2-(2-(methoxymethoxy)phenyl)ethanol $LiAlH_4$ (410 mg, 10.8 mmol) was added portionwise to a solution of give methyl 2-((3-bromo-5-morpholinophenyl)thio)-2-(2-(methoxymethoxy)phenyl)acetate (2.6 g, 5.4 mmol) in THF (50 mL) at 0° C. The reaction mixture was stirred at 0° C. for 30 min. The mixture was poured into ice-water (100 mL) slowly and extracted with ethyl acetate (50 mL×3). The combined organics were washed with brine (100 mL), dried over sodium sulfate, and concentrated. The residue was purified by silica gel column chromatography (petroleum ether/ethyl acetate=5:1) to give 2-(3-bromo-5-morpholinophenylthio)-2-(2-(methoxymethoxy)phenyl) ethanol (1.1 g, 45% yield). LC-MS: 455.77 $(M+H)^+$, $C_{20}H_{24}BrNO_4S$. $^1H$ NMR ($CDCl_3$, 400 MHz) δ: 7.30 (m, 1H), 7.23 (m, 1H), 7.12 (m, 1H), 6.96 (m, 2H), 6.84 (s, 1H), 6.71 (s, 1H), 5.21 (s, 2H), 4.85 (m, 1H), 3.90 (m, 2H), 3.78 (m, 4H), 3.48 (s, 3H), 3.06 (m, 4H).

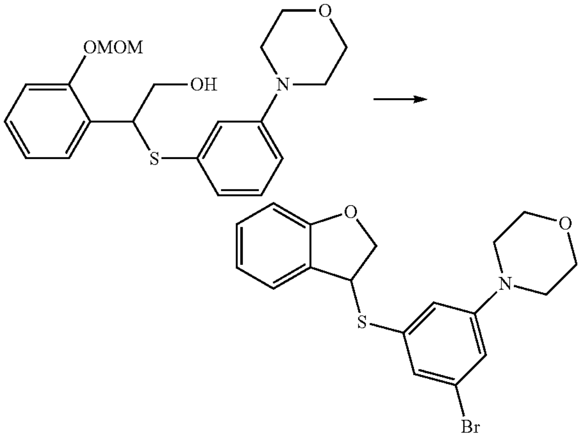

Step 4 (See Scheme H, Step 24): Synthesis of 4-(3-bromo-5-(2,3-dihydrobenzofuran-3-ylthio)phenyl) morpholine 6 N HCl/dioxane (5 mL) was added to a solution of 2-(3-bromo-5-morpholinophenylthio)-2-(2-

(methoxymethoxy)phenyl)ethanol (1.1 g, 2.4 mmol) in dioxane (5 mL). The reaction was stirred at rt for 30 min. The solvent was removed in vacuo. The residue was dissolved in ethyl acetate (20 mL) and washed with sat. sodium bicarbonate (10 mL). The organic phase was dried over anhydrous sodium sulfate and concentrated to give phenol analog (1.02 g, quantative yield). The phenol analog (1 g, 2.4 mmol) was dissolved in toluene (5 mL) and added to a solution of triphenylphosphine (640 mg, 2.4 mmol) and DEAD (425 mg, 2.4 mmol) in toluene (5 mL) at 0° C. The reaction was then stirred for 1 h at rt. The mixture was poured into water (20 mL) and extracted with ethyl acetate (20 mL×2). The organic extracts were combined, washed with brine (10 mL), dried over anhydrous sodium sulfate, and concentrated. The residue was purified by silica gel column chromatography (petroleum ether/ethyl acetate=20:1) to give 4-(3-bromo-5-(2,3-dihydrobenzofuran-3-ylthio)phenyl)morpholine (630 mg, 67% yield). LC-MS: 393.98 $(M+H)^+$, $C_{18}H_{18}BrNO_2S$. $^1H$ NMR ($CDCl_3$, 400 MHz) δ: 7.27 (m, 1H), 7.18 (m, 1H), 6.99 (s, 1H), 6.91 (m, 2H), 6.79 (d, J=84 Hz, 1H), 6.69 (s, 1H), 4.91 (m, 1H), 4.79 (m, 1H), 4.55 (m, 1H), 3.81 (m, 4H), 3.07 (m, 4H).

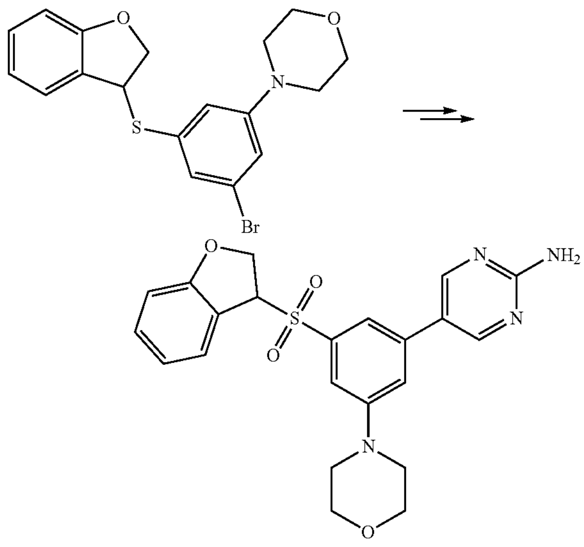

Compound 119

Step 5 (See Scheme H, Step 12a): Synthesis of 5-(3-((2,3-dihydrobenzofuran-3-yl)sulfonyl)-5-morpholinophenyl)pyrimidin-2-amine Oxidation of 4-(3-Bromo-5-(2,3-dihydrobenzofuran-3-ylthio)phenyl)morpholine with mCPBA, as seen in Example 11 for Compound 52, provided 4-(3-bromo-5-(2,3-dihydrobenzofuran-3-ylsulfonyl)phenyl)morpholine (500 mg, 46% yield). The compound was confirmed with LC-MS only: 426.37 $(M+H)^+$, $C_{18}H_{18}BrNO_4S$.

Step 6 (See Scheme H, Step 4c): Suzuki reaction of 4-(3-bromo-5-(2,3-dihydrobenzofuran-3-ylsulfonyl)phenyl)morpholine (500 mg, 1.2 mmol) with 5-(4,4,5,5-tetramethyl-1,3,2-dioxaborolan-2-yl)pyrimidin-2-amine (287 mg, 1.3 mmol), as described in Example 11 for Compound 52 afforded 5-(3-((2,3-dihydrobenzofuran-3-yl)sulfonyl)-5-morpholinophenyl)pyrimidin-2-amine (139 mg, 27% yield) as a white solid. ESMS+: 439.10 (M+H). $^1H$ NMR (DMSO-d6, 400 MHz) δ: 8.54 (s, 2H), 7.47 (s, 1H), 7.33 (m, 1H), 7.27 (m, 1H), 7.22 (s, 1H), 6.97 (m, 2H), 6.92 (s, 2H), 6.77 (d, J=8.0 Hz, 1H), 5.50 (m, 1H), 4.89 (m, 1H), 4.69 (m, 1H), 3.73 (m, 4H), 3.18 (m, 4H).

Example 17: 5-(6-morpholino-4-(phenylsulfonyl)pyridin-2-yl)pyrimidin-2-amine (Compound 115)

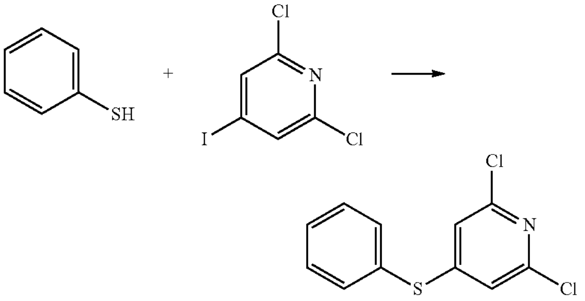

Step 1 (See Scheme I, Step 25): Synthesis of 2,6-dichloro-4-(phenylthio)pyridine $Pd_2(dba)_3$ (0.17 g, 0.18 mmol) was added to a mixture of 2,6-dichloro-4-iodopyridine (1 g, 3.66 mmol), thiophenol (0.44 g, 4.03 mmol), Xantphos (0.21 g, 0.37 mmol), and DIPEA (0.94 g, 7.32 mmol) in dioxane (20 mL) under $N_2$. The reaction was heated at 110° C. for 2 h. The mixture was cooled to rt, poured into water (20 mL), and extracted with ethyl acetate (20 mL×3). The combined organics were washed with brine (20 mL), dried over sodium sulfate, and concentrated. The residue was purified by silica gel column chromatography (petroleum ether) to give 2,6-dichloro-4-(phenylthio)pyridine (0.78 g, 83% yield) as an off-white solid. The compound was confirmed with LC-MS only: 256.16 $(M+H)^+$, $C_{11}H_7Cl_2NS$.

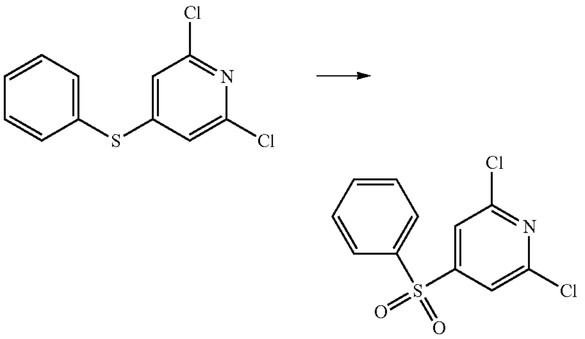

Step 2 (See Scheme I, Step 12a): Synthesis of 2,6-dichloro-4-(phenylsulfonyl)pyridine mCPBA mediated oxidation of 2,6-dichloro-4-(phenylthio)pyridine as described in Example 11 for Compound 52, provided 2,6-dichloro-4-(phenylsulfonyl)pyridine (0.69 g, 90% yield). The compound was confirmed with LC-MS only: 287.98 $(M+H)^+$, $C_{11}H_7Cl_2NO_2S$.

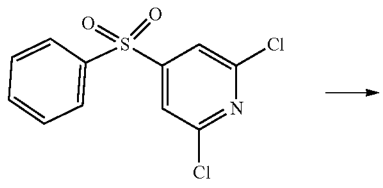

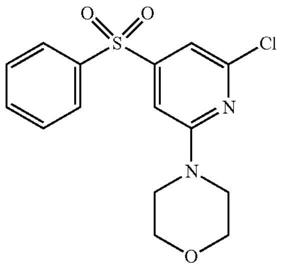

Step 3 (See Scheme I, Step 26): Synthesis of 4-(6-chloro-4-(phenylsulfonyl)pyridin-2-yl)morpholine A solution of 2,6-dichloro-4-(phenylsulfonyl)pyridine (0.69 g, 2.40 mmol), morpholine (0.23 g, 2.64 mmol), and DIPEA (0.40 g, 3.13 mmol) in dioxane (20 mL) was heated at 120° C. overnight. The reaction was cooled to rt and poured into water (100 mL). The mixture was extracted with ethyl acetate (100 mL×3). The organic extracts were combined, dried over sodium sulfate, and concentrated. The crude was purified by silica gel column chromatography (petroleum ether/ethyl acetate=60:1) to give 4-(6-chloro-4-(phenylsulfonyl)pyridin-2-yl)morpholine (700 mg, 86% yield). The compound was confirmed with LC-MS only: 339.74 $(M+H)^+$, $C_{15}H_{15}ClN_2O_3S$.

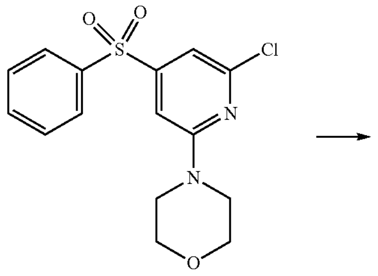

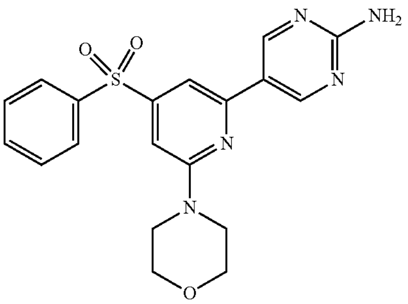

Compound 115

Step 4 (See Scheme I, Step 4c): Synthesis of 5-(6-morpholino-4-(phenylsulfonyl)pyridin-2-yl)pyrimidin-2-amine The Suzuki coupling of 4-(6-chloro-4-(phenylsulfonyl)pyridin-2-yl)morpholine (338 mg, 1 mmol) and 5-(4,4,5,5-tetramethyl-1,3,2-dioxaborolan-2-yl)pyrimidin-2-amine (442 mg, 2 mmol) as described in Example 11 for Compound 52 afforded 5-(6-morpholino-4-(phenylsulfonyl)pyridin-2-yl)pyrimidin-2-amine (220 mg, 55% yield). ESMS+: 398.27 (M+H). $^1H$ NMR (DMSO-d6, 400 MHz) δ: 8.94 (s, 2H), 8.11 (d, J=8.8 Hz, 2H), 7.73 (m, 1H), 7.65 (m, 2H), 7.55 (s, 1H), 7.11 (s, 3H), 3.70 (m, 4H), 3.60 (m, 4H).

The following compounds were prepared by methods analogous to the method described for Compound 115 and as described in Scheme I:

| Cmpd # | MS | $^1H$ NMR |
|---|---|---|
| 150 | 425.9 (M + H) | (DMSO-d6, 500 MHz) 8.92 (d, J = 5.3 Hz, 2H), 8.11 (m, 2H), 7.78 (m, 1H), 7.67-7.61 (m, 2H), 7.50 (d, J = 1.1 Hz, 1H), 7.15 (d, J = 1.2 Hz, 1H), 7.07 (s, 2H), 4.31 (d, J = 12.5 Hz, 1H), 4.04 (td, J = 6.5, 3.4 Hz, 1H), 3.72 (dd, J = 12.8, 3.5 Hz, 1H), 3.61 (m, 2H), 3.36 (m, 1H), 1.19 (d, J = 6.2 Hz, 3H), 1.16 (d, J = 6.4 Hz, 3H). |
| 151 | 423.9 (M + H) | (DMSO-d6, 500 MHz) δ 8.92 (s, 2H), 8.10 (m, 2H), 7.72(m, 1H), 7.63 (m, 2H), 7.51 (d, J = 1.1 Hz, 1H), 7.08 (s, 2H), 7.00 (d, J = 1.2 Hz, 1H), 4.45 (dq, J = 4.1, 2.1 Hz, 2H), 3.97 (d, J = 12.5 Hz, 2H), 3.05 (dd, J = 12.5, 2.7 Hz, 2H), 1.83 (dd, J = 8.4, 4.3 Hz, 2H), 1.73 (q, J = 7.2, 6.4 Hz, 2H). |

Example 18: 5-(4-morpholino-6-(phenylsulfonyl) pyridin-2-yl)pyrimidin-2-amine (Compound 117)

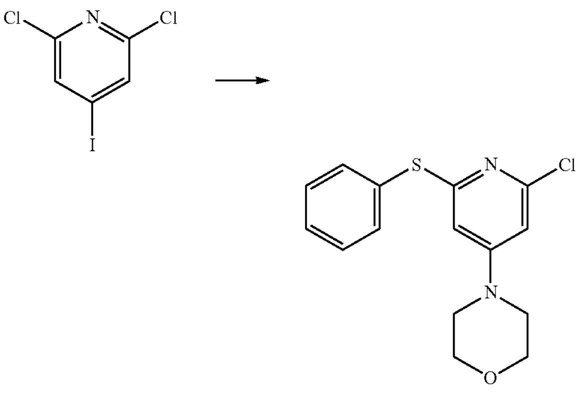

Step 1 (See Scheme J, Step 27): Synthesis of 4-(2-chloro-6-(phenylthio)pyridin-4-yl)morpholine $Pd_2(dba)_3$ (872 mg, 0.95 mmol) was added to a mixture of 2,6-dichloro-4-iodopyridine (2 g, 7.32 mmol), morpholine (764 mg, 8.78 mmol), Xantphos (550 mg, 0.95 mmol), and $Cs_2CO_3$ (3.1 g, 9.52 mmol) in dioxane (50 mL) under $N_2$. The reaction was heated at 140° C. for 1 h. The mixture was cooled to rt, poured into water (100 mL), and extracted with ethyl acetate (100 mL×3). The combined organics were washed with brine (100 mL), dried over sodium sulfate, and concentrated. The residue was purified by silica gel column chromatography (petroleum ether/ethyl acetate=3:1) to give 4-(2,6-dichloropyridin-4-yl)morpholine (1.19 g, 70% yield). LC-MS: 234.81 $(M+H)^+$, $C_9H_{10}Cl_2N_2O$. $^1H$ NMR ($CDCl_3$, 400 MHz) δ: 6.60 (s, 2H), 3.82 (t, J=5.0 Hz, 4H), 3.31 (m, J=5.0 Hz, 4H).

Step 2 (See Scheme J, Step 28): A mixture of 4-(2,6-dichloropyridin-4-yl)morpholine (1.1 g, 4.74 mmol), 1,2-diphenyldisulfane (0.62 g, 2.84 mmol), and sodium hydroxide (0.28 g, 7.11 mmol) in DMSO (10 mL) was heated at 120° C. overnight. The mixture was cooled to rt and poured into water (100 mL). The mixture was then extracted with ethyl acetate (100 mL×3). The organic extracts were combined, washed with brine (50 mL×2), dried over anhydrous sodium sulfate, and concentrated. The residue was purified by silica gel column chromatography (petroleum ether/ethyl acetate=3:1) to give 4-(2-chloro-6-(phenylthio)pyridin-4-yl) morpholine (1.12 g, 77% yield), which was used for next reaction without further purification. The compound was confirmed with LC-MS only: 306.98 $(M+H)^+$, $C_{15}H_{15}ClN_2OS$.

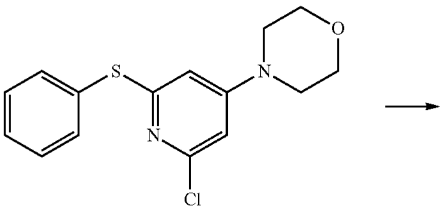

-continued

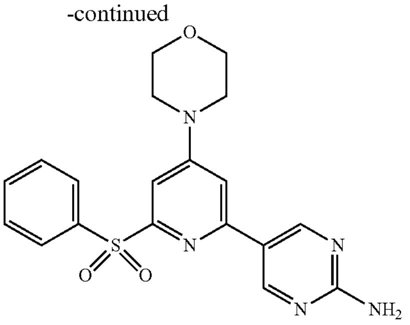

Compound 117

Step 3 (See Scheme J, Step 12a): 5-(4-morpholino-6-(phenylsulfonyl)pyridin-2-yl)pyrimidin-2-amine Oxidation of 4-(2-chloro-6-(phenylthio)pyridin-4-yl)morpholine as described in example 51 provided 4-(2-chloro-6-(phenylsulfonyl)pyridin-4-yl)morpholine (640 mg, 58% yield). The compound was confirmed by LC-MS only: 338.91 $(M+H)^+$, $C_{15}H_{15}ClN_2O_3S$.

Step 4 (See Scheme J, Step 4c): Suzuki coupling of 4-(2-chloro-6-(phenylsulfonyl)pyridin-4-yl)morpholine (600 mg, 1.78 mmol and, 5-(4,4,5,5-tetramethyl-1,3,2-dioxaborolan-2-yl)pyrimidin-2-amine (432 mg, 1.95 mmol), $K_2CO_3$ (490 mg, 3.55 mmol), and $Pd(dppf)Cl_2$ (145 mg, 0.18 mmol) in 1,4-dioxane (18 mL) and $H_2O$ (6 mL) was stirred at 95° C. for 1 h under $N_2$. The reaction mixture was poured into water (30 mL) and extracted with ethyl acetate (30 mL×3). The combined organics were washed with brine (20 mL), dried over sodium sulfate, concentrated. The crude was purified by silica gel column chromatography (dichloromethane/methanol=100:1) and washed with a combination of dichloromethane/methanol (50:1, 10 mL) to afford 5-(4-morpholino-6-(phenylsulfonyl)pyridin-2-yl)pyrimidin-2-amine (132 mg, 19% yield). ESMS+: 397.96 (M+H). $^1H$ NMR (DMSO-d6, 400 MHz) δ: 8.81 (s, 2H), 8.03 (d, J=7.2 Hz, 2H), 7.74 (m, 1H), 7.65 (m, 2H), 7.43 (s, 1H), 7.37 (s, 1H), 7.07 (s, 2H), 3.74 (m, 4H), 3.51 (m, 4H).

Example 19: 5-(2-morpholino-6-(phenylsulfonyl) pyridin-4-yl)pyrimidin-2-amine (Compound 118)

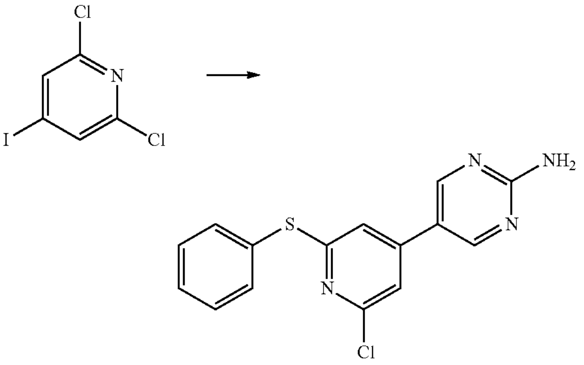

Step 1: Synthesis of 5-(2-chloro-6-(phenylthio)pyridin-4-yl)pyrimidin-2-amine

Palladium mediated Suzuki coupling of 2,6-dichloro-4-iodopyridine (1 g, 3.66 mmol) and 5-(4,4,5,5-tetramethyl- 1,3,2-dioxaborolan-2-yl)pyrimidin-2-amine (0.97 g, 4.40 mmol) was achieved as described in Example 11 for Compound 52 to give 5-(2,6-dichloropyridin-4-yl)pyrimidin-2-amine (700 mg, 80% yield). The compound was confirmed with LC-MS only: 240.98 $(M+H)^+$, $C_9H_6Cl_2N_4$.

Step 2 (See Scheme K, Step 29): A mixture of give 5-(2,6-dichloropyridin-4-yl)pyrimidin-2-amine (0.7 g, 2.92 mmol), thiophenol (321 mg, 2.92 mmol), and potassium carbonate (483 mg, 3.5 mmol) in DMF (20 mL) was heated at 110° C. overnight. The mixture was cooled to rt and poured into water (100 mL). The mixture was then extracted with ethyl acetate (100 mL×3). The organic extracts were combined, washed with brine (50 mL×2), dried over anhydrous sodium sulfate, and concentrated. The residue was purified by silica gel column chromatography (petroleum ether/ethyl acetate=60:1) to give 5-(2-chloro-6-(phenylthio)pyridin-4-yl)pyrimidin-2-amine (0.75 g, 82% yield). The compound was confirmed with LC-MS only: 314.99 $(M+H)^+$, $C_{15}H_{11}ClN_4S$.

-continued

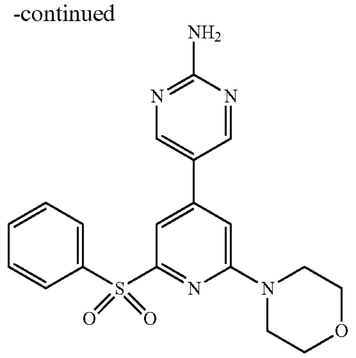

Compound 118

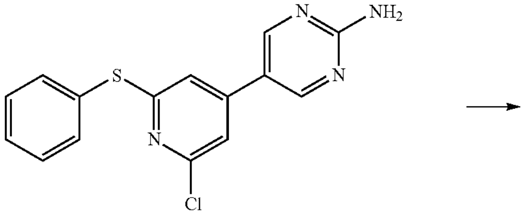

Step 3 (See Scheme K, Step 12a): 5-(2-morpholino-6-(phenylsulfonyl)pyridin-4-yl)pyrimidin-2-amine mCPBA oxidation of 5-(2-chloro-6-(phenylthio)pyridin-4-yl)pyrimidin-2-amine (0.75 g, 2.39 mmol), as described in Example 11 for Compound 52, gave 5-(2-chloro-6-(phenylsulfonyl)pyridin-4-yl)pyrimidin-2-amine (0.25 g, 30% yield). The compound was confirmed by LC-MS only: 346.97 $(M+H)^+$, $C_{15}H_{11}ClN_4O_2S$.

Step 4 (See Scheme K, Step 26): An SNAr reaction of 5-(2-chloro-6-(phenylsulfonyl)pyridin-4-yl)pyrimidin-2-amine (200 mg, 0.58 mmol) with morpholine (503 mg, 5.8 mmol) was done as described for 115 to afford 5-(2-morpholino-6-(phenylsulfonyl)pyridin-4-yl)pyrimidin-2-amine (37 mg, 16% yield). ESMS+: 398.07 (M+H). $^1H$ NMR (DMSO-d6, 400 MHz) δ: 8.78 (s, 2H), 7.99 (m, 2H), 7.73 (m, 1H), 7.63 (m, 3H), 7.55 (s, 1H), 7.14 (s, 2H), 3.64 (m, 4H), 3.50 (m, 4H).

The following compounds were prepared by methods analogous to the method described for Compound 118 and as described in Scheme K:

| Cmpd # | MS | $^1H$ NMR |
|---|---|---|
| 139 | 432.1 (M + H) | ($CDCl_3$ + MeOD, 400 MHz) δ: 8.86 (s, 2H), 8.36 (d, J = 7.6 Hz, 1H), 7.64 (m, 3H), 7.53 (m, 1H), 7.41 (m, 1H), 7.25 (s, 1H), 7.11 (s, 1H), 3.87 (m, 4H), 3.67 (m, 4H). |
| 144 | 464.9 (M + H) | (DMSO-d6, 500 MHz) δ 8.12 (s, 1H), 8.08-8.02 (m, 2H), 7.79-7.70 (m, 1H), 7.70-7.61 (m, 2H), 7.18 (d, J = 1.3 Hz, 1H), 7.11 (d, J = 1.2 Hz, 1H), 6.81 (s, 1H), 6.78 (s, 2H), 3.68 (dd, J = 5.9, 3.9 Hz, 4H), 3.55 (dd, J = 5.8, 3.9 Hz, 4H). |
| 145 | 439.9 (M + H) | (DMSO-d6, 500 MHz) δ 10.76 (s, 1H), 9.29 (s, 2H), 8.21-8.08 (m, 2H), 7.79-7.69 (m, 2H), 7.69-7.62 (m, 2H), 7.24 (d, J = 1.1 Hz, 1H), 3.72 (dd, J = 5.9, 3.7 Hz, 4H), 3.64 (dd, J = 5.7, 3.8 Hz, 4H), 2.23 (s, 3H). |
| 146 | 438.0 (M + H) | (DMSO-d6, 500 MHz) δ 9.06-8.91 (m, 2H), 8.13-8.06 (m, 2H), 7.82 (d, J = 3.8 Hz, 1H), 7.77-7.69 (m, 1H), 7.69-7.60 (m, 2H), 7.53 (d, J = 1.1 Hz, 1H), 7.11 (d, J = 1.2 Hz, 1H), 3.71 (dd, J = 5.9, 3.9 Hz, 4H), 3.60 (dd, J = 5.8, 3.9 Hz, 4H), 2.77 (tt, J = 7.4, 3.7 Hz, 1H), 0.69 (td, J = 7.0, 4.7 Hz, 2H), 0.53-0.47 (m, 2H). |

Example 20: 5-(6-morpholino-4-phenoxypyridin-2-yl)pyrimidin-2-amine (Compound 120)

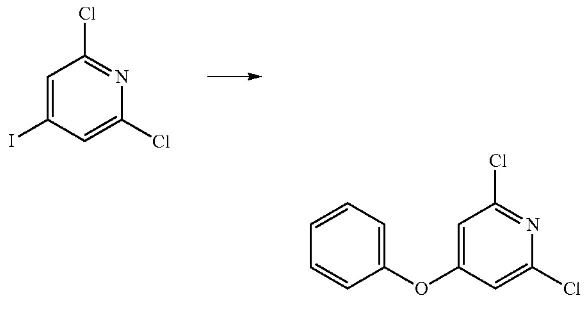

Step 1 (See Scheme L, Step 30): Synthesis of 2,6-dichloro-4-phenoxypyridine

A mixture of 2,6-dichloro-4-iodopyridine (600 mg, 2.20 mmol), phenol (207 mg, 2.20 mmol), and potassium carbonate (455 mg, 3.30 mmol) in DMSO (20 mL) was stirred at 100° C. for 3 h under $N_2$. The reaction mixture was poured into water (100 mL) and extracted with ethyl acetate (100 mL×3). The combined organics were washed with brine (50 mL×2), dried over sodium sulfate, and concentrated. The residue was purified by silica gel column chromatography (petroleum ether) to give 2,6-dichloro-4-phenoxypyridine (210 mg, 40% yield). The compound was confirmed with LC-MS only: 239.86 $(M+H)^+$, $C_{11}H_7Cl_2NO$.

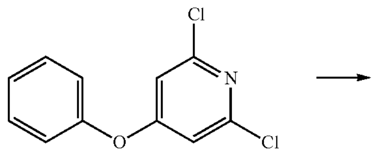

-continued

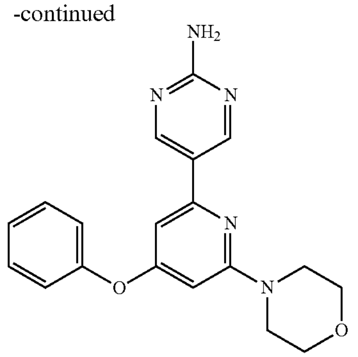

Compound 120

Step 2 (See Scheme L, Step 26): An SNAr reaction of 2,6-dichloro-4-phenoxypyridine (200 mg, 0.84 mmol) and morpholine (218 mg, 2.51 mmol) as described in Example 17 for Compound 115 gave 4-(6-chloro-4-phenoxypyridin-2-yl)morpholine (180 mg, 74% yield). The compound was confirmed with LC-MS only: 290.75 $(M+H)^+$, $C_{15}H_{15}ClN_2O_2$.

Step 3 (See Scheme L, Step 4c): A mixture of 4-(6-chloro-4-phenoxypyridin-2-yl)morpholine (180 mg, 0.62 mmol), 5-(4,4,5,5-tetramethyl-1,3,2-dioxaborolan-2-yl)pyrimidin-2-amine (151 mg, 0.68 mmol), $K_2CO_3$ (171 mg, 1.24 mmol), and $Pd(dppf)Cl_2$ (51 mg, 0.06 mmol) in 1,4-dioxane (6 mL) and $H_2O$ (2 mL) was stirred at 95° C. for 2 h under $N_2$. The reaction mixture was poured into water (20 mL) and extracted with dichloromethane (20 mL×3). The combined organics were washed with brine (20 mL), dried over sodium sulfate, and concentrated. The crude was purified by silica gel column chromatography (petroleum ether/ethyl acetate=2:1) to afford 5-(6-morpholino-4-phenoxypyridin-2-yl)pyrimidin-2-amine (150 mg, 69% yield). ESMS+: 350.2 (M+H). $^1$H NMR (DMSO-d6, 400 MHz) δ: 8.81 (s, 2H), 7.45 (m, 2H), 7.24 (m, 1H), 7.15 (m, 2H), 6.97 (s, 2H), 6.81 (s, 1H), 6.16 (s, 1H), 3.68 (m, 4H), 3.43 (m, 4H).

The following compounds were prepared by methods analogous to the method described for Compound 120 and as described in Scheme L:

| Cmpd # | MS | $^1$H NMR |
|---|---|---|
| 128 | 451.52 (M + H) | (DMSO-d6, 400 MHz) δ: 8.86 (s, 2H), 7.76 (d, J = 8.8 Hz, 1H), 7.61 (s, 1H), 7.45 (m, 1H), 7.00 (s, 2H), 6.93 (s, 1H), 6.36 (s, 1H), 3.69 (m, 4H), 3.49 (m, 4H). |
| 130 | 343.8 (M + H) | ( DMSO-d6, 500 MHz) δ 8.87 (s, 2H), 6.88 (s, 2H), 6.79 (d, J = 1.8 Hz, 1H), 6.18 (d, J = 1.8 Hz, 1H), 5.23 (tt, J = 4.7, 2.0 Hz, 1H), 3.92 (dd, J = 10.2, 4.5 Hz, 1H), 3.84 (td, J = 8.2, 7.0 Hz, 1H), 3.80-3.73 (m, 2H), 3.70 (t, J = 4.9 Hz, 4H), 3.49 (t, J = 4.9 Hz, 4H), 2.27 (dtd, J = 13.5, 8.3, 6.3 Hz, 1H), 1.99-1.91 (m, 1H). |
| 132 | 451.52 (M + H) | (DMSO-d6, 400 MHz) δ: 8.86 (s, 2H), 7.76 (d, J = 8.8 Hz, 1H), 7.61 (s, 1H), 7.45 (m, 1H), 7.00 (s, 2H), 6.93 (s, 1H), 6.36 (s, 1H), 3.69 (m, 4H), 3.49 (m, 4H). |
| 134 | 384.2 (M + H) | ($CDCl_3$, 400 MHz) δ: 8.85 (s, 2H), 7.52 (d, J = 7.6 Hz, 1H), 7.33 (d, J = 7.6 Hz, 1H), 7.23 (d, J = 7.6 Hz, 1H), 7.17 (d, J = 7.6 Hz, 1H), 6.47 (s, 1H), 6.05 (s, 1H), 5.86 (br, 2H), 3.81 (m, 4H), 3.52 (m, 4H). |
| 135 | 380.3 (M + H) | ($CDCl_3$, 400 MHz) δ: 8.83 (s, 2H), 7.26-7.19 (m, 1H), 7.11 (dd, J = 7.9, 1.7 Hz, 1H), 7.07-6.94 (m, 2H), 6.51 (d, J = 1.7 Hz, 1H), 6.07 (d, J = 1.6 Hz, 1H), 5.80 (s, 2H), 3.82 (d, J = 4.8 Hz, 7H), 3.51 (t, J = 4.9 Hz, 4H). |
| 136 | 434.3 (M + H) | ($CDCl_3$, 400 MHz) δ: 8.84 (s, 2H), 7.39 (m, 1H), 7.33 (m, 1H), 7.28 (m, 1H), 7.19 (m, 1H), 6.53 (s, 1H), 6.08 (s, 1H), 5.49 (br, 2H), 3.82 (m, 4H), 3.53 (m, 4H). |
| 137 | 364.3 (M + H) | ($CDCl_3$, 400 MHz) δ: 8.84 (s, 2H), 7.31 (m, 1H), 7.25 (m, 1H), 7.19 (m, 1H), 7.02 (m, 1H), 6.50 (s, 1H), 6.00 (s, 1H), 5.71 (br, 2H), 3.81 (m, 4H), 3.50 (m, 4H), 2.21 (s, 3H). |

-continued

| Cmpd # | MS | $^1$H NMR |
|---|---|---|
| 138 | 396.1 (M + H) | ($CDCl_3$, 400 MHz) δ: 8.89 (s, 2H), 7.51 (m, 2H), 7.43 (m, 2H), 7.17 (s, 1H), 6.92 (s, 1H), 5.51 (br, 2H), 3.85 (m, 4H), 3.62 (m, 4H). |

Example 21: (3-((2-(2-aminopyrimidin-5-yl)-6-morpholinopyridin-4-yl)oxy)azetidin-1-yl)(cyclopropyl) methanone (Compound 129)

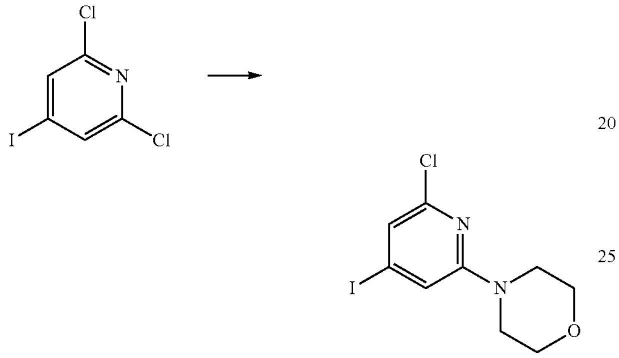

Step 1 (See Scheme L, Step 26): Synthesis of 4-(6-chloro-4-iodopyridin-2-yl)morpholine A solution of 2,6-dichloro-4-iodopyridine (3 g, 11.0 mmol), morpholine (1.05 g, 12.1 mmol), and DIPEA (1.86 g, 14.3 mmol) in dioxane (30 mL) was refluxed for 5 h. The solution was cooled to rt and poured into water (100 mL). The mixture was extracted with ethyl acetate (60 mL×3). The organic extracts were combined, washed with brine (30 mL×2), dried over anhydrous sodium sulfate, and concentrated. The residue was purified by silica gel column chromatography (petroleum ether/ethyl acetate=30:1) to give 4-(6-chloro-4-iodopyridin-2-yl)morpholine (2.5 g, 70% yield). The compound was confirmed with LC-MS only: 324.73 $(M+H)^+$, $C_9H_{10}ClIN_2O$.

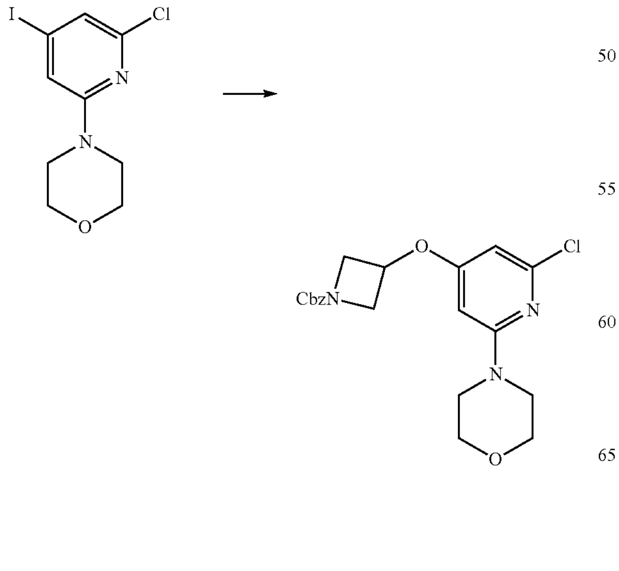

Step 2 (See Scheme L, Step 30): Synthesis of Benzyl 3-(2-chloro-6-morpholinopyridin-4-yloxy)azetidine-1-carboxylate tBuOK (340 mg, 3.04 mmol) was added to a solution of benzyl 3-hydroxyazetidine-1-carboxylate (500 mg, 2.42 mmol) in DMSO (10 mL). The reaction was stirred for 30 min and 4-(6-chloro-4-iodopyridin-2-yl)morpholine (650 mg, 2.0 mmol) was added. The reaction was stirred overnight at rt under $N_2$. The reaction mixture was poured into water (50 mL) and extracted with ethyl acetate (50 mL×3). The combined organics were washed with brine (50 mL×2), dried over sodium sulfate, and concentrated. The residue was purified by silica gel column chromatography (petroleum ether/ethyl acetate=20:1) to give benzyl 3-(2-chloro-6-morpholinopyridin-4-yloxy)azetidine-1-carboxylate (280 mg, 35% yield). The compound was confirmed with LC-MS only: 403.93 $(M+H)^+$, $C_{20}H_{22}ClN_3O_4$.

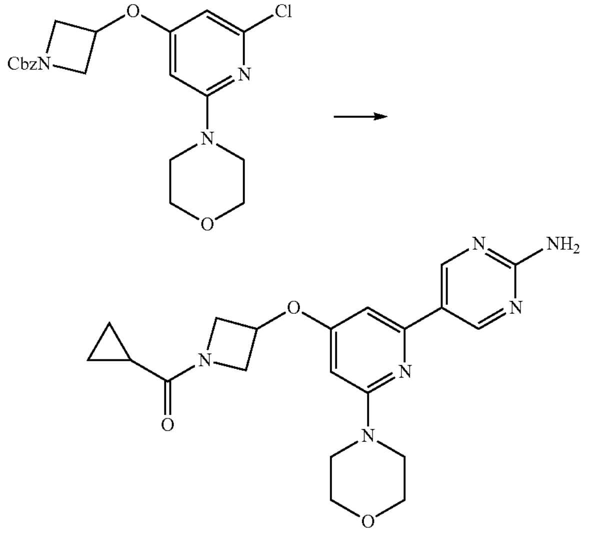

Compound 129

Step 3 (See Scheme L, Step 4c): Synthesis of benzyl 3-(2-(2-(tert-butoxycarbonylamino)pyrimidin-5-yl)-6-morpholinopyridin-4-yloxy)azetidine-1-carboxylate A mixture of benzyl 3-(2-chloro-6-morpholinopyridin-4-yloxy)azetidine-1-carboxylate (280 mg, 0.70 mmol), a mixture of tert-Butyl 5-(4,4,5,5-tetramethyl-1,3,2-dioxaborolan-2-yl)pyrimidin-2-ylcarbamate and its di-Boc analog (354 mg, ~1.04 mmol), $K_2CO_3$ (194 mg, 1.40 mmol), and $Pd(dppf)Cl_2$ (58 mg, 0.07 mmol) in 1,4-dioxane (9 mL) and $H_2O$ (3 mL) was stirred at 95° C. for 2 h under $N_2$. The reaction mixture was poured into water (20 mL) and extracted with dichloromethane (20 mL×3). The combined organics were washed with brine (20 mL), dried over sodium sulfate, and concentrated. The crude was purified by silica gel column chromatography (petroleum ether/ethyl acetate=5:1) to give 3-(2-(2-(tert-butoxycarbonylamino)pyrimidin-5-yl)-6-morpholinopyridin-4-yloxy)azetidine-1-carboxylate (50 mg) and its di-Boc analog (210 mg). The compounds were confirmed with LC-MS only: 3-(2-(2-(tert-butoxycarbonylamino)pyrimidin-5-yl)-6-morpholinopyridin-4-yloxy)azetidine-1-carboxylate –562.2 $(M+H)^+$, $C_{29}H_{34}N_6O_6$; benzyl 3-((2-(2-(di-BOC-amino)pyrimidin-5-yl)-6-morpholinopyridin-4-yl)oxy)azetidine-1-carboxylate –662.2 $(M+H)^+$, $C_{34}H_{42}N_6O_8$.

Step 4 (See Scheme L, Step 31): A solution of benzyl 3-((2-(2-(di-BOC-amino)pyrimidin-5-yl)-6-morpholinopyridin-4-yl)oxy)azetidine-1-carboxylate (210 mg, 0.32 mmol) in MeOH (20 mL) was hydrogenated in the presence of Pd/C overnight. Pd/C was filtered off and the filtrate was concentrated in vacuo. The residue was purified by silica gel column chromatography (dichloromethane/methanol=30:1) to give free amine (30 mg, 18% yield).

Step 5 (See Scheme L, Step 6): The free amine (30 mg, 0.06 mmol) was dissolved in dichloromethane (5 mL) and cooled to 0° C. TEA (0.02 mL, 0.14 mmol) and cyclopropanecarbonyl chloride (12 mg, 0.11 mmol) were added successively. The reaction was then stirred for 1 h at rt. The mixture was poured into water (10 mL) and extracted with dichloromethane (10 mL×3). The organic extracts were combined, dried over anhydrous sodium sulfate, and concentrated. The residue was purified by prep-TLC to give cyclopropyl(3-((2-(2-(di-Boc-amino)pyrimidin-5-yl)-6-morpholinopyridin-4-yl)oxy)azetidin-1-yl)methanone (30 mg, 89% yield), which was dissolved in dichloromethane (3 mL) and treated with TFA (0.5 mL) for 1 h. The solvent was removed in vacuo to afford (3-((2-(2-aminopyrimidin-5-yl)-6-morpholinopyridin-4-yl)oxy)azetidin-1-yl)(cyclopropyl)methanone-TFA (20 mg, 78% yield) as a yellow solid. ESMS+: 396.95 (M+H). $^1H$ NMR ($CDCl_3$, 400 MHz) δ: 8.86 (s, 2H), 6.43 (s, 1H), 5.88 (s, 1H), 5.34 (s, 2H), 5.06 (m, 1H), 4.66 (m, 1H), 4.42 (m, 1H), 4.34 (m, 1H), 4.10 (m, 1H), 3.84 (m, 4H), 3.55 (m, 4H), 1.41 (m, 1H), 0.99 (m, 2H), 0.77 (m, 2H).

Example 22: (2-(2-aminopyrimidin-5-yl)-6-morpholinopyridin-4-yl)(phenyl)methanone (Compound 122)

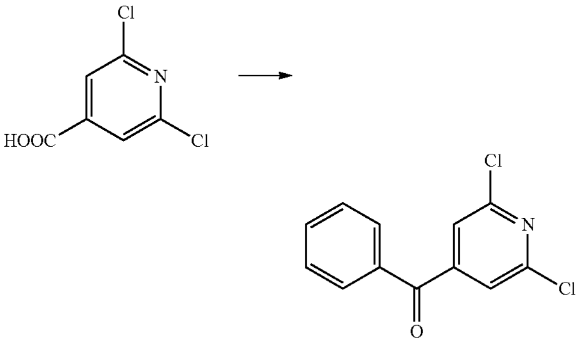

Step 1 (See Scheme M, Step 32): Synthesis of (2,6-dichloropyridin-4-yl)(phenyl)methanone CDI (3.44 g, 21.2 mmol) was added to a suspension of 2,6-dichloroisonicotinic acid (3.6 g, 18.8 mmol) in dichloromethane (20 mL). The solution was stirred for 2.5 h at rt. N,O-Dimethyl hydroxylamine·HCl (2.74 g, 28.2 mmol) was added and the reaction was stirred overnight at rt. The reaction was quenched with 1 N NaOH (10 mL) and extracted with dichloromethane (20 mL×3). The organic extracts were combined, washed with brined (20 mL), dried over anhydrous sodium sulfate, and concentrated. The residue was purified by silica gel column chromatography (petroleum ether/ethyl acetate=10:1) to give 2,6-dichloro-N-methoxy-N-methylisonicotinamide, 1 (3.8 g, 86% yield) as a white solid. The compound was confirmed with LC-MS only: 235.10 $(M+H)^+$, $C_8H_8Cl_2N_2O_2$.

Step 3 (See Scheme M, Step 33): Phenylmagnesium bromide (24.4 mL, 24.4 mmol, 1M in THF) was added dropwise to a solution of 2,6-dichloro-N-methoxy-N-methylisonicotinamide (3.8 g, 16.2 mmol) in THF (50 mL) at 0° C. under nitrogen protection. The reaction mixture stirred for 2 h at rt. The mixture was quenched with sat. ammonium chloride (100 mL) and extracted with ethyl acetate (60 mL×3). The combined organics were washed with brine (50 mL×2), dried over sodium sulfate, and concentrated. The crude was purified by silica gel column chromatography (petroleum ether/ethyl acetate=20:1) to give (2,6-dichloropyridin-4-yl)(phenyl)methanone (3.8 g, 93% yield) as a white solid. The compound was confirmed with LC-MS only: 251.91 $(M+H)^+$, $C_{12}H_7Cl_2NO$.

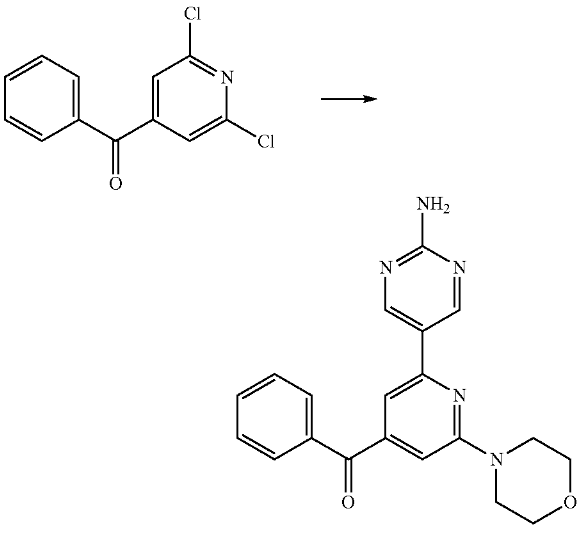

Compound 122

Step 2 (See Scheme M, Step 26): SNAr reaction of (2,6-dichloropyridin-4-yl)(phenyl)methanone (3.8 g, 15.1 mmol) and morpholine (5.2 g, 59.8 mmol) with DIPEA (7.7 g, 60.1 mmol), as described in Example 17 for Compound 115 gave (2-chloro-6-morpholinopyridin-4-yl)(phenyl) methanone (4.3 g, 94% yield) as a yellow solid. The compound was confirmed with LC-MS only: 303.26 $(M+H)^+$, $C_{16}H_{15}ClN_2O_2$.

Step 3 (See Scheme M, Step 4c): Suzuki coupling of (2-chloro-6-morpholinopyridin-4-yl)(phenyl)methanone (500 mg, 1.66 mmol) and 5-(4,4,5,5-tetramethyl-1,3,2-dioxaborolan-2-yl)pyrimidin-2-amine (360 mg, 1.66 mmol), as described in Example 11 for Compound 52 afforded (2-(2-aminopyrimidin-5-yl)-6-morpholinopyridin-4-yl) (phenyl)methanone (250 mg, 42% yield) as a yellow solid. ESMS+: 362.61 (M+H). $^1H$ NMR (DMSO-d6, 400 MHz) δ:

8.92 (s, 2H), 7.84 (d, J=8.0 Hz, 2H), 7.72 (m, 1H), 7.58 (m, 2H), 7.30 (s, 1H), 7.01 (s, 2H), 6.85 (s, 1H), 3.72 (m, 4H), 3.57 (m, 4H).

The following compounds were prepared by methods analogous to the method described for Compound 122 and as described in Scheme M:

| Cmpd # | MS | $^1$H NMR |
|---|---|---|
| 131 | 370.2 (M + H) | ($CDCl_3$, 400 MHz) δ: 8.94 (s, 2H), 7.29 (s, 1H), 6.96 (s, 1H), 5.41 (br, 2H), 4.07 (t, J-6.8 Hz, 1H), 4.05 (t, J = 6.4 Hz, 1H), 3.86 (m, 4H), 3.65 (m, 4H), 3.57 (m, 2H), 3.41 (m, 1H), 1.85 (m, 4H). |
| 133 | 391.91 (M + H) | ($CDCl_3$, 400 MHz) δ: 8.92 (s, 2H), 6.96 (s, 1H), 6.57 (s, 1H), 5.50 (s, 2H), 4.07-3.99 (m, 2H), 3.86 (t, J = 4.9 Hz, 4H), 3.80 (d, J = 4.5 Hz, 1H), 3.63 (t, J = 4.9 Hz, 4H), 3.35 (td, J = 11.2, 4.7 Hz, 2H), 2.22 (m, 2H), 2.00 (m, 2H). |
| 149 | 356.3 (M + H) | ($CDCl_3$, 400 MHz) δ 8.96 (s, 2H), 7.34 (s, 1H), 7.02 (s, 1H), 5.55 (s, 2H), 4.10 (t, J = 8.1 Hz, 1H), 4.03-3.89 (m, 4H), 3.87 (t, J = 5.0 Hz, 4H), 3.66 (t, J = 4.9 Hz, 4H), 2.36-2.20 (m, 2H). |

Example 23: 5-(4-(Difluoro(phenyl)methyl)-6-morpholinopyridin-2-yl)pyrimidin-2-amine (Compound 123)

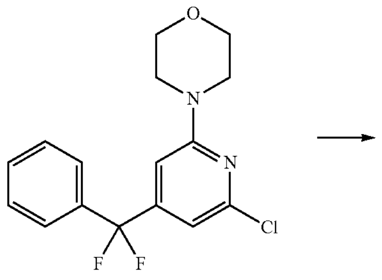

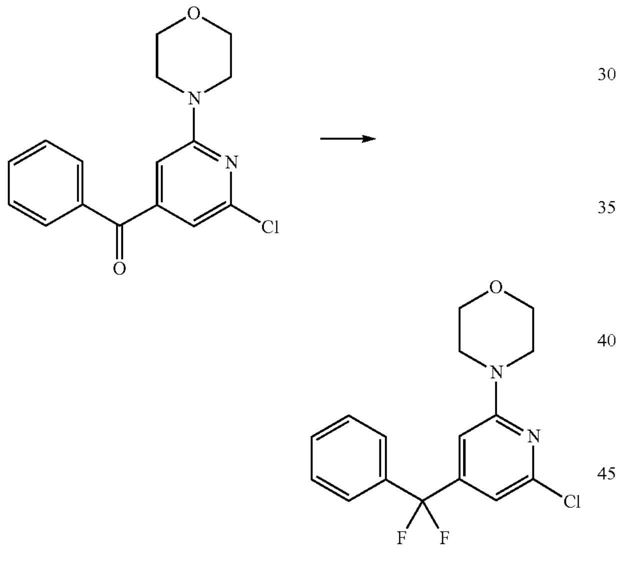

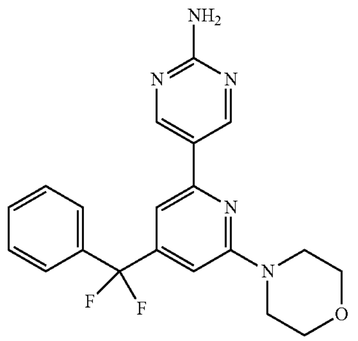

Step 1 (See Scheme M, Step 34): Synthesis of 4-(6-chloro-4-(difluoro(phenyl)methyl)pyridin-2-yl) morpholine DAST (1.07 g, 6.64 mmol) was added to a solution of (2-chloro-6-morpholinopyridin-4-yl)(phenyl)methanone (0.5 g, 1.66 mmol, for preparation, see procedure in Example 22 for Compound 122) in dichloromethane (10 mL) at 0° C. The reaction was stirred overnight at rt. The solution was poured into ice cold sat. sodium bicarbonate (50 mL) slowly and extracted with ethyl acetate (50 mL×3). The combined organics were washed with brine (50 mL), dried over sodium sulfate, and concentrated. The residue was purified by silica gel column chromatography (petroleum ether/ethyl acetate=50:1) to give 4-(6-chloro-4-(difluoro(phenyl)methyl)pyridin-2-yl)morpholine (80 mg, 15% yield). The compound was confirmed with LC-MS only: 324.89 $(M+H)^+$, $C_{16}H_{15}ClF_2N_2O$.

Step 2 (See Scheme M, Step 4c): Synthesis of 5-(4-(Difluoro(phenyl)methyl)-6-morpholinopyridin-2-yl)pyrimidin-2-amine A mixture of 4-(6-chloro-4-(difluoro(phenyl)methyl)pyridin-2-yl)morpholine (80 mg, 0.25 mmol), 5-(4,4,5,5-tetramethyl-1,3,2-dioxaborolan-2-yl)pyrimidin-2-amine (110 mg, 0.49 mmol), $K_2CO_3$ (103 mg, 0.74 mmol), and Pd(dppf)$Cl_2$ (20 mg, 0.03 mmol) in 1,4-dioxane (6 mL) and $H_2O$ (2 mL) was reacted and worked up as described in Example 11 for Compound 52 to afford 5-(4-(difluoro(phenyl)methyl)-6-morpholinopyridin-2-yl)pyrimidin-2-amine (69 mg, 73% yield). ESMS+: 384.2 (M+H). $^1$H NMR (DMSO-d6, 400 MHz) δ: 8.92 (s, 2H), 7.66 (m, 2H), 7.51 (m, 3H), 7.31 (s, 1H), 7.03 (s, 2H), 6.84 (s, 1H), 3.71 (m, 4H), 3.55 (m, 4H).

Example 24: 5-(6-morpholino-4-(1-phenylvinyl) pyridin-2-yl)pyrimidin-2-amine: 2,6-dichloro-4-(1-phenylvinyl)pyridine (Compound 126)

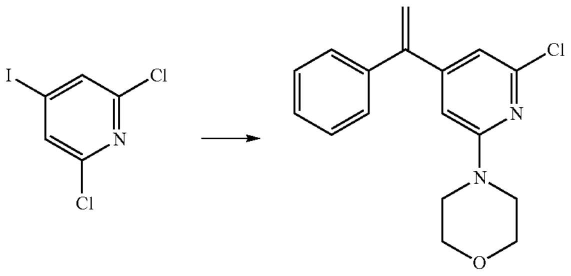 [SMILES: Clc1cc(I)cc(Cl)n1 ; C=C(c1ccccc1)c1cc(Cl)nc(N2CCOCC2)c1]

-continued

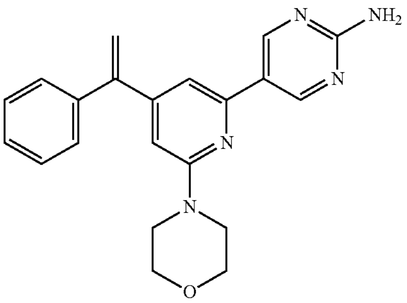

Compound 126

Step 1 (See Scheme N, Step 35): A mixture of 2,6-dichloro-4-iodopyridine (5 g, 18.2 mmol), 4,4,5,5-tetramethyl-2-(4,4,5,5-tetramethyl-1,3,2-dioxaborolan-2-yl)-1,3,2-dioxaborolane (5.6 g, 21.9 mmol), KOAc (3.6 g, 36.5 mmol), and $Pd(PPh_3)Cl_2$ (0.5 g, 0.73 mmol) in DMF (20 mL) was stirred at 100° C. for 1 h under $N_2$. The reaction mixture was poured into water (100 mL) and extracted with ethyl acetate (100 mL×3). The combined organics were washed with brine (100 mL), dried over sodium sulfate, and concentrated. The residue was purified by silica gel column chromatography (petroleum ether/ethyl acetate=200:1) to give 2,6-dichloro-4-(4,4,5,5-tetramethyl-1,3,2-dioxaborolan-2-yl)pyridine (3.6 g, 72% yield).

Step 2 (See Scheme N, Step 4c): A mixture of (1-bromovinyl)benzene (0.73 mg, 4.01 mmol), 2,6-dichloro-4-(4,4,5,5-tetramethyl-1,3,2-dioxaborolan-2-yl)pyridine (1.1 g, 4.03 mmol), $Pd(dppf)Cl_2$ (68 mg, 0.08 mmol), and potassium carbonate (1.1 g, 8.0 mmol) in dioxane/water (9 mL/3 mL) was treated and worked up as described in Example 11 for Compound 52 to give 2,6-dichloro-4-(1-phenylvinyl) pyridine (705 mg, 71% yield). The compound was confirmed with LC-MS only: 249.99 $(M+H)^+$, $C_{13}H_9Cl_2N$.

Step 3 (See Scheme I, Step 26): A solution of 2,6-dichloro-4-(1-phenylvinyl)pyridine (700 mg, 2.81 mmol), morpholine (490 mg, 5.63 mmol), and DIPEA (471 mg, 3.65 mmol) in 1,4-dioxane (20 mL) was treated and worked up as described in Example 17 for Compound 115 to give 4-(6-chloro-4-(1-phenylvinyl)pyridin-2-yl)morpholine (530 mg, 63% yield). The compound was confirmed with LC-MS only: 301.22 $(M+H)^+$, $C_{17}H_{17}ClN_2O$.

Step 4 (See Scheme N, Step 4C): A mixture of 2,6-dichloro-4-(1-phenylvinyl)pyridine (200 mg, 0.67 mmol) and 5-(4,4,5,5-tetramethyl-1,3,2-dioxaborolan-2-yl)pyrimidin-2-amine (300 mg, 1.36 mmol), underwent a Suzuki coupling as described in Example 11 for Compound 52 to afford 5-(6-morpholino-4-(1-phenylvinyl)pyridin-2-yl)pyrimidin-2-amine (98 mg, 41% yield). ESMS+: 360.2 (M+H). $^1H$ NMR ($CDCl_3$, 400 MHz) δ: 8.94 (s, 2H), 7.35 (m, 5H), 6.92 (s, 1H), 6.57 (s, 1H), 6.10 (br, 2H), 5.62 (s, 1H), 5.57 (s, 1H), 3.85 (m, 4H), 3.58 (m, 4H).

The following compound was prepared by methods analogous to the method described for Compound 126 and as described in Scheme N:

| Cmpd # | MS | $^1H$ NMR |
|---|---|---|
| 124 | 348.2 (M + H) | (DMSO-d6, 400 MHz) δ: 8.84 (s, 2H), 7.31 (m, 4H), 7.20 (m, 1H), 7.13 (s, 1H), 6.93 (s, 2H), 6.65 (s, 1H), 3.87 (s, 2H), 3.70 (m, 4H), 3.47 (m, 4H). |

Example 25: 5-(6-morpholino-4-(1-phenylethyl) pyridin-2-yl)pyrimidin-2-amine (Compound 125)

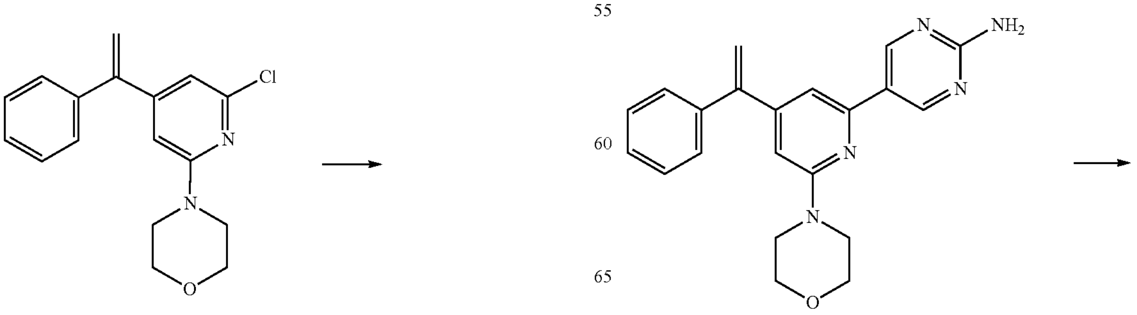

-continued

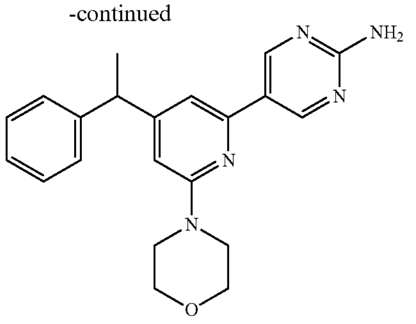

Compound 125

(See Scheme L, Step 31): A mixture of 5-(6-morpholino-4-(1-phenylvinyl)pyridin-2-yl)pyrimidin-2-amine (25 mg, 0.07 mmol) and Pd/C (5 mg) in methanol (5 mL) was hydrogenated for 1 h at rt and 1 atm $H_2$. Pd/C was filtered off and washed with methanol (3 mL). The filtrate and wash were combined and concentrated in vacuo to afford 5-(6-morpholino-4-(1-phenylethyl)pyridin-2-yl)pyrimidin-2-amine (19 mg, 76% yield). ESMS+: 362.04 (M+H). $^1H$ NMR ($CDCl_3$, 400 MHz) δ: 8.96 (s, 2H), 7.32 (m, 5H), 6.87 (br, 2H), 6.80 (s, 1H), 6.54 (s, 1H), 4.10 (q, J=7.1 Hz, 1H), 3.84 (m, 4H), 3.56 (m, 4H), 1.65 (d, J=7.2 Hz, 3H).

Example 26: 5-(6-morpholino-4-(1-phenylcyclopropyl)pyridin-2-yl)pyrimidin-2-amine (Compound 127)

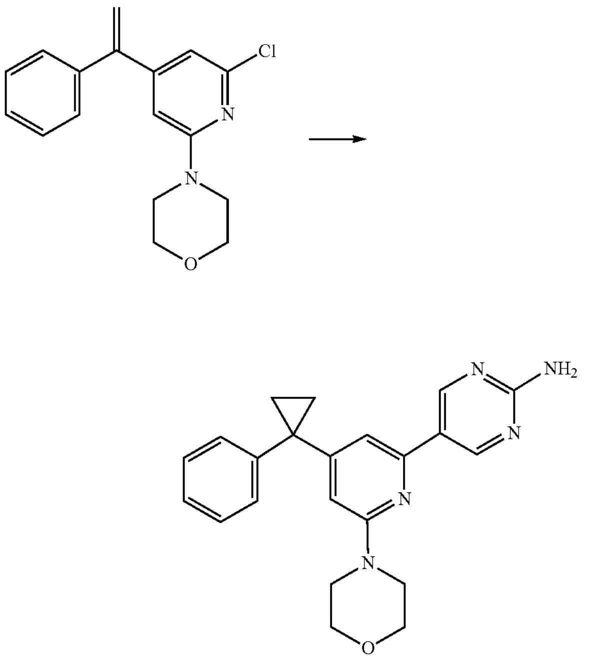

Compound 127

Step 1 (See Scheme N, Step 36): Sodium hydride (62 mg, 60% in mineral oil, 1.55 mmol) was added in portions to a solution of trimethylsulfoxonium iodide (341 mg, 1.55 mmol) in DMSO (10 mL) at rt. The reaction was stirred for 15 min and then a solution of 4-(6-chloro-4-(1-phenylvinyl)pyridin-2-yl)morpholine (310 mg, 1.03 mmol) in THF (5 mL) was added. The reaction was stirred overnight at rt. The reaction mixture was poured into water (50 mL) and extracted with ethyl acetate (50 mL×3). The organic extracts were combined, washed with brine (20 mL), dried over anhydrous sodium sulfate, and concentrated. The residue was purified by silica gel column chromatography (petroleum ther/ethyl acetate=50:1) to give 4-(6-chloro-4-(1-phenylcyclopropyl)pyridin-2-yl)morpholine (184 mg, 56% yield) as a white solid. The compound was confirmed with LC-MS only: 315.04 $(M+H)^+$, $C_{18}H_{19}ClN_2O$.

Step 2 (See Scheme N, Step 4c): A mixture of 4-(6-chloro-4-(1-phenylcyclopropyl)pyridin-2-yl)morpholine (184 mg, 0.59 mmol), 5-(4,4,5,5-tetramethyl-1,3,2-dioxaborolan-2-yl)pyrimidin-2-amine (259 mg, 1.17 mmol), underwent a Suzuki coupling as described in Example 11 for Compound 52 to afford 5-(6-morpholino-4-(1-phenylcyclopropyl)pyridin-2-yl)pyrimidin-2-amine (130 mg, 59% yield) as a yellow solid. ESMS+: 374.08 (M+H). $^1H$ NMR (DMSO-d6, 400 MHz) δ: 8.83 (s, 2H), 7.31 (m, 4H), 7.24 (m, 1H), 6.98 (s, 1H), 6.93 (s, 2H), 6.45 (s, 1H), 3.68 (m, 4H), 3.42 (m, 4H), 1.38 (m, 2H), 1.25 (m, 2H).

Example 27: 5-(4-(3,4-Dihydroquinolin-1(2H)-yl)-6-morpholinopyridin-2-yl)pyrimidin-2-amine (Compound 140)

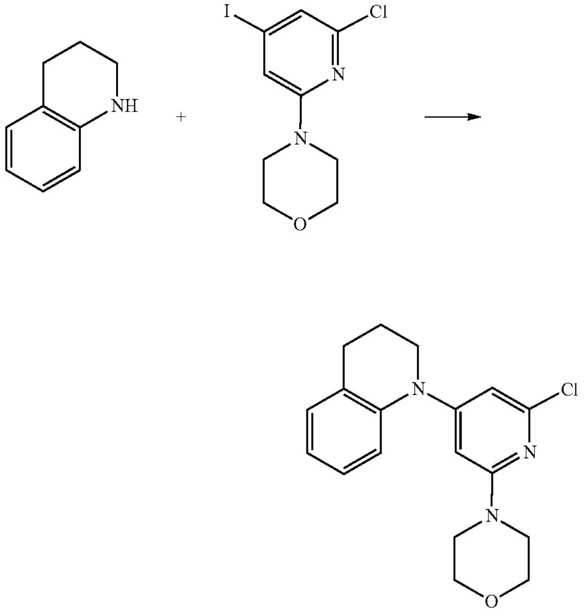 [SMILES: c1ccc2c(c1)CCCN2 ; Clc1cc(I)cc(N2CCOCC2)n1 ; Clc1cc(N2CCCc3ccccc32)cc(N2CCOCC2)n1]

Step 1 (See Scheme 0, Step 37): A mixture of 1,2,3,4-tetrahydroquinoline (133 mg, 1 mmol), 4-(6-chloro-4-iodopyridin-2-yl)morpholine (324 mg, 1 mmol), BINAP (62 mg, 0.1 mmol), t-BuONa (192 mg, 2 mmol), and $Pd_2dba_3$ (91.6 mg, 0.1 mmol) in toluene (10 mL) was refluxed for 2 h. The mixture was cooled to rt, diluted with water (30 mL), and extracted with ethyl acetate (30 mL×3). The organic extracts were combined, dried over anhydrous sodium sulfate, and concentrated. The residue was purified by prep-TLC to give 4-(6-chloro-4-(3,4-dihydroquinolin-1(2H)-yl)pyridin-2-yl)morpholine (57 mg, 17% yield). The compound was confirmed with LC-MS only: 300.28 $(M+H)^+$, $C_{18}H_{20}ClN_3O$.

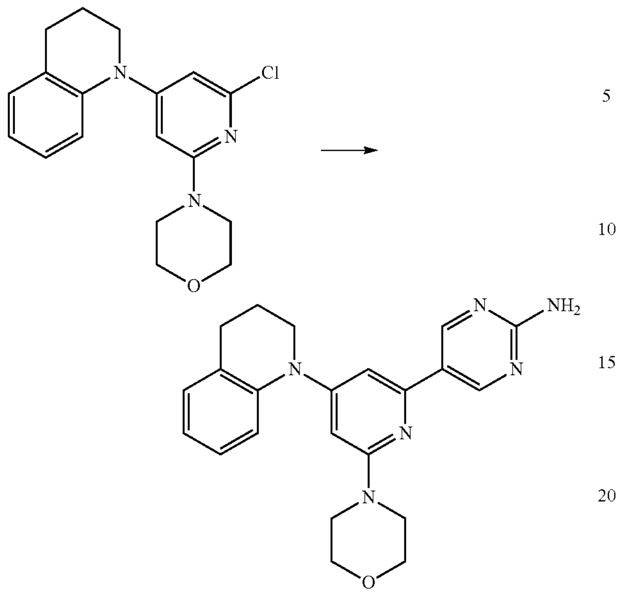

Compound 140

Step 2 (See Scheme N, Step 4c): Synthesis of 4-(6-argio-4-(3,4-dihydroquinolin-1(2H)-yl)pyridin-2-yl)morpholine. A mixture of 4-(6-chloro-4-(3,4-dihydroquinolin-1(2H)-yl) pyridin-2-yl)morpholine (55 mg, 0.17 mmol), 5-(4,4,5,5-tetramethyl-1,3,2-dioxaborolan-2-yl)pyrimidin-2-amine (74 mg, 0.33 mmol), $Na_2CO_3$ (71 mg, 0.67 mmol), and Pd(dppf) $Cl_2$ (27 mg, 0.03 mmol) in 1,4-dioxane (6 mL) and $H_2O$ (2 mL) was stirred at 95° C. for 2 h under $N_2$. The reaction mixture was poured into water (10 mL) and extracted with dichloromethane (10 mL×3). The combined organics were washed with brine (10 mL), dried over sodium sulfate, and concentrated. The crude was purified by prep-TLC to afford 4-(6-argio-4-(3,4-dihydroquinolin-1(2H)-yl)pyridin-2-yl) morpholine (11 mg, 81% yield). ESMS+: 389.1 (M+H). $^1H$ NMR ($CDCl_3$, 400 MHz) δ: 8.84 (s, 2H), 7.24 (m, 1H), 7.14 (m, 1H), 7.10 (m, 1H), 6.94 (m, 1H), 6.84 (s, 1H), 6.29 (s, 1H), 5.37 (br, 2H), 3.84 (m, 4H), 3.69 (m, 2H), 3.53 (m, 4H), 2.77 (m, 2H), 2.02 (m, 2H).

Example 28: 5-(6-morpholino-4-((tetrahydrofuran-3-yl)sulfonyl)pyridin-2-yl)pyrimidin-2-amine (Compound 142a)

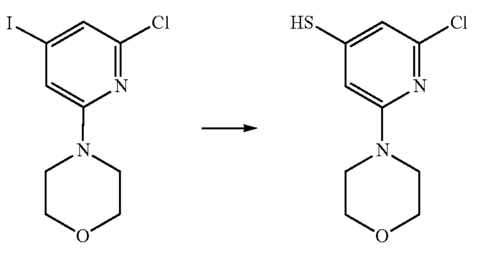 [SMILES: Clc1cc(I)cc(N2CCOCC2)n1 ; Sc1cc(Cl)nc(N2CCOCC2)c1]

Step 1 (See Scheme Q, Step 8): Synthesis of 2-chloro-6-morpholinopyridine-4-thiol: A mixture of 4-(6-chloro-4-iodopyridin-2-yl)morpholine (0.55 g, 2 mmol), BnSH (0.25 g, 2 mmol), and potassium carbonate (0.41 g, 3 mmol) in DMSO (5 mL) was heated at 55° C. for 2 h. The mixture was poured into water (20 mL) and extracted with ethyl acetate (20 mL×3). The organic extracts were combined, washed with brine (10 mL×2), dried over anhydrous sodium sulfate, and concentrated. The residue was purified by silica gel column chromatography (petroleum ether) to yield 4-(4-(benzylthio)-6-chloropyridin-2-yl)morpholine (310 mg, 58% yield). The compound was confirmed with LC-MS only: 321.21 $(M+H)^+$, $C_{16}H_{17}ClN_2OS$.

Step 2 (See Scheme Q, Step 10): $AlCl_3$ deprotection of the benzyl group was accomplished as outlined in Example 11 for Compound 52 to give 2-chloro-6-morpholinopyridine-4-thiol (150 mg, 75% yield) as an off-white solid. The compound was confirmed with LC-MS only: 179.84 $(M+H)^+$, $C_9H_{11}ClN_2OS$.

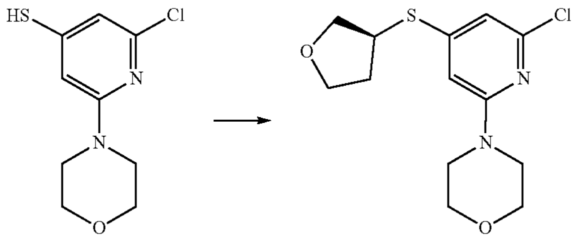 [SMILES: Sc1cc(Cl)nc(N2CCOCC2)c1 ; Clc1cc(S[C@H]2CCOC2)cc(N2CCOCC2)n1]

Step 3 (See Scheme Q, Step 11b): Synthesis of (S)-4-(6-chloro-4-(tetrahydrofuran-3-ylthio)pyridin-2-yl)morpholine: A mixture of 2-chloro-6-morpholinopyridine-4-thiol (195 mg, 0.85 mmol), (R)-3-bromotetrahydrofuran (375 mg, 2.5 mmol), and $CsCO_3$ (1.1 g, 3.39 mmol) in acetonitrile (20 mL) was heated at 60° C. overnight under nitrogen protection. The solid was filtered off and the filtrate was concentrated. The residue was purified by prep-TLC to give (S)-4-(6-chloro-4-(tetrahydrofuran-3-ylthio)pyridin-2-yl) morpholine (130 mg, 51% yield). The compound was confirmed with LC-MS only: 301.23 $(M+H)^+$, $C_{13}H_{17}ClN_2O_2S$.

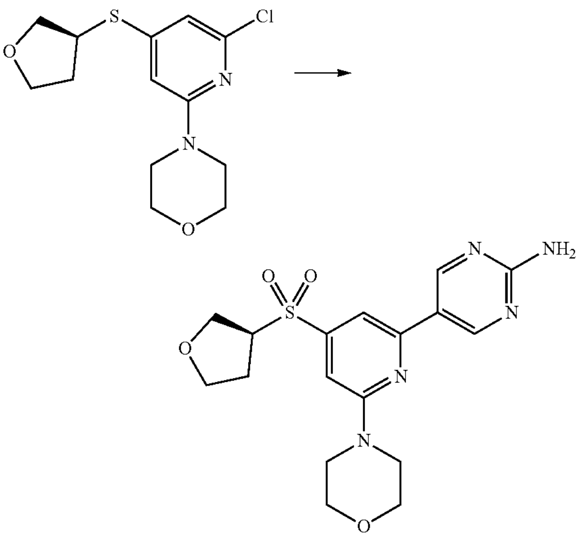

Compound 142a

Step 4 (See Scheme Q, Step 12a): Synthesis of (S)-5-(6-morpholino-4-((tetrahydrofuran-3-yl)sulfonyl)pyridin-2-yl) pyrimidin-2-amine: Oxidation of (S)-4-(6-chloro-4-(tetrahydrofuran-3-ylthio)pyridin-2-yl)morpholine with mCPBA was accomplished as outlined in Example 11 for Compound 52 to give (S)-4-(6-chloro-4-(tetrahydrofuran-3-ylsulfonyl)pyridin-2-yl)morpholine (70 mg, 49% yield) as an off-white solid. The compound was confirmed with LC-MS only: 333.18 $(M+H)^+$, $C_{13}H_{17}ClN_2O_4S$.

Step 5 (See Scheme Q, Step 4c): The coupling of (S)-4-(6-chloro-4-(tetrahydrofuran-3-ylsulfonyl)pyridin-2-yl)morpholine (70 mg, 0.21 mmol) and 5-(4,4,5,5-tetramethyl-1,3,2-dioxaborolan-2-yl)pyrimidin-2-amine (70 mg, 0.32 mmol) was carried out as described in Example 11 for Compound 52 to afford (S)-5-(6-morpholino-4-((tetrahydrofuran-3-yl)sulfonyl)pyridin-2-yl)pyrimidin-2-amine (Compound 142a) (13 mg, 16% yield). ESMS+: 392.2 (M+H). $^1$H NMR (DMSO-d6, 400 MHz) δ: 8.97 (s, 2H), 7.52 (s, 1H), 7.12 (br, 2H), 7.05 (s, 1H), 4.41 (m, 1H), 4.05 (m, 1H), 3.84 (m, 2H), 3.72 (m, 4H), 3.63 (m, 4H), 2.17 (m, 3H).

The following compounds were prepared by methods analogous to the method described for Compound 142a and as described in Scheme Q:

| Cmpd # | MS | $^1$H NMR |
|---|---|---|
| 142b | 392.4 (M + H) | (DMSO-d6, 400 MHz) δ: 8.97 (s, 2H), 7.51 (s, 1H), 7.11 (br, 2H), 7.05 (s, 1H), 4.41 (m, 1H), 4.05 (m, 1H), 3.84 (m, 2H), 3.72 (m, 4H), 3.67 (m, 1H), 3.64 (m, 4H), 2.17 (m, 2H). |
| 148 | 406.2 (M + H) | (DMSO-d6, 400 MHz) δ: 8.96 (s, 2H), 7.45 (s, 1H), 7.13 (br, 2H), 6.98 (s, 1H), 3.94 (m, 2H), 3.77 (m, 1H), 3.72 (m, 4H), 3.62 (m, 4H), 3.27 (m, 2H), 1.74 (m, 2H), 1.64 (m, 2H). |

Example 29: 5-(4-(chroman-4-ylsulfonyl)-6-morpholinopyridin-2-yl)pyrimidin-2-amine (Compound 143)

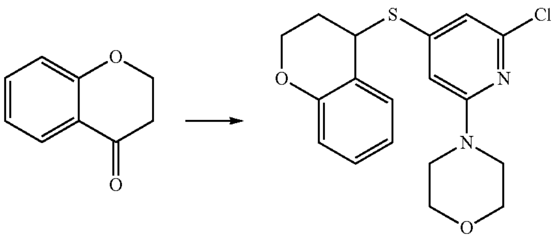 [SMILES: O=C1CCOc2ccccc21 ; Clc1cc(SC2CCOc3ccccc32)cc(N2CCOCC2)n1]

Step 1: Synthesis of (6-chloro-4-(chroman-4-ylthio)pyridin-2-yl)morpholine: BH3·$SMe_2$ (50 mL, 0.5 mol, 10 M) was added dropwise to a solution of chroman-4-one (10 g, 67.5 mmol) in THF (100 mL) at 0° C. The reaction was stirred for 1 h at 0° C. The reaction was quenched with methanol (10 mL) and concentrated. The residue was co-evaporated with DCM (100 mL×3) to give chroman-4-ol (11 g, quantative yield) as colorless oil, which was used for next reaction without further purification. The alcohol (3 g, 20.0 mmol) was dissolved in thionyl chloride (10 mL) and the reaction was stirred overnight at rt. The solvent was removed in vacuo and co-evaporated with dichloromethane twice to give 4-chlorochromane (3.3 g, 20.0 mmol), which was used crude in the next reaction. In a second flask, -chloro-6-morpholinopyridine-4-thiol (4.6 g, 20.0 mmol, for preparation, see procedure for Example 28, Compound 142a) was dissolved in DMF (20 mL) and added to a solution of NaH (1.2 mg, 30.0 mmol, 60% purity in mineral oil) in DMF (5 mL) at 0° C. The reaction was stirred for 5 min at 0° C. and a solution of the chloride in DMF (3 mL) was added followed by addition of KI (100 mg, 0.6 mmol). The reaction was stirred for 3 h at rt. The solution was poured into water (50 mL) and extracted with ethyl acetate (50 mL×3). The organic extracts were combined, washed with brine (50 mL), dried over anhydrous sodium sulfate, and concentrated. The residue was purified by silica gel column chromatography (petroleum ether/ethyl acetate=30:1 to 15:1) to give 4-(6-chloro-4-(chroman-4-ylthio)pyridin-2-yl)morpholine (5.33 g, 74% yield) as off-white solid.

The compound was confirmed with LC-MS only: 363.1 $(M+H)^+$, $C_{18}H_{19}ClN_2O_2S$.

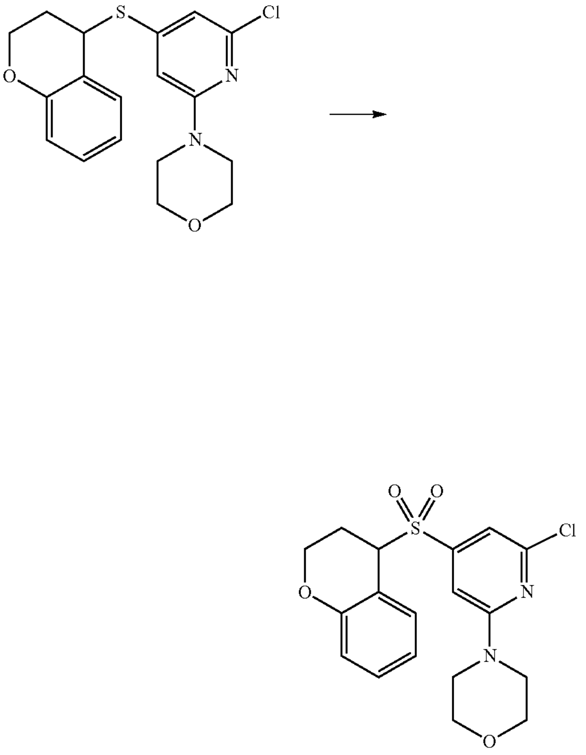

Step 2: Synthesis of 4-(6-chloro-4-(chroman-4-ylsulfonyl)pyridin-2-yl)morpholine: mCPBA (11.9 g, 58.8 mmol, 70% purity) was added portionwise to a solution of compound 13 (5.33 g, 14.7 mmol) in dichloromethane (100 mL). The mixture was stirred overnight at rt. 4,4,4',4',5,5,5',5'-octamethyl-2,2'-bi(1,3,2-dioxaborolane) (15 g, 58.8 mmol) was added and the mixture was stirred for another 30 min. The reaction mixture was diluted with dichloromethane (100 mL), washed with sat. $Na_2CO_3$ (100 mL×2), brine (50 mL), dried over sodium sulfate, and concentrated. The residue was purified by silica gel column chromatography (petroleum ether/ethyl acetate=20:1 to 5:1) to give 4-(6-chloro-4-(chroman-4-ylsulfonyl)pyridin-2-yl)morpholine (4.3 g, 74% yield) as light yellow solid. The compound was confirmed with LC-MS only: 395.7 $(M+H)^+$, $C_{18}H_{19}ClN_2O_4S$.

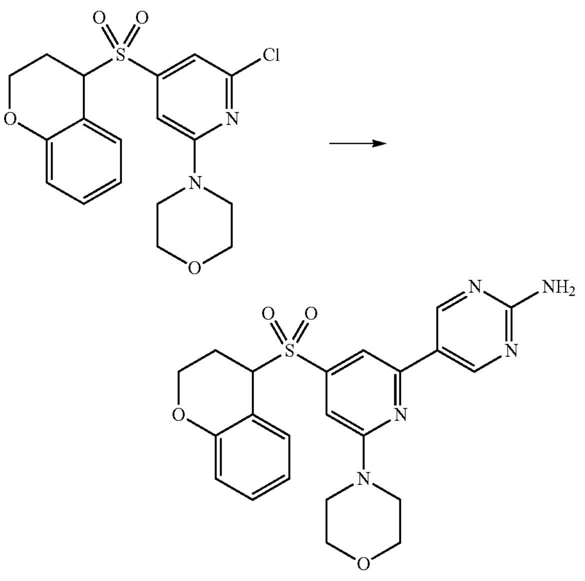

Compound 143

Step 3: A mixture of 4-(6-chloro-4-(chroman-4-ylsulfonyl)pyridin-2-yl)morpholine (4.3 g, 10.9 mmol), 5-(4,4,5,5-tetramethyl-1,3,2-dioxaborolan-2-yl)pyrimidin-2-amine (3.6 g, 16.4 mmol), $K_2CO_3$ (3 g, 21.8 mmol), and Pd(dppf)$Cl_2$ (0.89 g, 1.09 mmol) in 1,4-dioxane (30 mL) and $H_2O$ (10 mL) was stirred at 95° C. for 1 h under $N_2$. The reaction mixture was poured into water (50 mL) and extracted with ethyl acetate (50 mL×2). The combined organics were washed with brine (30 mL), dried over sodium sulfate, and concentrated. The crude was washed with petroleum ether/ethyl acetate (30 mL×2, 2:1) and DCM (10 mL×3) successively. The crude Compound 143 was redissolved in 10% methanol/dichloromethane and 1 w/w equivalent of Silica Thiol MS001 (Shanghai Chiral Chemistry Co., Ltd) was added and the mixture was stirred for 30 minutes at room temperature. The Silica Thiol MS001 was filtered off and washed with 10% methanol/dichloromethane. The combined filtrate and wash were evaporated under reduced pressure to give Compound 143 (3.7 g, 75% yield) as an off white solid. LC-MS: 454.4 $(M+H)^+$, $C_{22}H_{23}N_5O_4S$. 1H NMR (DMSO-d6, 400 MHz) δ: 8.96 (s, 2H), 7.51 (s, 1H), 7.36 (m, 1H), 7.30 (m, 1H), 7.14 (s, 2H), 7.01 (s, 1H), 6.94 (m, 1H), 6.88 (m, 1H), 5.04 (m, 1H), 4.34 (m, 1H), 4.19 (m, 1H), 3.72 (m, 4H), 3.62 (m, 4H), 2.14 (m, 2H).

Example 30: Enantiomeric separation of 5-(4-(chroman-4-ylsulfonyl)-6-morpholinopyridin-2-yl)pyrimidin-2-amine (Compound 143)

The racemate of Compound 143 was separated into 2 single enantiomers by chiral SFC. The racemate of Compound 143 (1.3 g) was dissolved in 60 mL of IPA/DMSO and injected in 1.1 mL aliquots (0.024 g/injection). The material was separated on a Regis IA column (5 μM, 250×21.1 mm). using 40/60-IPA/$CO_2$ at a flow rate of 32 mL/min IPA and 80 g/min $CO_2$. Two peaks were isolated. The solvent was removed under reduced pressure at 40° C. Residual DMSO was removed by adding a small amount of water, freezing and lyophilizing. The first eluting fraction, enantiomer 1, is drawn arbitrarily as (S) (534 mg, optical rotation [a]20=+104, c=0.1, DMSO). The second eluting fraction, enantiomer 2, is drawn arbitrarily as (R) (544 mg, optical rotation [a]20=−112, c=0.1, DMSO).

| Cmpd # | MS | $^1$H NMR |
|---|---|---|
| (+)143 | 453.9 (M + H) | (DMSO-d6, 500 MHz) δ 8.95 (s, 2H), 7.49 (d, J = 1.1 Hz, 1H), 7.36 (dd, J = 8.0, 1.7 Hz, 1H), 7.29 (ddd, J = 8.6, 7.2, 1.7 Hz, 1H), 7.11 (s, 2H), 7.00 (d, J = 1.1 Hz, 1H), 6.93 (td, J = 7.5, 1.3 Hz, 1H), 6.88 (dd, J = 8.2, 1.2 Hz, 1H), 5.03 (t, J = 4.3 Hz, 1H), 4.34 (m, 1H), 4.19 (m, 1H), 3.73 (dd, J = 5.7, 4.0 Hz, 4H), 3.61 (dd, J = 5.8, 3.9 Hz, 4H), 2.19-2.09 (m, 2H). |
| (−)143 | 453.9 (M + H) | (DMSO-d6, 500 MHz) δ 8.95 (s, 2H), 7.49 (d, J = 1.1 Hz, 1H), 7.36 (dd, J = 7.8, 1.7 Hz, 1H), 7.29 (ddd, J = 8.7, 7.3, 1.7 Hz, 1H), 7.11 (s, 2H), 7.00 (d, J = 1.2 Hz, 1H), 6.93 (td, J = 7.5, 1.2 Hz, 1H), 6.88 (dd, J = 8.2, 1.2 Hz, 1H), 5.03 (t, J = 4.3 Hz, 1H), 4.34 (ddd, J = 11.1, 8.9, 5.8 Hz, 1H), 4.18 (m, 1H), 3.73 (dd, J = 5.8, 4.0 Hz, 4H), 3.61 (t, J = 5.0 Hz, 4H), 2.16 (p, J = 4.5, 4.1 Hz, 2H). |

Additional compounds within the scope of Formula (I) may be prepared using methods analogous to those described herein. The mass spectrometry (MS) and nuclear magnetic resonance (NMR) characterization data for compounds described herein is shown in Table A.

TABLE A

| Cmpd # | MS | $^1$H NMR |
|---|---|---|
| 116 | 438.97 (M + H) | ($CDCl_3$, 400 MHz) δ: 8.47 (s, 2H), 7.48 (m, 1H), 7.41 (s, 2H), 7.29 (m, 2H), 7.04 (s, 1H), 5.21 (br, 2H), 4.63 (d, J = 8.8 Hz, 2H), 3.88 (m, 4H), 3.25 (m, 6H). |
| 141 | 390.1 (M + H) | ($CDCl_3$, 400 MHz) δ: 8.87 (s, 2H), 7.17 (m, 1H), 6.82-6.91 (m, 3H), 6.78 (s, 1H), 6.36 (s, 1H), 5.48 (br, 2H), 4.23 (m, 2H), 4.13 (m, 1H), 3.83 (m, 4H), 3.54 (m, 4H), 2.36 (m, 1H), 2.13 (m, 1H). |
| 147 | 440.3 (M + H) | (DMSO-d6, 400 MHz) δ: 8.93 (s, 2H), 7.45 (d, J = 7.2 Hz, 1H), 7.34 (m, 2H), 7.19 (m, 2H), 7.05 (m, 1H), 6.88 (d, J = 8.0 Hz, 1H), 6.84 (s, 1H), 5.66 (m, 1H), 4.99 (m, 1H), 4.77 (m, 1H), 3.76 (m, 4H), 3.59 (m, 4H). |

Biological Example B-1

Inhibition of PI3Kα

Quantification of ATP to ADP conversion as a measure of PI3Kα activity. Active PI3Kα (Life Technologies), in the presence or absence of PI3Kα inhibitor, was reacted with PIP2:PS (Life Technologies), a substrate specifically optimized for use with Class I PI3 kinases, and ultrapure ATP (Promega). The conversion of ATP to ADP by PI3Kα was measured as luminescence signal via Promega ADP-Glo kinase activity assay. Assay was validated using published PI3Kα inhibitors LY294002, PI-103, BYL719, GDC0198 and also DMSO vehicle control.

Compounds were prepared at 100× final concentration as a 12-point, 1:3 serial-dilution in DMSO series, with DMSO control as 12$^{th}$ point. Compound was then diluted in (25 mM HEPES pH 7.5, 1 mM EGTA, 0.3% CHAPS) prior to addition to PI3Kα. Active PI3Kα diluted to 0.24 ng/μL (1.1 nM) in (50 mM HEPES pH 7.5, 6 mM $MgCl_2$, 1 mM EGTA, 200 mM NaCl, 0.03% CHAPS, 8 mM DTT) was incubated with compound for 0 hr and 3 hr prior to the start of the reaction. 25 μM PIP2:PS and 60 μM ATP were diluted from stock in (25 mM HEPES pH 7.5, 1 mM EGTA, 0.3% CHAPS) and added to initiate the PI3Kα reaction. Reaction time was 30 minutes. ATP to ADP conversion was measured in Luminescence Counts on DTX880 Plate Reader (Beckman Coulter). Compound $IC_{50}$s were reported using GraphPad Prism software. Analytical method was non-linear regression, 4-parameter curve fit with bottom fit to validated PI3Kα inhibitor reference controls and no top fit (floating top). Data obtained from this assay are presented in Table 2.

TABLE 2

| Cmpd # | $PI3K_\alpha$ $IC_{50}$ (μM) |
|---|---|
| 1 | 0.61 |
| 2 | 5.0 |
| 3 | 2.0 |
| 4 | 11 |
| 5 | 12 |
| 6 | 3.8 |
| 7 | 1.8 |
| 8 | 1.3 |
| 9 | 1.5 |
| 10 | 0.46 |
| 11 | 1.40 |

TABLE 2-continued

| Cmpd # | $PI3K_\alpha$ $IC_{50}$ (μM) |
|---|---|
| 12 | 9.0 |
| 13 | 0.91 |
| 14 | 7.3 |
| 15 | 3.5 |
| 16 | 1.5 |
| 17 | 1.9 |
| 18 | 3.9 |
| 19 | 2.9 |
| 20 | 2.7 |
| 21 | 2.1 |
| 22 | 2.8 |
| 23 | 0.10 |
| 24 | 21 |
| 25 | 30 |
| 26 | 0.27 |
| 27 | 0.38 |
| 28 | 0.37 |
| 29 | 0.37 |
| 30 | 3.1 |
| 31 | 0.66 |
| 32 | 0.45 |
| 33 | 0.98 |
| 34 | 13 |
| 35 | 1.1 |
| 36 | 1.1 |
| 37 | 2.0 |
| 38 | 0.74 |
| 39 | 0.79 |
| 40 | 6.5 |
| 41 | 0.53 |
| 42 | 4.7 |
| 43 | 11 |
| 44 | 13 |
| 45 | 5.9 |
| 46 | 19 |
| 47 (as a HCl salt) | 1.2 |
| 48 (as a TFA salt) | 0.47 |
| 49 | 0.49 |
| 50 | 0.28 |
| 51 | 0.12 |
| 52 | 0.13 |
| 53 | 0.11 |
| 54 | 0.13 |
| 55 | 12 |
| 56 | 0.26 |

TABLE 2-continued

| Cmpd # | PI3K$_{\alpha}$ $IC_{50}$ (μM) |
|---|---|
| 57 (as a TFA salt) | 0.48 |
| 58 | 0.41 |
| 59 (as a TFA salt) | 0.46 |
| 60 | 0.81 |
| 61 | 0.50 |
| 62 | 0.33 |
| 63 | 0.47 |
| 64 | 1.1 |
| 65 | 0.87 |
| 66 | 1.3 |
| 67 | 0.80 |
| 68 | 0.047 |
| 69 | 0.54 |
| 70 | 7.6 |
| 71 | 9.1 |
| 72 | 0.46 |
| 73 | 1.5 |
| 74 | 1.0 |
| 75 | 0.25 |
| 76 | 0.30 |
| 77 | 0.10 |
| 78 | 0.18 |
| 79 | 0.21 |
| 80 | 0.66 |
| 81 | 0.062 |
| 82 | 0.29 |
| 83 | 0.34 |
| 84 | 0.60 |
| 85 | 1.0 |
| 86 | 0.58 |
| 87 | 0.21 |
| 88 | 0.53 |
| 89 | 2.5 |
| 90 | 7.22 |
| 91 | 0.18 |
| 92 | 0.15 |
| 93 | 0.088 |
| 94 | 0.11 |
| 95 | 0.12 |
| 96 | 1.4 |
| 97 | 0.51 |
| 98 | 12 |
| 99 | 4.3 |
| 100 | 1.6 |
| 101 | 0.88 |
| 102 | 0.54 |
| 103 | 0.68 |
| 104 | 1.3 |
| 105 | 1.7 |
| 106 | 0.10 |
| 107 | 0.067 |
| 108 | 0.69 |
| 109 | 1.2 |
| 110 | 0.40 |
| 111 | 0.38 |
| 112 | 2.3 |
| 113 | 1.1 |
| 114 | 2.4 |
| 115 | 0.066 |
| 116 | 2.3 |
| 117 | 3.3 |
| 118 | 0.88 |
| 119 | 0.11 |
| 120 | 0.091 |
| 121 | 0.84 |
| 122 | 0.037 |
| 123 | 0.046 |
| 124 | 0.12 |
| 125 | 0.21 |
| 126 | 0.27 |
| 127 | 0.056 |

TABLE 2-continued

| Cmpd # | PI3K$_{\alpha}$ $IC_{50}$ (μM) |
|---|---|
| 128 | 1.22 |
| 129 | 0.034 |
| 130 | 0.023 |
| 131 | 0.023 |
| 132 | 1.21 |
| 133 | 0.012 |
| 134 | 0.07 |
| 135 | 0.079 |
| 136 | 0.37 |
| 137 | 0.075 |
| 138 | 0.014 |
| 139 | 0.017 |
| 140 | 0.12 |
| 141 | 0.062 |
| 142a | 0.0057 |
| 142b | 0.0068 |
| 143 | 0.0017 |
| (+)143 | 0.0045 |
| (−)143 | 0.0010 |
| 144 | 0.39 |
| 145 | 0.39 |
| 146 | 0.37 |
| 147 | 0.0070 |
| 148 | 0.0130 |
| 149 | 0.0140 |
| 150 | 0.45 |
| 151 | 0.83 |

Biological Example B-2 mTor Assay Protocol

The substrate was prepared in base reaction buffer (20 mM Hepes (pH 7.5), 10 mM $MgCl_2$, 1 mM EGTA, 0.02% Brij35, 0.02 mg/mi BSA, 0.1 mM $Na_3VO_4$, 2 mM DTT, 1% DMSO), and required cofactors were added to the substrate solution. The mTor kinase was delivered into the substrate solution, and the solution was gently mixed. Testing compounds were dissolved in 100% DMSO to specific concentration. The serial dilution was conducted by Integra Viaflo Assist in DMSO. The compounds were delivered into the kinase reaction mixture by Acoustic technology (Echo550; nanoliter range), and the reaction mixture was incubated for 20 min at room temperature. Then, $_{33}$P-ATP (Specific activity 10 μCi/μl) was delivered into the reaction mixture to initiate the reaction. The reaction mixture was incubated for 2 hours at room temperature. Radioactivity was detected by a filter-binding method. Kinase activity data were expressed as the percent remaining kinase activity in test samples compared to vehicle (dimethyl sulfoxide) reactions. $IC_{50}$ values and curve fits were obtained using Prism (GraphPad Software). Data obtained from this assay are presented in Table 3.

Biological Example B-3 pAKT Protocol

Inhibition of the PI3K-AKT-mTOR pathway was measured by quantifying the loss of (Ser-473) pAKT using AlphaScreen (Perkin Elmer). B103 (Rat Neuroblastoma) cells were seeded in serum containing medium (High Glucose DMEM (−Phenol Red)+10% FBS+2× Glutamax+1 mM Sodium Pyruvate+10 mM HEPES+1× Non-Essential Amino Acids+1× Pen/Strep) on a 96-well tissue culture treated plate and grown for 20 hours. Cells were then serum starved in serum free medium (High Glucose DMEM (−Phenol Red)+1× Glutamax+1 mM Sodium Pyruvate+1× Pen/

Strep) for 6 hours prior to a 2-hour pretreatment with inhibitors of the pathway, including reference inhibitor LY294002. These inhibitors were prepared at a 200× final concentration as a 6-point, 1:3 serial dilution in DMSO series, with DMSO as the 7th point. The inhibitors were then diluted in experimental medium (High Glucose DMEM (−Phenol Red)$^+$1× Glutamax+1 mM Sodium Pyruvate+1× Pen/Strep+25 mM HEPES+0.1% BSA) and combined with the cells at 1× final concentration in 0.5% DMSO. The cells were then stimulated for 20 minutes with (2.5 μg/mL) insulin, an activator of the PI3K-AKT-mTOR pathway and a demonstrated (Ser-473) pAKT agonist. Cells were promptly lysed using Perkin Elmer proprietary lysis buffer and the (Ser-473) pAKT and total AKT contained in the lysate was measured by AlphaScreen. In AlphaScreen, donor beads were coated with streptavidin to capture one of the antibodies, which is biotinylated. Acceptor beads were coated with Protein A to immobilize the other antibody. In the presence of target protein, the two antibodies bring the donor and acceptor beads close together, generating signal. The amount of light emission is directly proportional to the amount of target protein present in the sample. For each inhibitor tested: the ratio of measured (Ser-473) pAKT/totalAKT was plotted in GraphPad Prism as a 7-point, non-linear regression, 4-parameter curve with bottom constrained to reference control bottom and unconstrained top anchored to DMSO. (Ser-473) pAKT $IC_{50}$ was calculated and reported, and the data obtained from this assay are presented in Table 3.

TABLE 3

| Example # | pAKT (μM) | mTor (μM) |
|---|---|---|
| 1 | 7.52 | 2.00 |
| 8 | 7.62 | 0.83 |
| 10 | 30.70 | 0.64 |
| 11 | 100.00 | 22.00 |
| 12 | 100.00 | 100.00 |
| 13 | 28.60 | 10.00 |
| 15 | 100.00 | 22.00 |
| 17 | 100.00 | 100.00 |
| 18 | 100.00 | 100.00 |
| 19 | 37.00 | 16.00 |
| 20 | 100.00 | 10.00 |
| 21 | 37.00 | 9.39 |
| 22 | 39.00 | 8.69 |
| 23 | 8.50 | 3.00 |
| 26 | 6.20 | 5.30 |
| 27 | 14.00 | 11.00 |
| 28 | 13.00 | 7.90 |
| 29 | 10.90 | 10.90 |
| 30 | 18.00 | 10.90 |
| 32 | 6.30 | >33 |
| 35 | 23.49 | 12.20 |
| 38 | 9.11 | 3.60 |
| 39 | 9.90 | 4.80 |
| 41 | 0.86 | 4.27 |
| 47 (as a HCl salt) | 2.18 | ND |
| 48 (as a TFA salt) | >50 | 6.39 |
| 49 | 31.10 | ND |
| 50 | >50 | 2.98 |
| 51 | 2.12 | 0.46 |
| 52 | 3.46 | 0.73 |
| 53 | 1.65 | 0.54 |
| 54 | 2.46 | 0.59 |
| 56 | 19.76 | 6.15 |
| 57 (as a TFA salt) | 19.75 | 3.44 |

TABLE 3-continued

| Example # | pAKT (μM) | mTor (μM) |
|---|---|---|
| 58 | 41.29 | 3.95 |
| 59 (as a TFA salt) | 36.09 | 4.60 |
| 60 | 31.12 | ND |
| 62 | 6.47 | 1.87 |
| 63 | 3.71 | ND |
| 68 | 4.66 | 1.21 |
| 70 | 4.02 | 7.61 |
| 71 | 11.20 | ND |
| 72 | 9.13 | ND |
| 75 | 6.40 | ND |
| 76 | 5.64 | ND |
| 77 | 3.19 | ND |
| 78 | 4.52 | ND |
| 79 | 5.02 | ND |
| 81 | 26.40 | ND |
| 82 | 10.78 | ND |
| 83 | 8.47 | ND |
| 87 | 1.00 | 1.44 |
| 88 | 6.54 | 2.46 |
| 91 | 7.33 | 2.58 |
| 92 | 2.91 | ND |
| 93 | 5.44 | 0.87 |
| 94 | 19.84 | ND |
| 95 | 5.19 | ND |
| 96 | 1.06 | ND |
| 97 | 12.37 | ND |
| 100 | 48.20 | ND |
| 101 | 8.53 | ND |
| 102 | 6.79 | ND |
| 103 | 5.81 | ND |
| 106 | 4.10 | 1.46 |
| 107 | 3.70 | 4.33 |
| 108 | 4.72 | ND |
| 109 | 15.00 | ND |
| 110 | 8.70 | 9.90 |
| 111 | 14.50 | 5.40 |
| 112 | 22.30 | ND |
| 113 | 14.30 | ND |
| 114 | 15.30 | ND |
| 115 | 0.57 | 0.063 |
| 116 | 22.90 | ND |
| 117 | 17.30 | ND |
| 118 | 13.80 | ND |
| 119 | 4.00 | 4.70 |
| 120 | 0.64 | 0.48 |
| 122 | 0.48 | 0.51 |
| 123 | 0.46 | 0.56 |
| 124 | 0.89 | ND |
| 125 | 0.81 | 0.27 |
| 126 | 0.49 | ND |
| 127 | 0.38 | 0.13 |
| 129 | 3.46 | 2.95 |
| 130 | 0.75 | 1.75 |
| 131 | 0.56 | 0.59 |
| 133 | 0.40 | 0.44 |
| 134 | 0.38 | 0.45 |
| 135 | 1.62 | 0.70 |
| 136 | 1.51 | 2.06 |
| 137 | 0.45 | 0.37 |
| 138 | 0.19 | 1.10 |
| 139 | 0.016 | ND |
| 140 | 0.31 | ND |

ND = not determined

The invention claimed is:

1. A method of interfering with, modulating, activating, increasing, or stimulating the process of autophagy in a cell, comprising contacting the cell with a compound of Formula (I):

(I)

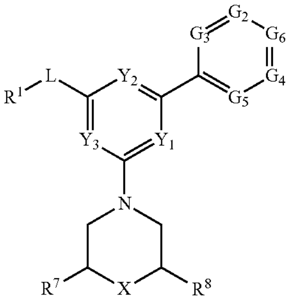

wherein $R^1$ is —$(CR^eR^f)_o$-heterocycloalkyl;

is 0, 1, or 2;

$R^e$ and $R^f$ are each independently H, halo, or $C_{1-4}$alkyl, each heterocycloalkyl present in $R^1$ is unsubstituted or substituted with one or two $R^x$ substituents;

wherein each $R^x$ substituent is independently halo, $C_{1-4}$alkyl, cycloalkyl, —$C_{1-2}$-haloalkyl, —OH, —$OC_{1-4}$alkyl, —O—$C_{1-2}$-haloalkyl, cyano, —C(O)$C_{1-4}$alkyl, —C(O)$NR^iR^j$, —$SO_2C_{1-4}$alkyl, —$SO_2NR^kR^l$, —$NR^qR^r$, —C(O)-cycloalkyl, —C(O)-aryl (optionally substituted with methyl or halo), —$CO_2C_{1-4}$alkyl, —$CO_2$aryl, —C(O)$CH_2$-aryl (optionally substituted with methyl or halo), —$CH_2$-aryl (optionally substituted with methyl or halo), or monocyclic heterocycloalkyl (optionally substituted with methyl, —C(O)$C_{1-4}$alkyl, or —$CO_2C_{1-4}$alkyl);

wherein $R^i$, $R^j$, $R^k$, and $R^l$ are each independently H, $C_{1-4}$alkyl, —$C_{1-4}$alkyl-OH, or —$C_{1-4}$alkyl-O—$C_{1-4}$alkyl, wherein $R^q$ and $R^r$ are each independently H, $C_{1-4}$alkyl, —$C_{1-4}$alkyl-OH, —$C_{1-4}$alkyl-O—$C_{1-4}$alkyl, —C(O)$C_{1-4}$alkyl, —$CO_2C_{1-4}$alkyl, or —$SO_2C_{1-4}$alkyl;

L is —$S(O)_2$—;

X is O;

one of $Y_1$, $Y_2$, and $Y_3$ is N and the other two are each CH, or $Y_1$, $Y_2$, and $Y_3$ are each CH;

$G_2$ is N;

$G_3$ is $CR^3$;

$G_4$ is N;

$G_5$ is $CR^5$; and $G_6$ is $CR^6$;

wherein $R^3$, $R^5$, and $R^6$ are each independently hydrogen, halogen, —OH, -alkyl, —O-alkyl, -haloalkyl, —O-haloalkyl, or —$NR^uR^v$;

$R^u$ is H or $C_{1-4}$alkyl;

$R^v$ is H, $C_{1-4}$alkyl, monocyclic cycloalkyl, —C(O)$C_{1-4}$alkyl, or —C(O)$NR^wR^y$;

wherein each alkyl present in $R^v$ is unsubstituted or substituted with —OH, —$NH_2$, —NH($C_{1-4}$alkyl), or —N($C_{1-4}$alkyl$)_2$, $R^w$ and $R^y$ are each independently H or $C_{1-4}$alkyl; and $R^7$ and $R^8$ are each independently hydrogen or $C_{1-4}$alkyl, or $R^7$ and $R^8$ are taken together to form —$CH_2CH_2$—; or a pharmaceutically acceptable salt thereof.

2. The method of claim 1, wherein o is 0.

3. The method of claim 1, wherein each heterocycloalkyl present in $R^1$ is unsubstituted.

4. The method of claim 1, wherein $R^6$ is —$NR^uR^v$.

5. The method of claim 1, wherein $R^7$ and $R^8$ are each hydrogen.

6. The method of claim 1, wherein the compound is

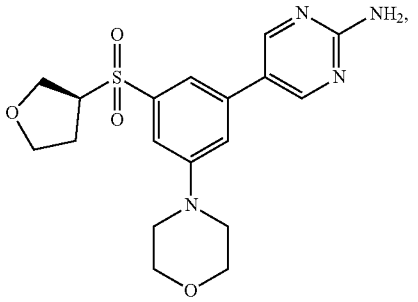 [SMILES: Nc1ncc(-c2cc(N3CCOCC3)cc(S(=O)(=O)[C@H]3CCOC3)c2)cn1]

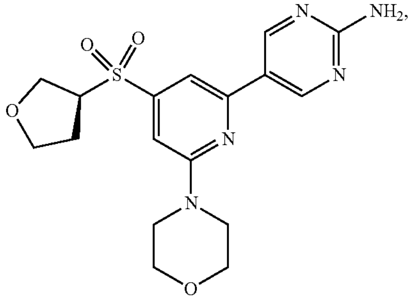 [SMILES: Nc1ncc(-c2cc(S(=O)(=O)[C@H]3CCOC3)cc(N3CCOCC3)n2)cn1]

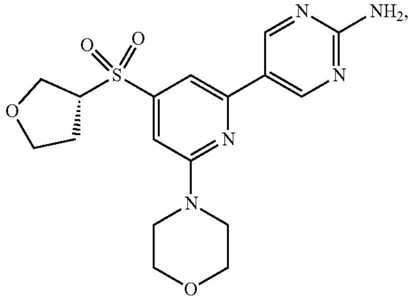 [SMILES: Nc1ncc(-c2cc(S(=O)(=O)[C@@H]3CCOC3)cc(N3CCOCC3)n2)cn1]

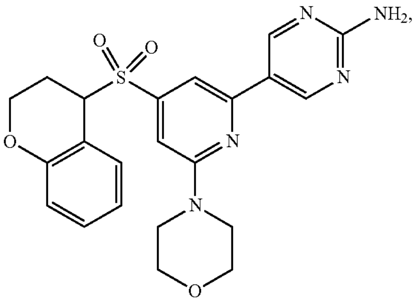

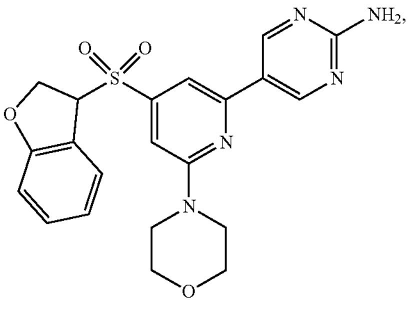

or

-continued

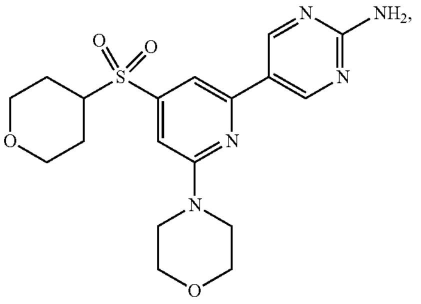

or a pharmaceutically acceptable salt thereof.

7. The method of claim 6, wherein the compound is

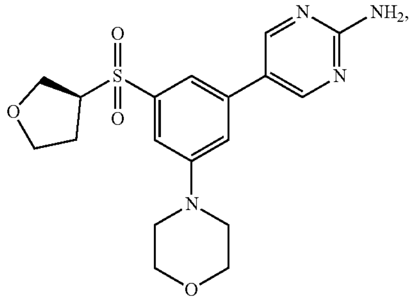

or a pharmaceutically acceptable salt thereof.

8. The method of claim 6, wherein the compound is

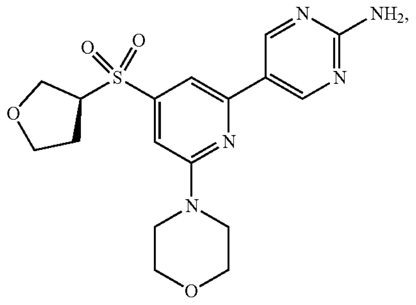

or a pharmaceutically acceptable salt thereof.

9. The method of claim 6, wherein the compound is

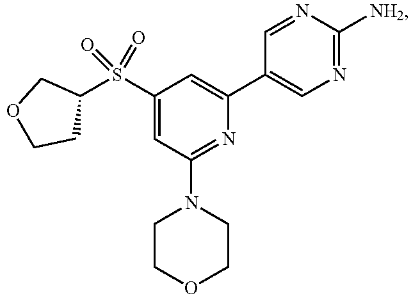

or a pharmaceutically acceptable salt thereof.

10. The method of claim 6, or a pharmaceutically acceptable salt thereof, wherein the compound is

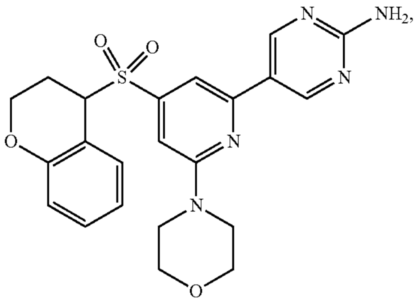 [SMILES: Nc1ncc(-c2cc(S(=O)(=O)C3CCOc4ccccc43)cc(N3CCOCC3)n2)cn1]

or a pharmaceutically acceptable salt thereof.

11. A method of method of preventing, reversing, slowing, or inhibiting the PI3K-AKT-mTOR pathway in a cell, comprising contacting the cell with a compound of Formula (I):

(I)

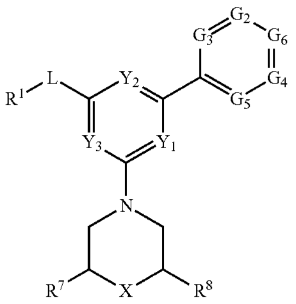

wherein $R^1$ is —$(CR^eR^f)_o$-heterocycloalkyl;

is 0, 1, or 2;

$R^e$ and $R^f$ are each independently H, halo, or $C_{1-4}$alkyl, each heterocycloalkyl present in $R^1$ is unsubstituted or substituted with one or two $R^x$ substituents;

wherein each $R^x$ substituent is independently halo, $C_{1-4}$alkyl, cycloalkyl, —$C_{1-2}$-haloalkyl, —OH, —$OC_{1-4}$alkyl, —O—$C_{1-2}$-haloalkyl, cyano, —$C(O)C_{1-4}$alkyl, —$C(O)NR^iR^j$, —$SO_2C_{1-4}$alkyl, —$SO_2NR^kR^l$, —$NR^qR^r$, —C(O)-cycloalkyl, —C(O)-aryl (optionally substituted with methyl or halo), —$CO_2C_{1-4}$alkyl, —$CO_2$aryl, —C(O)$CH_2$-aryl (optionally substituted with methyl or halo), —$CH_2$-aryl (optionally substituted with methyl or halo), or monocyclic heterocycloalkyl (optionally substituted with methyl, —C(O)$C_{1-4}$alkyl, or —$CO_2C_{1-4}$alkyl);

wherein $R^i$, $R^j$, $R^k$, and $R^l$ are each independently H, $C_{1-4}$alkyl, —$C_{1-4}$alkyl-OH, or —$C_{1-4}$alkyl-O—$C_{1-4}$alkyl, wherein $R^q$ and $R^r$ are each independently H, $C_{1-4}$alkyl, —$C_{1-4}$alkyl-OH, —$C_{1-4}$alkyl-O—$C_{1-4}$alkyl, —$C(O)C_{1-4}$alkyl, —$CO_2C_{1-4}$alkyl, or —$SO_2C_{1-4}$alkyl;

L is —$S(O)_2$—;

X is O;

one of $Y_1$, $Y_2$, and $Y_3$ is N and the other two are each CH, or $Y_1$, $Y_2$, and $Y_3$ are each CH;

$G_2$ is N;

$G_3$ is $CR^3$;

$G_4$ is N;

$G_5$ is $CR^5$; and $G_6$ is $CR^6$;

wherein $R^3$, $R^5$, and $R^6$ are each independently hydrogen, halogen, —OH, -alkyl, —O-alkyl, -haloalkyl, —O-haloalkyl, or —$NR^uR^v$;

$R^u$ is H or $C_{1-4}$alkyl;

$R^v$ is H, $C_{1-4}$alkyl, monocyclic cycloalkyl, —C(O)$C_{1-4}$alkyl, or —C(O)$NR^wR^y$;

wherein each alkyl present in $R^v$ is unsubstituted or substituted with —OH, —$NH_2$, —NH($C_{1-4}$alkyl), or —N($C_{1-4}$alkyl)$_2$, $R^w$ and $R^y$ are each independently H or $C_{1-4}$alkyl; and $R^7$ and $R^8$ are each independently hydrogen or $C_{1-4}$alkyl, or $R^7$ and $R^8$ are taken together to form —$CH_2CH_2$—;

or a pharmaceutically acceptable salt thereof.

12. The method of claim 11, wherein o is 0.

13. The method of claim 11, wherein each heterocycloalkyl present in $R^1$ is unsubstituted.

14. The method of claim 11, wherein $R^6$ is —$NR^uR^v$.

15. The method of claim 11, wherein $R^7$ and $R^8$ are each hydrogen.

16. The method of claim 11, wherein the compound is

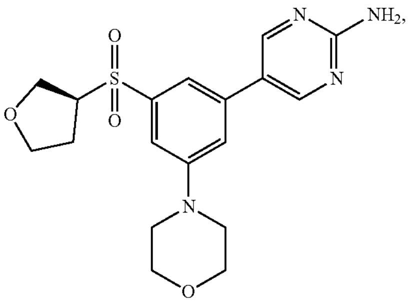

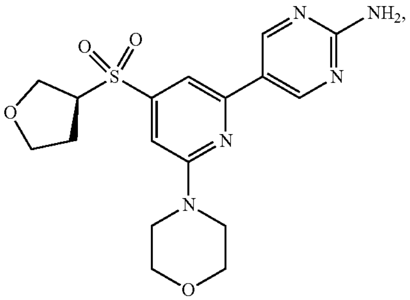

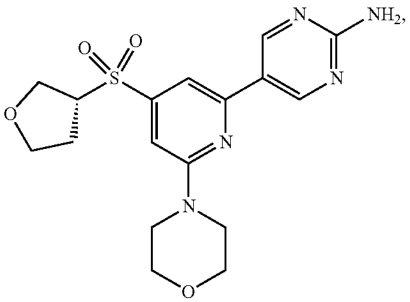

-continued

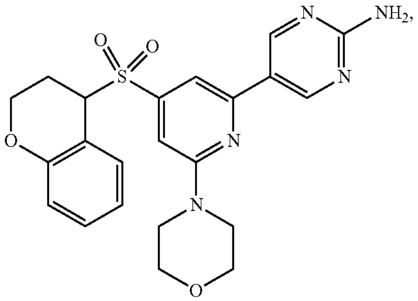

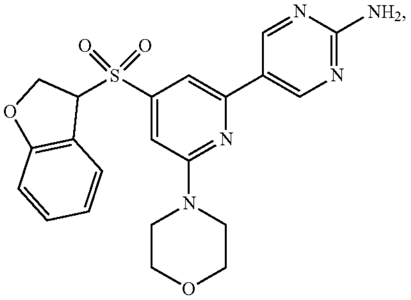

or

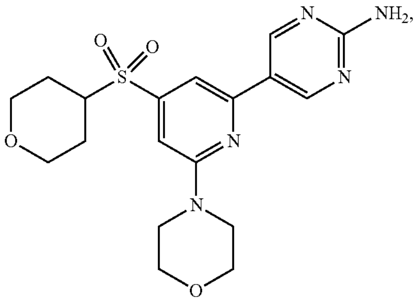

or a pharmaceutically acceptable salt thereof.

17. The method of claim 16, wherein the compound is

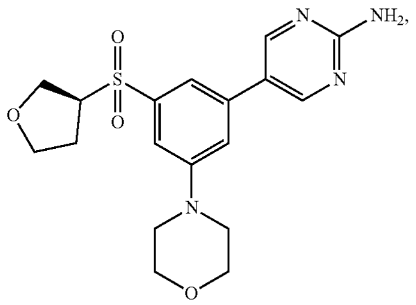 [SMILES: Nc1ncc(-c2cc(N3CCOCC3)cc(S(=O)(=O)[C@H]3CCOC3)c2)cn1]

or a pharmaceutically acceptable salt thereof.

18. The method of claim 16, wherein the compound is

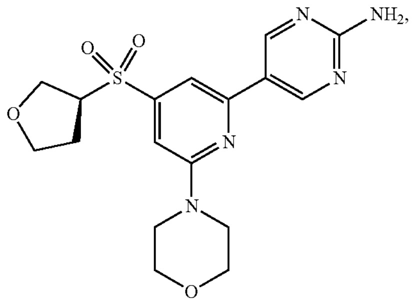 [SMILES: Nc1ncc(-c2cc(S(=O)(=O)[C@H]3CCOC3)cc(N3CCOCC3)n2)cn1]

or a pharmaceutically acceptable salt thereof.

19. The method of claim 16, wherein the compound is

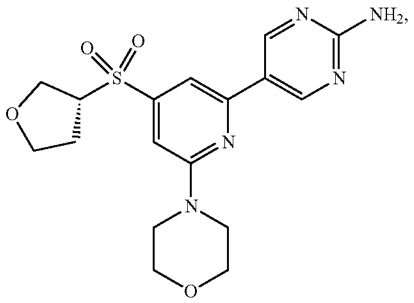 [SMILES: Nc1ncc(-c2cc(S(=O)(=O)[C@@H]3CCOC3)cc(N3CCOCC3)n2)cn1]

or a pharmaceutically acceptable salt thereof.

20. The method of claim 16, or a pharmaceutically acceptable salt thereof, wherein the compound is

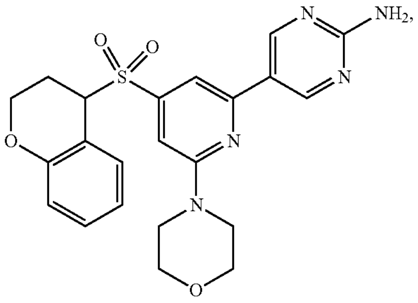 [SMILES: Nc1ncc(-c2cc(S(=O)(=O)C3CCOc4ccccc43)cc(N3CCOCC3)n2)cn1]

or a pharmaceutically acceptable salt thereof.

* * * * *